(12) United States Patent
Parks et al.

(10) Patent No.: US 12,251,105 B2
(45) Date of Patent: Mar. 18, 2025

(54) LOCKOUT ARRANGEMENTS FOR SURGICAL INSTRUMENTS

(71) Applicant: Cilag GmbH International, Zug (CH)

(72) Inventors: Darryl A. Parks, Mason, OH (US);
Scott A. Jenkins, Mason, OH (US);
Jeffery D. Bruns, Cincinnati, OH (US);
Jason M. Rector, Maineville, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/505,847

(22) Filed: Oct. 20, 2021

(65) Prior Publication Data

US 2023/0120209 A1   Apr. 20, 2023

(51) Int. Cl.
*A61B 17/072* (2006.01)
*A61B 17/068* (2006.01)

(52) U.S. Cl.
CPC ........ *A61B 17/072* (2013.01); *A61B 17/0682* (2013.01); *A61B 2017/07285* (2013.01)

(58) Field of Classification Search
CPC ............ A61B 17/072; A61B 17/07207; A61B 17/0682; A61B 2017/07285; A61B 2090/0814; A61B 2017/07271; A61B 2017/07278; A61B 2017/00473; A61B 2017/07228; A61B 2017/2927; A61B 2017/07214; A61B 2017/00398; A61B 2017/0725; A61B 34/30; A61B 17/068; A61B 2017/00477; A61B 2017/07264; A61B 2017/2933
USPC ..................................................... 227/180.1
See application file for complete search history.

(56) References Cited

U.S. PATENT DOCUMENTS

| | | |
|---|---|---|
| 3,490,675 A | 1/1970 | Green et al. |
| 3,494,533 A | 2/1970 | Green et al. |
| 3,643,851 A | 2/1972 | Green et al. |
| 3,662,939 A | 5/1972 | Bryan |
| 3,717,294 A | 2/1973 | Green |
| 3,819,100 A | 6/1974 | Noiles et al. |
| RE28,932 E | 8/1976 | Noiles et al. |
| 4,111,206 A | 9/1978 | Vishnevsky et al. |
| 4,272,002 A | 6/1981 | Moshofsky |

(Continued)

FOREIGN PATENT DOCUMENTS

| | | |
|---|---|---|
| AU | 2012200178 B2 | 7/2013 |
| CN | 2488482 Y | 5/2002 |

(Continued)

OTHER PUBLICATIONS

Disclosed Anonymously, "Motor-Driven Surgical Stapler Improvements," Research Disclosure Database No. 526041, Published: Feb. 2008.

(Continued)

*Primary Examiner* — Veronica Martin

(57) ABSTRACT

A surgical instrument including a first jaw that is configured to support a staple cartridge therein. An axially movable firing member is configured to move between a beginning position and an ending position by a first flexible drive member and a second flexible drive member. A firing member lock is configured to prevent the firing member from distally moving from the beginning position to the ending position unless an axially movable camming member in the staple cartridge that is supported in the first jaw is in a starting position.

20 Claims, 60 Drawing Sheets

(56) References Cited

U.S. PATENT DOCUMENTS

| | | |
|---|---|---|
| 4,305,539 A | 12/1981 | Korolkov et al. |
| 4,331,277 A | 5/1982 | Green |
| 4,379,457 A | 4/1983 | Gravener et al. |
| 4,383,634 A | 5/1983 | Green |
| 4,396,139 A | 8/1983 | Hall et al. |
| 4,397,311 A | 8/1983 | Kanshin et al. |
| 4,402,445 A | 9/1983 | Green |
| 4,415,112 A | 11/1983 | Green |
| 4,429,695 A | 2/1984 | Green |
| 4,434,796 A | 3/1984 | Karapetian et al. |
| 4,438,659 A | 3/1984 | Desplats |
| 4,475,679 A | 10/1984 | Fleury, Jr. |
| 4,489,875 A | 12/1984 | Crawford et al. |
| 4,500,024 A | 2/1985 | DiGiovanni et al. |
| 4,505,273 A | 3/1985 | Braun et al. |
| 4,505,414 A | 3/1985 | Filipi |
| 4,520,817 A | 6/1985 | Green |
| 4,522,327 A | 6/1985 | Korthoff et al. |
| 4,530,453 A | 7/1985 | Green |
| 4,566,620 A | 1/1986 | Green et al. |
| 4,573,622 A | 3/1986 | Green et al. |
| 4,580,712 A | 4/1986 | Green |
| 4,585,153 A | 4/1986 | Failla et al. |
| 4,605,001 A | 8/1986 | Rothfuss et al. |
| 4,605,004 A | 8/1986 | Di Giovanni et al. |
| 4,608,981 A | 9/1986 | Rothfuss et al. |
| 4,610,383 A | 9/1986 | Rothfuss et al. |
| 4,612,933 A | 9/1986 | Brinkerhoff et al. |
| 4,619,391 A | 10/1986 | Sharkany et al. |
| 4,629,107 A | 12/1986 | Fedotov et al. |
| 4,632,290 A | 12/1986 | Green et al. |
| 4,633,874 A | 1/1987 | Chow et al. |
| 4,634,419 A | 1/1987 | Kreizman et al. |
| 4,655,222 A | 4/1987 | Florez et al. |
| 4,662,555 A | 5/1987 | Thornton |
| 4,664,305 A | 5/1987 | Blake, III et al. |
| 4,669,647 A | 6/1987 | Storace |
| 4,671,445 A | 6/1987 | Barker et al. |
| 4,684,051 A | 8/1987 | Akopov et al. |
| 4,700,703 A | 10/1987 | Resnick et al. |
| 4,715,520 A | 12/1987 | Roehr, Jr. et al. |
| 4,719,917 A | 1/1988 | Barrows et al. |
| 4,727,308 A | 2/1988 | Huljak et al. |
| 4,728,020 A | 3/1988 | Green et al. |
| 4,747,820 A | 5/1988 | Hornlein et al. |
| 4,750,902 A | 6/1988 | Wuchinich et al. |
| 4,752,024 A | 6/1988 | Green et al. |
| 4,754,909 A | 7/1988 | Barker et al. |
| 4,767,044 A | 8/1988 | Green |
| 4,805,823 A | 2/1989 | Rothfuss |
| 4,809,695 A | 3/1989 | Gwathmey et al. |
| 4,817,847 A | 4/1989 | Redtenbacher et al. |
| 4,819,853 A | 4/1989 | Green |
| 4,821,939 A | 4/1989 | Green |
| 4,827,911 A | 5/1989 | Broadwin et al. |
| 4,844,068 A | 7/1989 | Arata et al. |
| 4,848,637 A | 7/1989 | Pruitt |
| 4,865,030 A | 9/1989 | Polyak |
| 4,869,414 A | 9/1989 | Green et al. |
| 4,869,415 A | 9/1989 | Fox |
| 4,896,678 A | 1/1990 | Ogawa |
| 4,931,047 A | 6/1990 | Broadwin et al. |
| 4,938,408 A | 7/1990 | Bedi et al. |
| 4,941,623 A | 7/1990 | Pruitt |
| 4,944,443 A | 7/1990 | Oddsen et al. |
| 4,978,333 A | 12/1990 | Broadwin et al. |
| 4,986,808 A | 1/1991 | Broadwin et al. |
| 5,002,553 A | 3/1991 | Shiber |
| 5,015,227 A | 5/1991 | Broadwin et al. |
| 5,038,109 A | 8/1991 | Goble et al. |
| 5,065,929 A | 11/1991 | Schulze et al. |
| 5,071,430 A | 12/1991 | de Salis et al. |
| 5,088,997 A | 2/1992 | Delahuerga et al. |
| 5,104,397 A | 4/1992 | Vasconcelos et al. |
| 5,122,156 A | 6/1992 | Granger et al. |
| 5,129,570 A | 7/1992 | Schulze et al. |
| 5,137,198 A | 8/1992 | Nobis et al. |
| 5,139,513 A | 8/1992 | Segato |
| 5,141,144 A | 8/1992 | Foslien et al. |
| 5,156,315 A | 10/1992 | Green et al. |
| 5,158,567 A | 10/1992 | Green |
| 5,190,517 A | 3/1993 | Zieve et al. |
| 5,221,036 A | 6/1993 | Takase |
| 5,221,281 A | 6/1993 | Klicek |
| 5,222,975 A | 6/1993 | Crainich |
| 5,236,440 A | 8/1993 | Hlavacek |
| 5,240,163 A | 8/1993 | Stein et al. |
| 5,258,009 A | 11/1993 | Conners |
| 5,258,012 A | 11/1993 | Luscombe et al. |
| 5,281,216 A | 1/1994 | Klicek |
| 5,282,829 A | 2/1994 | Hermes |
| 5,284,128 A | 2/1994 | Hart |
| 5,304,204 A | 4/1994 | Bregen |
| 5,312,023 A | 5/1994 | Green et al. |
| 5,312,329 A | 5/1994 | Beaty et al. |
| 5,333,772 A | 8/1994 | Rothfuss et al. |
| 5,342,395 A | 8/1994 | Jarrett et al. |
| 5,342,396 A | 8/1994 | Cook |
| 5,346,504 A | 9/1994 | Ortiz et al. |
| 5,350,400 A | 9/1994 | Esposito et al. |
| 5,358,506 A | 10/1994 | Green et al. |
| 5,364,001 A | 11/1994 | Bryan |
| 5,366,479 A | 11/1994 | McGarry et al. |
| 5,370,645 A | 12/1994 | Klicek et al. |
| 5,372,596 A | 12/1994 | Klicek et al. |
| 5,374,277 A | 12/1994 | Hassler |
| 5,381,943 A | 1/1995 | Allen et al. |
| 5,382,247 A | 1/1995 | Cimino et al. |
| 5,383,880 A | 1/1995 | Hooven |
| 5,389,104 A | 2/1995 | Hahnen et al. |
| 5,395,033 A | 3/1995 | Byrne et al. |
| 5,395,384 A | 3/1995 | Duthoit et al. |
| 5,397,046 A | 3/1995 | Savage et al. |
| 5,403,312 A | 4/1995 | Yates et al. |
| 5,405,072 A | 4/1995 | Zlock et al. |
| 5,405,344 A | 4/1995 | Williamson et al. |
| 5,413,267 A | 5/1995 | Solyntjes et al. |
| 5,413,272 A | 5/1995 | Green et al. |
| 5,413,573 A | 5/1995 | Koivukangas |
| 5,417,361 A | 5/1995 | Williamson, IV |
| 5,421,829 A | 6/1995 | Olichney et al. |
| 5,422,567 A | 6/1995 | Matsunaga |
| 5,423,471 A | 6/1995 | Mastri et al. |
| 5,423,809 A | 6/1995 | Klicek |
| 5,425,745 A | 6/1995 | Green et al. |
| 5,433,721 A | 7/1995 | Hooven et al. |
| 5,438,302 A | 8/1995 | Goble |
| 5,441,483 A | 8/1995 | Avitall |
| 5,447,265 A | 9/1995 | Vidal et al. |
| 5,447,417 A | 9/1995 | Kuhl et al. |
| 5,449,355 A | 9/1995 | Rhum et al. |
| 5,452,837 A | 9/1995 | Williamson, IV et al. |
| 5,462,215 A | 10/1995 | Viola et al. |
| 5,465,896 A | 11/1995 | Allen et al. |
| 5,466,020 A | 11/1995 | Page et al. |
| 5,472,442 A | 12/1995 | Klicek |
| 5,474,057 A | 12/1995 | Makower et al. |
| 5,474,566 A | 12/1995 | Alesi et al. |
| 5,478,354 A | 12/1995 | Tovey et al. |
| 5,480,089 A | 1/1996 | Blewett |
| 5,484,398 A | 1/1996 | Stoddard |
| 5,485,947 A | 1/1996 | Olson et al. |
| 5,485,952 A | 1/1996 | Fontayne |
| 5,487,499 A | 1/1996 | Sorrentino et al. |
| 5,489,058 A | 2/1996 | Plyley et al. |
| 5,496,312 A | 3/1996 | Klicek |
| 5,496,317 A | 3/1996 | Goble et al. |
| 5,497,933 A | 3/1996 | DeFonzo et al. |
| 5,503,320 A | 4/1996 | Webster et al. |
| 5,503,638 A | 4/1996 | Cooper et al. |
| 5,505,363 A | 4/1996 | Green et al. |
| 5,509,596 A | 4/1996 | Green et al. |
| 5,509,916 A | 4/1996 | Taylor |
| 5,520,678 A | 5/1996 | Heckele et al. |

(56) References Cited

U.S. PATENT DOCUMENTS

| | | |
|---|---|---|
| 5,529,235 A | 6/1996 | Boiarski et al. |
| 5,533,661 A | 7/1996 | Main et al. |
| 5,535,934 A | 7/1996 | Boiarski et al. |
| 5,535,935 A | 7/1996 | Vidal et al. |
| 5,535,937 A | 7/1996 | Boiarski et al. |
| 5,541,376 A | 7/1996 | Ladtkow et al. |
| 5,547,117 A | 8/1996 | Hamblin et al. |
| 5,553,765 A | 9/1996 | Knodel et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,564,615 A | 10/1996 | Bishop et al. |
| 5,571,285 A | 11/1996 | Chow et al. |
| 5,577,654 A | 11/1996 | Bishop |
| 5,579,978 A | 12/1996 | Green et al. |
| 5,580,067 A | 12/1996 | Hamblin et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,597,107 A | 1/1997 | Knodel et al. |
| 5,599,344 A | 2/1997 | Paterson |
| 5,601,224 A | 2/1997 | Bishop et al. |
| 5,605,272 A | 2/1997 | Witt et al. |
| 5,605,273 A | 2/1997 | Hamblin et al. |
| 5,607,094 A | 3/1997 | Clark et al. |
| 5,609,601 A | 3/1997 | Kolesa et al. |
| 5,611,709 A | 3/1997 | McAnulty |
| 5,613,966 A | 3/1997 | Makower et al. |
| 5,615,820 A | 4/1997 | Viola |
| 5,618,303 A | 4/1997 | Marlow et al. |
| 5,619,992 A | 4/1997 | Guthrie et al. |
| 5,628,446 A | 5/1997 | Geiste et al. |
| 5,628,743 A | 5/1997 | Cimino |
| 5,628,745 A | 5/1997 | Bek |
| 5,630,539 A | 5/1997 | Plyley et al. |
| 5,630,540 A | 5/1997 | Blewett |
| 5,632,432 A | 5/1997 | Schulze et al. |
| 5,634,584 A | 6/1997 | Okorocha et al. |
| 5,636,779 A | 6/1997 | Palmer |
| 5,636,780 A | 6/1997 | Green et al. |
| 5,639,008 A | 6/1997 | Gallagher et al. |
| 5,645,209 A | 7/1997 | Green et al. |
| 5,647,526 A | 7/1997 | Green et al. |
| 5,647,869 A | 7/1997 | Goble et al. |
| 5,651,491 A | 7/1997 | Heaton et al. |
| 5,653,373 A | 8/1997 | Green et al. |
| 5,653,374 A | 8/1997 | Young et al. |
| 5,655,698 A | 8/1997 | Yoon |
| 5,657,921 A | 8/1997 | Young et al. |
| 5,662,258 A | 9/1997 | Knodel et al. |
| 5,662,260 A | 9/1997 | Yoon |
| 5,662,667 A | 9/1997 | Knodel |
| 5,667,527 A | 9/1997 | Cook |
| 5,669,544 A | 9/1997 | Schulze et al. |
| 5,669,904 A | 9/1997 | Platt, Jr. et al. |
| 5,669,907 A | 9/1997 | Platt, Jr. et al. |
| 5,673,840 A | 10/1997 | Schulze et al. |
| 5,673,841 A | 10/1997 | Schulze et al. |
| 5,673,842 A | 10/1997 | Bittner et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,690,269 A | 11/1997 | Bolanos et al. |
| 5,692,668 A | 12/1997 | Schulze et al. |
| 5,693,020 A | 12/1997 | Rauh |
| 5,693,051 A | 12/1997 | Schulze et al. |
| 5,695,494 A | 12/1997 | Becker |
| 5,695,524 A | 12/1997 | Kelley et al. |
| 5,697,543 A | 12/1997 | Burdorff |
| 5,702,387 A | 12/1997 | Arts et al. |
| 5,704,534 A | 1/1998 | Huitema et al. |
| 5,706,997 A | 1/1998 | Green et al. |
| 5,706,998 A | 1/1998 | Plyley et al. |
| 5,709,334 A | 1/1998 | Sorrentino et al. |
| 5,709,680 A | 1/1998 | Yates et al. |
| 5,711,472 A | 1/1998 | Bryan |
| 5,713,895 A | 2/1998 | Lontine et al. |
| 5,715,604 A | 2/1998 | Lanzoni |
| 5,715,987 A | 2/1998 | Kelley et al. |
| 5,715,988 A | 2/1998 | Palmer |
| 5,718,359 A | 2/1998 | Palmer et al. |
| 5,720,744 A | 2/1998 | Eggleston et al. |
| 5,725,554 A | 3/1998 | Simon et al. |
| 5,730,758 A | 3/1998 | Allgeyer |
| 5,732,871 A | 3/1998 | Clark et al. |
| 5,732,872 A | 3/1998 | Bolduc et al. |
| 5,735,445 A | 4/1998 | Vidal et al. |
| 5,735,874 A | 4/1998 | Measamer et al. |
| 5,743,456 A | 4/1998 | Jones et al. |
| 5,749,893 A | 5/1998 | Vidal et al. |
| 5,752,644 A | 5/1998 | Bolanos et al. |
| 5,752,965 A | 5/1998 | Francis et al. |
| 5,762,255 A | 6/1998 | Chrisman et al. |
| 5,762,256 A | 6/1998 | Mastri et al. |
| 5,772,659 A | 6/1998 | Becker et al. |
| 5,776,130 A | 7/1998 | Buysse et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,748 A | 7/1998 | Palmer et al. |
| 5,785,232 A | 7/1998 | Vidal et al. |
| 5,794,834 A | 8/1998 | Hamblin et al. |
| 5,797,536 A | 8/1998 | Smith et al. |
| 5,797,537 A | 8/1998 | Oberlin et al. |
| 5,797,538 A | 8/1998 | Heaton et al. |
| 5,800,379 A | 9/1998 | Edwards |
| 5,807,393 A | 9/1998 | Williamson, IV et al. |
| 5,814,055 A | 9/1998 | Knodel et al. |
| 5,820,009 A | 10/1998 | Melling et al. |
| 5,826,776 A | 10/1998 | Schulze et al. |
| 5,827,271 A | 10/1998 | Buysse et al. |
| 5,830,598 A | 11/1998 | Patterson |
| 5,833,695 A | 11/1998 | Yoon |
| 5,836,503 A | 11/1998 | Ehrenfels et al. |
| 5,839,639 A | 11/1998 | Sauer et al. |
| 5,843,021 A | 12/1998 | Edwards et al. |
| 5,855,311 A | 1/1999 | Hamblin et al. |
| 5,860,975 A | 1/1999 | Goble et al. |
| 5,865,361 A | 2/1999 | Milliman et al. |
| 5,868,760 A | 2/1999 | McGuckin, Jr. |
| 5,878,937 A | 3/1999 | Green et al. |
| 5,878,938 A | 3/1999 | Bittner et al. |
| 5,893,506 A | 4/1999 | Powell |
| 5,894,979 A | 4/1999 | Powell |
| 5,897,552 A | 4/1999 | Edwards et al. |
| 5,901,895 A | 5/1999 | Heaton et al. |
| 5,902,312 A | 5/1999 | Frater et al. |
| 5,908,402 A | 6/1999 | Blythe |
| 5,918,791 A | 7/1999 | Sorrentino et al. |
| 5,937,951 A | 8/1999 | Izuchukwu et al. |
| 5,941,442 A | 8/1999 | Geiste et al. |
| 5,944,715 A | 8/1999 | Goble et al. |
| 5,947,984 A | 9/1999 | Whipple |
| 5,951,552 A | 9/1999 | Long et al. |
| 5,954,259 A | 9/1999 | Viola et al. |
| 5,988,479 A | 11/1999 | Palmer |
| 6,004,319 A | 12/1999 | Goble et al. |
| 6,010,054 A | 1/2000 | Johnson et al. |
| 6,012,494 A | 1/2000 | Balazs |
| 6,013,076 A | 1/2000 | Goble et al. |
| 6,015,406 A | 1/2000 | Goble et al. |
| 6,027,501 A | 2/2000 | Goble et al. |
| 6,032,849 A | 3/2000 | Mastri et al. |
| 6,033,399 A | 3/2000 | Gines |
| 6,039,734 A | 3/2000 | Goble |
| 6,050,172 A | 4/2000 | Corves et al. |
| 6,050,472 A | 4/2000 | Shibata |

(56) References Cited

U.S. PATENT DOCUMENTS

| | | |
|---|---|---|
| 6,050,996 A | 4/2000 | Schmaltz et al. |
| 6,068,627 A | 5/2000 | Orszulak et al. |
| 6,074,401 A | 6/2000 | Gardiner et al. |
| 6,079,606 A | 6/2000 | Milliman et al. |
| 6,083,191 A | 7/2000 | Rose |
| 6,083,242 A | 7/2000 | Cook |
| 6,093,186 A | 7/2000 | Goble |
| 6,099,551 A | 8/2000 | Gabbay |
| 6,109,500 A | 8/2000 | Alli et al. |
| 6,117,158 A | 9/2000 | Measamer et al. |
| 6,119,913 A | 9/2000 | Adams et al. |
| 6,131,789 A | 10/2000 | Schulze et al. |
| 6,131,790 A | 10/2000 | Piraka |
| 6,149,660 A | 11/2000 | Laufer et al. |
| 6,155,473 A | 12/2000 | Tompkins et al. |
| 6,156,056 A | 12/2000 | Kearns et al. |
| 6,162,208 A | 12/2000 | Hipps |
| 6,171,330 B1 | 1/2001 | Benchetrit |
| 6,187,003 B1 | 2/2001 | Buysse et al. |
| 6,202,914 B1 | 3/2001 | Geiste et al. |
| 6,210,403 B1 | 4/2001 | Klicek |
| 6,213,999 B1 | 4/2001 | Platt, Jr. et al. |
| 6,228,081 B1 | 5/2001 | Goble |
| 6,228,083 B1 | 5/2001 | Lands et al. |
| 6,241,139 B1 | 6/2001 | Milliman et al. |
| 6,250,532 B1 | 6/2001 | Green et al. |
| 6,261,286 B1 | 7/2001 | Goble et al. |
| 6,273,897 B1 | 8/2001 | Dalessandro et al. |
| 6,277,114 B1 | 8/2001 | Bullivant et al. |
| 6,302,311 B1 | 10/2001 | Adams et al. |
| 6,322,494 B1 | 11/2001 | Bullivant et al. |
| 6,325,799 B1 | 12/2001 | Goble |
| 6,325,805 B1 | 12/2001 | Ogilvie et al. |
| 6,325,810 B1 | 12/2001 | Hamilton et al. |
| 6,330,965 B1 | 12/2001 | Milliman et al. |
| 6,334,861 B1 | 1/2002 | Chandler et al. |
| 6,336,926 B1 | 1/2002 | Goble |
| 6,338,737 B1 | 1/2002 | Toledano |
| 6,358,224 B1 | 3/2002 | Tims et al. |
| 6,387,113 B1 | 5/2002 | Hawkins et al. |
| H2037 H | 7/2002 | Yates et al. |
| RE37,814 E | 8/2002 | Allgeyer |
| 6,439,446 B1 | 8/2002 | Perry et al. |
| 6,443,973 B1 | 9/2002 | Whitman |
| 6,450,391 B1 | 9/2002 | Kayan et al. |
| 6,488,196 B1 | 12/2002 | Fenton, Jr. |
| 6,488,197 B1 | 12/2002 | Whitman |
| 6,488,659 B1 | 12/2002 | Rosenman |
| 6,491,201 B1 | 12/2002 | Whitman |
| 6,491,690 B1 | 12/2002 | Goble et al. |
| 6,505,768 B2 | 1/2003 | Whitman |
| 6,517,528 B1 | 2/2003 | Pantages et al. |
| 6,517,565 B1 | 2/2003 | Whitman et al. |
| 6,517,566 B1 | 2/2003 | Hovland et al. |
| 6,533,157 B1 | 3/2003 | Whitman |
| 6,558,379 B1 | 5/2003 | Batchelor et al. |
| 6,569,085 B2 | 5/2003 | Kortenbach et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,597 B2 | 7/2003 | Grant et al. |
| 6,607,475 B2 | 8/2003 | Doyle et al. |
| 6,616,686 B2 | 9/2003 | Coleman et al. |
| 6,619,529 B2 | 9/2003 | Green et al. |
| 6,629,988 B2 | 10/2003 | Weadock |
| 6,638,297 B1 | 10/2003 | Huitema |
| 6,644,532 B2 | 11/2003 | Green et al. |
| 6,656,193 B2 | 12/2003 | Grant et al. |
| 6,669,073 B2 | 12/2003 | Milliman et al. |
| 6,676,660 B2 | 1/2004 | Wampler et al. |
| 6,681,978 B2 | 1/2004 | Geiste et al. |
| 6,695,198 B2 | 2/2004 | Adams et al. |
| 6,698,643 B2 | 3/2004 | Whitman |
| 6,716,233 B1 | 4/2004 | Whitman |
| 6,722,552 B2 | 4/2004 | Fenton, Jr. |
| 6,723,109 B2 | 4/2004 | Solingen |
| 6,749,560 B1 | 6/2004 | Konstorum et al. |
| 6,755,338 B2 | 6/2004 | Hahnen et al. |
| 6,761,685 B2 | 7/2004 | Adams et al. |
| 6,769,590 B2 | 8/2004 | Vresh et al. |
| 6,769,594 B2 | 8/2004 | Orban, III |
| 6,786,382 B1 | 9/2004 | Hoffman |
| 6,793,652 B1 | 9/2004 | Whitman et al. |
| 6,793,661 B2 | 9/2004 | Hamilton et al. |
| 6,817,508 B1 | 11/2004 | Racenet et al. |
| 6,817,509 B2 | 11/2004 | Geiste et al. |
| 6,817,974 B2 | 11/2004 | Cooper et al. |
| 6,830,174 B2 | 12/2004 | Hillstead et al. |
| 6,835,336 B2 | 12/2004 | Watt |
| 6,840,423 B2 | 1/2005 | Adams et al. |
| 6,843,403 B2 | 1/2005 | Whitman |
| 6,858,005 B2 | 2/2005 | Ohline et al. |
| 6,866,178 B2 | 3/2005 | Adams et al. |
| 6,874,669 B2 | 4/2005 | Adams et al. |
| 6,877,647 B2 | 4/2005 | Green et al. |
| 6,878,106 B1 | 4/2005 | Herrmann |
| 6,905,057 B2 | 6/2005 | Swayze et al. |
| 6,908,472 B2 | 6/2005 | Wiener et al. |
| 6,932,810 B2 | 8/2005 | Ryan |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,958,035 B2 | 10/2005 | Friedman et al. |
| 6,959,851 B2 | 11/2005 | Heinrich |
| 6,959,852 B2 | 11/2005 | Shelton, IV et al. |
| 6,964,363 B2 | 11/2005 | Wales et al. |
| 6,978,921 B2 | 12/2005 | Shelton, IV et al. |
| 6,981,628 B2 | 1/2006 | Wales |
| 6,984,231 B2 | 1/2006 | Goble et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,995,729 B2 | 2/2006 | Govari et al. |
| 7,000,818 B2 | 2/2006 | Shelton, IV et al. |
| 7,000,819 B2 | 2/2006 | Swayze et al. |
| 7,001,408 B2 | 2/2006 | Knodel et al. |
| 7,008,435 B2 | 3/2006 | Cummins |
| 7,018,357 B2 | 3/2006 | Emmons |
| 7,032,798 B2 | 4/2006 | Whitman et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,052,494 B2 | 5/2006 | Goble et al. |
| 7,055,730 B2 | 6/2006 | Ehrenfels et al. |
| 7,055,731 B2 | 6/2006 | Shelton, IV et al. |
| 7,056,330 B2 | 6/2006 | Gayton |
| 7,059,508 B2 | 6/2006 | Shelton, IV et al. |
| 7,070,083 B2 | 7/2006 | Jankowski |
| 7,077,856 B2 | 7/2006 | Whitman |
| 7,080,769 B2 | 7/2006 | Vresh et al. |
| 7,083,075 B2 | 8/2006 | Swayze et al. |
| 7,097,089 B2 | 8/2006 | Marczyk |
| 7,097,644 B2 | 8/2006 | Long |
| 7,108,709 B2 | 9/2006 | Cummins |
| 7,111,769 B2 | 9/2006 | Wales et al. |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,128,748 B2 | 10/2006 | Mooradian et al. |
| 7,133,601 B2 | 11/2006 | Phillips et al. |
| 7,137,981 B2 | 11/2006 | Long |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,147,139 B2 | 12/2006 | Schwemberger et al. |
| 7,147,637 B2 | 12/2006 | Goble |
| 7,147,650 B2 | 12/2006 | Lee |
| 7,150,748 B2 | 12/2006 | Ebbutt et al. |
| 7,156,863 B2 | 1/2007 | Sonnenschein et al. |
| 7,159,750 B2 | 1/2007 | Racenet et al. |

(56) References Cited

U.S. PATENT DOCUMENTS

| | | |
|---|---|---|
| 7,168,604 B2 | 1/2007 | Milliman et al. |
| 7,172,104 B2 | 2/2007 | Scirica et al. |
| 7,182,239 B1 | 2/2007 | Myers |
| 7,199,537 B2 | 4/2007 | Okamura et al. |
| 7,204,404 B2 | 4/2007 | Nguyen et al. |
| 7,204,835 B2 | 4/2007 | Latterell et al. |
| 7,207,471 B2 | 4/2007 | Heinrich et al. |
| 7,211,081 B2 | 5/2007 | Goble |
| 7,213,736 B2 | 5/2007 | Wales et al. |
| 7,220,272 B2 | 5/2007 | Weadock |
| 7,225,963 B2 | 6/2007 | Scirica |
| 7,225,964 B2 | 6/2007 | Mastri et al. |
| 7,237,708 B1 | 7/2007 | Guy et al. |
| 7,238,195 B2 | 7/2007 | Viola |
| 7,246,734 B2 | 7/2007 | Shelton, IV |
| 7,247,161 B2 | 7/2007 | Johnston et al. |
| 7,258,262 B2 | 8/2007 | Mastri et al. |
| 7,258,546 B2 | 8/2007 | Beier et al. |
| 7,278,562 B2 | 10/2007 | Mastri et al. |
| 7,282,048 B2 | 10/2007 | Goble et al. |
| 7,293,685 B2 | 11/2007 | Ehrenfels et al. |
| 7,296,722 B2 | 11/2007 | Ivanko |
| 7,296,724 B2 | 11/2007 | Green et al. |
| 7,300,450 B2 | 11/2007 | Vleugels et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,326,203 B2 | 2/2008 | Papineau et al. |
| 7,328,828 B2 | 2/2008 | Ortiz et al. |
| 7,328,829 B2 | 2/2008 | Arad et al. |
| 7,331,340 B2 | 2/2008 | Barney |
| 7,334,717 B2 | 2/2008 | Rethy et al. |
| 7,334,718 B2 | 2/2008 | McAlister et al. |
| 7,336,048 B2 | 2/2008 | Lohr |
| 7,354,447 B2 | 4/2008 | Shelton, IV et al. |
| 7,357,287 B2 | 4/2008 | Shelton, IV et al. |
| 7,357,806 B2 | 4/2008 | Rivera et al. |
| 7,364,060 B2 | 4/2008 | Milliman |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,398,908 B2 | 7/2008 | Holsten et al. |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,404,822 B2 | 7/2008 | Viart et al. |
| 7,407,074 B2 | 8/2008 | Ortiz et al. |
| 7,407,075 B2 | 8/2008 | Holsten et al. |
| 7,407,076 B2 | 8/2008 | Racenet et al. |
| 7,407,077 B2 | 8/2008 | Ortiz et al. |
| 7,407,078 B2 | 8/2008 | Shelton, IV et al. |
| 7,410,086 B2 | 8/2008 | Ortiz et al. |
| 7,416,101 B2 | 8/2008 | Shelton, IV et al. |
| RE40,514 E | 9/2008 | Mastri et al. |
| 7,419,080 B2 | 9/2008 | Smith et al. |
| 7,419,321 B2 | 9/2008 | Tereschouk |
| 7,422,136 B1 | 9/2008 | Marczyk |
| 7,422,139 B2 | 9/2008 | Shelton, IV et al. |
| 7,427,607 B2 | 9/2008 | Suzuki |
| 7,431,188 B1 | 10/2008 | Marczyk |
| 7,431,189 B2 | 10/2008 | Shelton, IV et al. |
| 7,431,694 B2 | 10/2008 | Stefanchik et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,209 B1 | 10/2008 | Hess et al. |
| 7,438,718 B2 | 10/2008 | Milliman et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,451,904 B2 | 11/2008 | Shelton, IV |
| 7,455,682 B2 | 11/2008 | Viola |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,253 B2 | 1/2009 | Dycus et al. |
| 7,481,347 B2 | 1/2009 | Roy |
| 7,481,348 B2 | 1/2009 | Marczyk |
| 7,481,349 B2 | 1/2009 | Holsten et al. |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,513,408 B2 | 4/2009 | Shelton, IV et al. |
| 7,517,356 B2 | 4/2009 | Heinrich |
| 7,547,312 B2 | 6/2009 | Bauman et al. |
| 7,549,563 B2 | 6/2009 | Mather et al. |
| 7,549,564 B2 | 6/2009 | Boudreaux |
| 7,549,998 B2 | 6/2009 | Braun |
| 7,552,854 B2 | 6/2009 | Wixey et al. |
| 7,556,185 B2 | 7/2009 | Viola |
| 7,559,449 B2 | 7/2009 | Viola |
| 7,559,450 B2 | 7/2009 | Wales et al. |
| 7,559,452 B2 | 7/2009 | Wales et al. |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,615,067 B2 | 11/2009 | Lee et al. |
| 7,624,902 B2 | 12/2009 | Marczyk et al. |
| 7,624,903 B2 | 12/2009 | Green et al. |
| 7,625,370 B2 | 12/2009 | Hart et al. |
| 7,631,793 B2 | 12/2009 | Rethy et al. |
| 7,631,794 B2 | 12/2009 | Rethy et al. |
| 7,635,074 B2 | 12/2009 | Olson et al. |
| 7,637,409 B2 | 12/2009 | Marczyk |
| 7,638,958 B2 | 12/2009 | Philipp et al. |
| 7,641,091 B2 | 1/2010 | Olson et al. |
| 7,641,092 B2 | 1/2010 | Kruszynski et al. |
| 7,641,093 B2 | 1/2010 | Doll et al. |
| 7,641,095 B2 | 1/2010 | Viola |
| 7,644,848 B2 | 1/2010 | Swayze et al. |
| 7,645,230 B2 | 1/2010 | Mikkaichi et al. |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,662,161 B2 | 2/2010 | Briganti et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,694,865 B2 | 4/2010 | Scirica |
| 7,695,485 B2 | 4/2010 | Whitman et al. |
| 7,699,204 B2 | 4/2010 | Viola |
| 7,699,846 B2 | 4/2010 | Ryan |
| 7,699,856 B2 | 4/2010 | Van Wyk et al. |
| 7,703,653 B2 | 4/2010 | Shah et al. |

(56) References Cited

U.S. PATENT DOCUMENTS

| | | |
|---|---|---|
| 7,708,180 B2 | 5/2010 | Murray et al. |
| 7,708,181 B2 | 5/2010 | Cole et al. |
| 7,708,182 B2 | 5/2010 | Viola |
| 7,708,758 B2 | 5/2010 | Lee et al. |
| 7,717,312 B2 | 5/2010 | Beetel |
| 7,717,313 B2 | 5/2010 | Criscuolo et al. |
| 7,717,846 B2 | 5/2010 | Zirps et al. |
| 7,721,930 B2 | 5/2010 | McKenna et al. |
| 7,721,931 B2 | 5/2010 | Shelton, IV et al. |
| 7,721,933 B2 | 5/2010 | Ehrenfels et al. |
| 7,721,934 B2 | 5/2010 | Shelton, IV et al. |
| 7,721,936 B2 | 5/2010 | Shalton, IV et al. |
| 7,726,537 B2 | 6/2010 | Olson et al. |
| 7,726,538 B2 | 6/2010 | Holsten et al. |
| 7,731,072 B2 | 6/2010 | Timm et al. |
| 7,731,073 B2 | 6/2010 | Wixey et al. |
| 7,735,703 B2 | 6/2010 | Morgan et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,744,627 B2 | 6/2010 | Orban, III et al. |
| 7,744,628 B2 | 6/2010 | Viola |
| 7,751,870 B2 | 7/2010 | Whitman |
| 7,753,245 B2 | 7/2010 | Boudreaux et al. |
| 7,753,904 B2 | 7/2010 | Shelton, IV et al. |
| 7,758,612 B2 | 7/2010 | Shipp |
| 7,766,209 B2 | 8/2010 | Baxter, III et al. |
| 7,766,210 B2 | 8/2010 | Shelton, IV et al. |
| 7,770,773 B2 | 8/2010 | Whitman et al. |
| 7,770,774 B2 | 8/2010 | Mastri et al. |
| 7,770,775 B2 | 8/2010 | Shelton, IV et al. |
| 7,770,776 B2 | 8/2010 | Chen et al. |
| 7,780,054 B2 | 8/2010 | Wales |
| 7,780,055 B2 | 8/2010 | Scirica et al. |
| 7,784,662 B2 | 8/2010 | Wales et al. |
| 7,784,663 B2 | 8/2010 | Shelton, IV |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,810,690 B2 | 10/2010 | Bilotti et al. |
| 7,810,691 B2 | 10/2010 | Boyden et al. |
| 7,810,692 B2 | 10/2010 | Hall et al. |
| 7,810,693 B2 | 10/2010 | Broehl et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,823,592 B2 | 11/2010 | Bettuchi et al. |
| 7,824,426 B2 | 11/2010 | Racenet et al. |
| 7,828,189 B2 | 11/2010 | Holsten et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,837,694 B2 | 11/2010 | Tethrake et al. |
| 7,842,028 B2 | 11/2010 | Lee |
| 7,845,533 B2 | 12/2010 | Marczyk et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,854,736 B2 | 12/2010 | Ryan |
| 7,857,183 B2 | 12/2010 | Shelton, IV |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,866,525 B2 | 1/2011 | Scirica |
| 7,866,527 B2 | 1/2011 | Hall et al. |
| 7,870,989 B2 | 1/2011 | Viola et al. |
| 7,886,951 B2 | 2/2011 | Hessler |
| 7,886,952 B2 | 2/2011 | Scirica et al. |
| 7,891,531 B1 | 2/2011 | Ward |
| 7,891,532 B2 | 2/2011 | Mastri et al. |
| 7,893,586 B2 | 2/2011 | West et al. |
| 7,896,877 B2 | 3/2011 | Hall et al. |
| 7,900,805 B2 | 3/2011 | Shelton, IV et al. |
| 7,905,380 B2 | 3/2011 | Shelton, IV et al. |
| 7,905,381 B2 | 3/2011 | Baxter, III et al. |
| 7,905,902 B2 | 3/2011 | Huitema et al. |
| 7,909,039 B2 | 3/2011 | Hur |
| 7,909,220 B2 | 3/2011 | Viola |
| 7,909,221 B2 | 3/2011 | Viola et al. |
| 7,913,891 B2 | 3/2011 | Doll et al. |
| 7,913,893 B2 | 3/2011 | Mastri et al. |
| 7,918,376 B1 | 4/2011 | Knodel et al. |
| 7,918,377 B2 | 4/2011 | Measamer et al. |
| 7,918,845 B2 | 4/2011 | Saadat et al. |
| 7,922,061 B2 | 4/2011 | Shelton, IV et al. |
| 7,922,063 B2 | 4/2011 | Zemlok et al. |
| 7,922,743 B2 | 4/2011 | Heinrich et al. |
| 7,926,691 B2 | 4/2011 | Viola et al. |
| 7,931,660 B2 | 4/2011 | Aranyi et al. |
| 7,934,630 B2 | 5/2011 | Shelton, IV et al. |
| 7,934,631 B2 | 5/2011 | Balbierz et al. |
| 7,935,773 B2 | 5/2011 | Hadba et al. |
| 7,938,307 B2 | 5/2011 | Bettuchi |
| 7,942,303 B2 | 5/2011 | Shah |
| 7,942,890 B2 | 5/2011 | D'Agostino et al. |
| 7,950,560 B2 | 5/2011 | Zemlok et al. |
| 7,950,561 B2 | 5/2011 | Aranyi |
| 7,951,071 B2 | 5/2011 | Whitman et al. |
| 7,954,682 B2 | 6/2011 | Giordano et al. |
| 7,954,684 B2 | 6/2011 | Boudreaux |
| 7,954,686 B2 | 6/2011 | Baxter et al. |
| 7,954,687 B2 | 6/2011 | Zemlok et al. |
| 7,959,050 B2 | 6/2011 | Smith et al. |
| 7,959,051 B2 | 6/2011 | Smith et al. |
| 7,963,432 B2 | 6/2011 | Knodel et al. |
| 7,966,799 B2 | 6/2011 | Morgan et al. |
| 7,967,180 B2 | 6/2011 | Scirica |
| 7,967,181 B2 | 6/2011 | Viola et al. |
| 7,967,839 B2 | 6/2011 | Flock et al. |
| 7,976,563 B2 | 7/2011 | Summerer |
| 7,980,443 B2 | 7/2011 | Scheib et al. |
| 7,988,026 B2 | 8/2011 | Knodel et al. |
| 7,988,027 B2 | 8/2011 | Olson et al. |
| 7,988,779 B2 | 8/2011 | Disalvo et al. |
| 7,992,757 B2 | 8/2011 | Wheeler et al. |
| 7,997,469 B2 | 8/2011 | Olson et al. |
| 8,002,795 B2 | 8/2011 | Beetel |
| 8,006,885 B2 | 8/2011 | Marczyk |
| 8,006,889 B2 | 8/2011 | Adams et al. |
| 8,011,550 B2 | 9/2011 | Aranyi et al. |
| 8,011,551 B2 | 9/2011 | Marczyk et al. |
| 8,011,553 B2 | 9/2011 | Mastri et al. |
| 8,016,176 B2 | 9/2011 | Kasvikis et al. |
| 8,016,177 B2 | 9/2011 | Bettuchi et al. |
| 8,016,178 B2 | 9/2011 | Olson et al. |
| 8,016,849 B2 | 9/2011 | Wenchell |
| 8,016,855 B2 | 9/2011 | Whitman et al. |
| 8,016,858 B2 | 9/2011 | Whitman |
| 8,020,742 B2 | 9/2011 | Marczyk |
| 8,020,743 B2 | 9/2011 | Shelton, IV |
| 8,025,199 B2 | 9/2011 | Whitman et al. |
| 8,028,883 B2 | 10/2011 | Stopek |
| 8,028,884 B2 | 10/2011 | Sniffin et al. |
| 8,033,438 B2 | 10/2011 | Scirica |
| 8,033,440 B2 | 10/2011 | Wenchell et al. |
| 8,034,077 B2 | 10/2011 | Smith et al. |
| 8,035,487 B2 | 10/2011 | Malackowski |
| 8,038,045 B2 | 10/2011 | Bettuchi et al. |
| 8,047,236 B2 | 11/2011 | Perry |
| 8,056,787 B2 | 11/2011 | Boudreaux et al. |
| 8,056,788 B2 | 11/2011 | Mastri et al. |
| 8,061,576 B2 | 11/2011 | Cappola |
| 8,062,330 B2 | 11/2011 | Prommersberger et al. |
| 8,066,167 B2 | 11/2011 | Measamer et al. |
| 8,066,168 B2 | 11/2011 | Vidal et al. |
| D650,074 S | 12/2011 | Hunt et al. |
| 8,083,118 B2 | 12/2011 | Milliman et al. |
| 8,083,119 B2 | 12/2011 | Prommersberger |
| 8,083,120 B2 | 12/2011 | Shelton, IV et al. |

(56) References Cited

U.S. PATENT DOCUMENTS

| | | |
|---|---|---|
| 8,091,756 B2 | 1/2012 | Viola |
| 8,092,932 B2 | 1/2012 | Phillips et al. |
| 8,096,458 B2 | 1/2012 | Hessler |
| 8,097,017 B2 | 1/2012 | Viola |
| 8,100,310 B2 | 1/2012 | Zemlok |
| 8,105,350 B2 | 1/2012 | Lee et al. |
| 8,109,426 B2 | 2/2012 | Milliman et al. |
| 8,113,405 B2 | 2/2012 | Milliman |
| 8,113,410 B2 | 2/2012 | Hall et al. |
| 8,114,100 B2 | 2/2012 | Smith et al. |
| 8,123,103 B2 | 2/2012 | Milliman |
| 8,127,975 B2 | 3/2012 | Olson et al. |
| 8,132,703 B2 | 3/2012 | Milliman et al. |
| 8,132,706 B2 | 3/2012 | Marczyk et al. |
| 8,136,712 B2 | 3/2012 | Zingman |
| 8,140,417 B2 | 3/2012 | Shibata |
| 8,141,762 B2 | 3/2012 | Bedi et al. |
| 8,146,790 B2 | 4/2012 | Milliman |
| 8,152,041 B2 | 4/2012 | Kostrzewski |
| 8,157,145 B2 | 4/2012 | Shelton, IV et al. |
| 8,157,148 B2 | 4/2012 | Scirica |
| 8,157,152 B2 | 4/2012 | Holsten et al. |
| 8,157,153 B2 | 4/2012 | Shelton, IV et al. |
| 8,161,977 B2 | 4/2012 | Shelton, IV et al. |
| 8,162,197 B2 | 4/2012 | Mastri et al. |
| 8,162,933 B2 | 4/2012 | Francischelli et al. |
| 8,167,185 B2 | 5/2012 | Shelton, IV et al. |
| 8,172,120 B2 | 5/2012 | Boyden et al. |
| 8,172,122 B2 | 5/2012 | Kasvikis et al. |
| 8,172,124 B2 | 5/2012 | Shelton, IV et al. |
| 8,177,797 B2 | 5/2012 | Shimoji et al. |
| 8,186,555 B2 | 5/2012 | Shelton, IV et al. |
| 8,186,560 B2 | 5/2012 | Hess et al. |
| 8,191,752 B2 | 6/2012 | Scirica |
| 8,196,795 B2 | 6/2012 | Moore et al. |
| 8,196,796 B2 | 6/2012 | Shelton, IV et al. |
| 8,201,720 B2 | 6/2012 | Hessler |
| 8,201,721 B2 | 6/2012 | Zemlok et al. |
| 8,205,780 B2 | 6/2012 | Sorrentino et al. |
| 8,205,781 B2 | 6/2012 | Baxter, III et al. |
| 8,210,411 B2 | 7/2012 | Yates et al. |
| 8,210,414 B2 | 7/2012 | Bettuchi et al. |
| 8,214,019 B2 | 7/2012 | Govari et al. |
| 8,215,531 B2 | 7/2012 | Shelton, IV et al. |
| 8,220,688 B2 | 7/2012 | Laurent et al. |
| 8,220,690 B2 | 7/2012 | Hess et al. |
| 8,231,040 B2 | 7/2012 | Zemlok et al. |
| 8,236,010 B2 | 8/2012 | Ortiz et al. |
| 8,241,322 B2 | 8/2012 | Whitman et al. |
| 8,245,898 B2 | 8/2012 | Smith et al. |
| 8,245,899 B2 | 8/2012 | Swensgard et al. |
| 8,245,900 B2 | 8/2012 | Scirica |
| 8,245,901 B2 | 8/2012 | Stopek |
| 8,246,637 B2 | 8/2012 | Viola et al. |
| 8,256,654 B2 | 9/2012 | Bettuchi et al. |
| 8,256,655 B2 | 9/2012 | Sniffin et al. |
| 8,267,300 B2 | 9/2012 | Boudreaux |
| 8,272,553 B2 | 9/2012 | Mastri et al. |
| 8,276,801 B2 | 10/2012 | Zemlok et al. |
| 8,286,845 B2 | 10/2012 | Perry et al. |
| 8,286,846 B2 | 10/2012 | Smith et al. |
| 8,292,151 B2 | 10/2012 | Viola |
| 8,292,155 B2 | 10/2012 | Shelton, IV et al. |
| 8,292,888 B2 | 10/2012 | Whitman |
| 8,308,040 B2 | 11/2012 | Huang et al. |
| 8,308,042 B2 | 11/2012 | Aranyi |
| 8,313,496 B2 | 11/2012 | Sauer et al. |
| 8,317,070 B2 | 11/2012 | Hueil et al. |
| 8,317,071 B1 | 11/2012 | Knodel |
| 8,317,074 B2 | 11/2012 | Ortiz et al. |
| 8,322,455 B2 | 12/2012 | Shelton, IV et al. |
| 8,322,589 B2 | 12/2012 | Boudreaux |
| 8,333,313 B2 | 12/2012 | Boudreaux et al. |
| 8,333,764 B2 | 12/2012 | Francischelli et al. |
| 8,336,753 B2 | 12/2012 | Olson et al. |
| 8,348,123 B2 | 1/2013 | Scirica et al. |
| 8,348,129 B2 | 1/2013 | Bedi et al. |
| 8,348,130 B2 | 1/2013 | Shah et al. |
| 8,348,131 B2 | 1/2013 | Omaits et al. |
| 8,348,972 B2 | 1/2013 | Soltz et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,360,296 B2 | 1/2013 | Zingman |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,365,973 B1 | 2/2013 | White et al. |
| 8,365,976 B2 | 2/2013 | Hess et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,377,029 B2 | 2/2013 | Nagao et al. |
| 8,393,513 B2 | 3/2013 | Jankowski |
| 8,393,514 B2 | 3/2013 | Shelton, IV et al. |
| 8,397,971 B2 | 3/2013 | Yates et al. |
| 8,403,945 B2 | 3/2013 | Whitfield et al. |
| 8,408,439 B2 | 4/2013 | Huang et al. |
| 8,413,870 B2 | 4/2013 | Pastorelli et al. |
| 8,414,577 B2 | 4/2013 | Boudreaux et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,424,741 B2 | 4/2013 | McGuckin, Jr. et al. |
| 8,439,246 B1 | 5/2013 | Knodel |
| 8,444,036 B2 | 5/2013 | Shelton, IV |
| 8,453,904 B2 | 6/2013 | Eskaros et al. |
| 8,453,907 B2 | 6/2013 | Laurent et al. |
| 8,453,908 B2 | 6/2013 | Bedi et al. |
| 8,453,912 B2 | 6/2013 | Mastri et al. |
| 8,453,914 B2 | 6/2013 | Laurent et al. |
| 8,459,520 B2 | 6/2013 | Giordano et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,469,973 B2 | 6/2013 | Meade et al. |
| 8,470,355 B2 | 6/2013 | Skalla et al. |
| 8,474,677 B2 | 7/2013 | Woodard, Jr. et al. |
| 8,475,454 B1 | 7/2013 | Alshemari |
| 8,479,969 B2 | 7/2013 | Shelton, IV |
| 8,485,412 B2 | 7/2013 | Shelton, IV et al. |
| 8,485,413 B2 | 7/2013 | Scheib et al. |
| 8,496,156 B2 | 7/2013 | Sniffin et al. |
| 8,499,993 B2 | 8/2013 | Shelton, IV et al. |
| 8,517,239 B2 | 8/2013 | Scheib et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,523,043 B2 | 9/2013 | Ullrich et al. |
| 8,529,600 B2 | 9/2013 | Woodard, Jr. et al. |
| 8,534,528 B2 | 9/2013 | Shelton, IV |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,133 B2 | 9/2013 | Bedi et al. |
| 8,550,984 B2 | 10/2013 | Takemoto |
| 8,556,151 B2 | 10/2013 | Viola |
| 8,561,870 B2 | 10/2013 | Baxter, III et al. |
| 8,561,873 B2 | 10/2013 | Ingmanson et al. |
| 8,567,656 B2 | 10/2013 | Shelton, IV et al. |
| 8,573,459 B2 | 11/2013 | Smith et al. |
| 8,573,461 B2 | 11/2013 | Shelton, IV et al. |
| 8,573,465 B2 | 11/2013 | Shelton, IV |
| 8,579,176 B2 | 11/2013 | Smith et al. |
| 8,579,937 B2 | 11/2013 | Gresham |
| 8,584,919 B2 | 11/2013 | Hueil et al. |
| 8,590,760 B2 | 11/2013 | Cummins et al. |
| 8,590,762 B2 | 11/2013 | Hess et al. |
| 8,602,287 B2 | 12/2013 | Yates et al. |
| 8,602,288 B2 | 12/2013 | Shelton, IV et al. |
| 8,608,043 B2 | 12/2013 | Scirica |
| 8,608,044 B2 | 12/2013 | Hueil et al. |
| 8,608,045 B2 | 12/2013 | Smith et al. |

(56) References Cited

U.S. PATENT DOCUMENTS

| | | |
|---|---|---|
| 8,608,046 B2 | 12/2013 | Laurent et al. |
| 8,616,431 B2 | 12/2013 | Timm et al. |
| 8,622,274 B2 | 1/2014 | Yates et al. |
| 8,622,275 B2 | 1/2014 | Baxter, III et al. |
| 8,627,993 B2 | 1/2014 | Smith et al. |
| 8,631,987 B2 | 1/2014 | Shelton, IV et al. |
| 8,631,993 B2 | 1/2014 | Kostrzewski |
| 8,632,462 B2 | 1/2014 | Yoo et al. |
| 8,632,525 B2 | 1/2014 | Kerr et al. |
| 8,632,535 B2 | 1/2014 | Shelton, IV et al. |
| 8,632,563 B2 | 1/2014 | Nagase et al. |
| 8,636,187 B2 | 1/2014 | Hueil et al. |
| 8,636,191 B2 | 1/2014 | Meagher |
| 8,636,736 B2 | 1/2014 | Yates et al. |
| 8,652,120 B2 | 2/2014 | Giordano et al. |
| 8,657,174 B2 | 2/2014 | Yates et al. |
| 8,657,176 B2 | 2/2014 | Shelton, IV et al. |
| 8,657,178 B2 | 2/2014 | Hueil et al. |
| 8,668,129 B2 | 3/2014 | Olson |
| 8,668,130 B2 | 3/2014 | Hess et al. |
| 8,672,206 B2 | 3/2014 | Aranyi et al. |
| 8,672,207 B2 | 3/2014 | Shelton, IV et al. |
| 8,672,208 B2 | 3/2014 | Hess et al. |
| 8,672,209 B2 | 3/2014 | Crainich |
| 8,672,951 B2 | 3/2014 | Smith et al. |
| 8,678,263 B2 | 3/2014 | Viola |
| 8,679,154 B2 | 3/2014 | Smith et al. |
| 8,679,156 B2 | 3/2014 | Smith et al. |
| 8,684,253 B2 | 4/2014 | Giordano et al. |
| 8,695,866 B2 | 4/2014 | Leimbach et al. |
| 8,701,958 B2 | 4/2014 | Shelton, IV et al. |
| 8,701,959 B2 | 4/2014 | Shah |
| 8,708,210 B2 | 4/2014 | Zemlok et al. |
| 8,708,213 B2 | 4/2014 | Shelton, IV et al. |
| 8,720,766 B2 | 5/2014 | Hess et al. |
| 8,721,630 B2 | 5/2014 | Ortiz et al. |
| 8,727,197 B2 | 5/2014 | Hess et al. |
| 8,727,199 B2 | 5/2014 | Wenchell |
| 8,733,612 B2 | 5/2014 | Ma |
| 8,733,613 B2 | 5/2014 | Huitema et al. |
| 8,734,478 B2 | 5/2014 | Widenhouse et al. |
| 8,740,034 B2 | 6/2014 | Morgan et al. |
| 8,740,037 B2 | 6/2014 | Shelton, IV et al. |
| 8,740,038 B2 | 6/2014 | Shelton, IV et al. |
| 8,746,529 B2 | 6/2014 | Shelton, IV et al. |
| 8,746,530 B2 | 6/2014 | Giordano et al. |
| 8,746,535 B2 | 6/2014 | Shelton, IV et al. |
| 8,747,238 B2 | 6/2014 | Shelton, IV et al. |
| 8,752,699 B2 | 6/2014 | Morgan et al. |
| 8,752,747 B2 | 6/2014 | Shelton, IV et al. |
| 8,752,749 B2 | 6/2014 | Moore et al. |
| 8,757,465 B2 | 6/2014 | Woodard, Jr. et al. |
| 8,758,391 B2 | 6/2014 | Swayze et al. |
| 8,763,875 B2 | 7/2014 | Morgan et al. |
| 8,763,877 B2 | 7/2014 | Schall et al. |
| 8,763,879 B2 | 7/2014 | Shelton, IV et al. |
| 8,770,458 B2 | 7/2014 | Scirica |
| 8,770,459 B2 | 7/2014 | Racenet et al. |
| 8,777,004 B2 | 7/2014 | Shelton, IV et al. |
| 8,783,541 B2 | 7/2014 | Shelton, IV et al. |
| 8,783,542 B2 | 7/2014 | Riestenberg et al. |
| 8,783,543 B2 | 7/2014 | Shelton, IV et al. |
| 8,789,737 B2 | 7/2014 | Hodgkinson et al. |
| 8,789,739 B2 | 7/2014 | Swensgard |
| 8,789,740 B2 | 7/2014 | Baxter, III et al. |
| 8,789,741 B2 | 7/2014 | Baxter, III et al. |
| 8,794,497 B2 | 8/2014 | Zingman |
| 8,795,308 B2 | 8/2014 | Valin |
| 8,800,837 B2 | 8/2014 | Zemlok |
| 8,800,838 B2 | 8/2014 | Shelton, IV |
| 8,800,840 B2 | 8/2014 | Jankowski |
| 8,800,841 B2 | 8/2014 | Ellerhorst et al. |
| 8,801,734 B2 | 8/2014 | Shelton, IV et al. |
| 8,801,735 B2 | 8/2014 | Shelton, IV et al. |
| 8,801,752 B2 | 8/2014 | Fortier et al. |
| 8,806,973 B2 | 8/2014 | Ross et al. |
| 8,808,311 B2 | 8/2014 | Heinrich et al. |
| 8,808,325 B2 | 8/2014 | Hess et al. |
| 8,814,024 B2 | 8/2014 | Woodard, Jr. et al. |
| 8,820,603 B2 | 9/2014 | Shelton, IV et al. |
| 8,820,605 B2 | 9/2014 | Shelton, IV |
| 8,827,133 B2 | 9/2014 | Shelton, IV et al. |
| 8,827,134 B2 | 9/2014 | Viola et al. |
| 8,827,903 B2 | 9/2014 | Shelton, IV et al. |
| 8,833,632 B2 | 9/2014 | Swensgard |
| 8,840,003 B2 | 9/2014 | Morgan et al. |
| 8,840,603 B2 | 9/2014 | Shelton, IV et al. |
| 8,844,789 B2 | 9/2014 | Shelton, IV et al. |
| 8,851,354 B2 | 10/2014 | Swensgard et al. |
| 8,857,693 B2 | 10/2014 | Schuckmann et al. |
| 8,857,694 B2 | 10/2014 | Shelton, IV et al. |
| 8,858,538 B2 | 10/2014 | Belson et al. |
| 8,858,571 B2 | 10/2014 | Shelton, IV et al. |
| 8,858,590 B2 | 10/2014 | Shelton, IV et al. |
| 8,864,007 B2 | 10/2014 | Widenhouse et al. |
| 8,864,009 B2 | 10/2014 | Shelton, IV et al. |
| 8,875,971 B2 | 11/2014 | Hall et al. |
| 8,875,972 B2 | 11/2014 | Weisenburgh, II et al. |
| 8,876,857 B2 | 11/2014 | Burbank |
| 8,893,946 B2 | 11/2014 | Boudreaux et al. |
| 8,893,949 B2 | 11/2014 | Shelton, IV et al. |
| 8,899,463 B2 | 12/2014 | Schall et al. |
| 8,899,465 B2 | 12/2014 | Shelton, IV et al. |
| 8,899,466 B2 | 12/2014 | Baxter, III et al. |
| 8,905,977 B2 | 12/2014 | Shelton et al. |
| 8,911,471 B2 | 12/2014 | Spivey et al. |
| 8,920,435 B2 | 12/2014 | Smith et al. |
| 8,920,443 B2 | 12/2014 | Hiles et al. |
| 8,925,782 B2 | 1/2015 | Shelton, IV |
| 8,925,788 B2 | 1/2015 | Hess et al. |
| 8,926,598 B2 | 1/2015 | Mollere et al. |
| 8,931,682 B2 | 1/2015 | Timm et al. |
| 8,945,163 B2 | 2/2015 | Voegele et al. |
| 8,956,390 B2 | 2/2015 | Shah et al. |
| 8,967,448 B2 | 3/2015 | Carter et al. |
| 8,968,310 B2 | 3/2015 | Twomey et al. |
| 8,973,803 B2 | 3/2015 | Hall et al. |
| 8,973,804 B2 | 3/2015 | Hess et al. |
| 8,974,440 B2 | 3/2015 | Farritor et al. |
| 8,978,954 B2 | 3/2015 | Shelton, IV et al. |
| 8,978,955 B2 | 3/2015 | Aronhalt et al. |
| 8,978,956 B2 | 3/2015 | Schall et al. |
| 8,991,676 B2 | 3/2015 | Hess et al. |
| 8,991,677 B2 | 3/2015 | Moore et al. |
| 8,992,422 B2 | 3/2015 | Spivey et al. |
| 8,998,058 B2 | 4/2015 | Moore et al. |
| 9,005,230 B2 | 4/2015 | Yates et al. |
| 9,005,238 B2 | 4/2015 | DeSantis et al. |
| 9,005,243 B2 | 4/2015 | Stopek et al. |
| 9,010,608 B2 | 4/2015 | Casasanta, Jr. et al. |
| 9,016,542 B2 | 4/2015 | Shelton, IV et al. |
| 9,028,494 B2 | 5/2015 | Shelton, IV et al. |
| 9,028,495 B2 | 5/2015 | Mueller et al. |
| 9,028,519 B2 | 5/2015 | Yates et al. |
| 9,033,203 B2 | 5/2015 | Woodard, Jr. et al. |
| 9,033,204 B2 | 5/2015 | Shelton, IV et al. |
| 9,044,227 B2 | 6/2015 | Shelton, IV et al. |
| 9,044,228 B2 | 6/2015 | Woodard, Jr. et al. |
| 9,044,229 B2 | 6/2015 | Scheib et al. |
| 9,044,230 B2 | 6/2015 | Morgan et al. |
| 9,050,083 B2 | 6/2015 | Yates et al. |
| 9,050,084 B2 | 6/2015 | Schmid et al. |
| 9,055,941 B2 | 6/2015 | Schmid et al. |
| 9,055,944 B2 | 6/2015 | Hodgkinson et al. |
| 9,060,770 B2 | 6/2015 | Shelton, IV et al. |
| 9,060,894 B2 | 6/2015 | Wubbeling |
| 9,072,515 B2 | 7/2015 | Hall et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,084,601 B2 | 7/2015 | Moore et al. |
| 9,084,602 B2 | 7/2015 | Gleiman |
| 9,089,326 B2 | 7/2015 | Krumanaker et al. |
| 9,089,330 B2 | 7/2015 | Widenhouse et al. |

(56) References Cited

U.S. PATENT DOCUMENTS

| | | |
|---|---|---|
| 9,089,352 B2 | 7/2015 | Jeong |
| 9,095,339 B2 | 8/2015 | Moore et al. |
| 9,095,362 B2 | 8/2015 | Dachs, II et al. |
| 9,101,358 B2 | 8/2015 | Kerr et al. |
| 9,101,385 B2 | 8/2015 | Shelton, IV et al. |
| 9,107,663 B2 | 8/2015 | Swensgard |
| 9,113,862 B2 | 8/2015 | Morgan et al. |
| 9,113,864 B2 | 8/2015 | Morgan et al. |
| 9,113,865 B2 | 8/2015 | Shelton, IV et al. |
| 9,113,874 B2 | 8/2015 | Shelton, IV et al. |
| 9,113,880 B2 | 8/2015 | Zemlok et al. |
| 9,113,883 B2 | 8/2015 | Aronhalt et al. |
| 9,113,884 B2 | 8/2015 | Shelton, IV et al. |
| 9,119,657 B2 | 9/2015 | Shelton, IV et al. |
| 9,125,654 B2 | 9/2015 | Aronhalt et al. |
| 9,125,662 B2 | 9/2015 | Shelton, IV |
| 9,131,940 B2 | 9/2015 | Huitema et al. |
| 9,138,225 B2 | 9/2015 | Huang et al. |
| 9,149,274 B2 | 10/2015 | Spivey et al. |
| 9,168,038 B2 | 10/2015 | Shelton, IV et al. |
| 9,179,911 B2 | 11/2015 | Morgan et al. |
| 9,179,912 B2 | 11/2015 | Yates et al. |
| 9,186,143 B2 | 11/2015 | Timm et al. |
| 9,198,661 B2 | 12/2015 | Swensgard |
| 9,198,662 B2 | 12/2015 | Barton et al. |
| 9,204,878 B2 | 12/2015 | Hall et al. |
| 9,204,879 B2 | 12/2015 | Shelton, IV |
| 9,204,880 B2 | 12/2015 | Baxter, III et al. |
| 9,211,120 B2 | 12/2015 | Scheib et al. |
| 9,211,122 B2 | 12/2015 | Hagerty et al. |
| 9,216,019 B2 | 12/2015 | Schmid et al. |
| 9,220,500 B2 | 12/2015 | Swayze et al. |
| 9,220,501 B2 | 12/2015 | Baxter, III et al. |
| 9,226,751 B2 | 1/2016 | Shelton, IV et al. |
| 9,232,941 B2 | 1/2016 | Mandakolathur Vasudevan et al. |
| 9,232,945 B2 | 1/2016 | Zingman |
| 9,237,891 B2 | 1/2016 | Shelton, IV |
| 9,241,714 B2 | 1/2016 | Timm et al. |
| 9,271,799 B2 | 3/2016 | Shelton, IV et al. |
| 9,272,406 B2 | 3/2016 | Aronhalt et al. |
| 9,277,919 B2 | 3/2016 | Timmer et al. |
| 9,282,962 B2 | 3/2016 | Schmid et al. |
| 9,282,966 B2 | 3/2016 | Shelton, IV et al. |
| 9,282,974 B2 | 3/2016 | Shelton, IV |
| 9,289,210 B2 | 3/2016 | Baxter, III et al. |
| 9,289,212 B2 | 3/2016 | Shelton, IV et al. |
| 9,289,225 B2 | 3/2016 | Shelton, IV et al. |
| 9,289,256 B2 | 3/2016 | Shelton, IV et al. |
| 9,295,464 B2 | 3/2016 | Shelton, IV et al. |
| 9,301,752 B2 | 4/2016 | Mandakolathur Vasudevan et al. |
| 9,301,753 B2 | 4/2016 | Aldridge et al. |
| 9,301,755 B2 | 4/2016 | Shelton, IV et al. |
| 9,301,759 B2 | 4/2016 | Spivey et al. |
| 9,307,965 B2 | 4/2016 | Ming et al. |
| 9,307,986 B2 | 4/2016 | Hall et al. |
| 9,307,988 B2 | 4/2016 | Shelton, IV |
| 9,307,989 B2 | 4/2016 | Shelton, IV et al. |
| 9,314,246 B2 | 4/2016 | Shelton, IV et al. |
| 9,314,247 B2 | 4/2016 | Shelton, IV et al. |
| 9,320,518 B2 | 4/2016 | Henderson et al. |
| 9,320,521 B2 | 4/2016 | Shelton, IV et al. |
| 9,320,523 B2 | 4/2016 | Shelton, IV et al. |
| 9,326,767 B2 | 5/2016 | Koch, Jr. et al. |
| 9,326,768 B2 | 5/2016 | Shelton, IV |
| 9,326,769 B2 | 5/2016 | Shelton, IV et al. |
| 9,326,770 B2 | 5/2016 | Shelton, IV et al. |
| 9,326,771 B2 | 5/2016 | Baxter, III et al. |
| 9,332,974 B2 | 5/2016 | Henderson et al. |
| 9,332,984 B2 | 5/2016 | Weaner et al. |
| 9,332,987 B2 | 5/2016 | Leimbach et al. |
| 9,345,477 B2 | 5/2016 | Anim et al. |
| 9,345,481 B2 | 5/2016 | Hall et al. |
| 9,351,726 B2 | 5/2016 | Leimbach et al. |
| 9,351,727 B2 | 5/2016 | Leimbach et al. |
| 9,351,730 B2 | 5/2016 | Schmid et al. |
| 9,358,003 B2 | 6/2016 | Hall et al. |
| 9,364,219 B2 | 6/2016 | Olson et al. |
| 9,364,230 B2 | 6/2016 | Shelton, IV et al. |
| 9,364,233 B2 | 6/2016 | Alexander, III et al. |
| 9,370,358 B2 | 6/2016 | Shelton, IV et al. |
| 9,370,364 B2 | 6/2016 | Smith et al. |
| 9,386,983 B2 | 7/2016 | Swensgard et al. |
| 9,386,984 B2 | 7/2016 | Aronhalt et al. |
| 9,386,988 B2 | 7/2016 | Baxter, III et al. |
| 9,393,015 B2 | 7/2016 | Laurent et al. |
| 9,398,911 B2 | 7/2016 | Auld |
| 9,402,626 B2 | 8/2016 | Ortiz et al. |
| 9,408,604 B2 | 8/2016 | Shelton, IV et al. |
| 9,408,606 B2 | 8/2016 | Shelton, IV |
| 9,414,838 B2 | 8/2016 | Shelton, IV et al. |
| 9,427,223 B2 | 8/2016 | Park et al. |
| 9,433,419 B2 | 9/2016 | Gonzalez et al. |
| 9,439,649 B2 | 9/2016 | Shelton, IV et al. |
| 9,439,651 B2 | 9/2016 | Smith et al. |
| 9,451,958 B2 | 9/2016 | Shelton, IV et al. |
| 9,463,260 B2 | 10/2016 | Stopek |
| 9,468,438 B2 | 10/2016 | Baber et al. |
| 9,480,476 B2 | 11/2016 | Aldridge et al. |
| 9,486,213 B2 | 11/2016 | Altman et al. |
| 9,486,214 B2 | 11/2016 | Shelton, IV |
| 9,492,167 B2 | 11/2016 | Shelton, IV et al. |
| 9,492,170 B2 | 11/2016 | Bear et al. |
| 9,510,925 B2 | 12/2016 | Hotter et al. |
| 9,517,063 B2 | 12/2016 | Swayze et al. |
| 9,517,068 B2 | 12/2016 | Shelton, IV et al. |
| 9,522,029 B2 | 12/2016 | Yates et al. |
| 9,549,732 B2 | 1/2017 | Yates et al. |
| 9,554,794 B2 | 1/2017 | Baber et al. |
| 9,561,032 B2 | 2/2017 | Shelton, IV et al. |
| 9,561,038 B2 | 2/2017 | Shelton, IV et al. |
| 9,566,061 B2 | 2/2017 | Aronhalt et al. |
| 9,572,577 B2 | 2/2017 | Lloyd et al. |
| 9,574,644 B2 | 2/2017 | Parihar |
| 9,585,657 B2 | 3/2017 | Shelton, IV et al. |
| 9,585,660 B2 | 3/2017 | Laurent et al. |
| 9,592,050 B2 | 3/2017 | Schmid et al. |
| 9,592,052 B2 | 3/2017 | Shelton, IV |
| 9,592,053 B2 | 3/2017 | Shelton, IV et al. |
| 9,592,054 B2 | 3/2017 | Schmid et al. |
| 9,597,075 B2 | 3/2017 | Shelton, IV et al. |
| 9,597,080 B2 | 3/2017 | Milliman et al. |
| 9,603,595 B2 | 3/2017 | Shelton, IV et al. |
| 9,603,598 B2 | 3/2017 | Shelton, IV et al. |
| 9,603,991 B2 | 3/2017 | Shelton, IV et al. |
| 9,615,826 B2 | 4/2017 | Shelton, IV et al. |
| 9,629,623 B2 | 4/2017 | Lytle, IV et al. |
| 9,629,626 B2 | 4/2017 | Soltz et al. |
| 9,629,629 B2 | 4/2017 | Leimbach et al. |
| 9,629,814 B2 | 4/2017 | Widenhouse et al. |
| 9,642,620 B2 | 5/2017 | Baxter, III et al. |
| 9,649,110 B2 | 5/2017 | Parihar et al. |
| 9,649,111 B2 | 5/2017 | Shelton, IV et al. |
| 9,655,614 B2 | 5/2017 | Swensgard et al. |
| 9,655,624 B2 | 5/2017 | Shelton, IV et al. |
| 9,675,355 B2 | 6/2017 | Shelton, IV et al. |
| 9,675,372 B2 | 6/2017 | Laurent et al. |
| 9,675,375 B2 | 6/2017 | Houser et al. |
| 9,681,873 B2 | 6/2017 | Smith et al. |
| 9,687,230 B2 | 6/2017 | Leimbach et al. |
| 9,687,231 B2 | 6/2017 | Baxter, III et al. |
| 9,687,236 B2 | 6/2017 | Leimbach et al. |
| 9,700,309 B2 | 7/2017 | Jaworek et al. |
| 9,700,315 B2 | 7/2017 | Chen et al. |
| 9,700,317 B2 | 7/2017 | Aronhalt et al. |
| 9,700,321 B2 | 7/2017 | Shelton, IV et al. |
| 9,706,991 B2 | 7/2017 | Hess et al. |
| 9,724,091 B2 | 8/2017 | Shelton, IV et al. |
| 9,730,692 B2 | 8/2017 | Shelton, IV et al. |
| 9,743,928 B2 | 8/2017 | Shelton, IV et al. |
| 9,757,123 B2 | 9/2017 | Giordano et al. |
| 9,757,130 B2 | 9/2017 | Shelton, IV |
| 9,770,245 B2 | 9/2017 | Swayze et al. |
| 9,775,613 B2 | 10/2017 | Shelton, IV et al. |
| 9,782,169 B2 | 10/2017 | Kimsey et al. |

(56) References Cited

U.S. PATENT DOCUMENTS

| | | |
|---|---|---|
| 9,788,834 B2 | 10/2017 | Schmid et al. |
| 9,795,382 B2 | 10/2017 | Shelton, IV |
| 9,795,384 B2 | 10/2017 | Weaner et al. |
| 9,801,626 B2 | 10/2017 | Parihar et al. |
| 9,808,244 B2 | 11/2017 | Leimbach et al. |
| 9,814,460 B2 | 11/2017 | Kimsey et al. |
| 9,814,462 B2 | 11/2017 | Woodard, Jr. et al. |
| 9,826,976 B2 | 11/2017 | Parihar et al. |
| 9,833,236 B2 | 12/2017 | Shelton, IV et al. |
| 9,839,420 B2 | 12/2017 | Shelton, IV et al. |
| 9,839,427 B2 | 12/2017 | Swayze et al. |
| 9,844,368 B2 | 12/2017 | Boudreaux et al. |
| 9,844,373 B2 | 12/2017 | Swayze et al. |
| 9,848,873 B2 | 12/2017 | Shelton, IV |
| 9,848,875 B2 | 12/2017 | Aronhalt et al. |
| 9,848,877 B2 | 12/2017 | Shelton, IV et al. |
| 9,861,359 B2 | 1/2018 | Shelton, IV et al. |
| 9,861,361 B2 | 1/2018 | Aronhalt et al. |
| 9,867,612 B2 | 1/2018 | Parihar et al. |
| 9,883,860 B2 | 2/2018 | Leimbach et al. |
| 9,888,919 B2 | 2/2018 | Leimbach et al. |
| 9,888,924 B2 | 2/2018 | Ebersole et al. |
| 9,980,630 B2 | 5/2018 | Larkin et al. |
| 9,999,408 B2 | 6/2018 | Boudreaux et al. |
| 10,004,498 B2 | 6/2018 | Morgan et al. |
| 10,010,322 B2 | 7/2018 | Shelton, IV et al. |
| 10,039,529 B2 | 8/2018 | Kerr et al. |
| 10,045,781 B2 | 8/2018 | Cropper et al. |
| 10,052,099 B2 | 8/2018 | Morgan et al. |
| 10,052,100 B2 | 8/2018 | Morgan et al. |
| 10,058,963 B2 | 8/2018 | Shelton, IV et al. |
| 10,071,452 B2 | 9/2018 | Shelton, IV et al. |
| 10,123,798 B2 | 11/2018 | Baxter, III et al. |
| 10,130,359 B2 | 11/2018 | Hess et al. |
| 10,136,887 B2 | 11/2018 | Shelton, IV et al. |
| 10,136,890 B2 | 11/2018 | Shelton, IV et al. |
| 10,149,680 B2 | 12/2018 | Parihar et al. |
| 10,154,841 B2 | 12/2018 | Weaner et al. |
| 10,159,482 B2 | 12/2018 | Swayze et al. |
| 10,166,025 B2 | 1/2019 | Leimbach et al. |
| 10,188,393 B2 | 1/2019 | Smith et al. |
| 10,213,198 B2 | 2/2019 | Aronhalt et al. |
| 10,335,144 B2 | 7/2019 | Shelton, IV et al. |
| 10,342,533 B2 | 7/2019 | Shelton, IV et al. |
| 10,390,823 B2 | 8/2019 | Shelton, IV et al. |
| 10,405,854 B2 | 9/2019 | Schmid et al. |
| 10,405,857 B2 | 9/2019 | Shelton, IV et al. |
| 10,433,918 B2 | 10/2019 | Shelton, IV et al. |
| 10,441,369 B2 | 10/2019 | Shelton, IV et al. |
| 10,470,762 B2 | 11/2019 | Leimbach et al. |
| 10,492,787 B2 | 12/2019 | Smith et al. |
| 10,660,640 B2 | 5/2020 | Yates et al. |
| 10,695,057 B2 | 6/2020 | Shelton, IV et al. |
| 10,729,441 B2 | 8/2020 | Cropper et al. |
| 10,736,629 B2 | 8/2020 | Shelton, IV et al. |
| 10,973,520 B2 | 4/2021 | Shelton, IV et al. |
| 10,980,536 B2 | 4/2021 | Weaner et al. |
| 11,006,951 B2 | 5/2021 | Giordano et al. |
| 11,083,458 B2 | 8/2021 | Harris et al. |
| 11,096,688 B2 | 8/2021 | Shelton, IV et al. |
| 11,129,611 B2 | 9/2021 | Shelton, IV et al. |
| 11,166,716 B2 | 11/2021 | Shelton, IV et al. |
| 11,197,668 B2 | 12/2021 | Shelton, IV et al. |
| 11,207,067 B2 | 12/2021 | Shelton, IV et al. |
| 11,213,294 B2 | 1/2022 | Shelton, IV et al. |
| 11,219,453 B2 | 1/2022 | Shelton, IV et al. |
| 11,259,806 B2 | 3/2022 | Shelton, IV et al. |
| 11,278,280 B2 | 3/2022 | Shelton, IV et al. |
| 11,406,382 B2 | 8/2022 | Shelton, IV et al. |
| 11,471,156 B2 | 10/2022 | Shelton, IV et al. |
| 11,547,410 B2 | 1/2023 | Cropper et al. |
| 11,589,865 B2 | 2/2023 | Shelton, IV et al. |
| 11,638,582 B2 | 5/2023 | Bakos et al. |
| 11,660,090 B2 | 5/2023 | Bakos et al. |
| 11,737,748 B2 | 8/2023 | Witte |
| 2002/0117534 A1 | 8/2002 | Green et al. |
| 2003/0009193 A1 | 1/2003 | Corsaro |
| 2003/0039689 A1 | 2/2003 | Chen et al. |
| 2003/0096158 A1 | 5/2003 | Takano et al. |
| 2003/0181900 A1 | 9/2003 | Long |
| 2003/0236505 A1 | 12/2003 | Bonadio et al. |
| 2004/0068161 A1 | 4/2004 | Couvillon |
| 2004/0102783 A1 | 5/2004 | Sutterlin et al. |
| 2004/0108357 A1 | 6/2004 | Milliman et al. |
| 2004/0147909 A1 | 7/2004 | Johnston et al. |
| 2004/0164123 A1 | 8/2004 | Racenet et al. |
| 2004/0167572 A1 | 8/2004 | Roth et al. |
| 2004/0225186 A1 | 11/2004 | Horne et al. |
| 2004/0232201 A1 | 11/2004 | Wenchell et al. |
| 2004/0267310 A1 | 12/2004 | Racenet et al. |
| 2005/0059997 A1 | 3/2005 | Bauman et al. |
| 2005/0070929 A1 | 3/2005 | Dalessandro et al. |
| 2005/0080342 A1 | 4/2005 | Gilreath et al. |
| 2005/0125897 A1 | 6/2005 | Wyslucha et al. |
| 2005/0139636 A1 | 6/2005 | Schwemberger et al. |
| 2005/0143759 A1 | 6/2005 | Kelly |
| 2005/0216055 A1 | 9/2005 | Scirica et al. |
| 2005/0228224 A1 | 10/2005 | Okada et al. |
| 2005/0263563 A1 | 12/2005 | Racenet et al. |
| 2006/0049229 A1 | 3/2006 | Milliman et al. |
| 2006/0052825 A1 | 3/2006 | Ransick et al. |
| 2006/0089535 A1 | 4/2006 | Raz et al. |
| 2006/0173470 A1 | 8/2006 | Oray et al. |
| 2006/0180634 A1 | 8/2006 | Shelton et al. |
| 2006/0201989 A1 | 9/2006 | Ojeda |
| 2006/0235368 A1 | 10/2006 | Oz |
| 2006/0271102 A1 | 11/2006 | Bosshard et al. |
| 2006/0287576 A1 | 12/2006 | Tsuji et al. |
| 2006/0289602 A1 | 12/2006 | Wales et al. |
| 2006/0291981 A1 | 12/2006 | Viola et al. |
| 2007/0027468 A1 | 2/2007 | Wales et al. |
| 2007/0051375 A1 | 3/2007 | Milliman |
| 2007/0073341 A1 | 3/2007 | Smith et al. |
| 2007/0084897 A1 | 4/2007 | Shelton et al. |
| 2007/0093869 A1 | 4/2007 | Bloom et al. |
| 2007/0102472 A1 | 5/2007 | Shelton |
| 2007/0106317 A1 | 5/2007 | Shelton et al. |
| 2007/0134251 A1 | 6/2007 | Ashkenazi et al. |
| 2007/0170225 A1 | 7/2007 | Shelton et al. |
| 2007/0173687 A1 | 7/2007 | Shima et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0194079 A1 | 8/2007 | Hueil et al. |
| 2007/0194082 A1 | 8/2007 | Morgan et al. |
| 2007/0203510 A1 | 8/2007 | Bettuchi |
| 2007/0225562 A1 | 9/2007 | Spivey et al. |
| 2007/0246505 A1 | 10/2007 | Pace-Floridia et al. |
| 2007/0276409 A1 | 11/2007 | Ortiz et al. |
| 2007/0279011 A1 | 12/2007 | Jones et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078802 A1 | 4/2008 | Hess et al. |
| 2008/0082125 A1 | 4/2008 | Murray et al. |
| 2008/0086078 A1 | 4/2008 | Powell et al. |
| 2008/0135600 A1 | 6/2008 | Hiranuma et al. |
| 2008/0140115 A1 | 6/2008 | Stopek |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0172087 A1 | 7/2008 | Fuchs et al. |
| 2008/0190989 A1 | 8/2008 | Crews et al. |
| 2008/0197167 A1 | 8/2008 | Viola et al. |
| 2008/0200762 A1 | 8/2008 | Stokes et al. |
| 2008/0249536 A1 | 10/2008 | Stahler et al. |
| 2008/0296346 A1 | 12/2008 | Shelton, IV et al. |
| 2008/0308602 A1 | 12/2008 | Timm et al. |
| 2008/0308603 A1 | 12/2008 | Shelton et al. |
| 2009/0001121 A1 | 1/2009 | Hess et al. |
| 2009/0001130 A1 | 1/2009 | Hess et al. |
| 2009/0005809 A1 | 1/2009 | Hess et al. |
| 2009/0078736 A1 | 3/2009 | Van Lue |

(56) References Cited

U.S. PATENT DOCUMENTS

| | | |
|---|---|---|
| 2009/0090763 A1 | 4/2009 | Zemlok et al. |
| 2009/0099876 A1 | 4/2009 | Whitman |
| 2009/0149871 A9 | 6/2009 | Kagan et al. |
| 2009/0188964 A1 | 7/2009 | Orlov |
| 2009/0204108 A1 | 8/2009 | Steffen |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0242610 A1 | 10/2009 | Shelton, IV et al. |
| 2009/0255974 A1 | 10/2009 | Viola |
| 2009/0308907 A1 | 12/2009 | Nalagatla et al. |
| 2010/0069942 A1 | 3/2010 | Shelton, IV |
| 2010/0133317 A1 | 6/2010 | Shelton, IV et al. |
| 2010/0147921 A1 | 6/2010 | Olson |
| 2010/0147922 A1 | 6/2010 | Olson |
| 2010/0193566 A1 | 8/2010 | Scheib et al. |
| 2010/0222901 A1 | 9/2010 | Swayze et al. |
| 2011/0006101 A1 | 1/2011 | Hall et al. |
| 2011/0024477 A1 | 2/2011 | Hall |
| 2011/0024478 A1 | 2/2011 | Shelton, IV |
| 2011/0036891 A1 | 2/2011 | Zemlok et al. |
| 2011/0060363 A1 | 3/2011 | Hess et al. |
| 2011/0087276 A1 | 4/2011 | Bedi et al. |
| 2011/0091515 A1 | 4/2011 | Zilberman et al. |
| 2011/0114697 A1 | 5/2011 | Baxter, III et al. |
| 2011/0125176 A1 | 5/2011 | Yates et al. |
| 2011/0147433 A1 | 6/2011 | Shelton, IV et al. |
| 2011/0163146 A1 | 7/2011 | Ortiz et al. |
| 2011/0174861 A1 | 7/2011 | Shelton, IV et al. |
| 2011/0192882 A1 | 8/2011 | Hess et al. |
| 2011/0275901 A1 | 11/2011 | Shelton, IV |
| 2011/0276083 A1 | 11/2011 | Shelton, IV et al. |
| 2011/0278343 A1 | 11/2011 | Knodel et al. |
| 2011/0290856 A1 | 12/2011 | Shelton, IV et al. |
| 2011/0293690 A1 | 12/2011 | Griffin et al. |
| 2011/0295295 A1 | 12/2011 | Shelton, IV et al. |
| 2012/0029272 A1 | 2/2012 | Shelton, IV et al. |
| 2012/0074200 A1 | 3/2012 | Schmid et al. |
| 2012/0080336 A1 | 4/2012 | Shelton, IV et al. |
| 2012/0080344 A1 | 4/2012 | Shelton, IV |
| 2012/0080478 A1 | 4/2012 | Morgan et al. |
| 2012/0080498 A1 | 4/2012 | Shelton, IV et al. |
| 2012/0125792 A1 | 5/2012 | Cassivi |
| 2012/0175398 A1 | 7/2012 | Sandborn et al. |
| 2012/0234895 A1 | 9/2012 | O'Connor et al. |
| 2012/0234897 A1 | 9/2012 | Shelton, IV et al. |
| 2012/0248169 A1 | 10/2012 | Widenhouse et al. |
| 2012/0283707 A1 | 11/2012 | Giordano et al. |
| 2012/0292367 A1 | 11/2012 | Morgan et al. |
| 2012/0298722 A1 | 11/2012 | Hess et al. |
| 2013/0020375 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0087597 A1 | 4/2013 | Shelton, IV et al. |
| 2013/0116669 A1 | 5/2013 | Shelton, IV et al. |
| 2013/0153641 A1 | 6/2013 | Shelton, IV et al. |
| 2013/0175317 A1 | 7/2013 | Yates et al. |
| 2013/0233906 A1 | 9/2013 | Hess et al. |
| 2013/0256373 A1 | 10/2013 | Schmid et al. |
| 2013/0256380 A1 | 10/2013 | Schmid et al. |
| 2013/0270322 A1 | 10/2013 | Scheib et al. |
| 2013/0334283 A1 | 12/2013 | Swayze et al. |
| 2013/0334285 A1 | 12/2013 | Swayze et al. |
| 2013/0341374 A1 | 12/2013 | Shelton, IV et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005718 A1 | 1/2014 | Shelton, IV et al. |
| 2014/0014705 A1 | 1/2014 | Baxter, III |
| 2014/0048580 A1 | 2/2014 | Merchant et al. |
| 2014/0151433 A1 | 6/2014 | Shelton, IV et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0175152 A1 | 6/2014 | Hess et al. |
| 2014/0224857 A1 | 8/2014 | Schmid |
| 2014/0243865 A1 | 8/2014 | Swayze et al. |
| 2014/0246475 A1 | 9/2014 | Hall et al. |
| 2014/0249557 A1 | 9/2014 | Koch, Jr. et al. |
| 2014/0263541 A1 | 9/2014 | Leimbach et al. |
| 2014/0263552 A1 | 9/2014 | Hall et al. |
| 2014/0284371 A1 | 9/2014 | Morgan et al. |
| 2014/0291379 A1 | 10/2014 | Schellin et al. |
| 2014/0291383 A1 | 10/2014 | Spivey et al. |
| 2014/0299648 A1 | 10/2014 | Shelton, IV et al. |
| 2014/0303645 A1 | 10/2014 | Morgan et al. |
| 2014/0330161 A1 | 11/2014 | Swayze et al. |
| 2015/0173756 A1 | 6/2015 | Baxter, III et al. |
| 2015/0272576 A1* | 10/2015 | Cappola ............... A61B 17/072 227/175.2 |
| 2016/0174969 A1 | 6/2016 | Kerr et al. |
| 2016/0345971 A1* | 12/2016 | Bucciaglia ....... A61B 17/07207 |
| 2019/0137349 A1* | 5/2019 | Collins ............ A61B 17/07207 |
| 2019/0192161 A1 | 6/2019 | Leimbach et al. |
| 2019/0298353 A1 | 10/2019 | Shelton, IV et al. |
| 2020/0222044 A1* | 7/2020 | Baxter, III ......... A61B 17/0644 |
| 2022/0031315 A1 | 2/2022 | Bakos et al. |
| 2022/0031319 A1 | 2/2022 | Witte et al. |
| 2022/0031320 A1 | 2/2022 | Hall et al. |
| 2022/0031322 A1 | 2/2022 | Parks |
| 2022/0031323 A1 | 2/2022 | Witte |
| 2022/0031324 A1 | 2/2022 | Hall et al. |
| 2022/0031346 A1 | 2/2022 | Parks |
| 2022/0031350 A1 | 2/2022 | Witte |
| 2022/0031351 A1 | 2/2022 | Moubarak et al. |
| 2022/0133299 A1 | 5/2022 | Baxter, III |
| 2022/0133300 A1 | 5/2022 | Leimbach et al. |

FOREIGN PATENT DOCUMENTS

| | | |
|---|---|---|
| CN | 1634601 A | 7/2005 |
| CN | 201949071 U | 8/2011 |
| DE | 273689 C | 5/1914 |
| DE | 1775926 A | 1/1972 |
| DE | 3036217 A1 | 4/1982 |
| DE | 3210466 A1 | 9/1983 |
| DE | 3709067 A1 | 9/1988 |
| DE | 19851291 A1 | 1/2000 |
| DE | 19924311 A1 | 11/2000 |
| DE | 20016423 U1 | 2/2001 |
| DE | 20112837 U1 | 10/2001 |
| DE | 20121753 U1 | 4/2003 |
| DE | 10314072 A1 | 10/2004 |
| DE | 202007003114 U1 | 6/2007 |
| EP | 0000756 A1 | 2/1979 |
| EP | 0122046 A1 | 10/1984 |
| EP | 0129442 B1 | 11/1987 |
| EP | 0169044 B1 | 6/1991 |
| EP | 0594148 A1 | 4/1994 |
| EP | 0646357 A1 | 4/1995 |
| EP | 0505036 B1 | 5/1995 |
| EP | 0669104 A1 | 8/1995 |
| EP | 0705571 A1 | 4/1996 |
| EP | 0528478 B1 | 5/1996 |
| EP | 0770355 A1 | 5/1997 |
| EP | 0625335 B1 | 11/1997 |
| EP | 0879742 A1 | 11/1998 |
| EP | 0650701 B1 | 3/1999 |
| EP | 0923907 A1 | 6/1999 |
| EP | 0484677 B2 | 7/2000 |
| EP | 1034747 A1 | 9/2000 |
| EP | 1034748 A1 | 9/2000 |
| EP | 1053719 A1 | 11/2000 |
| EP | 1055399 A1 | 11/2000 |
| EP | 1055400 A1 | 11/2000 |
| EP | 1080694 A1 | 3/2001 |

(56) References Cited

FOREIGN PATENT DOCUMENTS

| | | |
|---|---|---|
| EP | 1090592 A1 | 4/2001 |
| EP | 1095627 A1 | 5/2001 |
| EP | 0806914 B1 | 9/2001 |
| EP | 1284120 A1 | 2/2003 |
| EP | 0869742 B1 | 5/2003 |
| EP | 1374788 A1 | 1/2004 |
| EP | 1407719 A2 | 4/2004 |
| EP | 0996378 B1 | 6/2004 |
| EP | 1157666 B1 | 9/2005 |
| EP | 0880338 B1 | 10/2005 |
| EP | 1158917 B1 | 11/2005 |
| EP | 1344498 B1 | 11/2005 |
| EP | 1330989 B1 | 12/2005 |
| EP | 1632191 A2 | 3/2006 |
| EP | 1082944 B1 | 5/2006 |
| EP | 1253866 B1 | 7/2006 |
| EP | 1285633 B1 | 12/2006 |
| EP | 1011494 B1 | 1/2007 |
| EP | 1767163 A1 | 3/2007 |
| EP | 1837041 A1 | 9/2007 |
| EP | 0922435 B1 | 10/2007 |
| EP | 1599146 B1 | 10/2007 |
| EP | 1330201 B1 | 6/2008 |
| EP | 2039302 A2 | 3/2009 |
| EP | 1719461 B1 | 6/2009 |
| EP | 1769754 B1 | 6/2010 |
| EP | 1627605 B1 | 12/2010 |
| EP | 2517638 A1 | 10/2012 |
| FR | 459743 A | 11/1913 |
| FR | 999646 A | 2/1952 |
| FR | 1112936 A | 3/1956 |
| FR | 2598905 A1 | 11/1987 |
| FR | 2765794 A1 | 1/1999 |
| FR | 2815842 A1 | 5/2002 |
| GB | 939929 A | 10/1963 |
| GB | 1210522 A | 10/1970 |
| GB | 1217159 A | 12/1970 |
| GB | 1339394 A | 12/1973 |
| GB | 2024012 A | 1/1980 |
| GB | 2109241 A | 6/1983 |
| GB | 2272159 A | 5/1994 |
| GB | 2336214 A | 10/1999 |
| GR | 930100110 A | 11/1993 |
| JP | S5033988 U | 4/1975 |
| JP | H0584252 A | 4/1993 |
| JP | H05130998 A | 5/1993 |
| JP | H0630945 A | 2/1994 |
| JP | H06237937 A | 8/1994 |
| JP | H07124166 A | 5/1995 |
| JP | H07255735 A | 10/1995 |
| JP | H07285089 A | 10/1995 |
| JP | H0833642 A | 2/1996 |
| JP | H08164141 A | 6/1996 |
| JP | H08182684 A | 7/1996 |
| JP | H08507708 A | 8/1996 |
| JP | H08229050 A | 9/1996 |
| JP | H10118090 A | 5/1998 |
| JP | 2000014632 A | 1/2000 |
| JP | 2000033071 A | 2/2000 |
| JP | 2000112002 A | 4/2000 |
| JP | 2000166932 A | 6/2000 |
| JP | 2000171730 A | 6/2000 |
| JP | 2000287987 A | 10/2000 |
| JP | 2000325303 A | 11/2000 |
| JP | 2001087272 A | 4/2001 |
| JP | 2001514541 A | 9/2001 |
| JP | 2002051974 A | 2/2002 |
| JP | 2002143078 A | 5/2002 |
| JP | 2002528161 A | 9/2002 |
| JP | 2003135473 A | 5/2003 |
| JP | 2003521301 A | 7/2003 |
| JP | 2004147702 A | 5/2004 |
| JP | 2004162035 A | 6/2004 |
| JP | 2004229976 A | 8/2004 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005137423 A | 6/2005 |
| JP | 2005328882 A | 12/2005 |
| JP | 2005335432 A | 12/2005 |
| JP | 2005342267 A | 12/2005 |
| JP | 2006187649 A | 7/2006 |
| JP | 2006281405 A | 10/2006 |
| JP | 2006346445 A | 12/2006 |
| JP | 2009189838 A | 8/2009 |
| JP | 2009539420 A | 11/2009 |
| JP | 2010098844 A | 4/2010 |
| RU | 1814161 C | 5/1993 |
| RU | 2008830 C1 | 3/1994 |
| RU | 2052979 C1 | 1/1996 |
| RU | 2098025 C1 | 12/1997 |
| RU | 2141279 C1 | 11/1999 |
| RU | 2144791 C1 | 1/2000 |
| RU | 2161450 C1 | 1/2001 |
| RU | 2181566 C2 | 4/2002 |
| RU | 2187249 C2 | 8/2002 |
| RU | 32984 U1 | 10/2003 |
| RU | 2225170 C2 | 3/2004 |
| RU | 42750 U1 | 12/2004 |
| RU | 61114 U1 | 2/2007 |
| RU | 61122 U1 | 2/2007 |
| SU | 189517 A | 1/1967 |
| SU | 328636 A | 9/1972 |
| SU | 674747 A1 | 7/1979 |
| SU | 1009439 A | 4/1983 |
| SU | 1333319 A2 | 8/1987 |
| SU | 1377053 A1 | 2/1988 |
| SU | 1509051 A1 | 9/1989 |
| SU | 1561964 A1 | 5/1990 |
| SU | 1708312 A1 | 1/1992 |
| SU | 1722476 A1 | 3/1992 |
| SU | 1752361 A1 | 8/1992 |
| SU | 1814161 A1 | 5/1993 |
| WO | WO-9315648 A1 | 8/1993 |
| WO | WO-9420030 A1 | 9/1994 |
| WO | WO-9517855 A1 | 7/1995 |
| WO | WO-9520360 A1 | 8/1995 |
| WO | WO-9623448 A1 | 8/1996 |
| WO | WO-9635464 A1 | 11/1996 |
| WO | WO-9639086 A1 | 12/1996 |
| WO | WO-9639088 A1 | 12/1996 |
| WO | WO-9724073 A1 | 7/1997 |
| WO | WO-9734533 A1 | 9/1997 |
| WO | WO-9903407 A1 | 1/1999 |
| WO | WO-9903409 A1 | 1/1999 |
| WO | WO-9948430 A1 | 9/1999 |
| WO | WO-0024322 A1 | 5/2000 |
| WO | WO-0024330 A1 | 5/2000 |
| WO | WO-0053112 A2 | 9/2000 |
| WO | WO-0057796 A1 | 10/2000 |
| WO | WO-0105702 A1 | 1/2001 |
| WO | WO-0154594 A1 | 8/2001 |
| WO | WO-0158371 A1 | 8/2001 |
| WO | WO-0162164 A2 | 8/2001 |
| WO | WO-0162169 A2 | 8/2001 |
| WO | WO-0191646 A1 | 12/2001 |
| WO | WO-0219932 A1 | 3/2002 |
| WO | WO-0226143 A1 | 4/2002 |
| WO | WO-0236028 A1 | 5/2002 |
| WO | WO-03055402 A1 | 7/2003 |
| WO | WO-03094747 A1 | 11/2003 |
| WO | WO-03079909 A3 | 3/2004 |
| WO | WO-2004019803 A1 | 3/2004 |
| WO | WO-2004032783 A1 | 4/2004 |
| WO | WO-2004047626 A1 | 6/2004 |
| WO | WO-2004047653 A2 | 6/2004 |
| WO | WO-2004056277 A1 | 7/2004 |
| WO | WO-2004078050 A2 | 9/2004 |
| WO | WO-2004078051 A2 | 9/2004 |
| WO | WO-2004096015 A2 | 11/2004 |
| WO | WO-2006044581 A2 | 4/2006 |
| WO | WO-2006051252 A1 | 5/2006 |

(56) References Cited

FOREIGN PATENT DOCUMENTS

| WO | WO-2006059067 A1 | 6/2006 |
|----|------------------|--------|
| WO | WO-2007137304 A2 | 11/2007 |
| WO | WO-2007142625 A2 | 12/2007 |
| WO | WO-2008021969 A2 | 2/2008 |
| WO | WO-2008089404 A2 | 7/2008 |
| WO | WO-2009067649 A2 | 5/2009 |
| WO | WO-2009091497 A2 | 7/2009 |
| WO | WO-2011008672 A2 | 1/2011 |
| WO | WO-2011044343 A2 | 4/2011 |
| WO | WO-2012044606 A2 | 4/2012 |

OTHER PUBLICATIONS

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20., pp. 1744-1748.
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).
Biomedical Coatings, Fort Wayne Metals, Research Products Corporation, obtained online at www.fwmetals.com on Jun. 21, 2010 (1 page).
Van Meer et al., "A Disposable Plastic Compact Wrist for Smart Minimally Invasive Surgical Tools," LAAS/CNRS (Aug. 2005).
Breedveld et al., "A New, Easily Miniaturized Sterrable Endoscope," IEEE Engineering in Medicine and Biology Magazine (Nov./Dec. 2005).
D. Tuite, Ed., "Get The Lowdown On Ultracapacitors," Nov. 15, 2007; [online] URL: http://electronicdesign.com/Articles/Print.cfm?ArticleID=17465, accessed Jan. 15, 2008 (5 pages).
Datasheet for Panasonic TK Relays Ultra Low Profile 2 A Polarized Relay, Copyright Matsushita Electric Works, Ltd. (Known of at least as early as Aug. 17, 2010), 5 pages.
ASTM procedure D2240-00, "Standard Test Method for Rubber Property-Durometer Hardness," (Published Aug. 2000).
ASTM procedure D2240-05, "Standard Test Method for Rubber Property-Durometer Hardness," (Published Apr. 2010).
Covidien Brochure, "Endo GIA™ Reloads with Tri-Staple™ Technology," (2010), 1 page.
Covidien Brochure, "Endo GIA™ Reloads with Tri-Staple™ Technology and Endo GIA™ Ultra Universal Staplers," (2010), 2 pages.
Covidien Brochure, "Endo GIA™ Black Reload with Tri-Staple™ Technology," (2012), 2 pages.
Covidien Brochure, "Endo GIA™ Curved Tip Reload with Tri-Staple™ Technology," (2012), 2 pages.
Covidien Brochure, "Endo GIA™ Reloads with Tri-Staple™ Technology," (2010), 2 pages.
Covidien Brochure, "Endo GIA™ Ultra Universal Stapler," (2010), 2 pages.
Miyata et al., "Biomolecule-Sensitive Hydrogels," Advanced Drug Delivery Reviews, 54 (2002) pp. 79-98.
Jeong et al., "Thermosensitive Sol-Gel Reversible Hydrogels," Advanced Drug Delivery Reviews, 54 (2002) pp. 37-51.
Byrne et al., "Molecular Imprinting Within Hydrogels," Advanced Drug Delivery Reviews, 54 (2002) pp. 149-161.
Qiu et al., "Environment-Sensitive Hydrogels for Drug Delivery," Advanced Drug Delivery Reviews, 53 (2001) pp. 321-339.
Hoffman, "Hydrogels for Biomedical Applications," Advanced Drug Delivery Reviews, 43 (2002) pp. 3-12.
Hoffman, "Hydrogels for Biomedical Applications," Advanced Drug Delivery Reviews, 54 (2002) pp. 3-12.
Peppas, "Physiologically Responsive Hydrogels," Journal of Bioactive and Compatible Polymers, vol. 6 (Jul. 1991) pp. 241-246.
Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.
Peppas, Editor "Hydrogels in Medicine and Pharmacy," vol. I, Fundamentals, CRC Press, 1986.
Matsuda, "Thermodynamics of Formation of Porous Polymeric Membrane from Solutions," Polymer Journal, vol. 23, No. 5, pp. 435-444 (1991).
Young, "Microcellular foams via phase separation," Journal of Vacuum Science & Technology A 4(3), (May/Jun. 1986).
Chen et al., "Elastomeric Biomaterials for Tissue Engineering," Progress in Polymer Science 38 (2013), pp. 584-671.
Pitt et al., "Attachment of Hyaluronan to Metallic Surfaces," J. Biomed. Mater. Res. 68A: pp. 95-106, 2004.
Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).
Solorio et al., "Gelatin Microspheres Crosslinked with Genipin for Local Delivery of Growth Factors," J. Tissue Eng. Regen. Med. (2010), 4(7): pp. 514-523.
The Sodem Aseptic Battery Transfer Kit, Sodem Systems, 2000, 3 pages.

\* cited by examiner

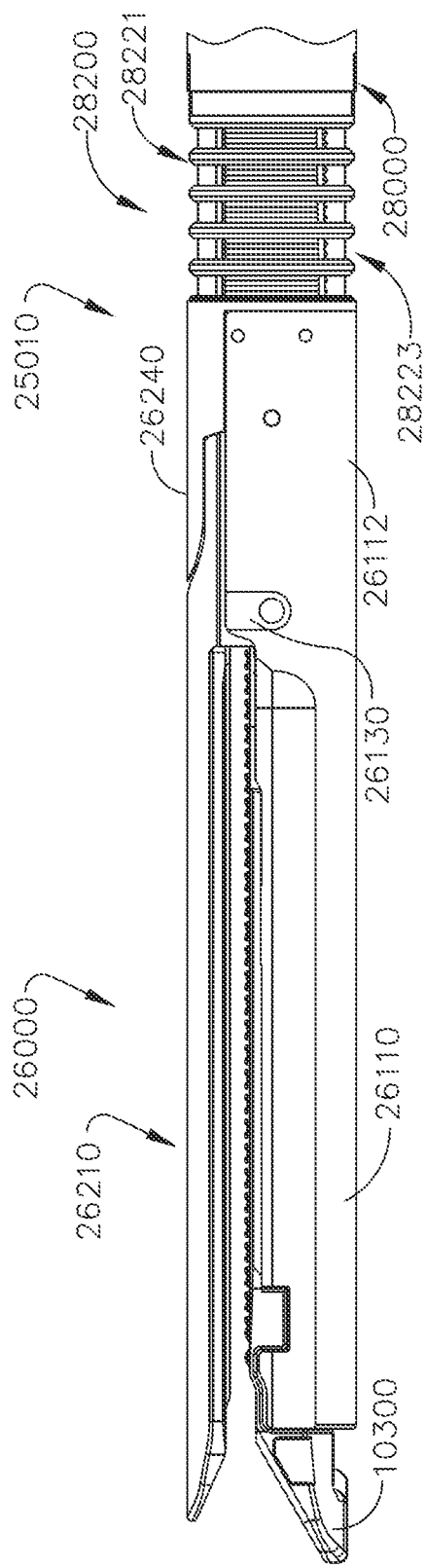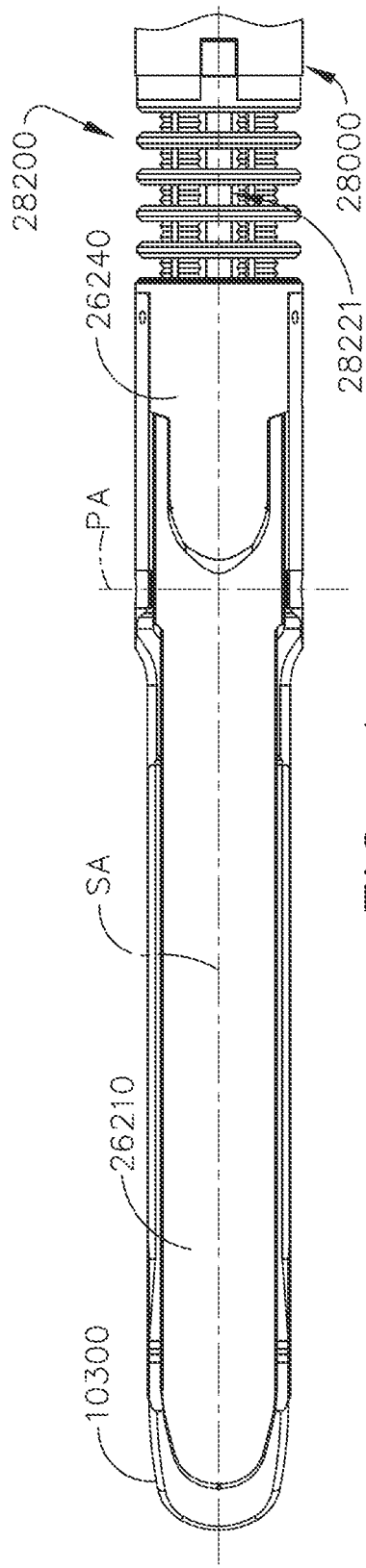
FIG. 3
FIG. 4

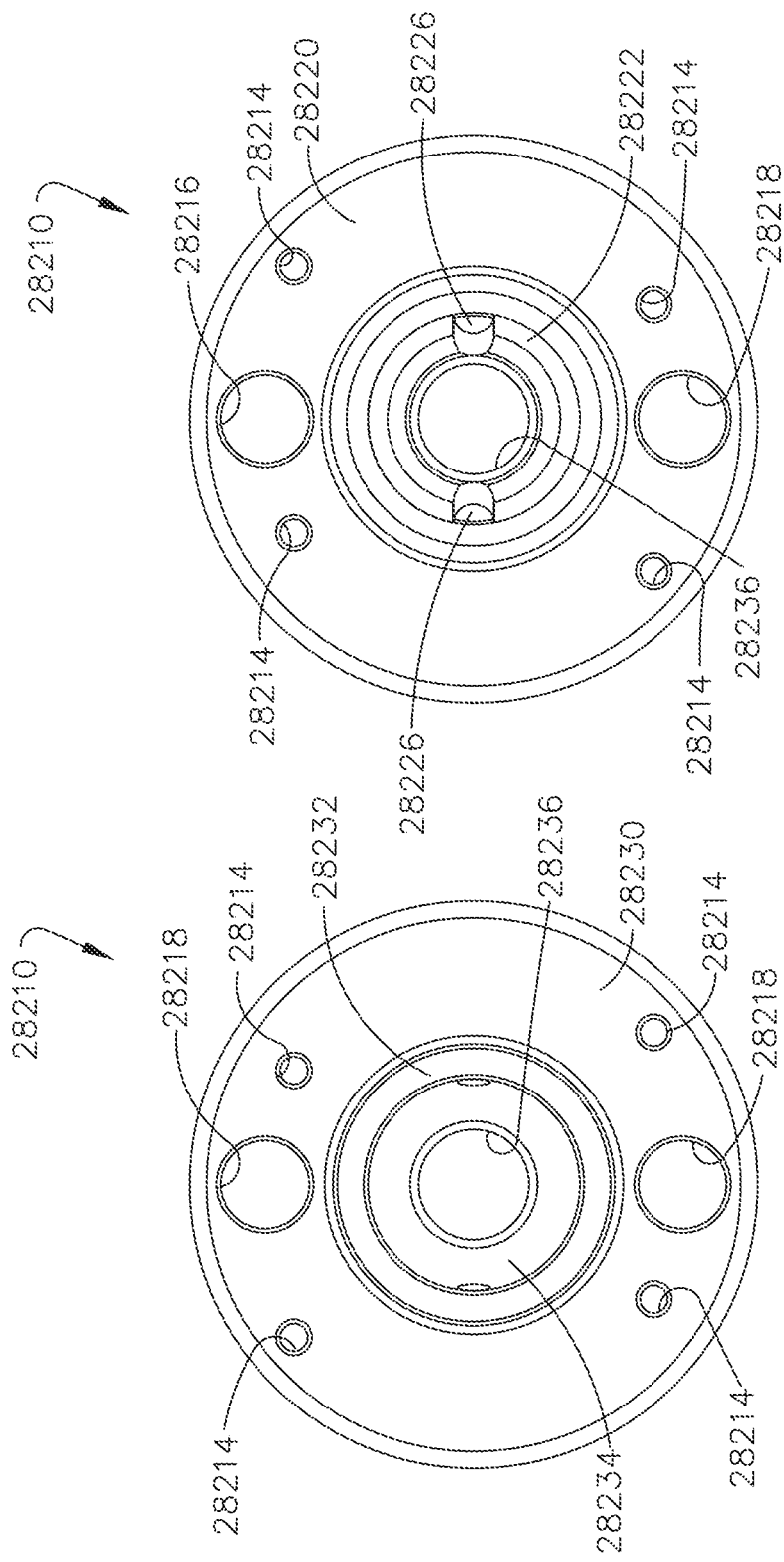

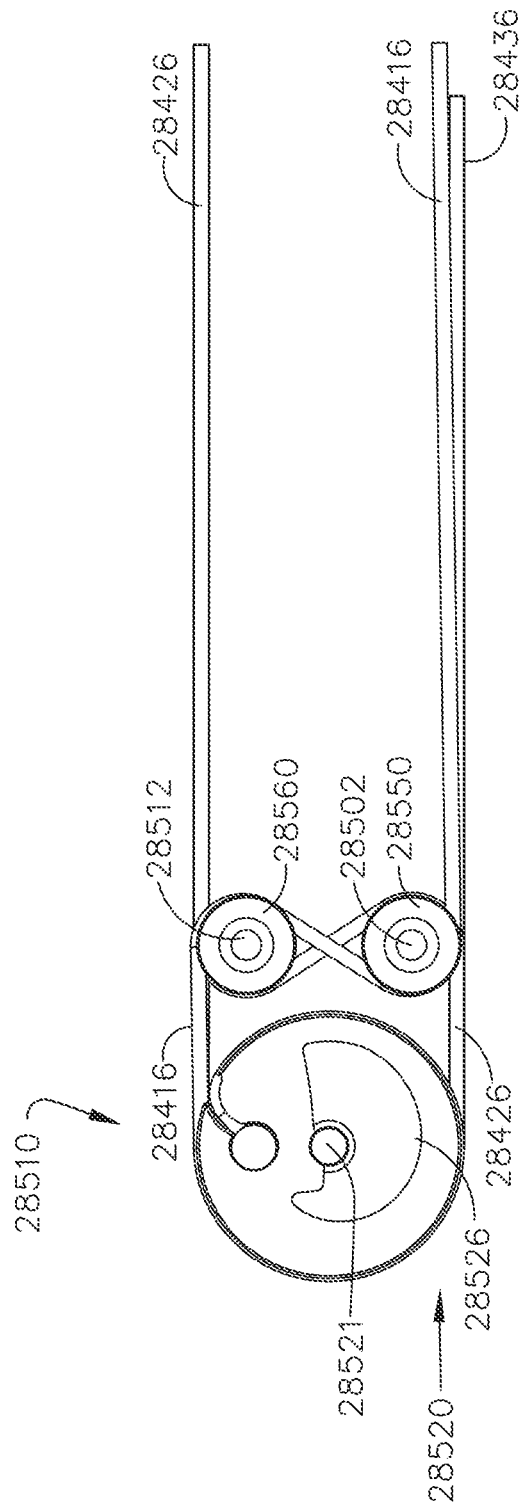
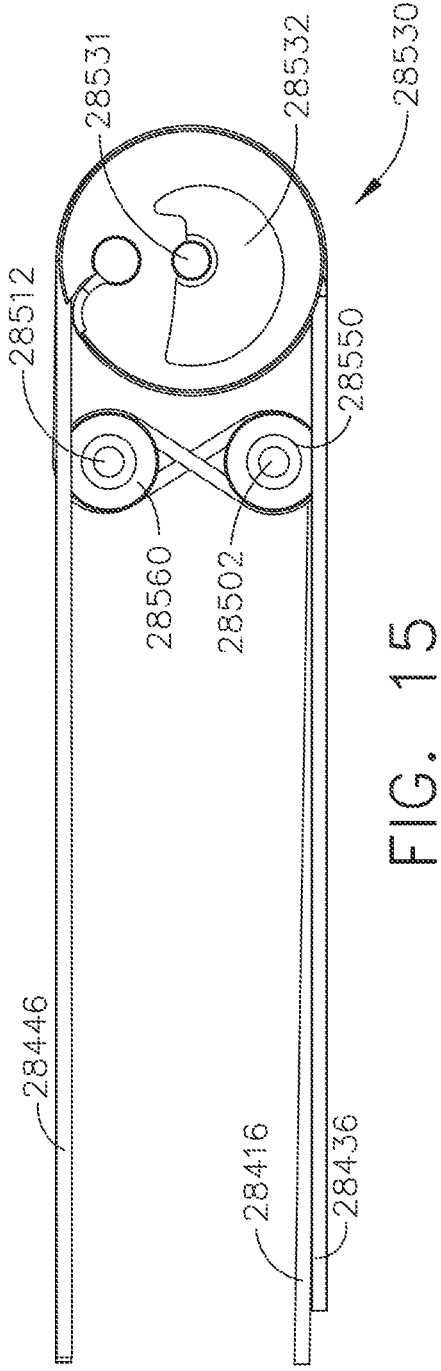
FIG. 14
FIG. 15

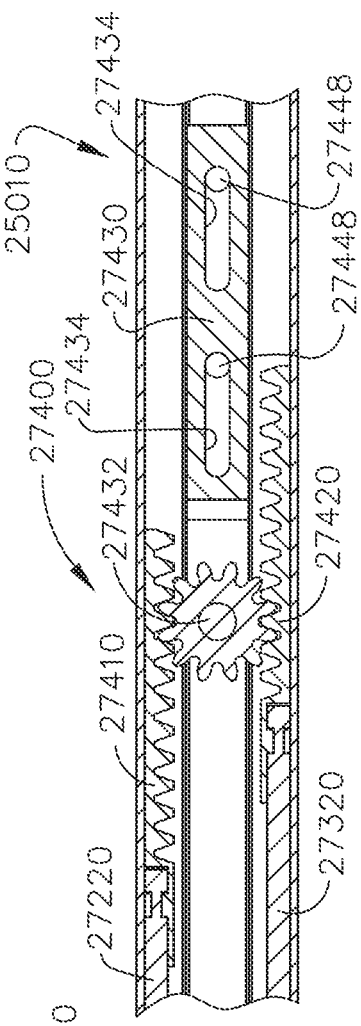
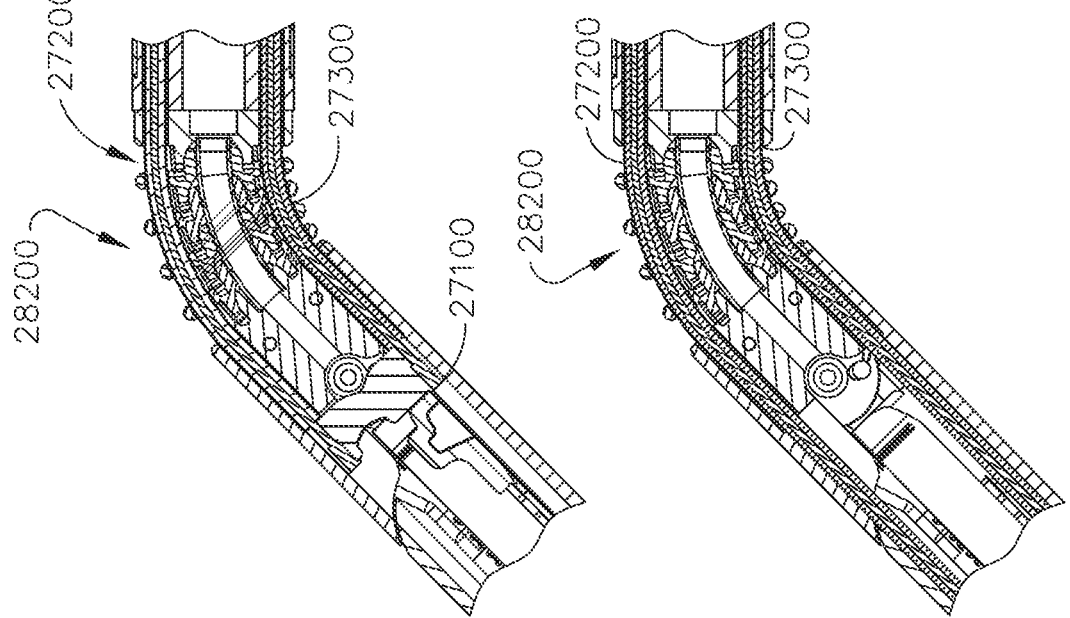
FIG. 24
FIG. 25

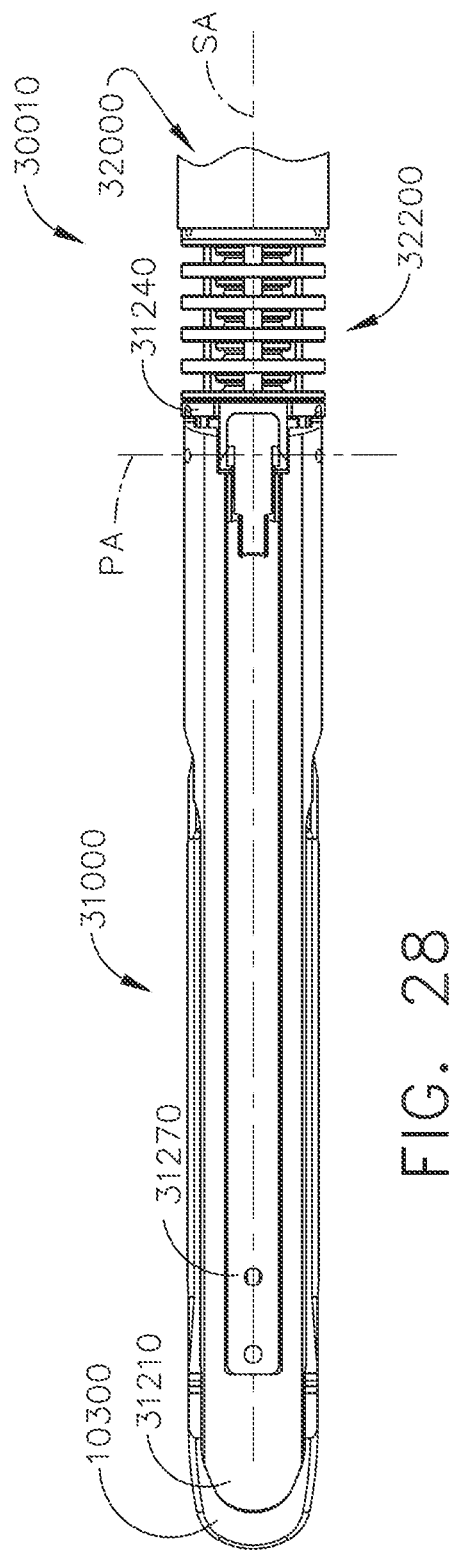
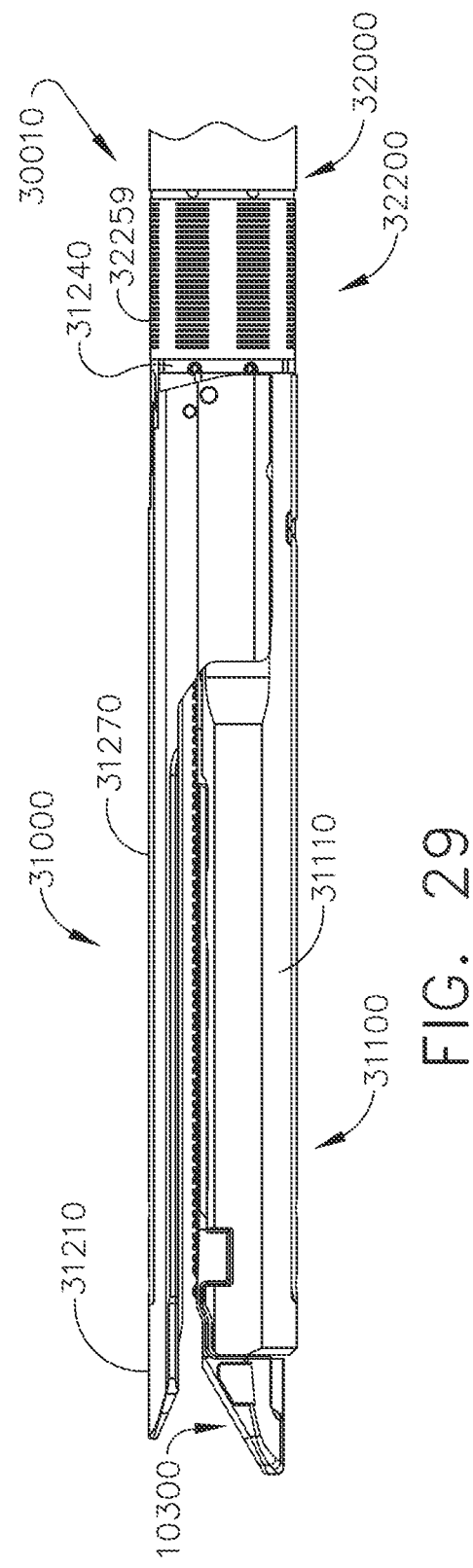
FIG. 28
FIG. 29

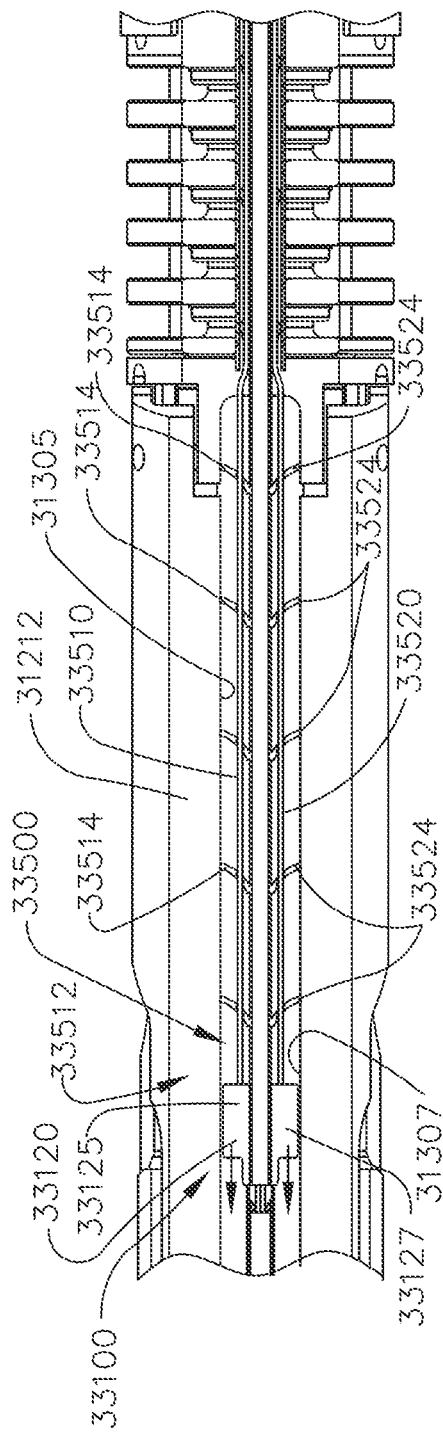
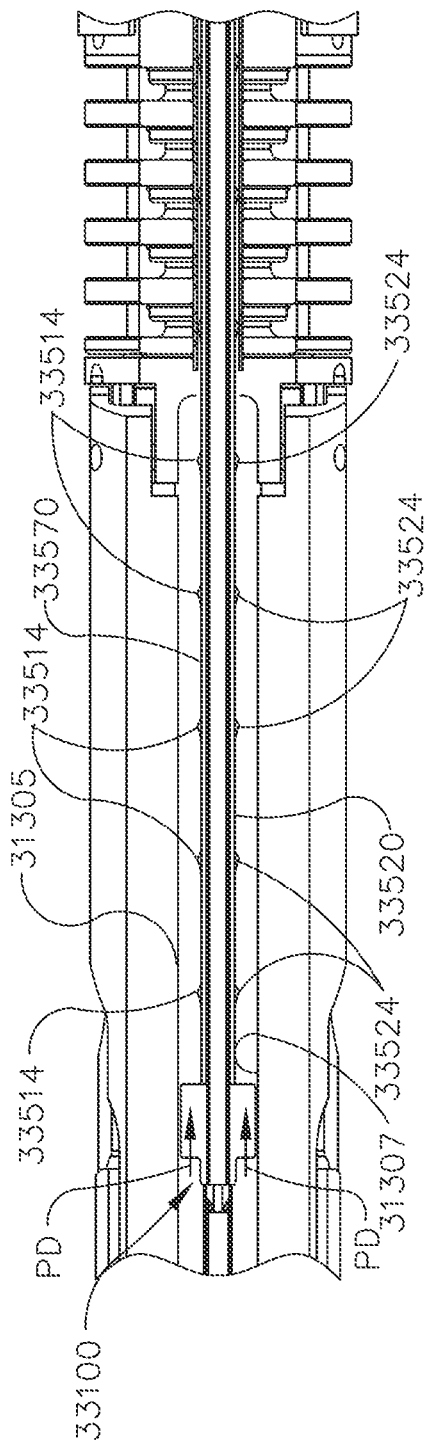

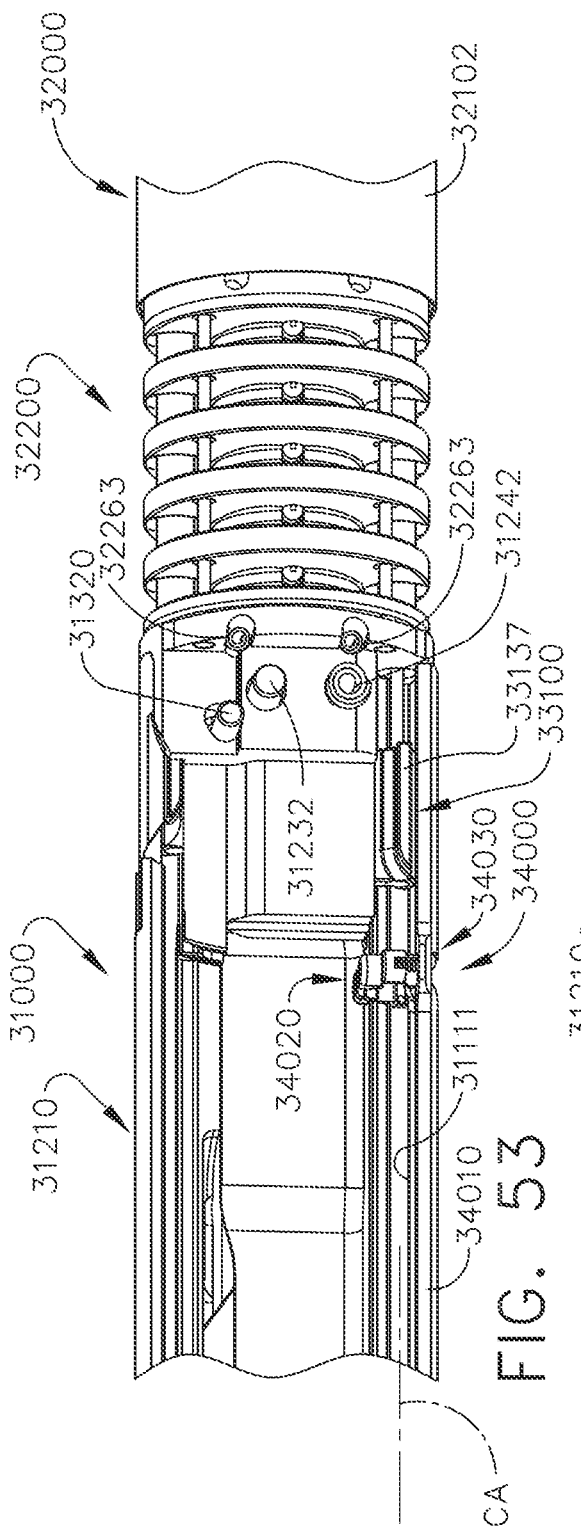
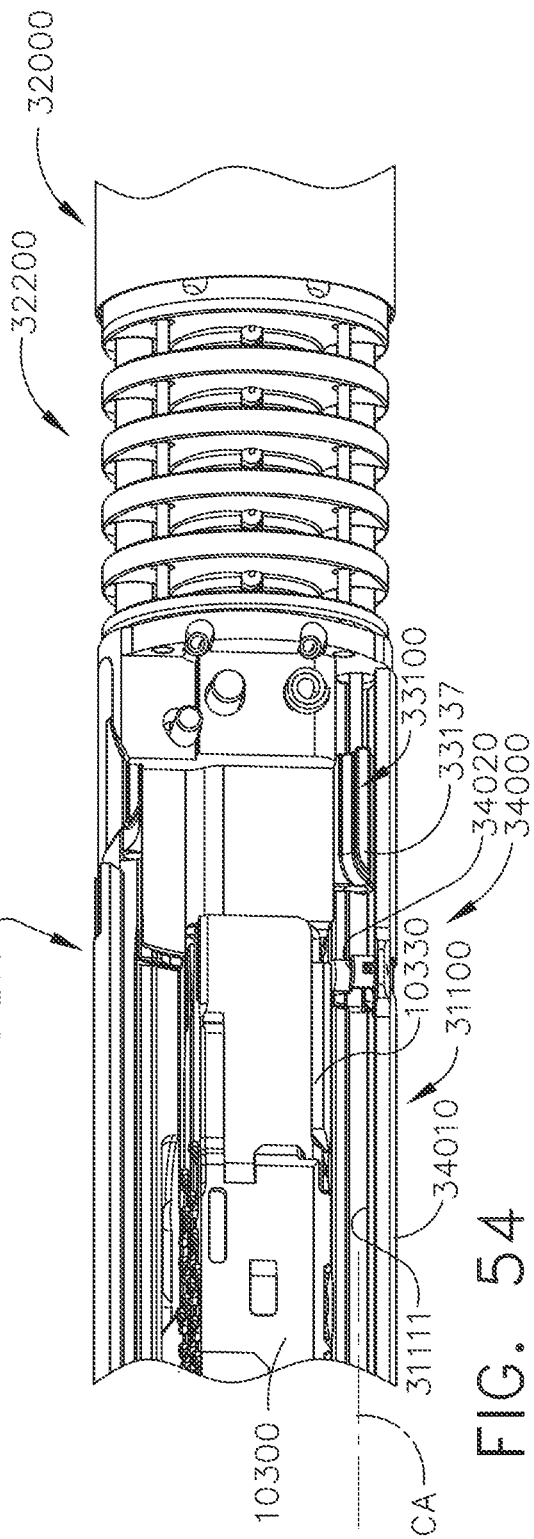
FIG. 53
FIG. 54

LOCKOUT ARRANGEMENTS FOR SURGICAL INSTRUMENTS

BACKGROUND

The present invention relates to surgical instruments and, in various arrangements, to surgical stapling and cutting instruments and staple cartridges for use therewith that are designed to staple and cut tissue. The surgical instruments may be configured for use in open surgical procedures, but have applications in other types of surgery, such as laparoscopic, endoscopic, and robotic-assisted procedures and may include end effectors that are articulatable relative to a shaft portion of the instrument to facilitate precise positioning within a patient.

BRIEF DESCRIPTION OF THE DRAWINGS

The novel features of the various aspects are set forth with particularity in the appended claims. The described aspects, however, both as to organization and methods of operation, may be best understood by reference to the following description, taken in conjunction with the accompanying drawings in which:

FIG. 3 is a side elevational view of the surgical end effector of FIG. 2, with an anvil thereof in a closed position;

FIG. 4 is a top view of the surgical end effector of FIG. 3;

FIG. 10 is a view of a distal face of the annular disc member of FIG. 8;

FIG. 11 is a view of a proximal face of the annular disc member of FIG. 8;

FIG. 14 is a side elevational view of the pulley unit of FIG. 12;

FIG. 15 is another side elevational view of the pulley unit of FIG. 12;

FIG. 24 is another partial cross sectional view of the surgical instrument of FIG. 1 with the surgical end effector thereof in an articulated position;

FIG. 25 is another partial cross sectional view of the surgical instrument of FIG. 1 with the surgical end effector thereof in an articulated position;

FIG. 28 is a top view of the surgical end effector of FIG. 26;

FIG. 29 is a side view of the surgical end effector of FIG. 26 with an anvil thereof in a closed position;

FIG. 49 is a partial top cross-sectional view of the surgical end effector of FIG. 48 illustrating distal advancement of the firing member within the surgical end effector;

FIG. 50 is another partial top cross-sectional view of the surgical end effector of FIG. 48 illustrating proximal retraction of the firing member within the surgical end effector;

FIG. 53 is a cross-sectional side view of a portion of another surgical end effector prior to installation of an unspent staple cartridge therein and with a firing member lockout system thereof in a locked orientation;

FIG. 54 is another cross-sectional side view of the surgical end effector of FIG. 54 with an unspent staple cartridge seated therein and with the firing member lockout system in an unlocked orientation;

DETAILED DESCRIPTION

Figure 1:
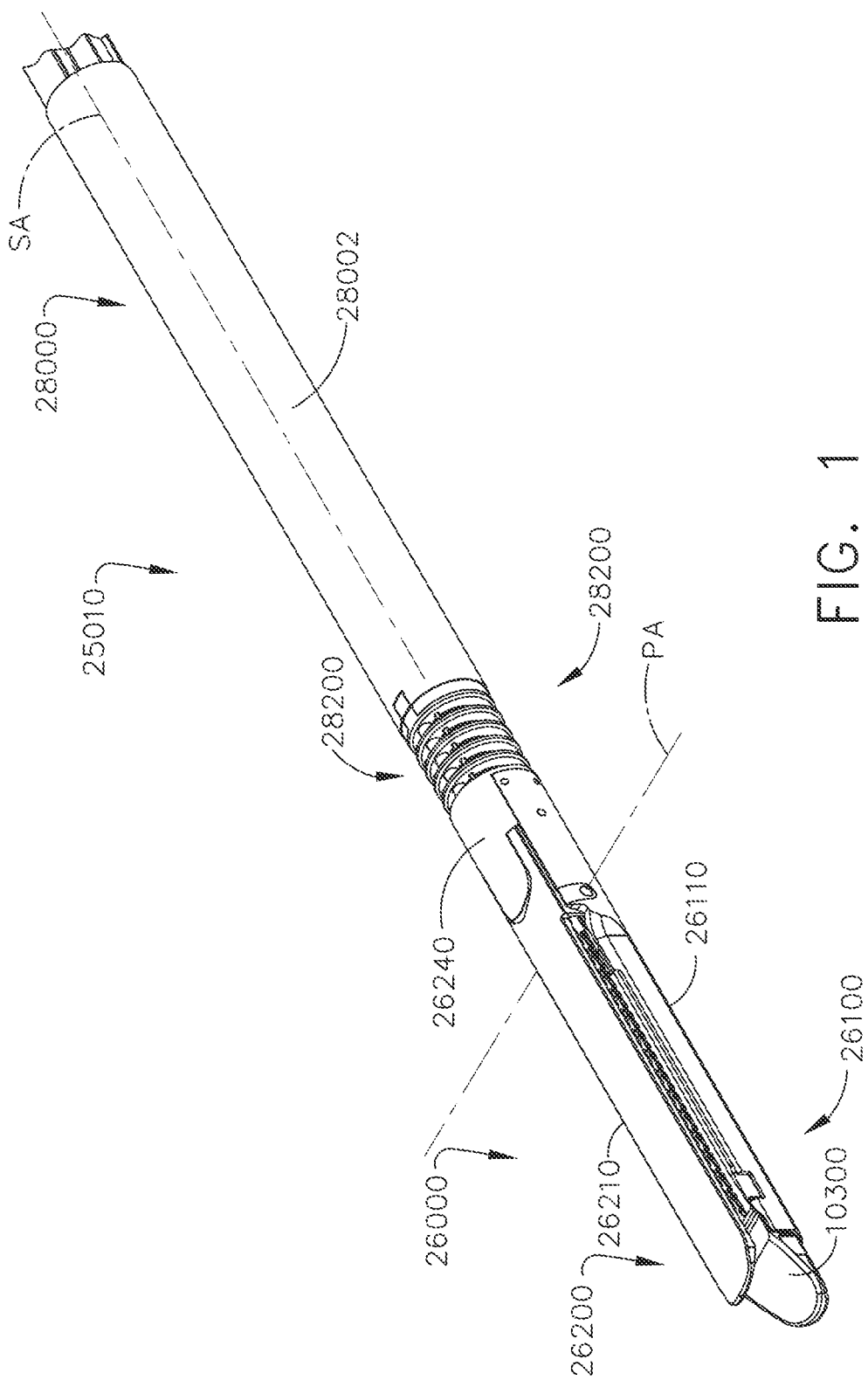
FIG. 1 is a perspective view of a portion of a surgical instrument embodiment.
Figure 2:
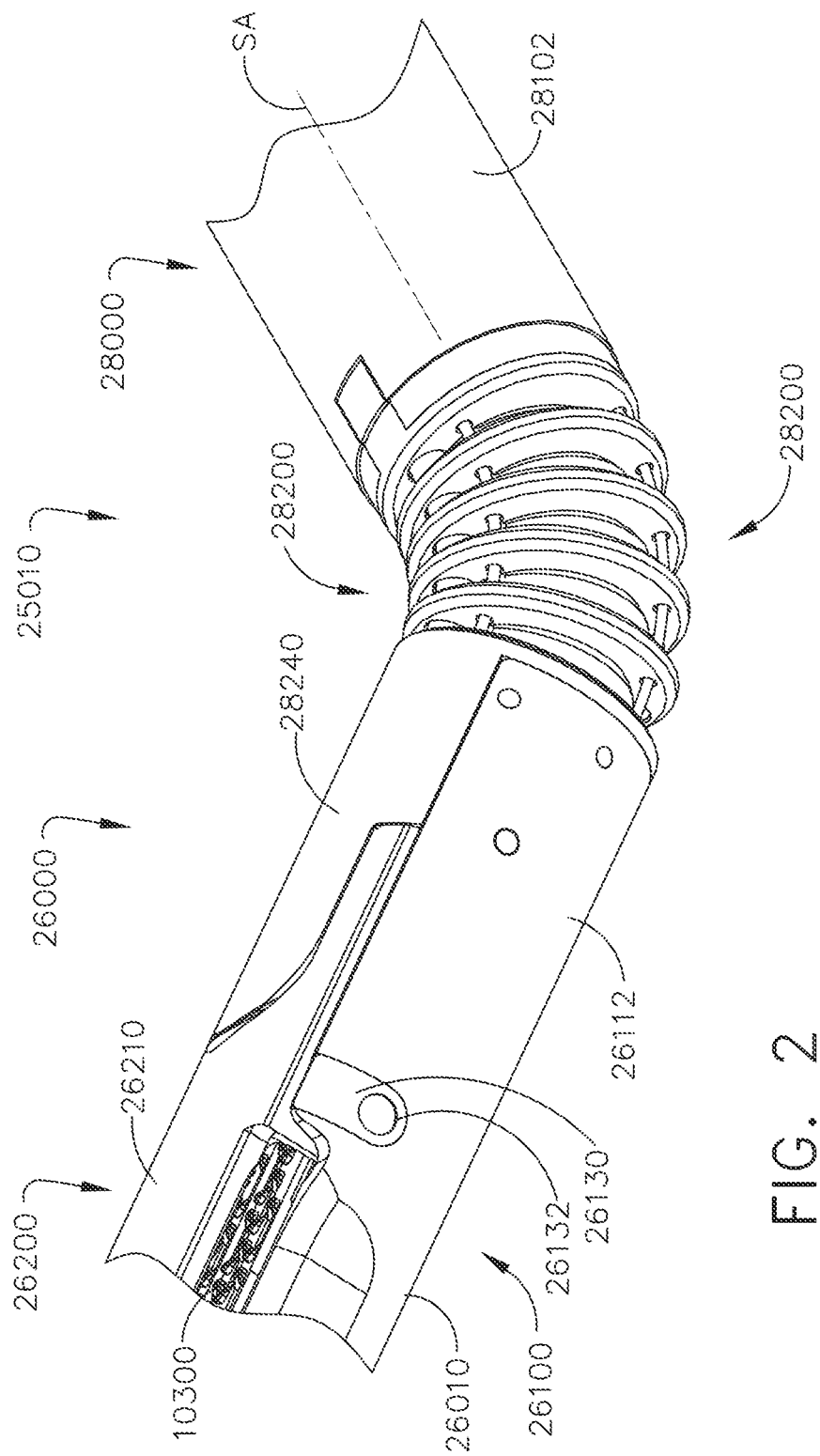
FIG. 2 is a perspective view of a portion of the surgical instrument of FIG. 1 with a surgical end effector portion thereof in an articulated position relative to an elongate shaft portion thereof.

The following U.S. Patent Applications were filed on Jun. 28, 2021 and are each incorporated by reference herein in their respective entireties:

U.S. patent application Ser. No. 17/360,133, entitled SURGICAL INSTRUMENTS WITH TORSION SPINE DRIVE ARRANGEMENTS;

U.S. patent application Ser. No. 17/360,139, entitled SURGICAL INSTRUMENTS WITH FIRING MEMBER CLOSURE FEATURES;

U.S. patent application Ser. No. 17/360,149, entitled SURGICAL INSTRUMENTS WITH SEGMENTED FLEXIBLE DRIVE ARRANGEMENTS;

U.S. patent application Ser. No. 17/360,162, entitled SURGICAL INSTRUMENTS WITH FLEXIBLE BALL CHAIN DRIVE ARRANGEMENTS;

U.S. patent application Ser. No. 17/360,176, entitled SURGICAL INSTRUMENTS WITH DOUBLE SPHERICAL ARTICULATION JOINTS WITH PIVOTABLE LINKS;

U.S. patent application Ser. No. 17/360,192, entitled SURGICAL INSTRUMENTS WITH DOUBLE PIVOT ARTICULATION JOINT ARRANGEMENTS;

U.S. patent application Ser. No. 17/360,197, entitled SURGICAL INSTRUMENTS WITH COMBINATION FUNCTION ARTICULATION JOINT ARRANGEMENTS;

U.S. patent application Ser. No. 17/360,199, entitled METHOD OF OPERATING A SURGICAL INSTRUMENT;

U.S. patent application Ser. No. 17/360,211, entitled SURGICAL INSTRUMENTS WITH DUAL SPHERICAL ARTICULATION JOINT ARRANGEMENTS;

U.S. patent application Ser. No. 17/360,220, entitled SURGICAL INSTRUMENTS WITH FLEXIBLE FIRING MEMBER ACTUATOR CONSTRAINT ARRANGEMENTS;

U.S. patent application Ser. No. 17/360,244, entitled ARTICULATABLE SURGICAL INSTRUMENTS WITH ARTICULATION JOINTS COMPRISING FLEXIBLE EXOSKELETON ARRANGEMENTS; and U.S. patent application Ser. No. 17/360,249, entitled SURGICAL INSTRUMENTS WITH DIFFERENTIAL ARTICULATION JOINT ARRANGEMENTS FOR ACCOMMODATING FLEXIBLE ACTUATORS.

Applicant of the present application owns the following U.S. Patent Applications that were filed on Feb. 21, 2019 which are each herein incorporated by reference in their respective entireties:

U.S. patent application Ser. No. 16/281,658, entitled METHODS FOR CONTROLLING A POWERED SURGICAL STAPLER THAT HAS SEPARATE ROTARY CLOSURE AND FIRING SYSTEMS;

U.S. patent application Ser. No. 16/281,670, entitled STAPLE CARTRIDGE COMPRISING A LOCKOUT KEY CONFIGURED TO LIFT A FIRING MEMBER;

U.S. patent application Ser. No. 16/281,675, entitled SURGICAL STAPLERS WITH ARRANGEMENTS FOR MAINTAINING A FIRING MEMBER THEREOF IN A LOCKED CONFIGURATION UNLESS A COMPATIBLE CARTRIDGE HAS BEEN INSTALLED THEREIN;

U.S. patent application Ser. No. 16/281,685, entitled SURGICAL INSTRUMENT COMPRISING CO-OPERATING LOCKOUT FEATURES;

U.S. patent application Ser. No. 16/281,693, entitled SURGICAL STAPLING ASSEMBLY COMPRISING A LOCKOUT AND AN EXTERIOR ACCESS ORIFICE TO PERMIT ARTIFICIAL UNLOCKING OF THE LOCKOUT;

U.S. patent application Ser. No. 16/281,704, entitled SURGICAL STAPLING DEVICES WITH FEATURES FOR BLOCKING ADVANCEMENT OF A CAMMING ASSEMBLY OF AN INCOMPATIBLE CARTRIDGE INSTALLED THEREIN;

U.S. patent application Ser. No. 16/281,707, entitled SURGICAL INSTRUMENT COMPRISING A DEACTIVATABLE LOCKOUT;

U.S. patent application Ser. No. 16/281,741, entitled SURGICAL INSTRUMENT COMPRISING A JAW CLOSURE LOCKOUT;

U.S. patent application Ser. No. 16/281,762, entitled SURGICAL STAPLING DEVICES WITH CARTRIDGE COMPATIBLE CLOSURE AND FIRING LOCKOUT ARRANGEMENTS;

U.S. patent application Ser. No. 16/281,660, entitled SURGICAL STAPLE CARTRIDGE WITH FIRING MEMBER DRIVEN CAMMING ASSEMBLY THAT HAS AN ONBOARD TISSUE CUTTING FEATURE;

U.S. patent application Ser. No. 16/281,666, entitled SURGICAL STAPLING DEVICES WITH IMPROVED ROTARY DRIVEN CLOSURE SYSTEMS;

U.S. patent application Ser. No. 16/281,672, entitled SURGICAL STAPLING DEVICES WITH ASYMMETRIC CLOSURE FEATURES;

U.S. patent application Ser. No. 16/281,678, entitled ROTARY DRIVEN FIRING MEMBERS WITH DIFFERENT ANVIL AND FRAME ENGAGEMENT FEATURES; and U.S. patent application Ser. No. 16/281,682, entitled SURGICAL STAPLING DEVICE WITH SEPARATE ROTARY DRIVEN CLOSURE AND FIRING SYSTEMS AND FIRING MEMBER THAT ENGAGES BOTH JAWS WHILE FIRING.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating a handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or", etc.

Recitation of ranges of values herein are not intended to be limiting, referring instead individually to any and all values falling within the range, unless otherwise indicated herein, and each separate value within such a range is incorporated into the disclosure as if it were individually recited herein. The words "about," "approximately" or the like, when accompanying a numerical value, are to be construed as indicating a deviation as would be appreciated by one of ordinary skill in the art to operate satisfactorily for an intended purpose. Similarly, words of approximation such as "approximately" or "substantially" when used in reference to physical characteristics, should be construed to contemplate a range of deviations that would be appreciated by one of ordinary skill in the art to operate satisfactorily for a corresponding use, function, purpose or the like.

The use of any and all examples, or exemplary language ("e.g.," "such as," or the like) provided herein, is intended merely to better illuminate the embodiments and does not pose a limitation on the scope of the embodiments. No language in the specification should be construed as indicating any unclaimed element as essential to the practice of the embodiments.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

It is common practice during various laparoscopic surgical procedures to insert a surgical end effector portion of a surgical instrument through a trocar that has been installed in the abdominal wall of a patient to access a surgical site located inside the patient's abdomen. In its simplest form, a trocar is a pen-shaped instrument with a sharp triangular point at one end that is typically used inside a hollow tube, known as a cannula or sleeve, to create an opening into the body through which surgical end effectors may be introduced. Such arrangement forms an access port into the body cavity through which surgical end effectors may be inserted. The inner diameter of the trocar's cannula necessarily limits the size of the end effector and drive-supporting shaft of the surgical instrument that may be inserted through the trocar.

Regardless of the specific type of surgical procedure being performed, once the surgical end effector has been inserted into the patient through the trocar cannula, it is often necessary to move the surgical end effector relative to the shaft assembly that is positioned within the trocar cannula in order to properly position the surgical end effector relative to the tissue or organ to be treated. This movement or positioning of the surgical end effector relative to the portion of the shaft that remains within the trocar cannula is often referred to as "articulation" of the surgical end effector. A variety of articulation joints have been developed to attach a surgical end effector to an associated shaft in order to facilitate such articulation of the surgical end effector. As one might expect, in many surgical procedures, it is desirable to employ a surgical end effector that has as large a range of articulation as possible.

Due to the size constraints imposed by the size of the trocar cannula, the articulation joint components must be sized so as to be freely insertable through the trocar cannula. These size constraints also limit the size and composition of various drive members and components that operably interface with the motors and/or other control systems that are supported in a housing that may be handheld or comprise a portion of a larger automated system. In many instances, these drive members must operably pass through the articulation joint to be operably coupled to or operably interface with the surgical end effector. For example, one such drive member is commonly employed to apply articulation control motions to the surgical end effector. During use, the articulation drive member may be unactuated to position the surgical end effector in an unarticulated position to facilitate insertion of the surgical end effector through the trocar and then be actuated to articulate the surgical end effector to a desired position once the surgical end effector has entered the patient.

Thus, the aforementioned size constraints form many challenges to developing an articulation system that can effectuate a desired range of articulation, yet accommodate a variety of different drive systems that are necessary to operate various features of the surgical end effector. Further, once the surgical end effector has been positioned in a desired articulated position, the articulation system and articulation joint must be able to retain the surgical end effector in that locked position during the actuation of the end effector and completion of the surgical procedure. Such articulation joint arrangements must also be able to withstand external forces that are experienced by the end effector during use.

A variety of surgical end effectors exist that are configured to cut and staple tissue. Such surgical end effectors commonly include a first jaw feature that supports a surgical staple cartridge and a second jaw that comprises an anvil. The jaws are supported relative to each other such that they can move between an open position and a closed position to position and clamp target tissue therebetween. Many of these surgical end effectors employ an axially moving firing member. In some end effector designs, the firing member is configured to engage the first and second jaws such that as the firing member is initially advanced distally, the firing member moves the jaws to the closed position. Other end effector designs employ a separate closure system that is independent and distinct from the system that operates the firing member.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The staple drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a camming member or "sled". The sled is movable between a proximal position adjacent the proximal end and a distal position adjacent the distal end. The sled comprises a plurality of ramped surfaces (cams) that are configured to slide under the drivers and lift the drivers, and the staples supported thereon, toward the anvil.

Further to the above, in these surgical end effectors, the sled is moved distally by the firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

Many surgical end effectors employ an axially movable firing beam that is attached to the firing member and is used to apply axial firing and retraction motions to the firing member. Many of such firing beams comprise a laminated construction that affords the firing beam with some degree of flexure about the articulation joint. As the firing beam traverses the articulation joint, the firing beam can apply de-articulation forces to the joint and can cause the beam to buckle. To prevent the firing beam from buckling under pressure, the articulation joint is commonly provided with lateral supports or "blow-out" plate features to support the portion of the beam that traverses the articulation joint. To advance the firing beam through an angle of greater than sixty degrees, for example, a lot of axial force is required. This axial force must be applied to the firing member in a balanced manner to avoid the firing member from binding with the jaws as the firing member moves distally. Any binding of the firing member with the jaws can lead to component damage and wear as well as require an increased amount of axial drive force to drive the firing member through the clamped tissue.

Other end effector designs employ a firing member that is rotary powered. In many of such designs, a rotary drive shaft extends through the articulation joint and interfaces with a rotatable firing member drive shaft that is rotatably supported within one of the jaws. The firing member threadably engages the rotatable firing member drive shaft and, as the rotatable firing member drive shaft is rotated, the firing member is driven through the end effector. Such arrangements require the supporting jaw to be larger to accommodate the firing member drive shaft. In such devices, a lower end of the firing member commonly operably interfaces with the drive shaft which can also result in an application of forces that can tend to unbalance the firing member as it is driven distally.

FIGS. 1-25 illustrate one form of surgical instrument 25010 that may address many of the challenges facing surgical instruments that comprise end effectors that are articulatable to large articulation angles and that are configured to cut and fasten tissue. In various embodiments, the surgical instrument 25010 may comprise a handheld device. In other embodiments, the surgical instrument 25010 may comprises an automated system sometimes referred to as a "robotically-controlled" system, for example. In various forms, the surgical instrument 25010 comprises a surgical end effector 26000 that is operably coupled to an elongate shaft assembly 28000. The elongate shaft assembly 28000 may be operably attached to a housing. In one embodiment, the housing may comprise a handle that is configured to be grasped, manipulated, and actuated by the clinician. In other embodiments, the housing may comprise a portion of a robotic system that houses or otherwise operably supports at least one drive system that is configured to generate and apply at least one control motion which could be used to actuate the surgical end effectors disclosed herein and their respective equivalents. In addition, various components may be "housed" or contained in the housing or various components may be "associated with" a housing. In such instances, the components may not be contained with the housing or supported directly by the housing. For example, the surgical instruments disclosed herein may be employed with various robotic systems, instruments, components and methods disclosed in U.S. Pat. No. 9,072,535, entitled SURGICAL STAPLING INSTRUMENTS WITH ROTATABLE STAPLE DEPLOYMENT ARRANGEMENTS, which is incorporated by reference herein in its entirety.

In one form, the surgical end effector 26000 comprises a first jaw 26100 and a second jaw 26200. In the illustrated arrangement, the first jaw 26100 comprises an elongate channel 26110 that comprises a proximal end 26112 and a distal end 26114 and is configured to operably support a surgical staple cartridge 10300 therein. The surgical staple cartridge 10300 comprises a cartridge body 10302 that has an elongate slot 10304 therein. A plurality of surgical staples or fasteners are stored therein on drivers (not shown) that are arranged in rows on each side of the elongate slot 10304. The drivers are each associated with corresponding staple cavities 10308 that open through a cartridge deck surface 10306. The surgical staple cartridge 10300 may be replaced after the staples/fasteners have been discharged therefrom.

Figure 5:
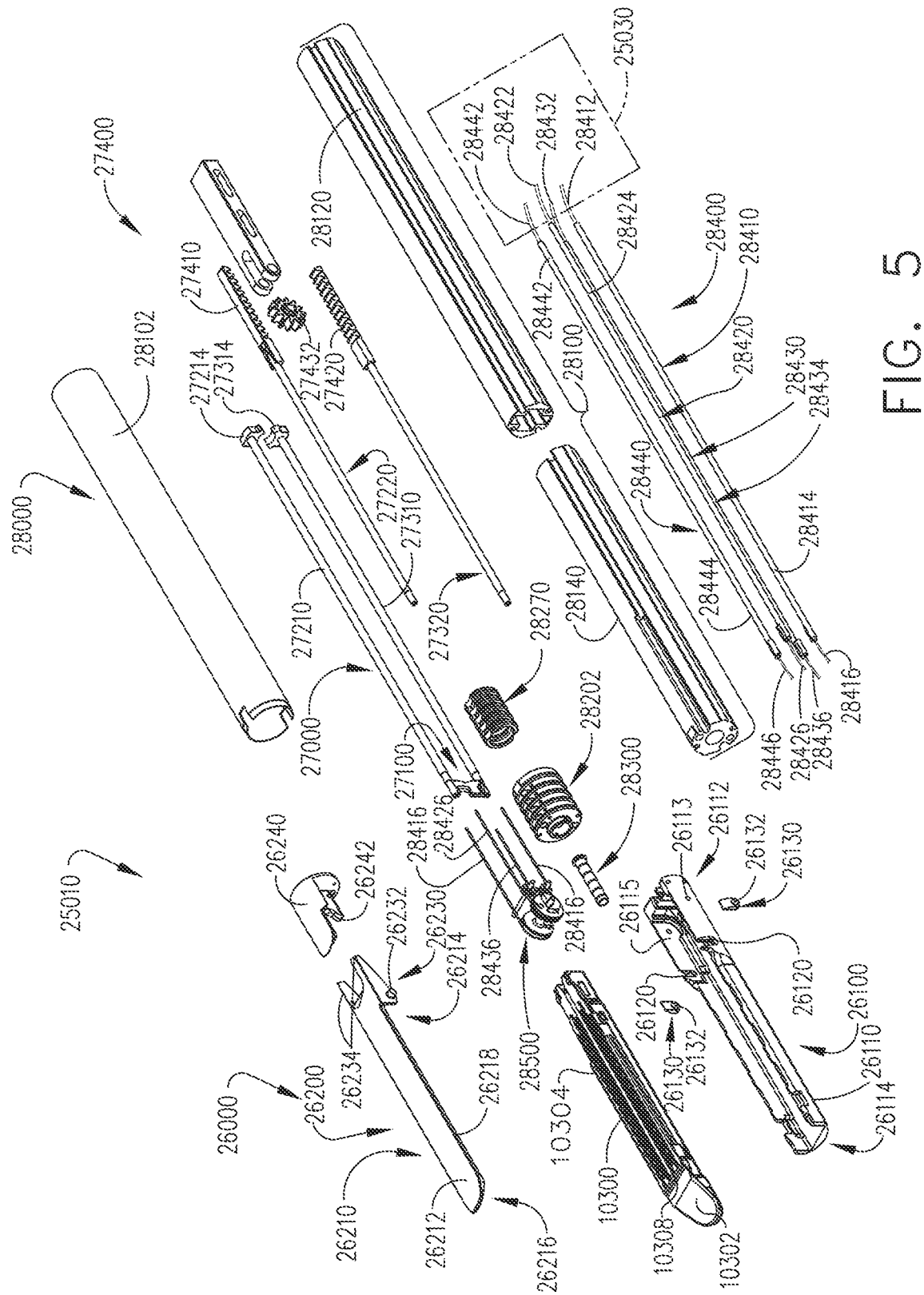
FIG. 5 is an exploded assembly perspective view of a portion of the surgical instrument of FIG. 1.

The second jaw 26200 comprises an anvil 26210 that comprises an elongate anvil body 26212 that has a proximal end 26214 and a distal end 26216. The anvil body 26212 comprises a staple-forming undersurface 26218 that faces the first jaw 26100 and may include a series of staple-forming pockets (not shown) that corresponds to each of the staples or fasteners in the surgical staple cartridge 10300. As can be seen in FIG. 5, the proximal end 26214 of the anvil body 26212 comprises an anvil mounting portion 26230 that comprises a pair of laterally extending mounting pins 26232. The mounting pins 26232 are configured to be received in corresponding mounting inserts 26130 that are configured to be retainingly received within mounting cradles 26120 that are formed in a proximal end 26112 of the elongate channel 26110. The mounting pins 26232 are pivotally received within pivot holes 26132 in the mounting inserts 26130 and then the mounting inserts 26130 are inserted into their corresponding cradle 26120 and affixed to the elongate channel 26110 by welding, adhesive, snap fit, etc. Such arrangement facilitates pivotal travel of the anvil 26210 relative to the elongate channel 26110 about a fixed pivot axis PA. See FIG. 1. As stated above, as used in this context, the term "fixed" means that the pivot axis PA is non-translating or non-moving relative to the elongate channel 26110.

In the illustrated arrangement, the elongate shaft assembly 28000 defines a shaft axis SA and comprises a shaft spine assembly 28100 that is received in a hollow outer shaft tube 28102. See FIG. 5. The shaft spine assembly 28100 may operably interface with a housing of a control portion (e.g., handheld unit, robotic tool driver, etc.) of the surgical instrument 25010 and in one example, comprises a proximal spine segment 28120 and a distal spine segment 28140.

Figure 6:
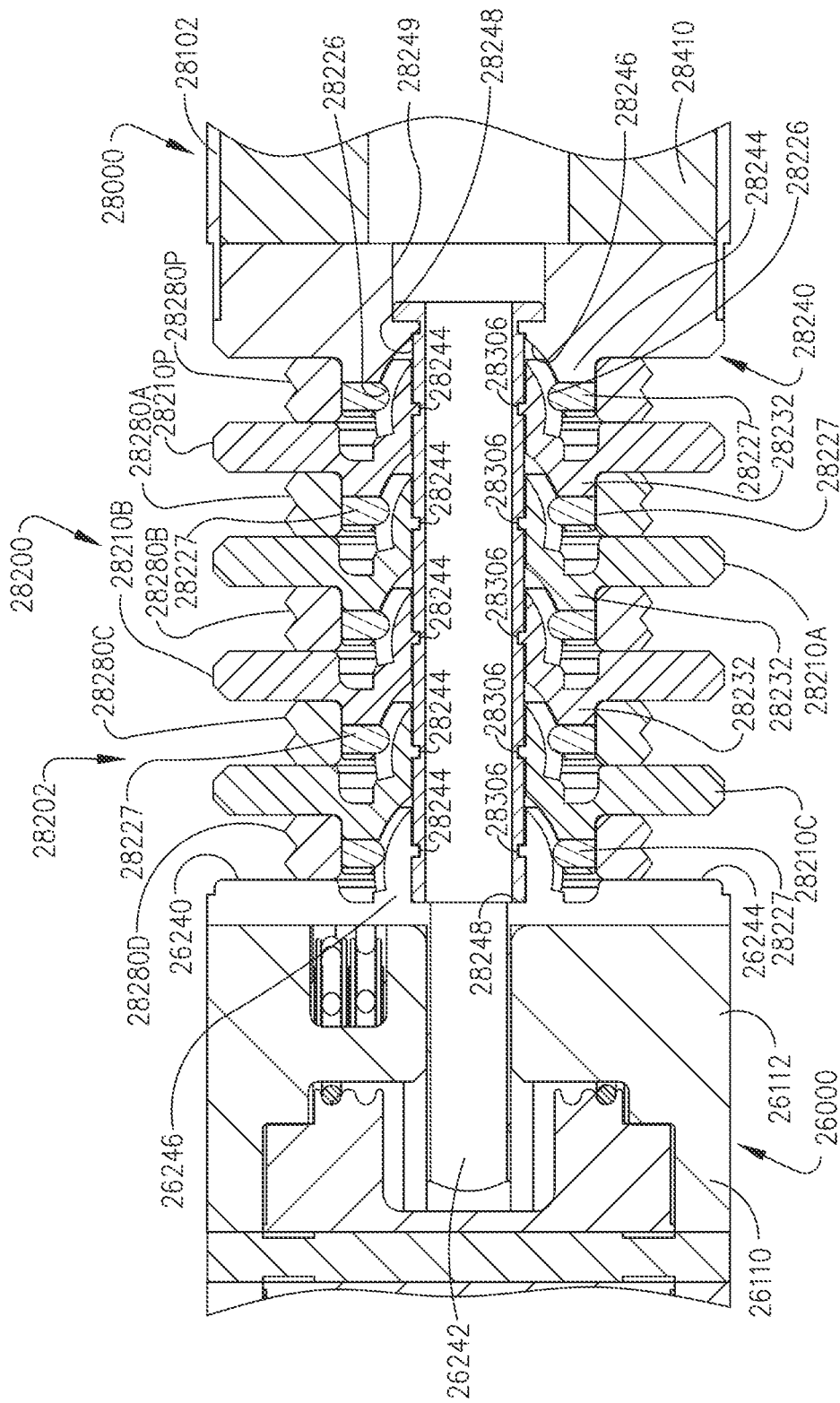
FIG. 6 is a bottom cross sectional view of an articulation joint and portions of the anvil of the surgical instrument of FIG. 1.
Figure 7:
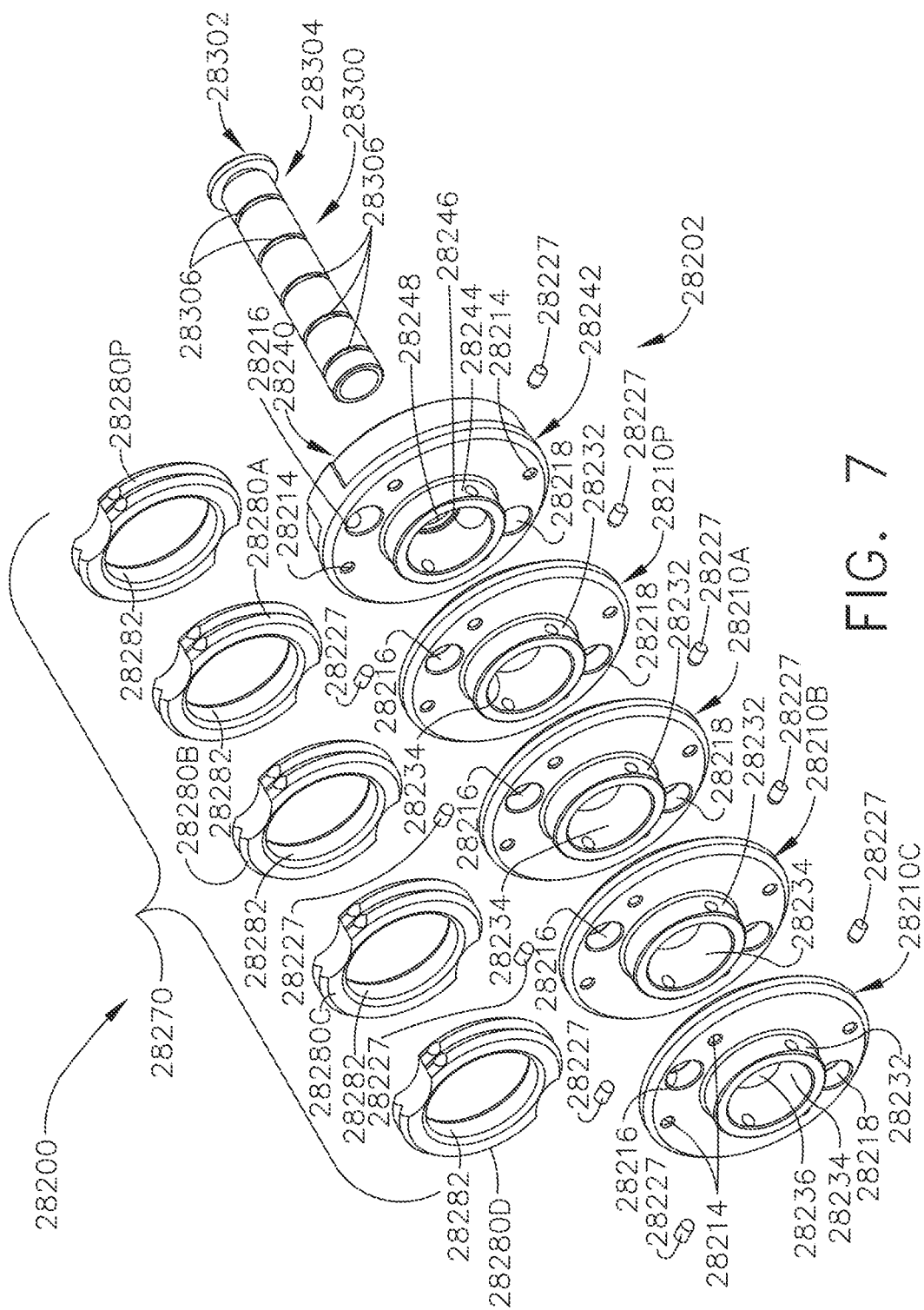
FIG. 7 is an exploded assembly view of the articulation joint of FIG. 6.
Figures 8, 9:
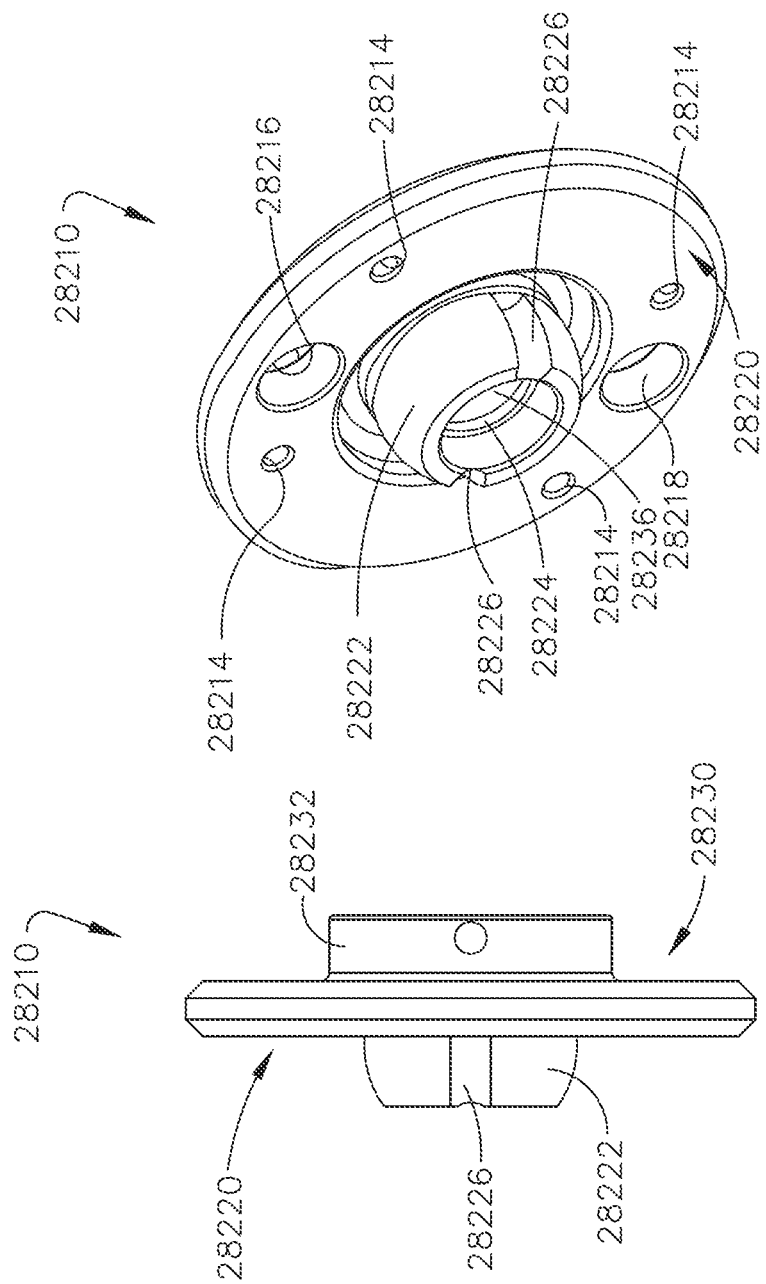
FIG. 8 is a side view of an annular disc member of the articulation joint of FIG. 7.
FIG. 9 is a perspective view of the annular disc member of FIG. 8.

The elongate shaft assembly 28000 further comprises an articulation joint 28200 that may be attached to the distal spine segment 28140 as well as the surgical end effector 26000 to facilitate selective articulation of the surgical end effector 26000 relative to the elongate shaft assembly 28000 in multiple articulation planes. Turning now to FIGS. 6-11, the articulation joint 28200 comprises a series 28202 of movably interfacing annular disc members 28210. As can be seen in FIGS. 8, 9, and 11, each annular disc member 28210 comprises a "first" or proximal face 28220 that comprises a centrally-disposed spherical feature or protrusion 28222. Each annular disc member 28210 further comprises a second or distal face 28230 that comprises an annular hub portion 28232 that defines a concave socket 28234 therein. See FIG. 10. Each annular disc member 28210 further has a central shaft passage 28236 therethrough. As can be seen in FIGS. 6 and 7, the articulation joint 28200 further comprises a proximal attachment disc assembly 28240 that is configured to be attached to a distal end of the distal spine segment 28140 by welding, adhesive, or other suitable fastener arrangement. The proximal attachment disc assembly 28240 comprises a distal face 28242 that includes an annular hub portion 28244 that defines a concave socket 28246 therein. The proximal attachment disc 28240 further has a central shaft passage 28248 therethrough.

Also in the illustrated arrangement, an anvil mounting bracket 26240 is configured to operably interface with the articulation joint 28200. The anvil mounting bracket 26240 is attached to the proximal end 26112 of the elongate channel 26110 of the surgical end effector 26000 by welding, adhesive or other suitable fastener arrangements and comprises a proximal face 26244 that has a centrally-disposed spherical feature or protrusion 26246 protruding therefrom. See FIG. 6. The anvil mounting bracket 26240 further has a central shaft passage 26248 therethrough.

In at least one embodiment, the articulation joint further comprises a series 28270 of elastomeric annular spacer members 28280 that serve to space and provide elastic support between each annular disc member 28210. The elastomeric annular spacer members 28280 define a spacer opening 28282 such that each elastomeric spacer member 28280 may be journaled on an annular hub portion 28232 of a corresponding annular disc member 28210. Each annular disc member 28210 is journaled on a central elastomeric support or continuum shaft 28300 that is mounted to the proximal attachment disc assembly 28240 and the anvil mounting bracket 26240. In one arrangement, the central continuum shaft 28300 is fabricated from an elastomeric material (e.g., rubber, polymer, etc.) and comprises a flanged proximal end 28302 and a cylindrical body portion 28304. The cylindrical body portion 28304 comprises a series of annular grooves 28306 therein. Each annular groove 28306 corresponds to one of the annular disc members 28210. The annular disc members 28210 and annular spacer members 28280 are journaled on the central continuum shaft 28300 as shown in FIG. 6. The flanged proximal end 28302 of the central continuum shaft 28300 is supported in a proximal passage 28249 in the proximal attachment disc 28240. The cylindrical body portion 28304 of the central continuum shaft 28300 extends through the central passage 28236 in each of the annular disc members 28210 in the series 28202 of movably interfacing annular disc members 28210. Each centrally-disposed spherical feature or protrusion 28222 comprises an annular key member 28224 that is configured to be received in a corresponding annular groove 28306 in the central continuum shaft 28300. See FIG. 6. Such arrangement may serve to orient each annular disc member 28210 in a desired spacing orientation on the central continuum shaft 28300, for example.

Still referring to FIG. 6, a proximal-most elastomeric spacer member 28280P is journaled on the annular hub portion 28244 of the proximal attachment disc assembly 28240 such that it is positioned between a proximal-most annular disc member 28210P and the proximal attachment disc 28240. The annular key member 28224 of the proximal-most annular disc member 28210P is received within a corresponding annular groove 28306 in the central continuum shaft 28300 to position the centrally-disposed spherical feature or protrusion 28222 of the proximal-most annular disc member 28210P within the concave socket 28246 in the annular hub portion 28244 of the proximal attachment disc 28240. As can further be seen in FIG. 6, another elastomeric spacer member 28280A is journaled on the annular hub portion 28232 of the proximal-most annular disc member 28210P such that is positioned between the next annular disc member 28210A in the series 28202 of movably interfacing annular disc members 28202 and the proximal-most annular disc member 28210P. The annular key member 28224 of the annular disc member 28210A is received within a corresponding annular groove 28306 in the central continuum shaft 28300 to position the centrally-disposed spherical feature or protrusion 28222 of the annular disc member 28210A within the concave socket 28246 in the annular hub portion 28244 of the proximal attachment disc 28210P. Still referring to FIG. 6, another elastomeric spacer member 28280B is journaled on the annular hub portion 28232 of the annular disc member 28210A such that is positioned between the next annular disc member 28210B in the series 28202 of movably interfacing annular disc members 28210. The annular key member 28224 of the annular disc member 28210B is received within a corresponding annular groove 28306 in the central continuum shaft 28300 to position the centrally-disposed spherical feature or protrusion 28222 of the annular disc member 28210B within the concave socket 28246 in the annular hub portion 28244 of the annular disc member 28210A. Also in this arrangement, another elastomeric spacer member 28280C is journaled on the annular hub portion 28232 of the annular disc member 28210B such that is positioned between the distal-most annular disc member 28210C in the series of movably interfacing annular disc members 28202. The annular key member 28224 of the distal-most annular disc member 28210C is received within a corresponding annular groove 28306 in the central continuum shaft 28300 to position the centrally-disposed spherical feature or protrusion 28222 of the distal-most annular disc member 28210C within the concave socket 28246 in the annular hub portion 28244 of the annular disc member 28210B. Finally, another elastomeric spacer member 28280D is journaled on the annular hub portion 28232 of the distal-most annular disc member 28210C such that is positioned between the anvil mounting bracket 26240 and the distal-most annular disc member 28210C. The annular key member 28224 of the centrally-disposed spherical feature or protrusion 26246 of the anvil mounting bracket 26240 is received within a corresponding annular groove 28306 in the central continuum shaft 28300 to position the centrally-disposed spherical feature or protrusion 226246 of the anvil mounting bracket 26240 within the concave socket 28246 in the annular hub portion 28244 of the distal-most annular disc member 28210C.

In at least one arrangement, to limit pivotal travel of the annular disc members 28210P, 28210A, 28210B, 28210C to a range of relative pivotal travel and prevent complete relative rotation of the annular disc members relative to each other, the centrally-disposed spherical feature or protrusion 28222 of each of the annular disc member 28210P, 28210A, 28210B, 28210C, as well as the distal spherical feature or protrusion 26246 of the anvil mounting bracket 26240, includes a pair of arcuate pin grooves 28226 therein. As can be seen in FIG. 6, a corresponding travel-limiting pin member 28227 is pressed into or otherwise attached to each annular hub portion 28232 and is received within the corresponding pin groove 28226 in the centrally-disposed spherical feature or protrusions 28222, 26246.

Returning to FIG. 5, in the illustrated example, the articulation joint 28200 may be operably controlled by an articulation system 28400 that comprises four cable assemblies 28410, 28420, 28430, and 28440 that extend through the elongate shaft assembly 28000. In one arrangement, the cable assembly 28410 comprises a proximal cable portion 28412 that is attached to an articulation rod 28414 that is supported in a corresponding axial groove in the shaft spine assembly 28100 for axial travel therein. A distal cable portion 28416 is attached to the articulation rod 28414. The cable assembly 28420 comprises a proximal cable portion 28422 that is attached to an articulation rod 28424 that is supported in a corresponding axial groove in the shaft spine assembly 28100 for axial travel therein. A distal cable portion 28426 is attached to the articulation rod 28424. The cable assembly 28430 comprises a proximal cable portion 28432 that is attached to an articulation rod 28434 that is supported in a corresponding axial groove in the shaft spine assembly 28100 for axial travel therein. A distal cable portion 28436 is attached to the articulation rod 28434. The cable assembly 28440 comprises a proximal cable portion 28442 that is attached to an articulation rod 28444 that is supported in a corresponding axial groove in the shaft spine assembly 28100 for axial travel therein. A distal cable portion 28446 is attached to the articulation rod 28444.

The proximal cable portions 28412, 28422, 28432, 28442 may operably interface with a portion of a cable control system 25030 that is supported within or is otherwise associated with a housing of the surgical instrument 25010. The cable control system 25030 may comprise a plurality of cable support members/capstans, pulleys, etc. that are controlled by one or more corresponding motors that are controlled by a control circuit portion of the surgical instrument 25010. In various embodiments, the cable control system 25030 is configured to manage the tensioning (pulling) and paying out of cables at precise times during the articulation process. In addition, in at least one arrangement, the cable control system 25030 may be employed to control the opening and closing of the anvil 26210 as will be discussed in further detail below.

Figure 12:
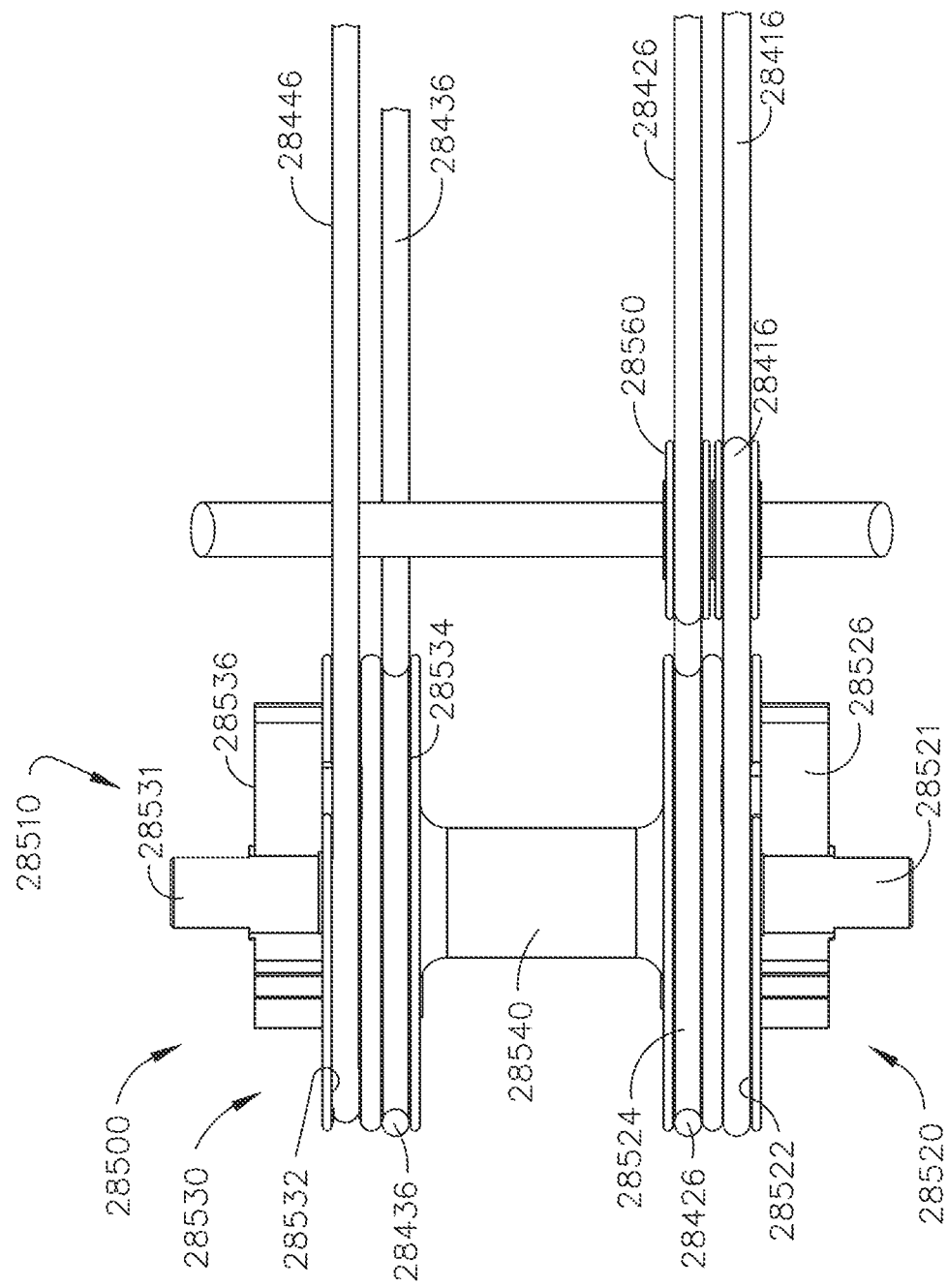
FIG. 12 is a top view of a pulley unit of the surgical instrument of FIG. 1.

Turning now to FIG. 12, the distal cable portions 28416, 28426, 28436, 28446 are configured to operably interface with a closure system 28500 that is rotatably mounted in the proximal end 26112 of the elongate channel 26110. As can be seen in FIG. 12, the closure system 28500 comprises a pulley unit 28510 that comprises a first lateral alpha wrap pulley 28520 and a second lateral alpha wrap pulley 28530 that are interconnected by a central shaft 28540. The pulley unit 28510 is rotatably supported within the proximal end 26112 of the elongate channel 26110 and retained therein by an anvil mounting bracket 26240 that is attached to the proximal end 26112 of the elongate channel 26112. See FIG. 5. The anvil mounting bracket 26240 may be attached to the proximal end 26112 of the elongate channel 26110 by welding, adhesive, snap features, etc. The anvil mounting bracket 26240 comprises a shaft cradle 26242 that is configured to rotatably support the central shaft 28540 within the elongate channel 26110. In the illustrated arrangement, a first pivot shaft 28521 protrudes from the first lateral alpha wrap pulley 28520 and is pivotally supported in a pivot hole 26113 in the proximal end of the elongate channel. Similarly, a second pivot shaft 28531 protrudes from the second lateral alpha wrap pulley 28530 and is pivotally supported in a pivot hole 26115 in the proximal end 26112 of the elongate channel 26110.

As can be seen in FIG. 12, the first alpha wrap pulley 28520 comprises a first circumferential groove 28522 and a second circumferential groove 28524. In the illustrated example, the first distal cable portion 28416 is received in the first circumferential groove 28522 and is attached thereto and the second distal cable portion 28426 is received in the second circumferential groove 28524 and is attached thereto. Pulling on the first distal cable portion 28416 will result in the rotation of the first lateral alpha wrap pulley 28520 in a first direction and pulling the second distal cable portion 28426 will result in the rotation of the first lateral alpha wrap pulley 28520 in a second opposite direction. Similarly, the second lateral alpha wrap pulley 28530 comprises a first circumferential groove 28532 and a second circumferential groove 28534. In the illustrated arrangement, the distal cable portion 28446 is received in the first circumferential groove 28532 and is attached thereto and the third distal cable portion 28436 is received in the second circumferential groove 28534 and is attached thereto. Pulling on the fourth distal cable portion 28446 will result in the rotation of the second alpha wrap pulley 28530 in the first direction and pulling the third distal cable portion 28436 will result in the rotation of the second lateral alpha wrap pulley 28530 in the second opposite direction. In accordance with one aspect, the lateral alpha wrap pulleys 28520, 28530 can rotate approximately three hundred thirty degrees. This range of rotational travel is in contrast to a normal pulley that may have a range of rotational travel that is less than one hundred eighty degrees of rotation.

Each of the first and second lateral alpha wrap pulleys 28520, 28530 also comprise a corresponding spiral closure cam that is configured to apply closure motions to the anvil 26210. As can be seen in FIG. 12, the first lateral alpha wrap pulley 28520 includes a first spiral closure cam 28526 and the second lateral alpha wrap pulley 28530 has a second spiral closure cam 28536 thereon. The spiral closure cams 28526, 28536 are configured to cammingly interact with corresponding anvil closure arms 26234 on the anvil mounting portion 26230 of the anvil 26210 to apply closure motions thereto. See FIG. 5. Rotation of the pulley unit 28510 in a first rotary direction will cause the spiral closure cams 28526, 28536 to cam the anvil 26210 to the closed position. To open the anvil 26210, the pulley unit 28510 is rotated in opposite direction to position the spiral closure cams 28526, 28536 in positions wherein the anvil 26210 can be pivoted open by an anvil spring (not shown).

In the illustrated arrangement, the proximal attachment disc 28240, the proximal-most annular disc member 28210P, annular proximal disc members 28210A, 28210B, 28210C and anvil mounting bracket 26240 all include fourth articulation cable passages 28214 that are configured to permit each of the distal cable portions 28416, 28426, 28436, and

Figure 13:
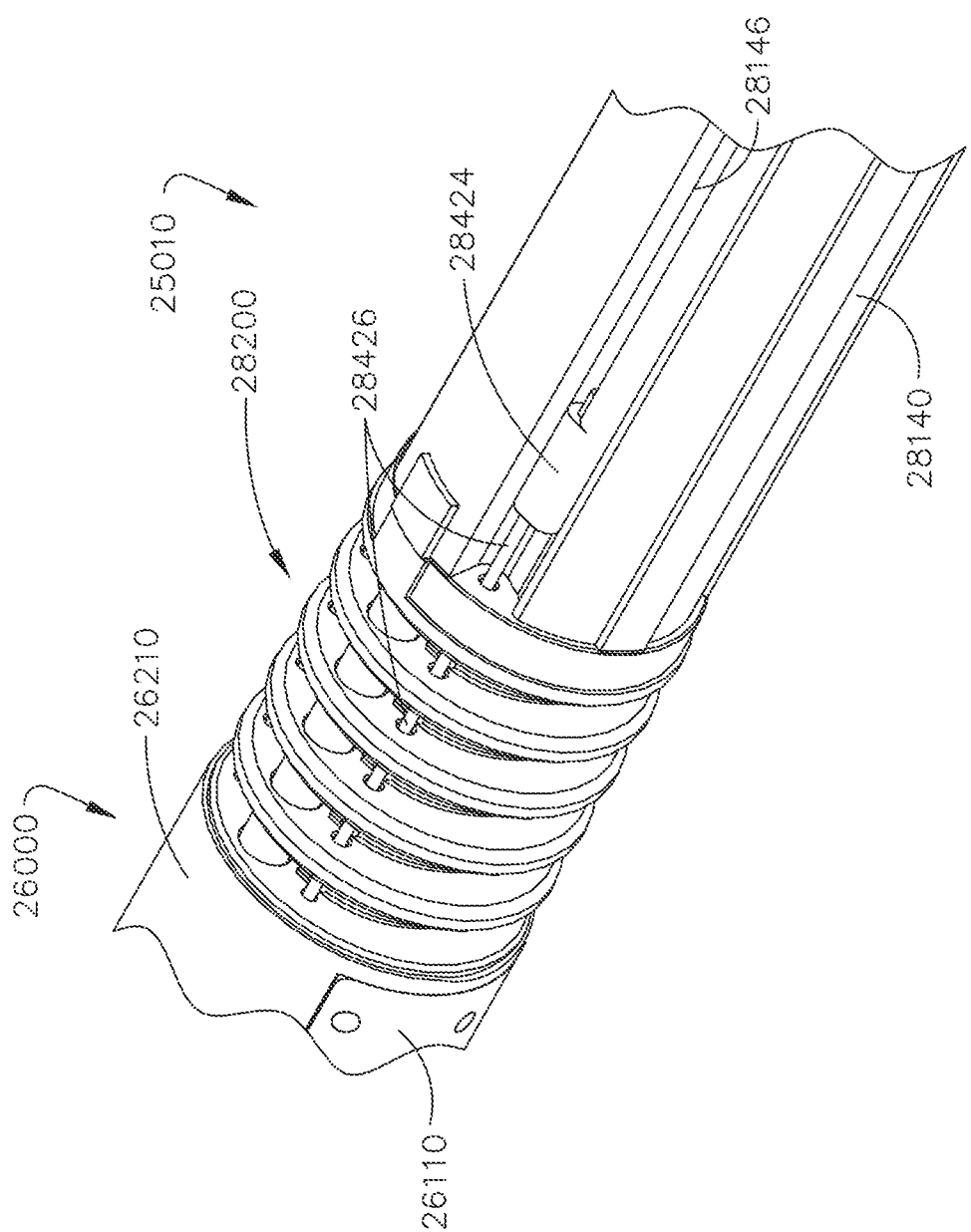
FIG. 13 is a perspective view of a portion of the articulation joint and elongate shaft assembly of the surgical instrument of FIG. 1, with an outer shaft tube omitted for clarity.
Figure 16:
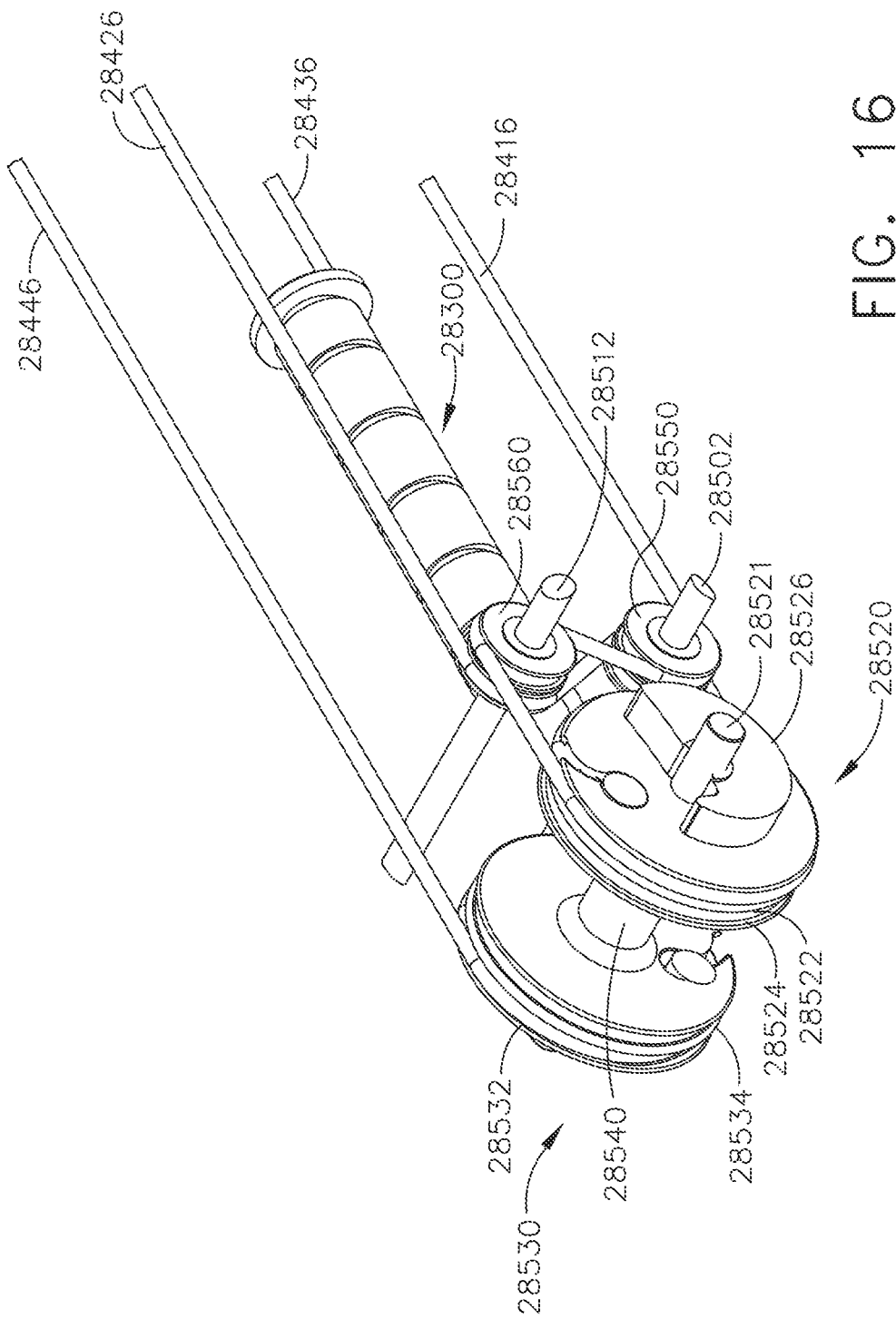
FIG. 16 is a perspective view of the pulley unit of FIG. 12 and a continuum shaft of the articulation joint of the surgical instrument of FIG. 1.
Figure 17:
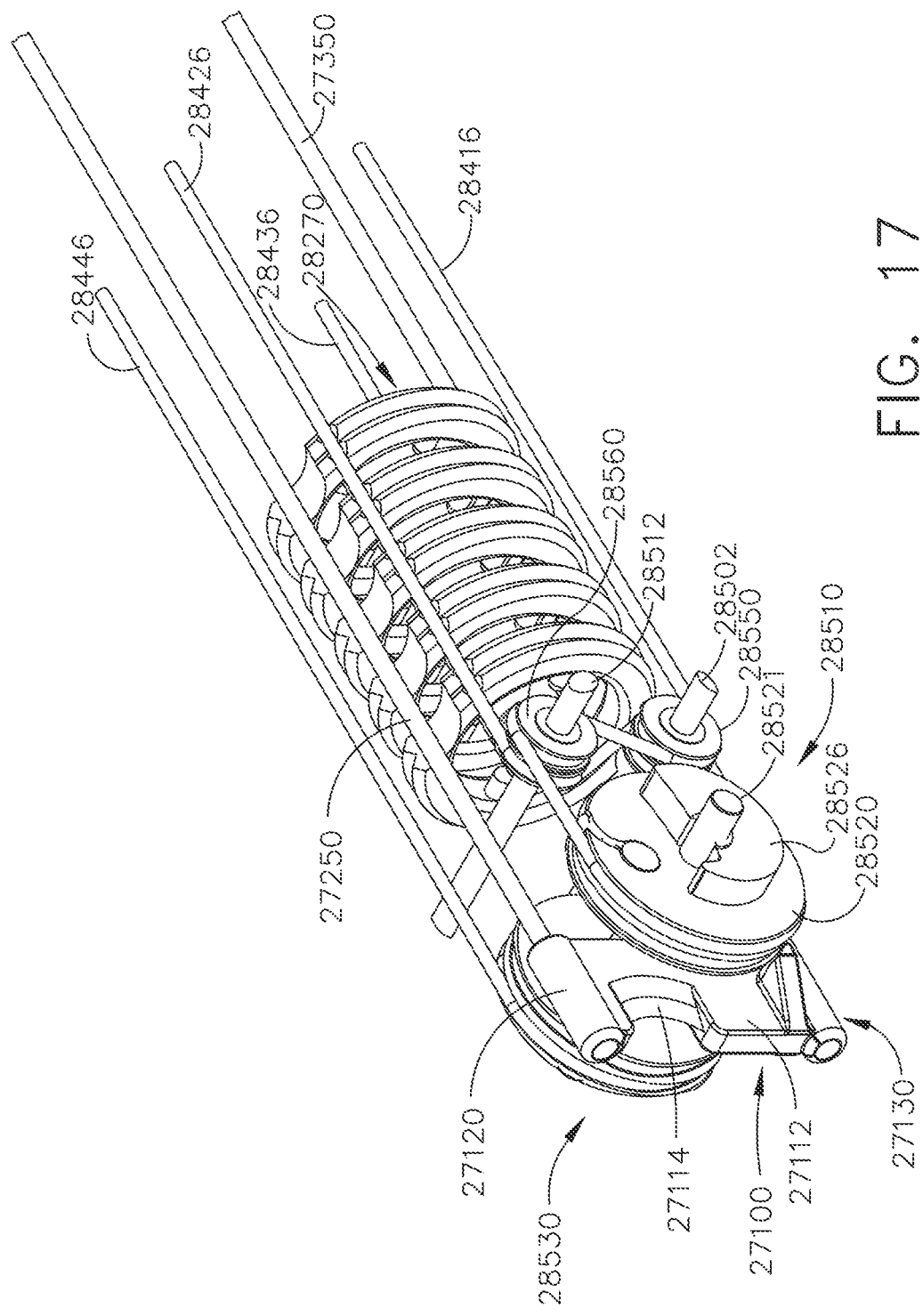
FIG. 17 is another perspective view of the pulley unit of FIG. 12 and a series of elastomeric annular spacer members of the articulation joint of the surgical instrument of FIG. 1.
Figure 18:
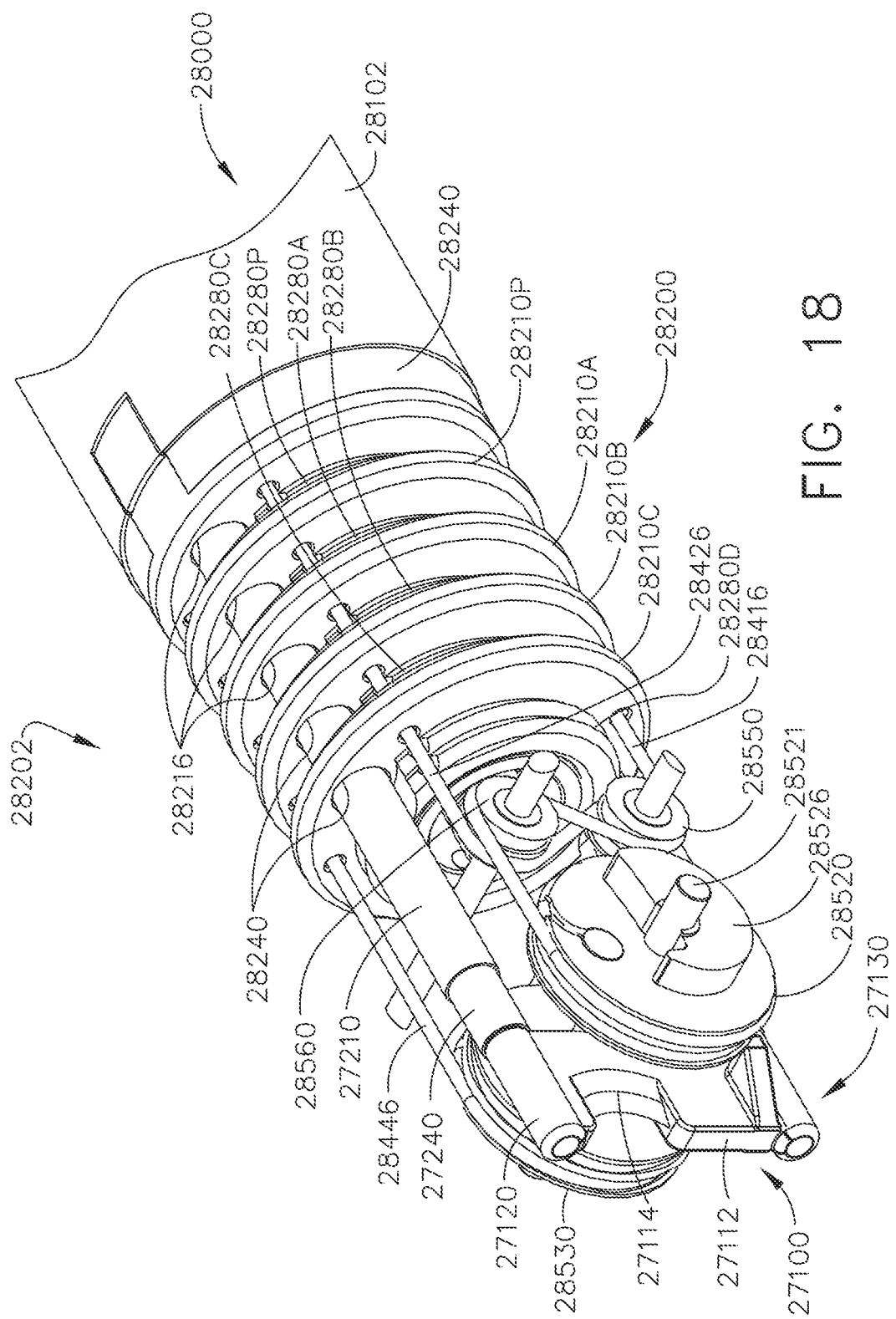
FIG. 18 is another perspective view of the pulley unit, portions of a firing system and the articulation joint of the surgical instrument of FIG. 1.

28446 to pass therethrough. FIG. 13 illustrates the articulation rod 28424 slidably supported in a corresponding axial groove 28146 in the distal spine segment 28140 for axial travel therein. Each of the other articulation rods 28414, 28434, 28444 is similarly supported in axial grooves in the distal spine segment 28140 as well as corresponding grooves in the proximal spine segment 28120.

Referring now to FIGS. 5 and 14-16, the distal cable portion 28416 extends from the articulation rod 28414 through the articulation joint 28200 and is looped around two redirect pulleys 28550, 28560 that are supported on shafts 28502, 28512 that are rotatably mounted in the proximal end 26112 of the elongate channel 26110. The distal cable portion 28416 exits the articulation joint 28200 to be received within the first circumferential groove 28522 in the first lateral alpha wrap pulley 28520 where it is secure therein. The distal cable portion 28426 extends from the articulation rod 28424 through the articulation joint 28200 to be looped around the redirect pulleys 28560, 28550 to be received within the second circumferential groove 28524 in the first lateral alpha wrap pulley 28520 where it is secure therein.

In the illustrated example, distal cable portion 28436 extends from the articulation rod 28434 through the articulation joint 28200 to be received within a corresponding circumferential groove 28534 in the second lateral alpha wrap pulley 28530 where it is secured therein. In addition, the distal cable portion 28446 extends from the articulation rod 28444 through the articulation joint 28200 to be received within a corresponding circumferential groove 28532 in the second lateral alpha wrap pulley 28530 where it is secure therein.

In at least one example, to articulate the surgical end effector 26000 relative to the elongate shaft assembly 28000 through a first articulation plane, the cable control system 25030 is actuated to pull on the distal cable portion 28426 and the distal cable portion 28446 simultaneously with a same amount of tension being applied to each distal cable portion 28426, 28446. Because the distal cable portions 28426, 28446 apply equal amounts of tension on both sides of the pulley unit 28510, the pulley unit 28510 does not rotate. However, the pulling action of the distal cable portions 28426, 28446 is translated through the articulation joint 28200 to the surgical end effector 26000 which results in the articulation of the articulation joint 28200 through a first articulation plane. To articulate the surgical end effector 26000 through a second plane of articulation that is transverse to the first plane of articulation, the cable control system 25030 is actuated to pull the distal cable portion 28436 and the distal cable portion 28446 simultaneously with a same amount of tension being applied to each distal cable portion 28436, 28446. Because the distal cable portions 28436, 28446 apply equal amounts of tension on both sides of the second lateral alpha wrap pulley 25830 of the pulley unit 28510, the pulley unit 28510 does not rotate. However, the pulling action of the distal cable portions 28436, 28446 is translated through the articulation joint 28200 to the surgical end effector 26000 which results in the articulation of the articulation joint 28200 in a second articulation plane.

The cable control system 25030 may also be used to control the opening and closing of the anvil 26210 in the following manner. As indicated above, when the spiral closure cams 28526 on the first lateral alpha wrap pulley 28520 and the second lateral alpha wrap pulley 28530 are in a first position, the anvil 26210 may be pivoted to an open position by an anvil spring or springs (not shown) that are positioned in the proximal end 26112 of the elongate channel 26110 and are position to contact the anvil mounting portion 26230 or anvil closure arms 26234 to pivot the anvil 26210 to the open position. To close the anvil 26210 from that position, the cable control system 25030 is actuated to pull the distal cable portion 28416 and the distal cable portion 28446 simultaneously with a same amount of tension being applied to each distal cable portion 28416 and 28446. These distal cable portions 28416, 28446 will cause the pulley unit 28510 to rotate causing the spiral closure cams 28526, 28536 to contact the anvil closure arms 26234 and cam the anvil 26210 to a closed position. It will be appreciated that by applying equal amounts of tension into the distal cable portions 28416, 28446, no moment is applied to the articulation joint 28200 because there are equal amounts of tension being applied on each side of the shaft axis SA. Such arrangement allows the jaw closure to be profiled as desired. This cable-control system 25030 may allow for a faster closure when the anvil 26210 is fully open. The cable-control system 25030 can also function as a lower speed/higher force generating closure mechanism for clamping onto tissue. The present cable controlled system 25030 may not produce the backlash that commonly occurs with other cable-controlled systems and thus can also be used to control the articulation position of the end effector. The above-described articulation joint 28200 and cable controlled system 25030 can facilitate multiple plane articulation while also supplying an additional actuation motion to the surgical end effector 26000.

As was discussed above, many surgical end effectors employ a firing member that is pushed distally through a surgical staple cartridge by an axially movable firing beam. The firing beam is commonly attached to the firing member in the center region of the firing member body. This attachment location can introduce an unbalance to the firing member as it is advanced through the end effector. Such unbalance can lead to undesirable friction between the firing member and the end effector jaws. The creation of this additional friction may require an application of a higher firing force to overcome such friction as well as can cause undesirable wear to portions of the jaws and/or the firing member. An application of higher firing forces to the firing beam may result in unwanted flexure in the firing beam as it traverses the articulation joint. Such additional flexure may cause the articulation joint to de-articulate—particularly when the surgical end effector is articulated at relatively high articulation angles. The surgical instrument 25010 employs a firing system 27000 that may address many if not all of such issues.

Figure 19:
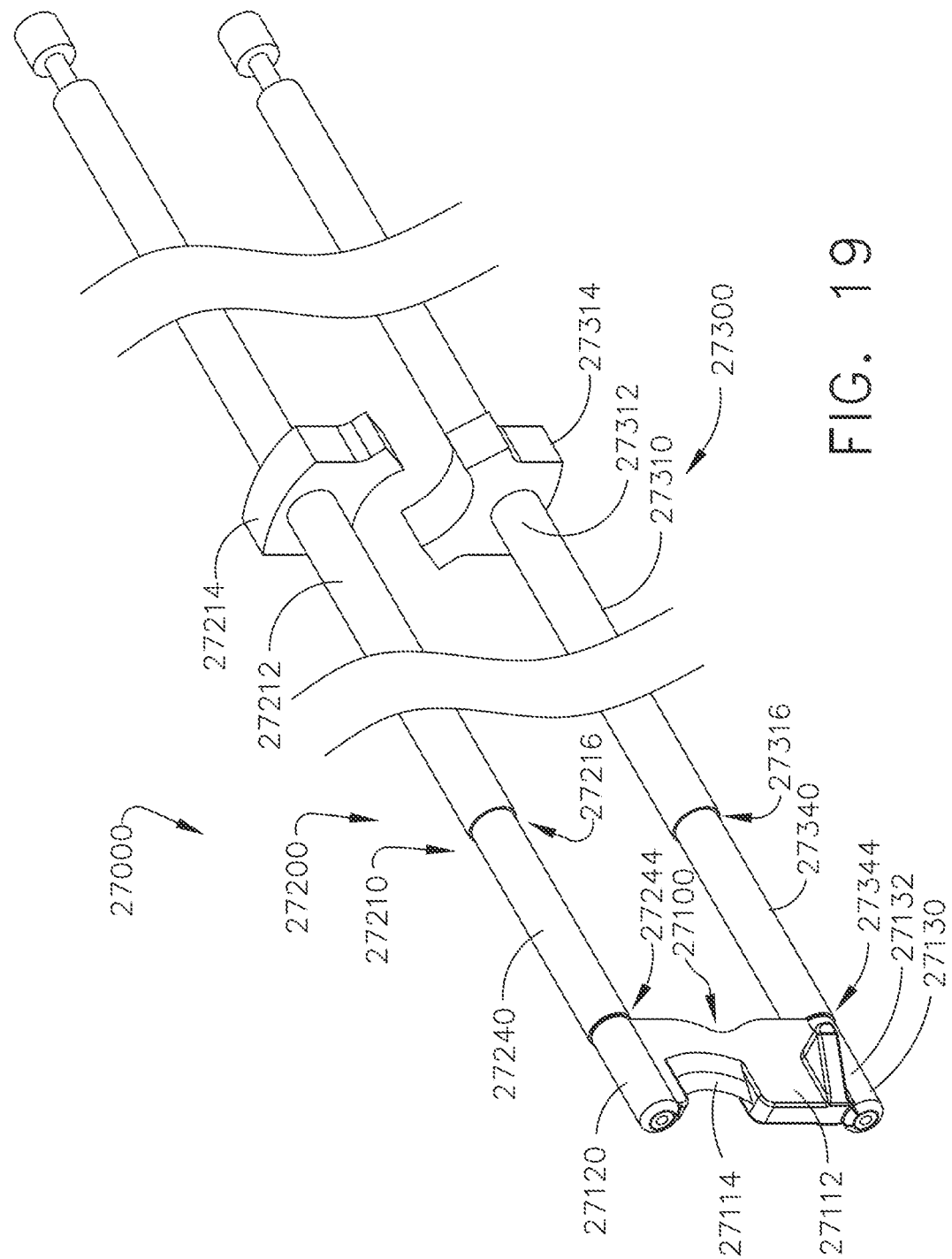
FIG. 19 is a perspective view of a portion of a firing system of the surgical instrument of FIG. 1.
Figure 20:
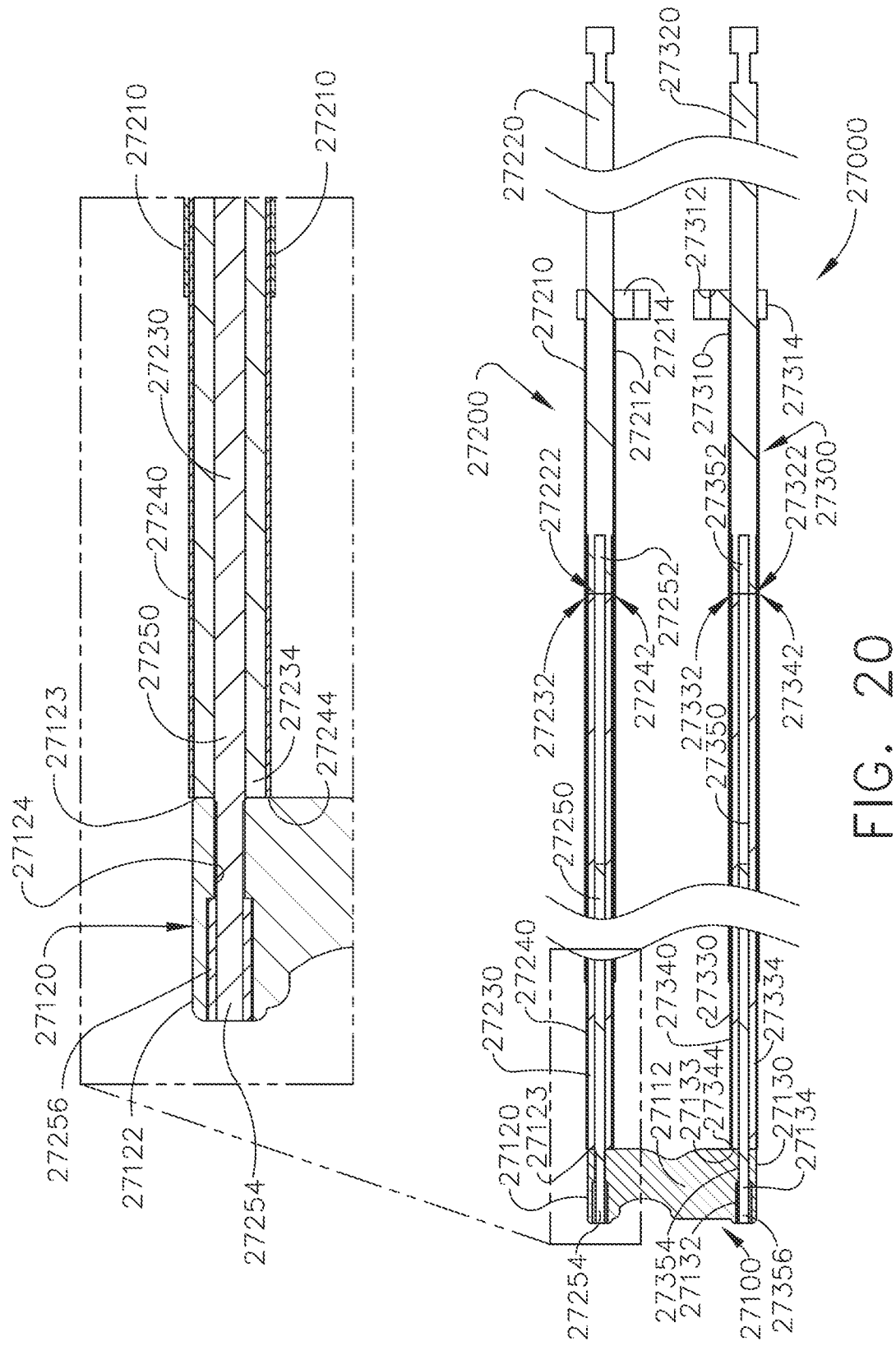
FIG. 20 is a partial cross-sectional view of the firing system of FIG. 19.
Figure 21:
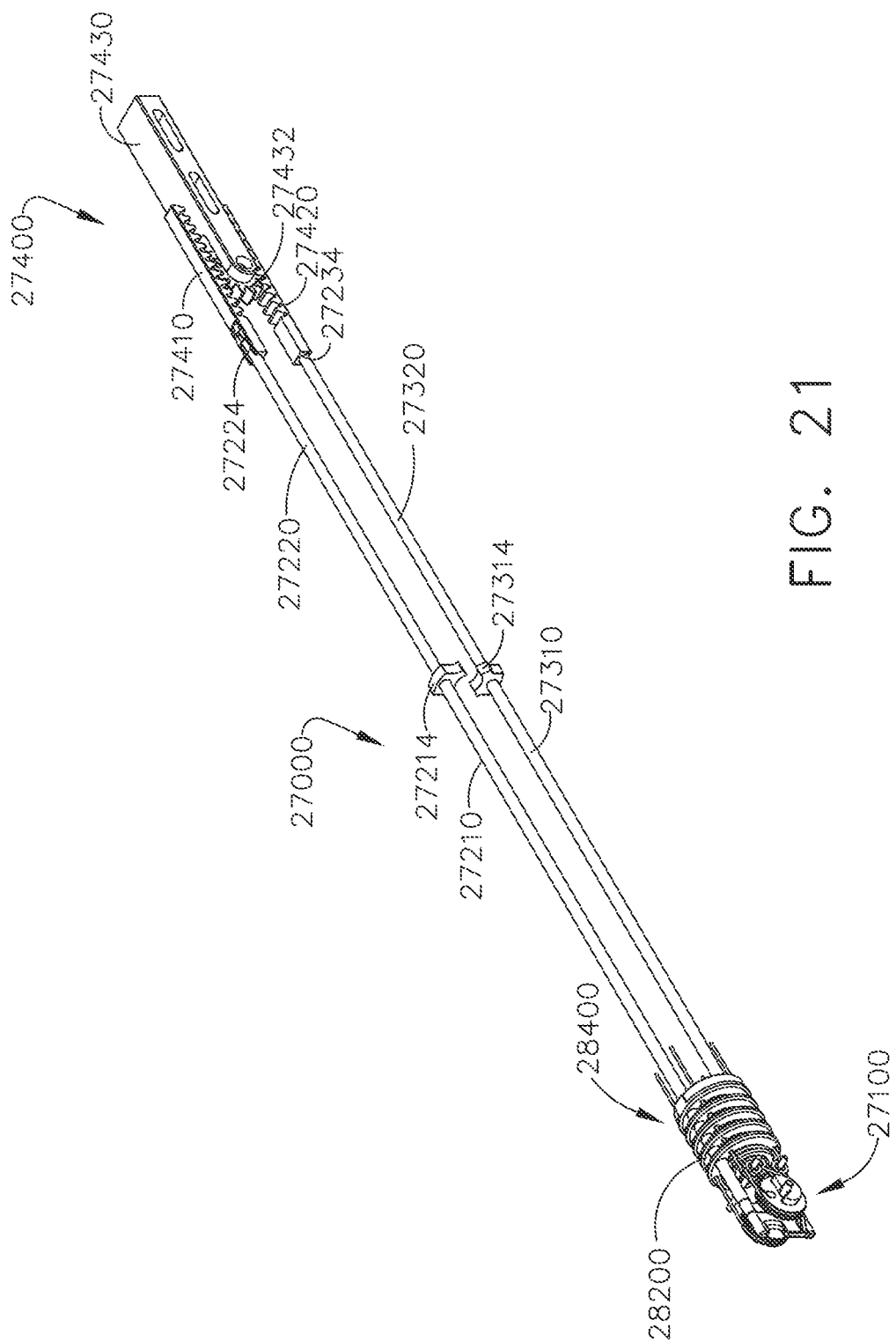
FIG. 21 is a perspective view of the firing system, articulation joint, and a closure system of the surgical instrument of FIG. 1.

Referring now to FIGS. 19 and 20, in at least one embodiment, the firing system 27000 comprises a firing member 27100 that includes a vertically-extending firing member body 27112 that comprises a top firing member feature 27120 and a bottom firing member feature 27130. A tissue cutting blade 27114 is attached to or formed in the vertically-extending firing member body 27112. In at least one arrangement, the top firing member feature 27120 comprises a top tubular body 27122 that has a top axial passage 27124 extending therethrough. See FIG. 20. The bottom firing member feature 27130 comprises a bottom tubular body 27132 that has a bottom axial passage 27134 extending therethrough. In at least one arrangement, the top firing member feature 27120 and the bottom firing member feature 27130 are integrally formed with the vertically-extending firing member body 27112. In at least one example, the anvil body 26212 comprises an axially extending anvil slot that has a cross-sectional shape that resembles a "keyhole" to accommodate passage of the top firing member feature 27120 in the various manners discussed herein. Similarly, the elongate channel 26110 comprises an axially extending channel slot that also has a keyhole cross-sectional shape for accommodating passage of the bottom firing member feature 27130 as described above.

In the illustrated arrangement, the firing system 27000 comprises an upper firing assembly 27200 that operably interfaces with the top firing member feature 27120. The upper firing assembly 27200 includes an upper flexible outer tube or conduit 27210 that has a proximal end 27212 that is fixed to an upper insert 27214 that is non-movably attached to the shaft spine assembly 28100. For example, the upper insert 27214 may be welded to the shaft spine assembly 28100 or otherwise be attached thereto by adhesive or other appropriate fastening means. The flexible outer tube or conduit 27210 extends through upper passages 28216 provided through the proximal attachment disc assembly 28240, the proximal-most annular disc member 28210P, the annular disc members 28210A, 28210B, 28210C and the anvil mounting bracket 26240. A distal end 27216 of the flexible outer tube or conduit 27210 may be affixed to the anvil mounting bracket 26240.

In the illustrated embodiment, the upper firing assembly 27200 further includes an upper push rod 27220 that is slidably supported in a corresponding axial passage in the shaft spine assembly 28100. The upper firing assembly 27200 further comprises an upper push coil 27230 that is supported in an inner flexible upper sleeve 27240 which extends through the upper flexible outer tube or conduit 27210. A proximal end 27232 of the upper push coil 27230 and a proximal end 27242 of the inner flexible upper sleeve 27240 abut a distal end 27222 of the upper push rod 27220. The upper push coil 27230 is hollow and may comprise a coil spring that is fabricated from Nitinol, titanium, stainless steel, etc. In other arrangements, the upper push coil 27230 comprises a laser cut "hypotube" that essentially comprises a hollow tubular member with offset laser cuts therein which enable the hypotube to flex and bend while being capable of transmitting axial forces or motions. The inner flexible upper sleeve 27240 may be fabricated from a polymer or similar material and prevent tissue, fluid, and/or debris from infiltrating into the upper push coil 27230 which may hamper its ability to flex and bend during articulation of the surgical end effector relative to the elongate shaft assembly.

As can be seen in FIG. 20, a distal end 27234 of the upper push coil 27230 as well as a distal end 27244 of the inner flexible upper sleeve 27240 abut a proximal end 27123 of the top tubular body 27122 or the top firing member feature 27120. Also in the illustrated arrangement, the upper firing assembly further comprises an upper push coil cable 27250 that extends through the hollow upper push coil 27230. The upper push coil cable 27250 comprises an upper cable proximal end 27252 that is secured to the distal end 27222 of the upper push rod 27220 and an upper cable distal end 27254 that is secured within the top axial passage 27124 in the top tubular body 27122 of the top firing member feature 27120 by an upper attachment lug 27256. The upper push coil cable 27250 is held in tension between the top firing member feature 27120 an the upper push rod 27220 which serves to retain the distal end 27234 of the upper push coil 27230 as well as a distal end 27244 of the inner flexible upper sleeve 27240 in abutting contact with the proximal end 27123 of the top tubular body 27122 of the top firing member feature 27120 and the proximal end 27232 of the upper push coil 27230 and a proximal end 27242 of the inner flexible upper sleeve 27240 in abutting contact with the distal end 27222 of the upper push rod 27220.

In the illustrated example, the firing system 27000 further comprises a lower firing assembly 27300 that operably interfaces with the bottom firing member feature 27130. The lower firing assembly 27300 includes a lower flexible outer tube or conduit 27310 that has a proximal end 27312 that is fixed to a lower insert 27314 that is non-movably attached to the shaft spine assembly 28100. For example, the lower insert 27314 may be welded to the shaft spine assembly 28100 or otherwise be attached thereto by adhesive or other appropriate fastening means. The lower flexible outer tube or conduit 27310 extends through lower passages 28218 provided in each of the proximal attachment disc assembly 28240, the proximal-most annular disc member 28210P, annular disc members 28210A, 28210B, 28210C and anvil mounting bracket 26240. A distal end 27316 of the flexible outer tube or conduit 27310 is affixed to the anvil mounting bracket 26240.

In the illustrated embodiment, the lower firing assembly 27300 further includes a lower push rod 27320 that is slidably supported in a corresponding axial passage in the shaft spine assembly 28100. The lower firing assembly 27300 further comprises a lower push coil 27330 that is supported in an inner flexible lower sleeve 27340 which extends through the lower flexible outer tube or conduit 27310. A proximal end 27332 of the lower push coil 27330 and a proximal end 27342 of the inner flexible lower sleeve 27340 abut a distal end 27322 of the lower push rod 27320. The lower push coil 27330 is hollow and may comprise a coil spring that is fabricated from Nitinol, titanium, stainless steel, etc. In other arrangements, the lower push coil 27330 comprises a laser cut hypotube that essentially comprises a hollow tubular member with offset laser cuts therein which enable the hypotube to flex and bend. The inner flexible lower sleeve 27340 may be fabricated from a polymer or similar material and prevent tissue, fluid, and/or debris from infiltrating into the lower push coil 27330 which may hamper its ability to flex during articulation.

As can be seen in FIG. 20, a distal end 27334 of the lower push coil 27330 as well as a distal end 27344 of the inner flexible lower sleeve 27340 abut a proximal end 27133 of the bottom tubular body 27132 of the bottom firing member feature 27130. Also in the illustrated arrangement, the lower firing assembly 27300 further comprises a lower push coil cable 27350 that extends through the hollow lower push coil 27330. The lower push coil cable 27350 comprises a lower cable proximal end 27352 that is secured to the distal end 27322 of the lower push rod 27320 and a lower cable distal end 27354 that is secured within the bottom axial passage 27134 in the bottom tubular body 27132 of the bottom firing member feature 27130 by a lower attachment lug 27356. The lower push coil cable 27350 is held in tension between the bottom firing member feature 27130 an the lower push rod 27320 which serves to retain the distal end 27334 of the lower push coil 27330 as well as a distal end 27344 of the inner flexible lower sleeve 27340 in abutting contact with the proximal end 27133 of the bottom tubular body 27132 of the bottom firing member feature 27130 and the proximal end 27332 of the lower push coil 27330 and a proximal end 27342 of the inner flexible lower sleeve 27340 in abutting contact with the distal end 27322 of the lower push rod 27320.

In the illustrated arrangement, the firing system 27000 further comprises a differential drive assembly 27400 that is configured to axially drive the upper firing assembly 27200 and the lower firing assembly 27300. Turning to FIGS.

Figure 22:
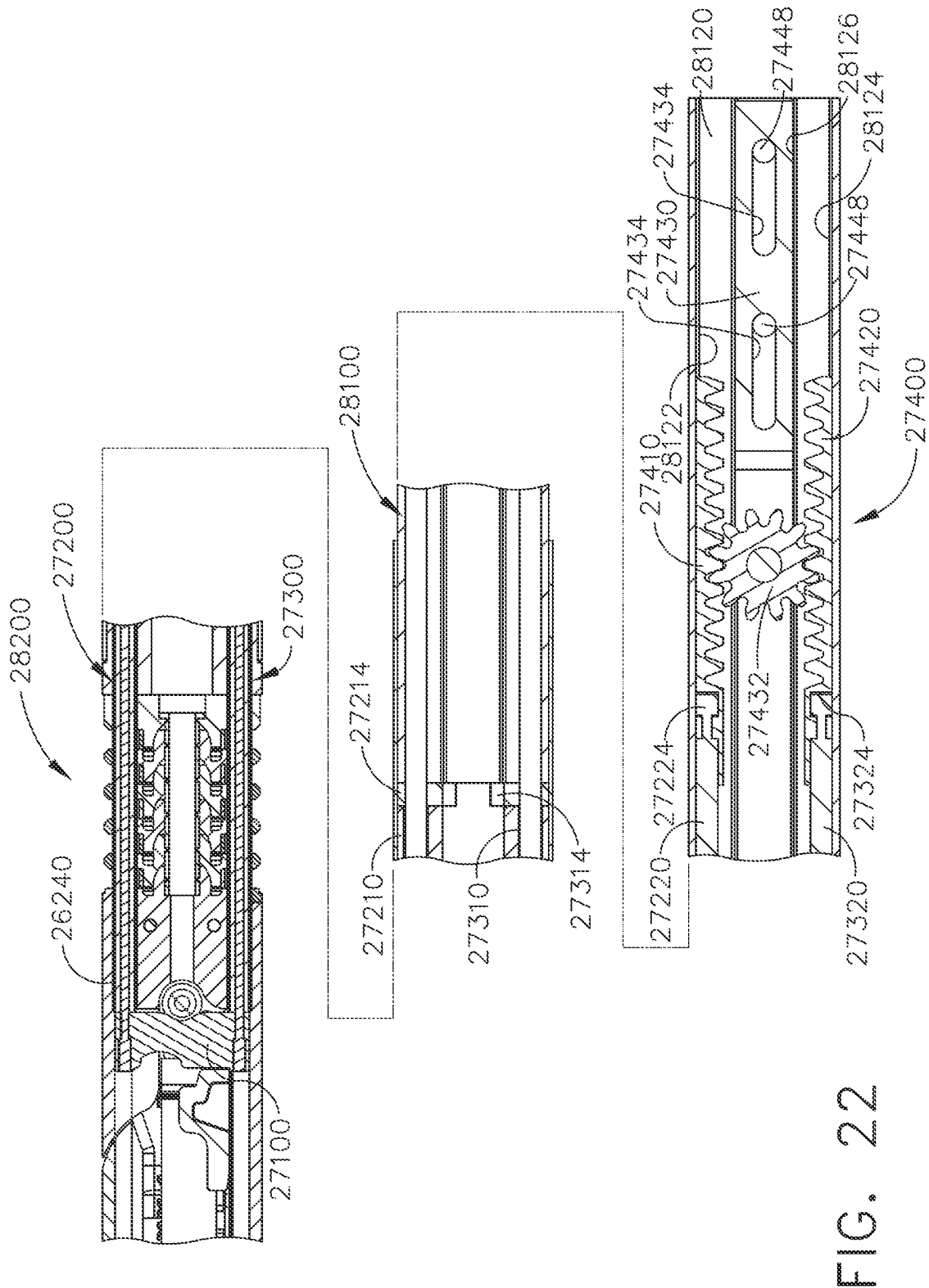
FIG. 22 is a partial cross sectional view of the surgical instrument of FIG. 1 with the surgical end effector thereof in an unarticulated position.
Figure 23:
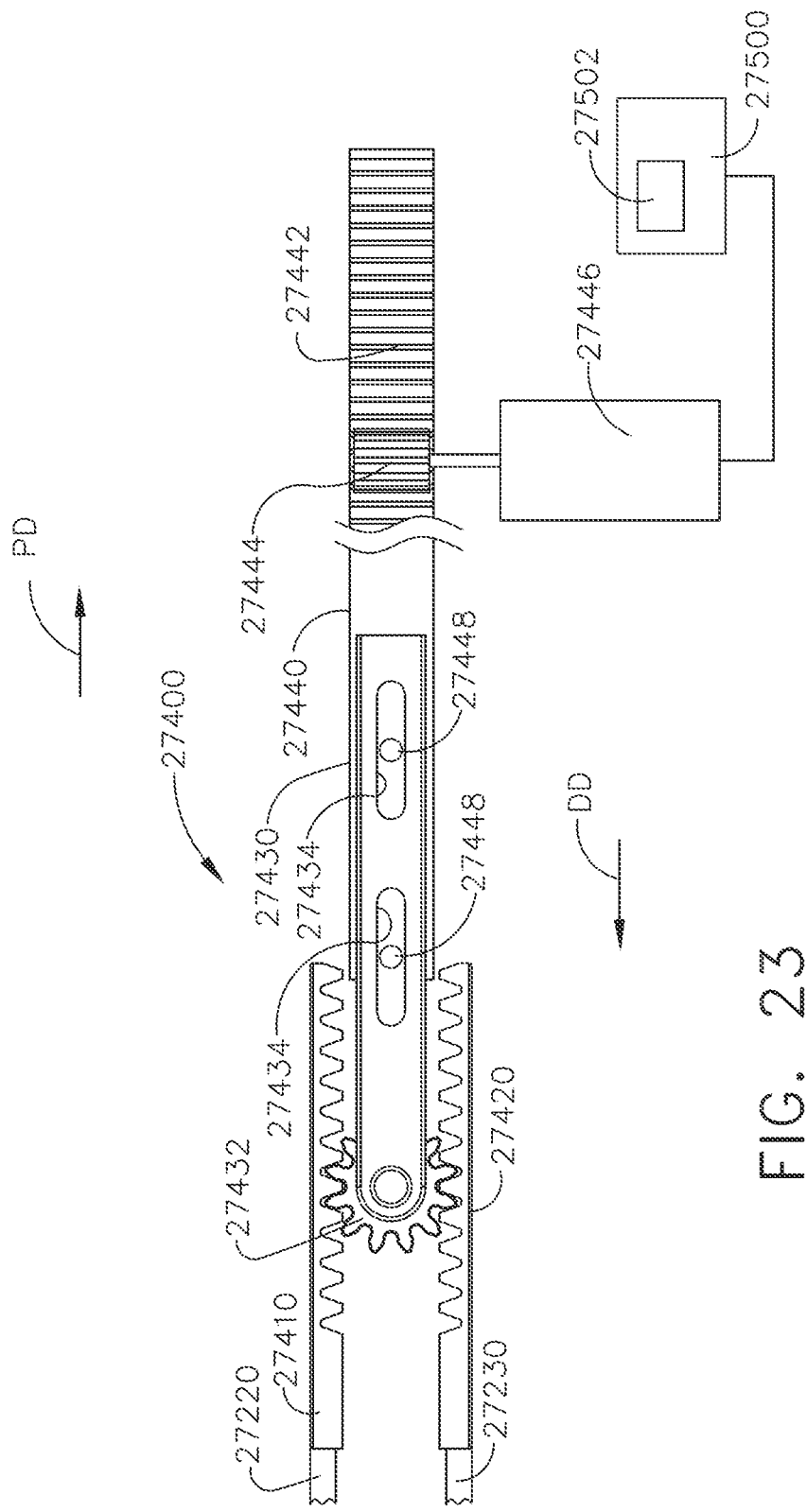
FIG. 23 is a partial view of a differential drive assembly embodiment of the firing system of the surgical instrument of FIG. 1.
Figure 26:
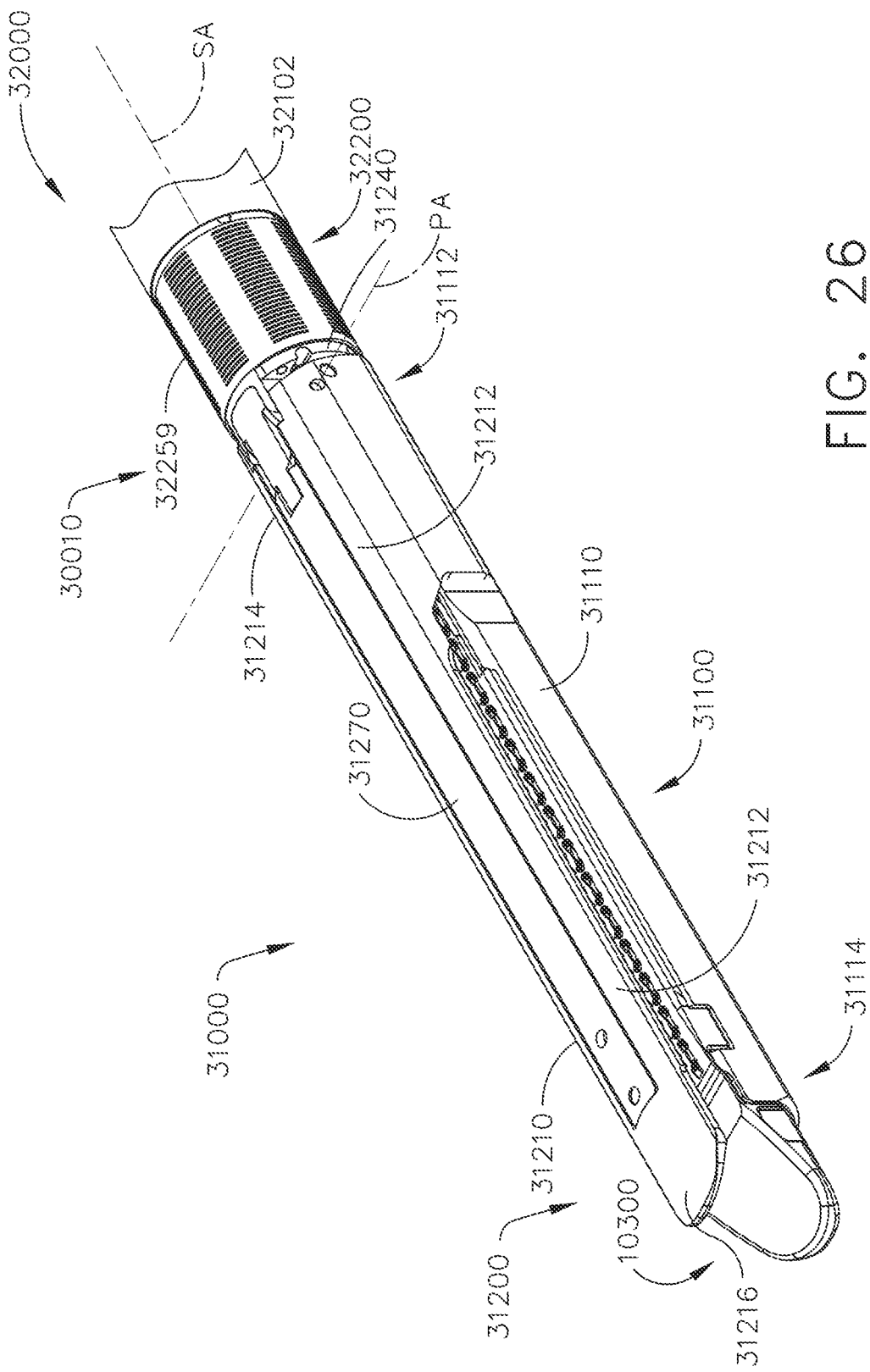
FIG. 26 is a perspective view of a surgical end effector of another surgical instrument in accordance with another general aspect of the present disclosure.
Figure 27:
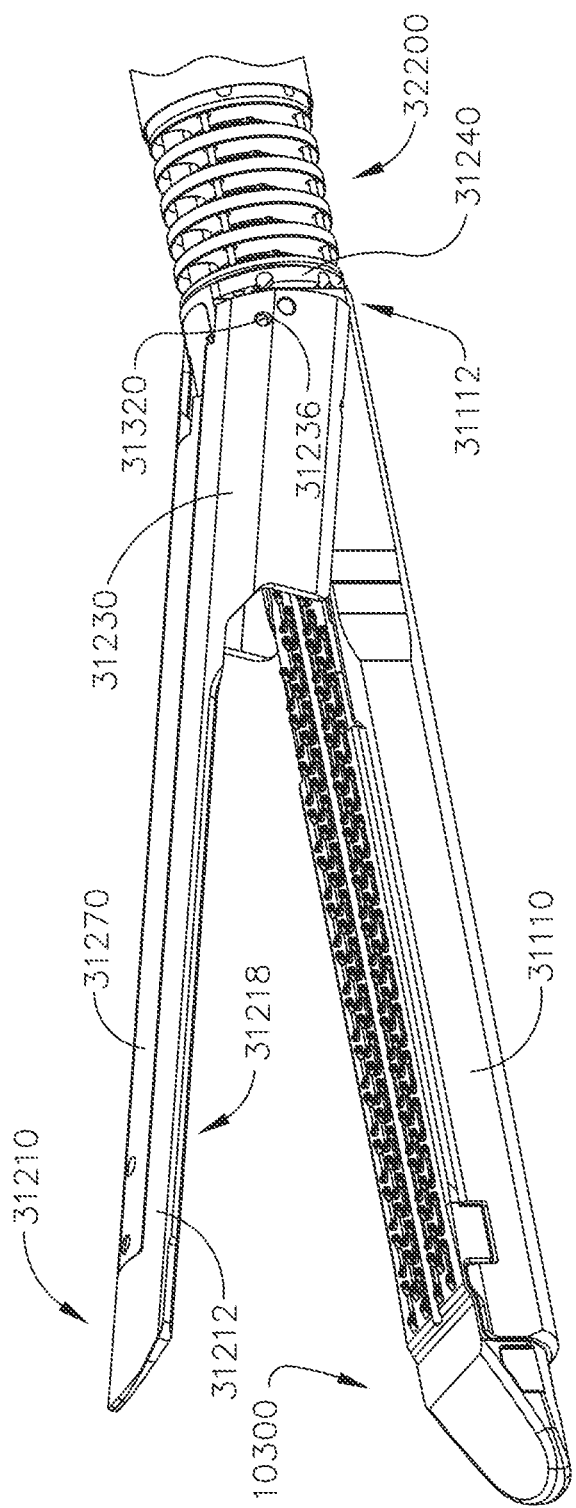
FIG. 27 is another perspective view of the surgical end effector of FIG. 26 with an anvil thereof in an open position.

21-25, in at least one arrangement, a proximal end 27224 of the upper push rod 27220 is coupled to a first or upper gear rack 27410 of the differential drive assembly 27400. As can be seen in FIG. 22, the first or upper gear rack 27410 is slidably supported in an upper proximal axial cavity 28122 in the proximal spine segment 28120. Similarly, a proximal end 27324 of the lower push rod 27320 is coupled to a second or lower gear rack 27420 that is supported for axial travel within a lower proximal axial cavity 28124 in the proximal spine segment 28120. The differential drive assembly 27400 further comprises an axially movable carrier member 27430 that is centrally disposed between the first or upper gear rack 27410 and the second or lower gear rack 27420 and is supported for axial travel within a proximal axial cavity 28126 in the proximal spine segment 28120. See FIG. 22.

Still referring to FIGS. 22-25, a pinion gear 27432 is pivotally pinned to the axially movable carrier member 27430 such that the pinion gear 27432 is meshing engagement with the first or upper gear rack 27410 and the second or lower gear rack 27420. The axially movable carrier member 27430 is driven axially within the proximal axial cavity 28126 in the proximal spine segment 28120 by a firing drive actuator 27440. See FIG. 23. In one arrangement, the firing drive actuator 27440 comprises a firing drive gear rack 27442 that drivingly interfaces with a drive gear 27444 that is driven by a firing motor 27446 that may be operably supported in or otherwise associated with the housing of the surgical instrument 25010. In one arrangement, the firing motor 27446 is controlled by a motor control system 27500 that may comprise a microprocessor-controlled control circuit 27502 that may be housed in an instrument housing 40002, associated with an instrument housing, and/or comprise a portion of a robotic system or other automated surgical system. In other arrangements, the firing drive actuator 27440 may be axially driven distally and proximally by a cylinder arrangement or other suitable actuator interfacing therewith.

As can be seen in FIGS. 22-25, the firing drive actuator 27440 may be attached to the axially movable carrier member 27430 by a pair of spaced coupler pins 27448 that are attached to the firing drive actuator 27440 and are received within corresponding axial slots 27434 in the axially movable carrier member 27430. Such arrangement permits some relative axial movement between the firing drive actuator 27440 and the axially movable carrier member 27430. For example, when the firing drive actuator 27440 is driven distally in the distal direction DD, the axially movable carrier member 27430 will not move distally until the coupler pins 27448 reach the distal ends of their corresponding axial slots 27434 at which point the axially movable carrier member 27430 will move distally. Likewise, the when the firing drive actuator 27440 is driven in the proximal direction PD, the axially movable carrier member 27430 will not move proximally until the coupler pins 27448 reach the proximal ends of their corresponding axial slots 27434 at which point the axially movable carrier member 27430 will move proximally.

Surgical stapling devices need to apply a high force on the firing member over a long displacement to form the staples and cut tissue. Transmitting that force through an articulated joint is especially challenging because it is difficult to redirect the forces in the desired direction and withstand the loads applied to it. The differential drive assembly 27400 described herein addresses and solves many, if not all, of such challenges by employing two flexible outer tubes or conduits 27210, 27310 to constrain the paths of the flexible push coils 27230, 27330, respectively. As described herein, the upper flexible outer tube or conduit 27210 surrounds a portion of the upper push coil 27230 and the upper flexible outer tube or conduit 27310 surrounds a portion of the lower push coil 27330. Each of the outer tubes or conduits 27210, 27310 can bend but they also can resolve an axial tensile load. The ability to bend allows for the firing member force to be redirected through the articulated joint, and the ability to resolve tension allows for it to change the direction in which the push coil goes. When the push coil 27230, 27330 is put in compression, the flexible outer tube or conduit 27210, 27310 is put in tension. The outer tubes or conduits 27210, 27310 prevent the push coils 27230, 27330 from buckling. The outer tubes 27210, 27310 are terminated in a manner to resolve the tensile loads.

As described above, the distal end 27216 of the flexible outer tube or conduit 27210 and the distal end 27316 of the flexible outer tube or conduit 27310 are both affixed to the anvil mounting bracket 26240. The proximal end 27212 of the flexible outer tube or conduit 27210 and the proximal end 27312 of the flexible outer tube or conduit 27310 are both affixed to the shaft spine assembly 28100. The pinion gear 27432 is in meshing engagement with the first or upper gear rack 27410 and the second or lower gear rack 27420 such that when one of the racks 27410, 27420 moves in one axial direction, the other rack 27410, 27420 axially moves in an opposite direction. As can be seen in FIGS. 24 and 25, during articulation, the pinion gear 27432 rotates so the flexible outer tubes or conduits 27210, 27310 can move to account for the change in path length. However, when the firing drive actuator 27440 is driven in the distal direction DD, the axially movable carrier member 27430 is actuated to push the push coils 27230, 27330 distally through the outer tubes or conduits 27210, 27310 to fire (i.e., drive the firing member 27100 distally) the tensile loads in the two flexible outer tubes or conduits 27210, 27310 react against one another without any motion of the pinion gear 27432.

In accordance with one general aspect, the upper passages 28216 form an upper pathway 28221 (FIG. 3) through the articulation joint 28200. Similarly, the lower passages 28218 form a lower pathway 28223 through the articulation joint 28200. When the surgical end effector 26000 is in an unarticulated position (i.e., the surgical end effector is axially aligned with the elongate shaft assembly 28000 on the shaft axis SA—FIGS. 1, 3, 4), the upper pathway 28221 and the lower pathway 28223 are parallel to each other. See FIG. 3. When the surgical end effector 26000 is in an articulated position relative to the elongate shaft assembly 28000, the upper pathway 28221 and the lower pathway 28223 are concentric to each other. See FIG. 2.

When the surgical end effector 26000 is in the unarticulated position, the firing system 27000 may be actuated to drive the firing member 27100 from a starting position within the proximal end 26112 of the elongate channel 26100 to an ending position within the distal end 26114 of the elongate channel 26110. When the surgical end effector 26000 is in the unarticulated position, and the firing system 27000 is actuated, the differential drive assembly 27400 drives the upper firing assembly 27200 and the lower firing assembly 27300 equal axial distances in a same axial direction (i.e., the distal direction DD) to apply an upper axial drive motion and a lower axial drive motion to the firing member 27100. The upper axial drive motion and the lower axial drive motion are substantially equal in magnitude which serves to distally advance the firing member 27100 through the surgical end effector 26000 without binding which might otherwise occur should the upper axial drive motion and the lower axial drive motions be different in magnitude. Similarly, when the surgical end effector 26000 is in an articulated position relative to the elongate shaft assembly 28000, the firing system 27000 may be actuated to drive the firing member 27100 from the starting position to the ending position. In such instances, the differential drive assembly 27400 is configured to permit the upper firing assembly 27200 and the lower firing assembly 27300 to move in substantially equal distances in opposite axial directions to accommodate the articulated position. The differential drive assembly 27400 may then apply an upper axial drive motion and a lower axial drive motion that are equal to each other to the firing member 27100. For example, depending upon the articulated position of the surgical end effector 26000 relative to the elongate shaft assembly 28000, the upper firing assembly 27200, upon articulation of the surgical end effector 26000, may be moved proximally a first distance and the lower firing assembly 27300 may be positioned relative thereto distally a second distance that is substantially equal to the first distance by the pinion gear 27432. Thereafter, distal actuation of the firing drive actuator 27440 will cause the upper firing assembly 27200 and the lower firing assembly 27300 to apply an upper axial drive motion and a lower axial drive motion that are equal to each other to the firing member 27100. As used herein, when the carrier is moved distally, the carrier may apply "axial control motions" to the upper firing assembly 27200 and the lower firing assembly 27300. Thus, when the surgical end effector 26000 is in an unarticulated configuration, the carrier may apply equal amounts of axial control motions to the upper firing member 27200 and the lower firing member 27300 in the same axial direction (distal direction DD) and when the surgical end effector 26000 is in an articulated configuration, the carrier may apply "other equal amounts" of axial control motions to the upper firing member 27200 and the lower firing member 27300 in the same axial direction (distal direction DD) to move the firing member 27100 from the starting position to the ending position.

FIGS. 26-30 illustrate another form of surgical instrument 30010 that, in many aspects, is very similar and identical to surgical instrument 25010 described above. The detailed descriptions of the construction and operation of those components and features of surgical instrument 30010 that are identical or very similar in construction and operation to those components of surgical instrument 25010 described in detail above will not be repeated again herein. In various embodiments, the surgical instrument 30010 may comprise a handheld device. In other embodiments, the surgical instrument 30010 may comprise an automated system sometimes referred to as a "robotically-controlled" system, for example. In various forms, the surgical instrument 30010 comprises a surgical end effector 31000 that is operably coupled to an elongate shaft assembly 32000. The elongate shaft assembly 32000 may be operably attached to a housing. In one embodiment, the housing may comprise a handle that is configured to be grasped, manipulated, and actuated by the clinician. In other embodiments, the housing may comprise a portion of a robotically-controlled system that houses or otherwise operably supports at least one drive system that is configured to generate and apply at least one control motion which could be used to actuate the surgical end effectors disclosed herein and their respective equivalents. In addition, various components may be "housed" or contained in the housing or various components may be "associated with" a housing. In such instances, the components may not be contained with the housing or supported directly by the housing. For example, the surgical instruments disclosed herein may be employed with various robotic systems, instruments, components and methods disclosed in U.S. Pat. No. 9,072,535, entitled SURGICAL STAPLING INSTRUMENTS WITH ROTATABLE STAPLE DEPLOYMENT ARRANGEMENTS, which is incorporated by reference herein in its entirety.

In one form, the surgical end effector 31000 comprises a first jaw 31100 and a second jaw 31200. In the illustrated arrangement, the first jaw 31100 comprises an elongate channel 31110 that comprises a proximal end 31112 and a distal end 31114 and is configured to operably support a surgical staple cartridge 10300 therein. The second jaw 31200 comprises an anvil 31210 that comprises an elongate anvil body 31212 that has a proximal end 31214 and a distal end 31216. The anvil body 31212 comprises a staple-forming underside 31218 that faces or "confronts" the first jaw 31100 and may include a series of staple-forming pockets (not shown) that correspond to each of the staples or fasteners in the surgical staple cartridge 10300.

In at least one arrangement, an anvil mounting bracket 31240 that is attached to the proximal end 31112 of the elongate channel 31110. See FIGS. 27-30. The anvil mounting bracket 31240 is attached to the proximal end 31112 of the elongate channel 31110 by a spring pin 31242. See FIG. 30. In other arrangements, the anvil mounting bracket 31240 may be attached to the proximal end 31112 of the elongate channel 31110 by welding, adhesive, snap features, etc. The anvil mounting bracket 31240 may be similar to anvil mounting bracket 26240 described above except for the differences discussed herein.

Figure 30:
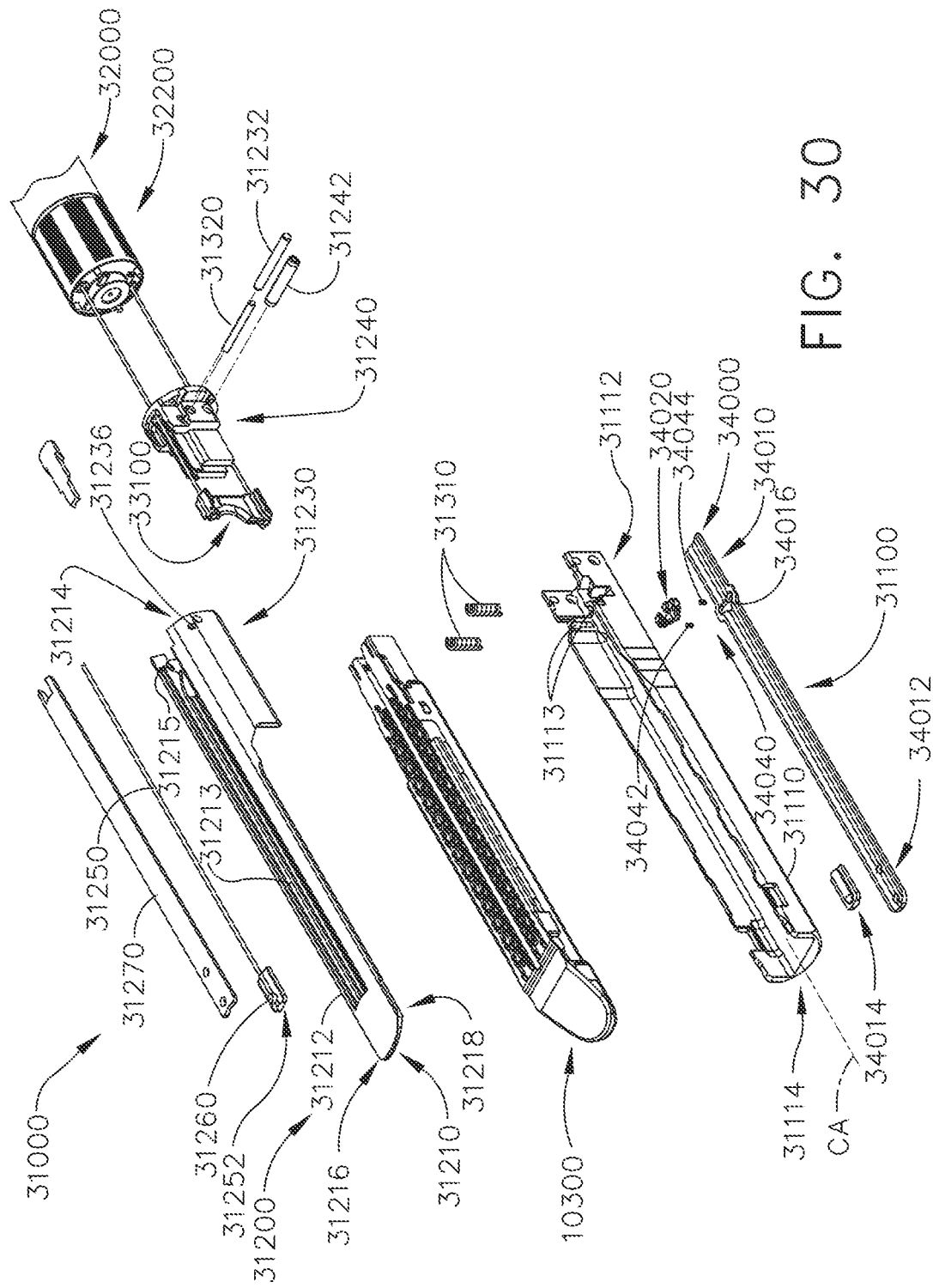
FIG. 30 is an exploded perspective view of the surgical end effector and surgical instrument of FIG. 26.

As can be seen in FIG. 30, the proximal end 31214 of the anvil body 31212 comprises an anvil mounting portion 31230 that is configured to be pivotably pinned to the anvil mounting bracket 31240 by a pin 31232. Such arrangement facilitates pivotal travel of the anvil 31210 relative to the elongate channel 31110 about a fixed pivot axis PA. See FIGS. 26 and 28. As stated above, as used in this context, the term "fixed" means that the pivot axis PA is non-translating or non-moving relative to the elongate channel 31110.

In the illustrated arrangement, the elongate shaft assembly 32000 defines a shaft axis SA and comprises a shaft spine assembly 32100 that is received in a hollow outer shaft tube 32102. See FIG. 31. The shaft spine assembly 32100 may operably interface with a housing of the control portion (e.g., handheld unit, robotic tool driver, etc.) of the surgical instrument 31010. In at least one arrangement, the shaft spine assembly 32100 is in many aspects very similar to or essentially identical to the shaft spine assembly 28100 described above. The shaft spine assembly 32100 will not be described in detail herein beyond what is necessary to understand the operation of the surgical instrument 31010. The elongate shaft assembly 32000 further comprises an articulation joint 32200 that may be attached to the shaft spine assembly 32100 in the various manners described above. The articulation joint 32200 is in many aspects very similar to or essentially identical to the articulation joint 28200 described above. The articulation joint 28200 will not be described in detail herein beyond what is necessary to understand the operation of the surgical instrument 31010. The articulation joint 32200 facilitates selective articulation of the surgical end effector 31000 relative to the elongate shaft assembly 32000 in multiple articulation planes in the various manners disclosed herein.

Figure 31:
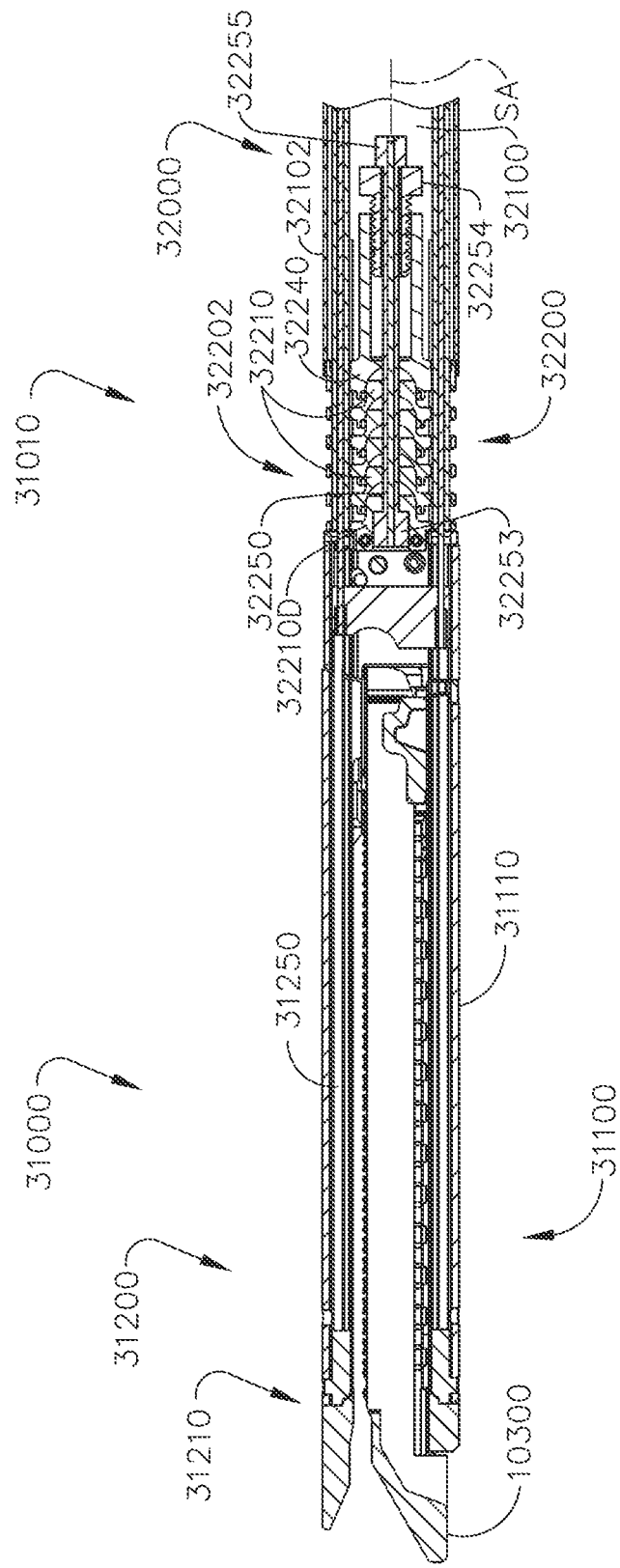
FIG. 31 is a cross-sectional side elevational view of the surgical end effector and surgical instrument of FIG. 26.
Figure 32:
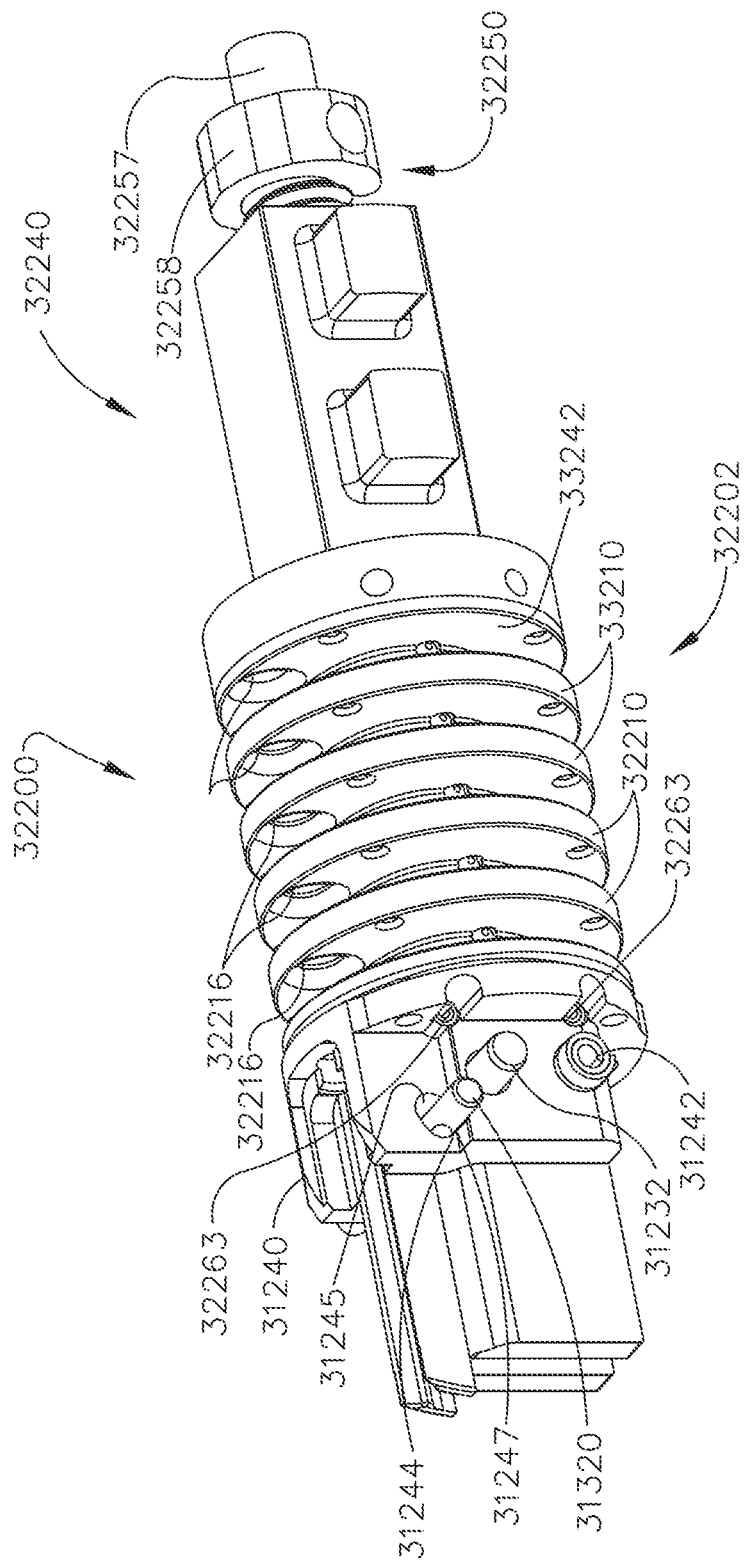
FIG. 32 is a perspective view of a portion of an articulation joint of the surgical instrument of FIG. 26.
Figure 33:
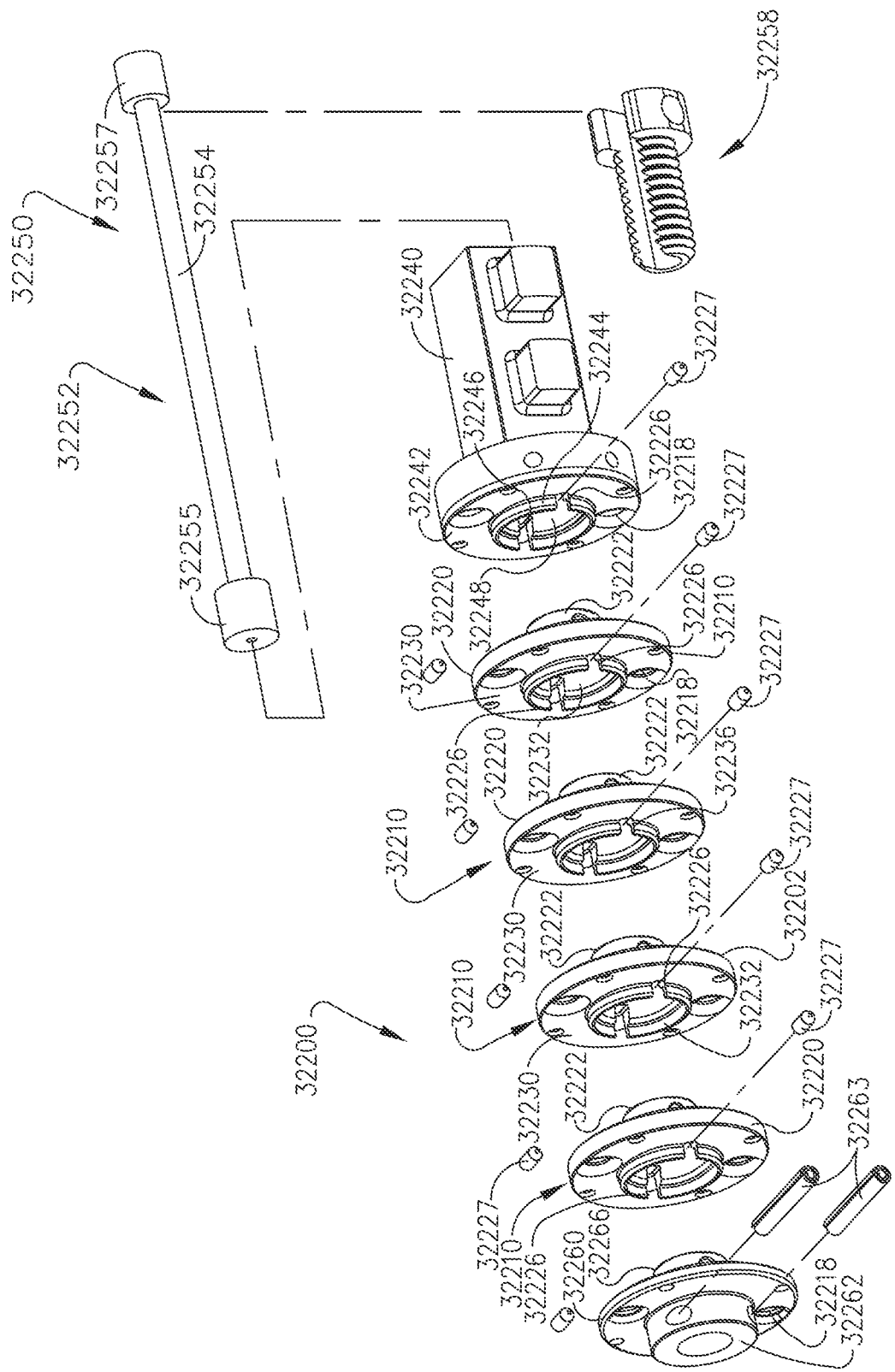
FIG. 33 is an exploded perspective view of the articulation joint of FIG. 32.
Figure 34:
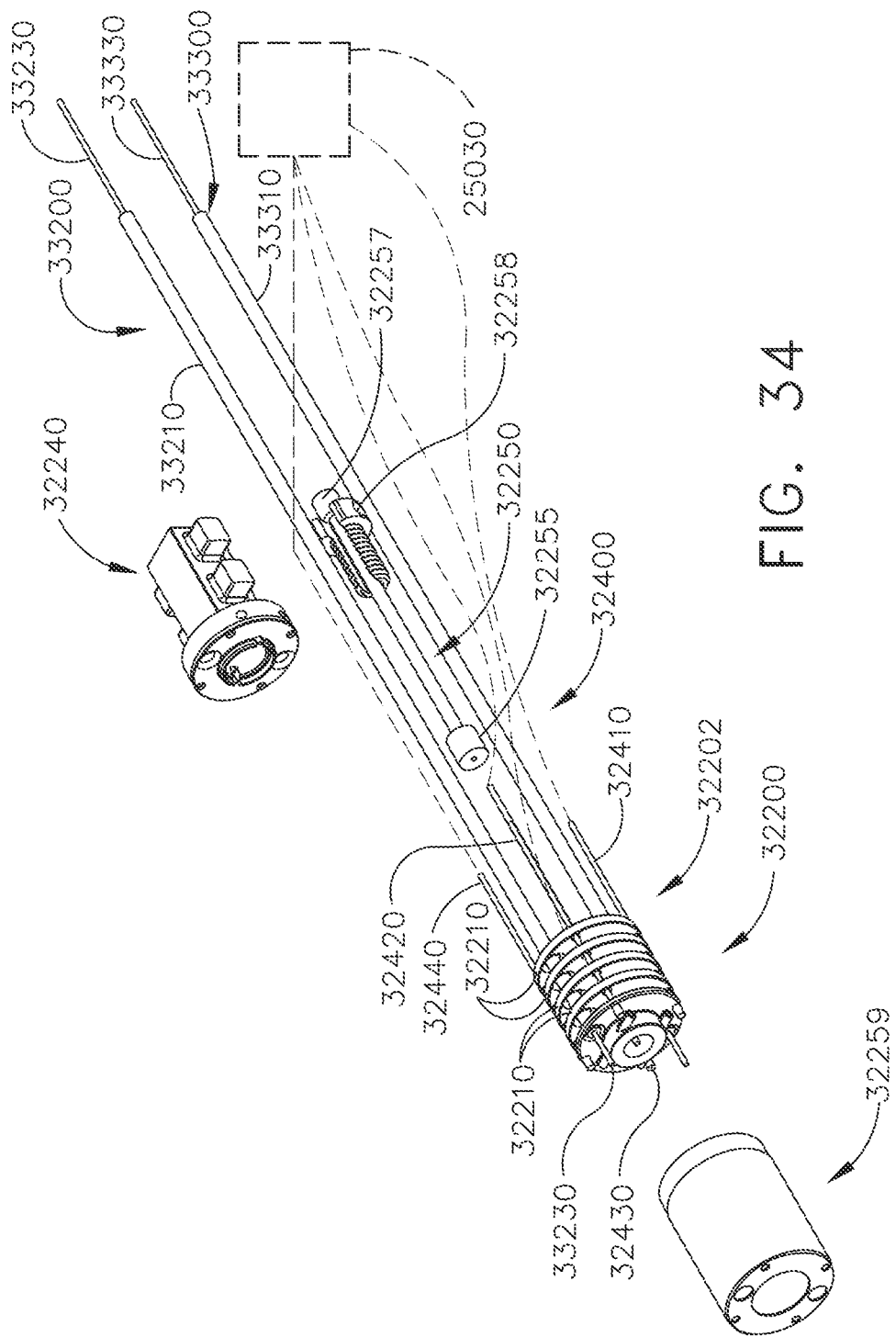
FIG. 34 is another exploded perspective view of the articulation joint of FIG. 32.

Turning now to FIGS. 31-35, the articulation joint 32200 comprises a series 32202 of movably interfacing annular disc members 32210. As can be seen in FIG. 33, each annular disc member 32210 comprises a "first" or proximal face 32220 that comprises a centrally-disposed spherical feature or protrusion 32222. Each annular disc member 32210 further comprises a second or distal face 32230 that comprises an annular hub portion 32232 that defines a concave socket 32234 therein. See FIG. 35. Each annular disc member 32210 further has a central shaft passage 32236 therethrough. As can be seen in FIG. 31, the articulation joint 32200 further comprises a proximal attachment disc assembly 32240 that is configured to be supported in a distal end of the shaft spine assembly 32100. The proximal attachment disc assembly 32240 comprises a distal face 32242 that includes an annular hub portion 32244 that defines a concave socket 32246 therein. The proximal attachment disc assembly 32240 further has a central shaft passage 32248 therethrough.

The articulation joint 32200 operably interfaces with and is coupled to the anvil mounting bracket 31240. See FIG. 32. In at least one arrangement for example, the anvil mounting bracket 31240 comprises a cavity 31243 configured to receive therein a distal attachment hub 32262 that is formed on a distal attachment disc 32260. See FIG. 36. The distal attachment hub 32262 is secured to the anvil mounting bracket 31240 by a pair of spring pins 32263. The distal attachment disc 32260 further comprises a "first" or proximal face 32264 that comprises a centrally-disposed spherical feature or protrusion 32266 that is configured to be rotatably received in the concave socket 32234 in the annular hub portion 32232 of the adjacent annular disc member 32210.

Figure 35:
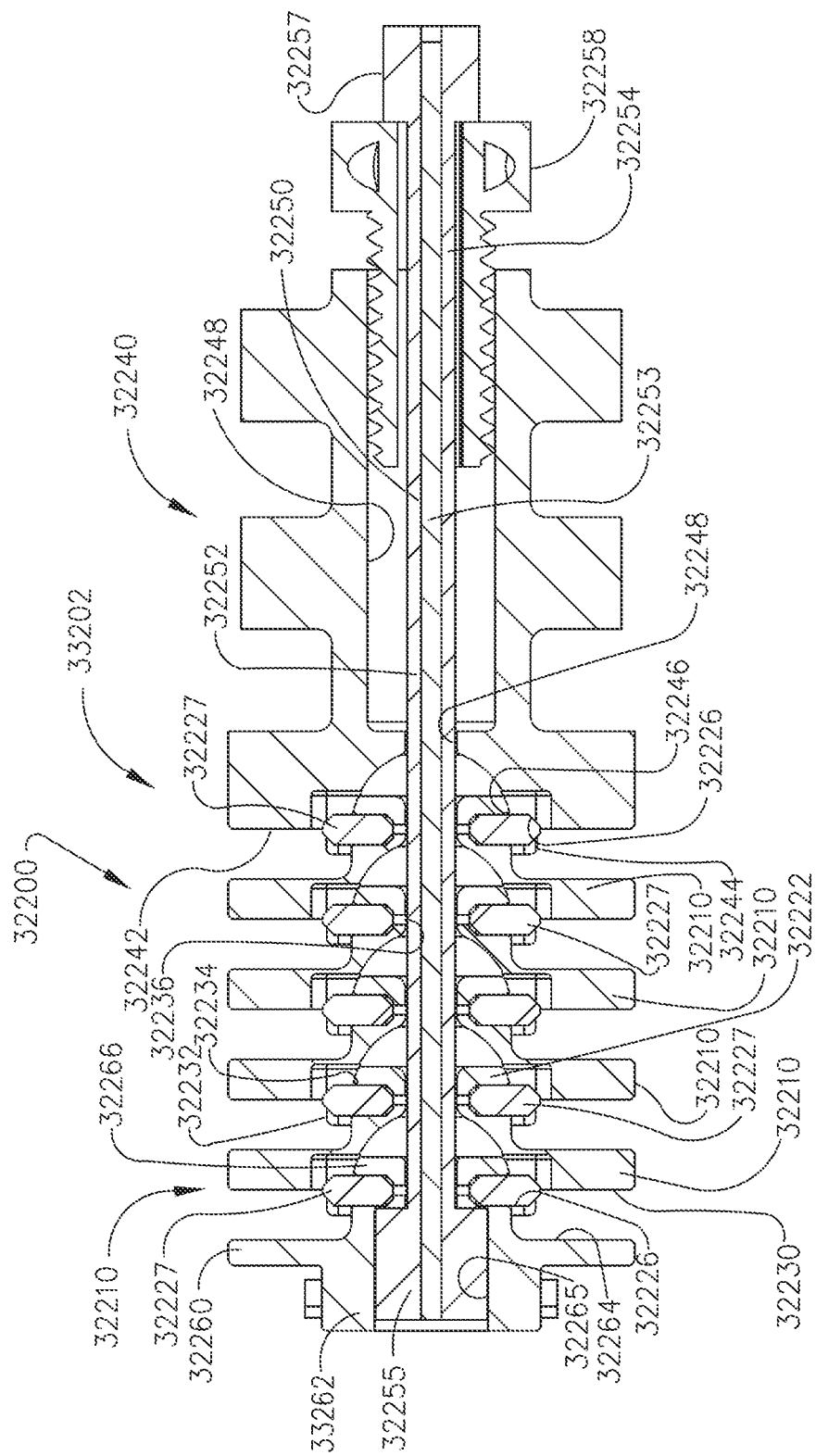
FIG. 35 is a cross-sectional view of the articulation joint of FIG. 32.

As can be seen in FIG. 35, in at least one arrangement, the articulation joint 32200 includes a flexible tensioner assembly 32250 for retaining the annular disc members 32210 in "floating" or movable engagement with each other and comprises a central tensioner 32252 that extends through the series 32202 of annular disc members 32210. In one arrangement, the central tensioner 32252 comprises a central rod member 32253 that extends through a tensioner body portion 32254. In one arrangement, the central rod member 32253 may comprise a flexible NiTi rod that is configured to prevent buckling. The tensioner body portion 32254 may comprise an elastomeric material and include a distal lug 32255 that is configured to be received in a lug cavity 32265 in the distal attachment disc 32260. The tensioner body portion 32254 may further comprise a proximal lug 32257 that is configured to engage a threaded adjustment member 32258. The threaded adjustment member 32258 is configured for threaded engagement with the proximal attachment disc assembly 32240. Rotation of the threaded adjustment member 32258 in a first rotary direction will cause the threaded adjustment member 32258 to move in a proximal direction to increase the amount of compression applied to the series 32202 of the annular disc members 32210 and rotation of the threaded adjustment member 32258 in an opposite direction will reduce the amount of compression that is applied to the series 32202 of annular disc members 32210.

In at least one arrangement, to limit pivotal travel of the annular disc members 32210 to a range of relative pivotal travel and prevent complete relative rotation of the annular disc members 32210 relative to each other, the centrally-disposed spherical feature or protrusion 32222 of each of the annular disc member 32210, as well as the centrally-disposed spherical feature or protrusion 32266 of the distal attachment disc 32260 include a pair of diametrically opposed pins 32227 that are pressed into or otherwise attached thereto. Each pin 32227 is configured to be movably received in corresponding open-ended slot 32226 in each annular hub portion 32232.

In at least one arrangement, the articulation joint 32200 also comprises a flexible, elastomeric joint cover assembly 32259 that is configured to prevent infiltration of fluids and debris into the articulation joint 32200. See FIG. 26. In one example, the articulation joint 32200 may be operably controlled by an articulation system 32400 that is similar to or identical to the articulation system 28400 described above.

Returning to FIG. 34, in the illustrated example, the articulation joint 32200 may be operably controlled by an articulation system 32400 that comprises four cable assemblies 32410, 32420, 32430, and 32440 that extend through the elongate shaft assembly 32000. The articulation system 32400 may be very similar to the articulation system 28400 described above except for the noted differences. In this embodiment, the cable assemblies 32410, 32420, 32430, 32440 are attached to the anvil mounting bracket 31240. The cable assemblies 32410, 32420, 32430, 32440 may operably interface with a portion of a cable control system 25030 that is supported within or is otherwise associated with a housing of the surgical instrument 30010. As described above, one form of a cable control system 25030 may comprise a plurality of cable support members/capstans, pulleys, etc. that are controlled by one or more corresponding motors that are controlled by a control circuit portion of the surgical instrument 30010. In various embodiments, the cable control system 25030 is configured to manage the tensioning (pulling) and paying out of cables at precise times during the articulation process.

Figure 37:
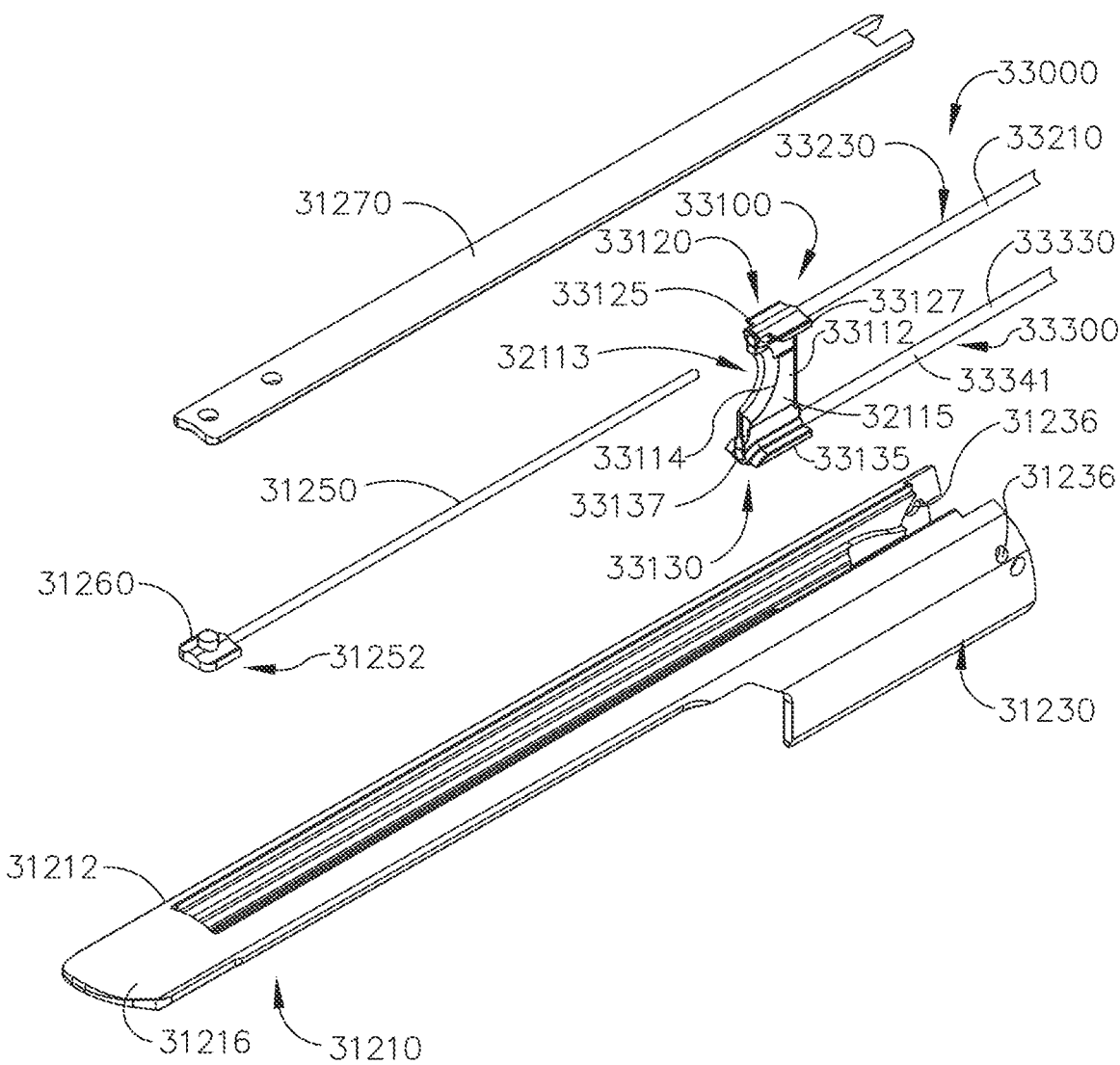
FIG. 37 is an exploded perspective view of an anvil arrangement of the surgical end effector of FIG. 26.
Figure 38:
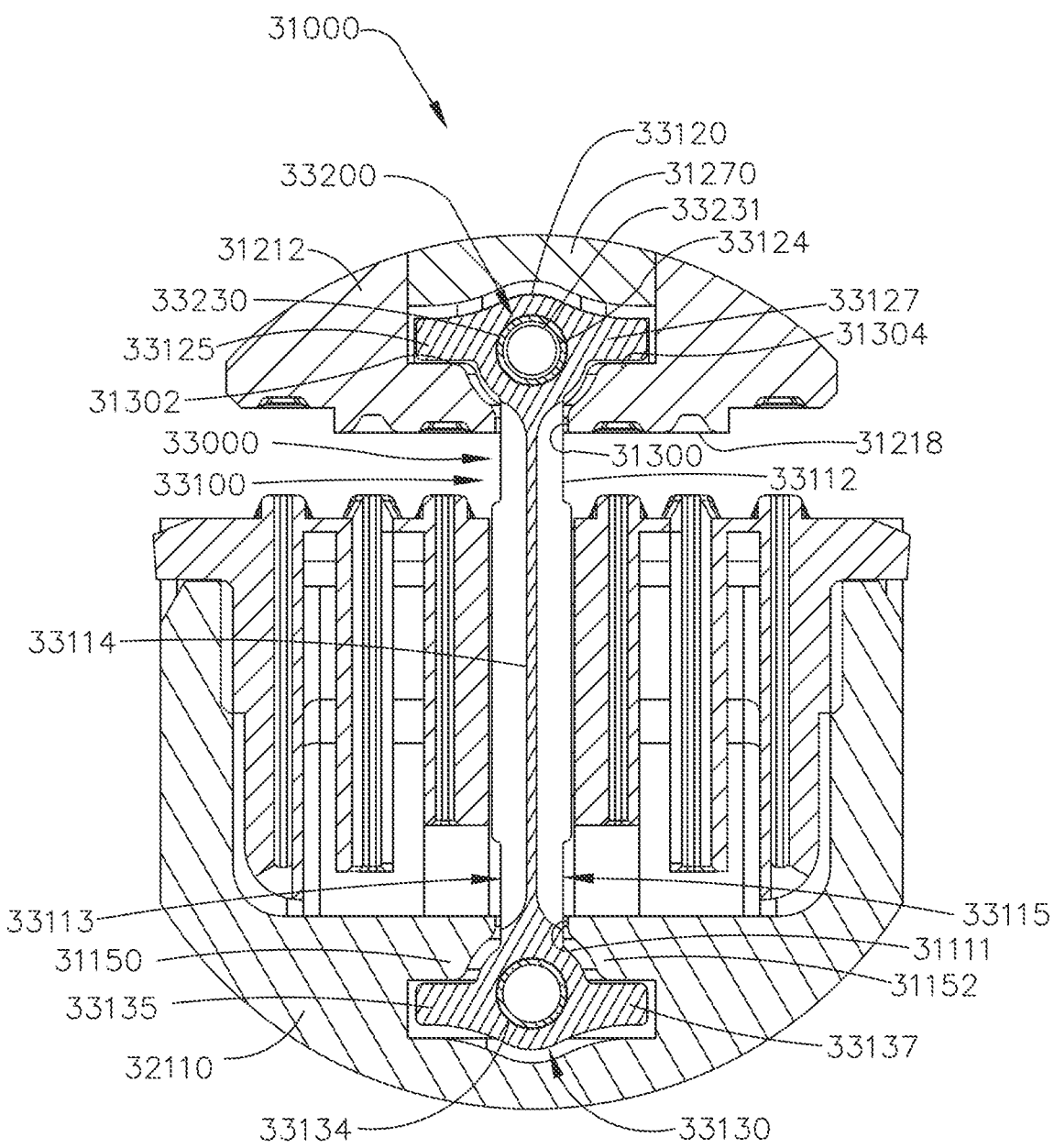
FIG. 38 is a cross-sectional end view of the surgical end effector of FIG. 26 with the anvil thereof in a closed position.

In at least one example, the surgical instrument 30010 further comprises a firing system 33000 that is in most if not all aspects very similar or identical to firing system 27000 described in detail above. As can be seen in FIGS. 37 and 38, the firing system 33000 comprises a firing member 33100 that includes a vertically-extending firing member body 33112 that comprises a top firing member feature 33120 and a bottom firing member feature 33130. A tissue cutting blade or tissue cutting surface 33114 is attached to or formed in the vertically-extending firing member body 33112. In at least one arrangement, the top firing member feature 33120 has a top axial passage 33124 extending therethrough and the bottom firing member feature 33130 has a bottom axial passage 33134 extending therethrough. In at least one arrangement, the top firing member feature 33120 and the bottom firing member feature 33130 are integrally formed with the vertically-extending firing member body 33112.

In at least one embodiment, anvil body 31212 comprises a centrally-disposed axially extending anvil slot 31300 that is configured to permit the firing member body 33112 to pass therethrough during firing and retraction strokes. Similarly, the elongate channel 32110 comprises an axially extending channel slot 31111 that is configured to permit the firing member body 33112 to pass therethrough. See FIG. 38. In one arrangement, the firing member body 33112 comprises a right or "first" lateral side 33113 and a left or "second" lateral side 33115. The top firing member feature 33120 further comprises a right or "first" top tab 33125 that protrudes laterally from the first lateral side 32113 and a left or "second" top tab 33127 that protrudes laterally from the second lateral side 32115. The first top tab 33125 and the second top tab 33127 are configured to engage corresponding axially extending ledges 31302, 31304, respectively that are formed on each side of the anvil slot 31300. See FIG. 38. Similarly, the bottom firing member feature 33130 further comprises right or "first" bottom tab 33135 that protrudes laterally from the first lateral side 33113 and a left or "second" bottom tab 33137 that protrudes laterally from the second lateral side 33115. The first bottom tab 33135 and the second bottom tab 33137 are configured to engage correspondingly axially extending ledges 31150, 31152, respectively that are formed on each side of the channel slot 31111.

In the illustrated arrangement, the firing system 33000 comprises an upper firing assembly 33200 that operably interfaces with the top firing member feature 33120 and in many aspects is similar to the upper firing assembly 27200. The upper firing assembly 33200 includes an upper flexible outer tube or conduit 33210 that has a proximal end that is fixed to an upper insert 33214 that is non-movably attached to the shaft spine assembly 32100 in the various manner described in detail above. The flexible outer tube or conduit 33210 extends through upper passages 32216 provided through the articulation joint 32200. See FIG. 32. A distal end 33212 of the flexible outer tube or conduit 33210 may be affixed to the anvil mounting bracket 31240. In the illustrated embodiment, the upper firing assembly 33200 further includes an upper push rod 33220 that is slidably supported in a corresponding axial passage in the shaft spine assembly 28100. In one arrangement, the upper firing assembly 33200 comprises an upper push coil 33230 that extends through the flexible outer tube or conduit 33210. See FIGS. 40-42. A proximal end of the upper push coil 33230 is coupled to a distal end of the upper push rod 33220. The upper push coil 33230 is hollow and may comprise a coil spring that is fabricated from Nitinol, titanium, stainless steel, etc. In other arrangements, the upper push coil 33230 comprises a laser cut "hypotube" that essentially comprises a hollow tubular member with offset laser cuts therein which enable the hypotube to flex and bend while being capable of transmitting axial forces or motions. The inner flexible upper sleeve may be fabricated from a polymer or similar material and prevent tissue, fluid, and/or debris from infiltrating into the upper push coil 33230 which may hamper its ability to flex and bend during articulation of the surgical end effector relative to the elongate shaft assembly.

As was discussed above, a distal end of the upper push coil 33230 as well as a distal end of the inner flexible upper sleeve abut a proximal end of the top firing member feature 33120. Also in the illustrated arrangement, the upper firing assembly 33200 may further comprise an upper push coil cable that extends through the hollow upper push coil. The upper push coil cable comprises an upper cable proximal end that is secured to the distal end of the upper push rod 33220 and an upper cable distal end that is secured within the top axial passage in the top firing member feature 33120 by an upper attachment lug. The upper push coil and inner sleeve arrangement of this embodiment is essentially identical to the upper push coil and inner sleeve arrangement depicted in FIG. 20 and described in detail above.

In addition, the firing system 33000 further comprises a lower firing assembly 33300 that operably interfaces with the bottom firing member feature 33130. The lower firing assembly 33300 includes a lower flexible outer tube or conduit 33310 that has a proximal end that is fixed to a lower insert 33314 that is non-movably attached to the shaft spine assembly 32100. The lower flexible outer tube or conduit 33310 extends through lower passages 32218 provided in each of the proximal attachment disc assembly 32240, the annular disc members 32210 and the anvil mounting bracket 31240. A distal end of the flexible outer tube or conduit 33310 may be affixed to the anvil mounting bracket 31240. In the illustrated embodiment, the lower firing assembly 33300 further includes a lower push rod 33320 that is slidably supported in a corresponding axial passage in the shaft spine assembly 32100. See FIG. 39. The lower firing assembly 33300 further comprises a lower push coil 33330 that may be supported in an inner flexible lower sleeve which extends through the lower flexible outer tube or conduit 33310. A proximal end of the lower push coil 33330 and a proximal end of the inner flexible lower sleeve abut and/or are attached to a distal end of the lower push rod 33320. The lower push coil 33330 is hollow and may comprise a coil spring that is fabricated from Nitinol, titanium, stainless steel, etc. In other arrangements, the lower push coil comprises a laser cut hypotube that essentially comprises a hollow tubular member with offset laser cuts therein which enable the hypotube to flex and bend. The inner flexible lower sleeve may be fabricated from a polymer or similar material and prevent tissue, fluid, and/or debris from infiltrating into the lower push coil which may hamper its ability to flex during articulation. A distal end of the lower push coil 33330 as well as a distal end of the inner flexible lower sleeve abut a proximal end of the bottom firing member feature 33130. The lower firing assembly 33300 further comprises a lower push coil cable that extends through the hollow lower push coil 33330. The lower push coil cable comprises a lower cable proximal end that is secured to the distal end of the lower push rod 33320 and a lower cable distal end that is secured to the bottom firing member feature 33130. The lower push coil 33330 and inner lower sleeve arrangement of this embodiment is essentially identical to the lower push coil and inner lower sleeve arrangement depicted in FIG. 20 and described in detail above.

Figure 39:
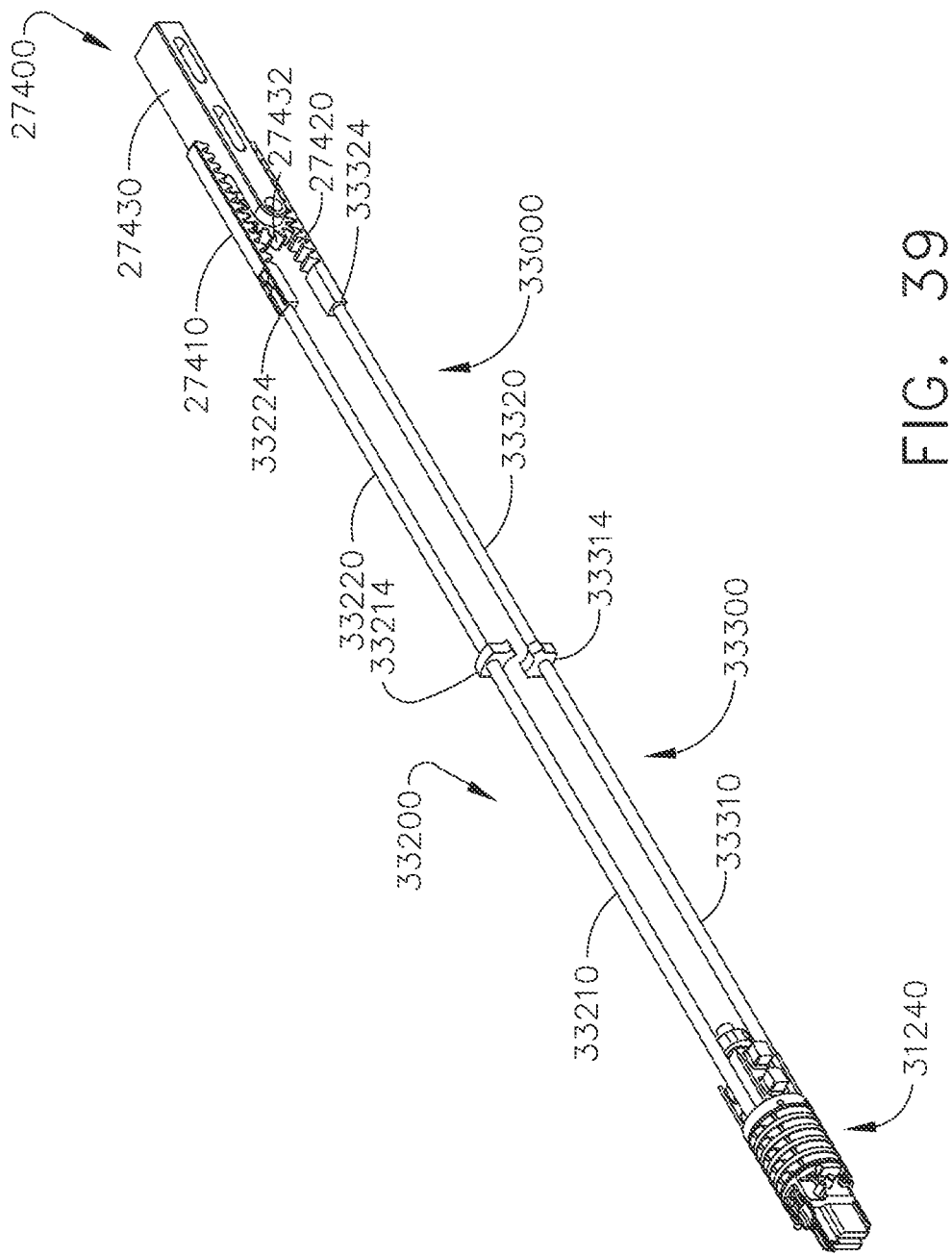
FIG. 39 is a perspective view of a portion of a firing system of the surgical instrument of FIG. 26.

As can be seen in FIG. 39, the firing system 33000 further comprises a differential drive assembly 27400 that is configured to axially drive the upper firing assembly 33200 and the lower firing assembly 33300. A proximal end 33224 of the upper push rod 33220 is coupled to a first or upper gear rack 27410 of the differential drive assembly 27400. Further construction and operation of the differential drive assembly 27400 was described in detail above (see also, FIGS. 20-25) and will not be repeated again.

As indicated above, the anvil 31210 is pivotally coupled to the proximal end 31112 of the elongate channel 31110 by a pin 31232 that defines the fixed pivot axis PA. See FIG. 40. In one arrangement, a pair of anvil opening springs 31310 are supported in pockets 31113 that are formed in the elongate channel 31110. See FIG. 30. The anvil opening springs 31310 are configured to apply opening motions to the anvil 31210 to cause the anvil 31210 to pivot open. In addition, in at least one arrangement, an anvil opening pin or feature 31320 operably interfaces with the anvil mounting portion 31230. See FIGS. 36 and 40-42. In particular, the anvil opening pin 31320 extends through holes 31236 in the anvil mounting portion 31230 and an oblong or elongated slot 31244 in the anvil mounting bracket 31240. FIG. 41 illustrates the firing member 33100 in a proximal-most or "beginning" position. When the firing member 33100 is driven in the proximal direction back to the beginning position, the firing member 33100 contacts the anvil opening pin 31320 and moves the anvil opening pin 31320 to the proximal end 31245 of the elongated slot 31244 in the anvil mounting bracket 31240. Such movement of the anvil opening pin 31320 applies additional pivotal opening motions to the anvil mounting portion 31320 to fully move and retain the anvil 31210 in that fully opened position. See FIG. 41.

Figure 36:
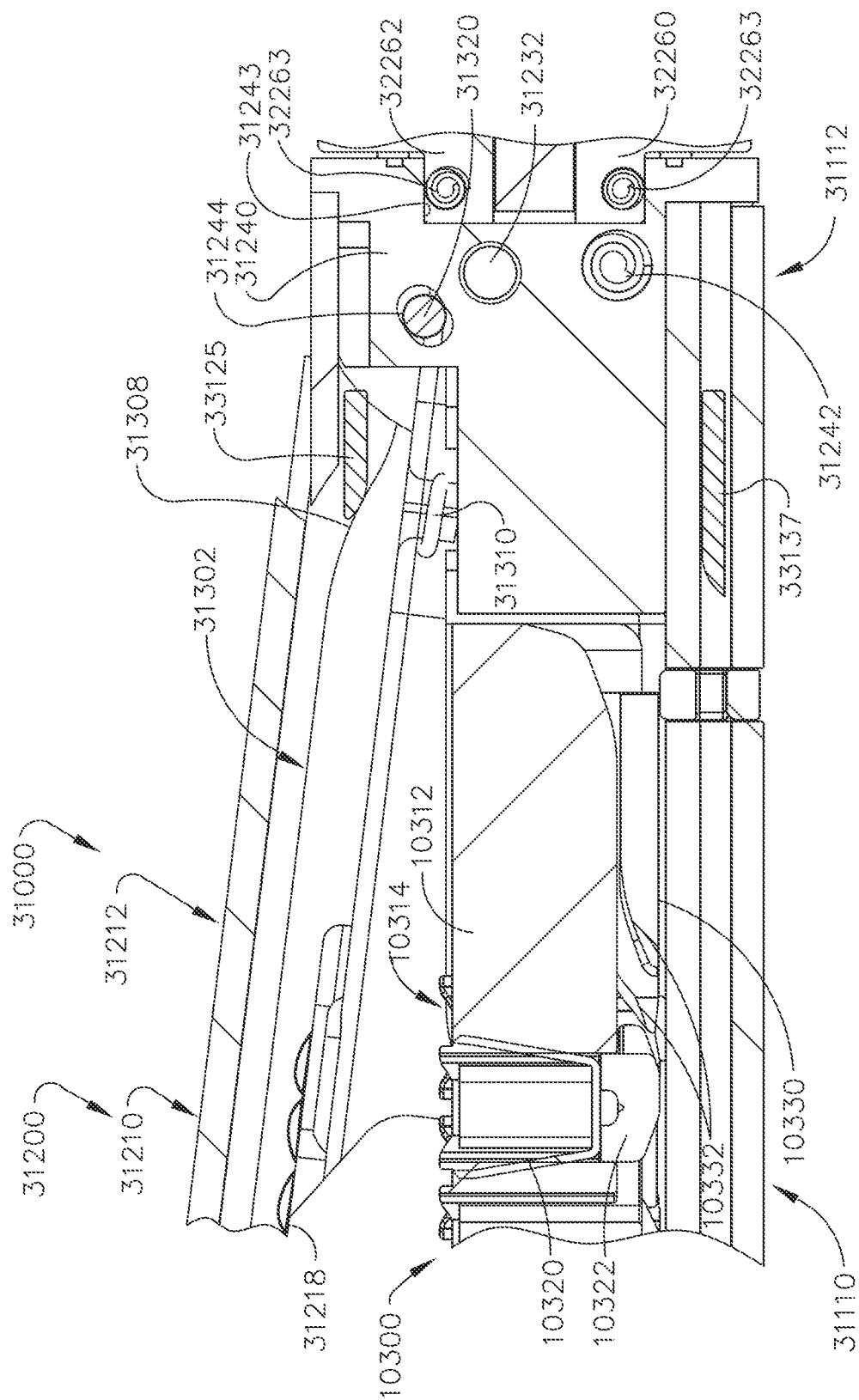
FIG. 36 is a partial cross-sectional side view of the surgical end effector of FIG. 26 with an anvil thereof in a partially open position.

In at least one arrangement, the anvil 31210 is moved from the fully open position (FIG. 41) to a closed position (FIG. 42) when the firing member 33100 is moved distally from the beginning position. In particular, as can be seen in FIG. 36, a proximal end of the axially extending ledge 31302 in the anvil 31210 is formed with a closure ramp 31308 thereon. A proximal end of the axially extending ledge 31304 has a similar closure ramp 31308 formed thereon. As the firing member 33100 is driven distally from the beginning position, the first top tab 33125 and the second top tab 33127 contact corresponding closure ramps 31308 and begin to pivot the anvil 31210 to the closed position against the bias of the anvil opening springs 31310. When the firing member 33100 has reached the position depicted in FIG. 42, the first top tab 33125 and the second top tab 33127 have sufficiently engaged the anvil ledges 31302, 31304 respectively to move the anvil 31210 to that closed position. As can also be seen in FIG. 42, when the anvil 31210 is in the closed position, the anvil opening pin 31320 is positioned in the distal end 31247 of the elongated slot 31244 in the anvil mounting bracket 31240.

Figure 42:
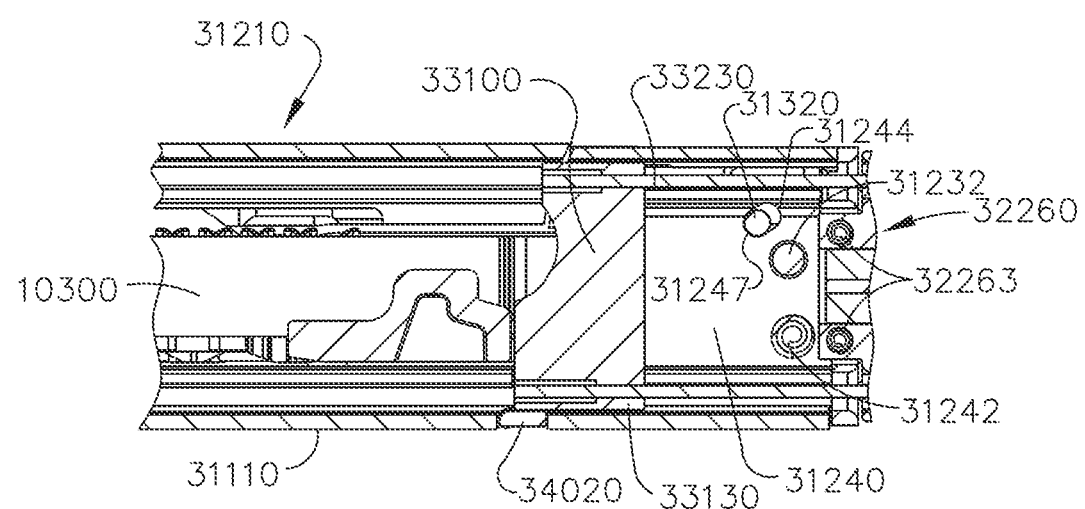
FIG. 42 is another cross-sectional side view of the surgical end effector of FIG. 26 with the anvil thereof in a closed position.

Thus, in one arrangement, the surgical instrument 30010 may be operated as follows. For example, to insert the surgical end effector 31000 through a cannula of a trocar that has been installed in the patient, the clinician must first close the anvil 31210. To accomplish that task, the clinician may actuate the differential drive assembly 27400 in the various manners described herein to cause the upper push coil 33230 and the lower push coil 33330 to distally drive the firing member 33100 from the beginning position to an "intermediate closure position" (FIG. 42). Once the firing member 33100 has reached the intermediate closure position, the differential drive assembly 27400 is deactivated. The position of the firing member 33100 may be determined by sensors (not shown) in the surgical end effector or activating the differential drive assembly 27400 for a known time period necessary to distally drive the firing member 33100 to that intermediate closure position from the beginning period. As can be seen in FIG. 42, when in the intermediate closure position, the firing member 33100 has moved distally from the beginning position to a position wherein the anvil 31210 has moved to a closed position, but the firing member 33100 has not actuated or operably interfaced with a camming member 10330 in a surgical staple cartridge 10300 that has been loaded (operably seated) into the surgical end effector 31000.

Once the surgical end effector 31000 has completely entered the patient and is moved to the desired area, the differential drive assembly is activated to return the firing member 33100 to the beginning position to move the anvil 31210 to the fully open position. At this time or prior to the moving of the anvil 31210 to the fully open position, the clinician may activate the cable control system 25030 in the various manners described herein to apply tension and relieve tension in the various cable assemblies 32410, 32420, 32430, 32440 that are attached to the anvil mounting bracket 31240 to cause the surgical end effector 31000 to articulate into a desired orientation in which the target tissue may be clamped between the anvil 31210 and the surgical staple cartridge 10300 that is supported in the surgical end effector 31000. Once the surgical end effector 31000 has been articulated into the desired position, the cable control system 25030 may be deactivated.

After the clinician (or robotic system) has positioned the surgical end effector 31000 in a desired orientation, the clinician (or robotic system) may once again activate the differential drive assembly 27400 to drive the firing member 33100 distally from the beginning position. The firing member 33100 may be stopped in the intermediate closure position to enable the clinician to assess whether the target tissue has been properly clamped in the surgical end effector 31000 before proceeding to cut and staple the tissue or the clinician may permit the firing member 33100 to continue moving distally until the firing member 33100 has reached the ending position within the surgical end effector 31000 wherein the target tissue has been fully cut and stapled. Stated another way, when the firing member 33100 has reached a distal-most position within the surgical end effector 31000 wherein all of the surgical staples stored in the surgical staple cartridge 10300 have been forced through the target tissue into forming contact with the staple-forming underside 31218 of the anvil 31210, the distal advancement of the firing member 33100 is discontinued.

Figure 40:
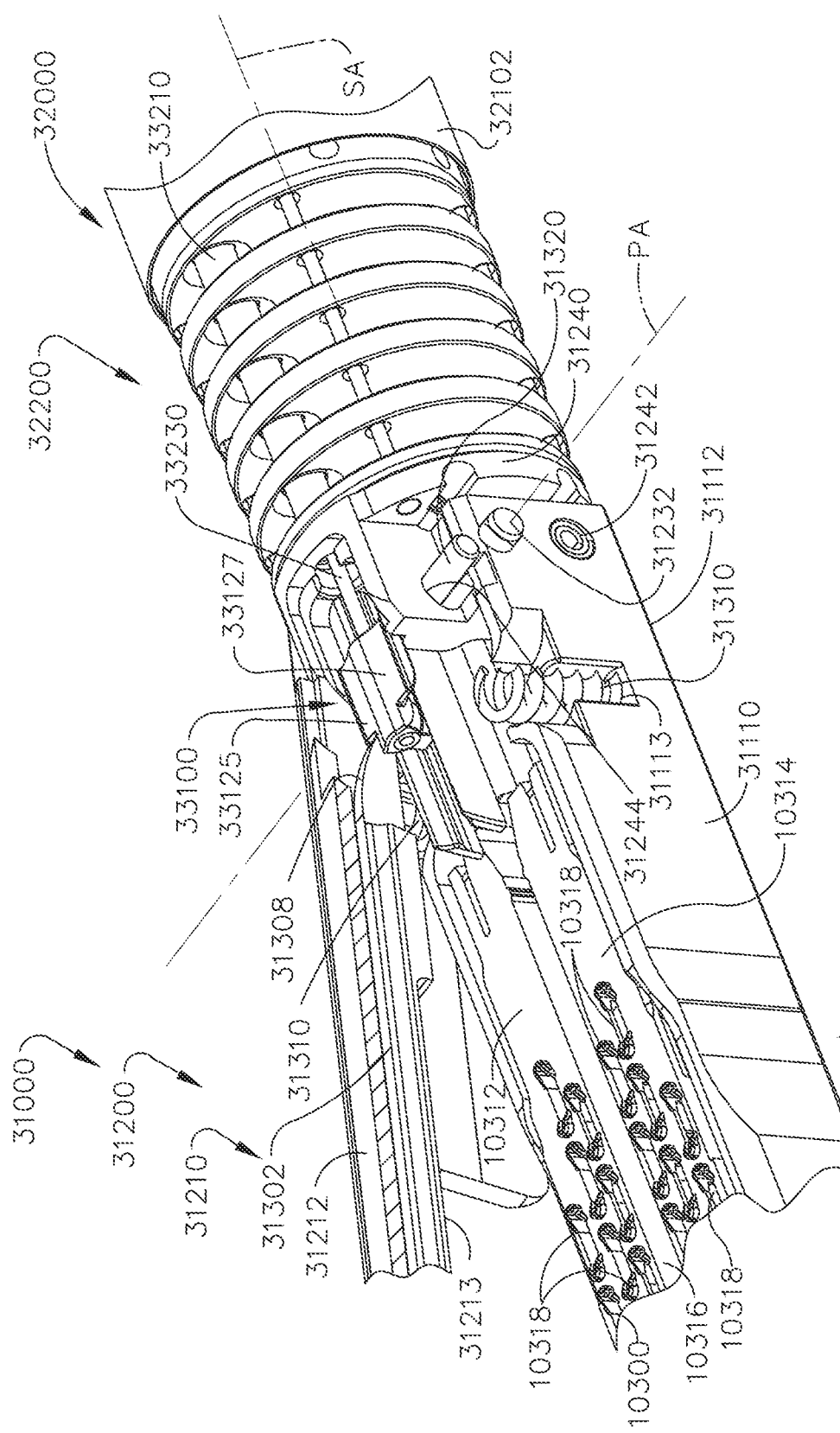
FIG. 40 is a partial cross-sectional view of a portion of the surgical end effector and surgical instrument of FIG. 26 with a staple cartridge therein and the anvil in an open position.
Figure 41:
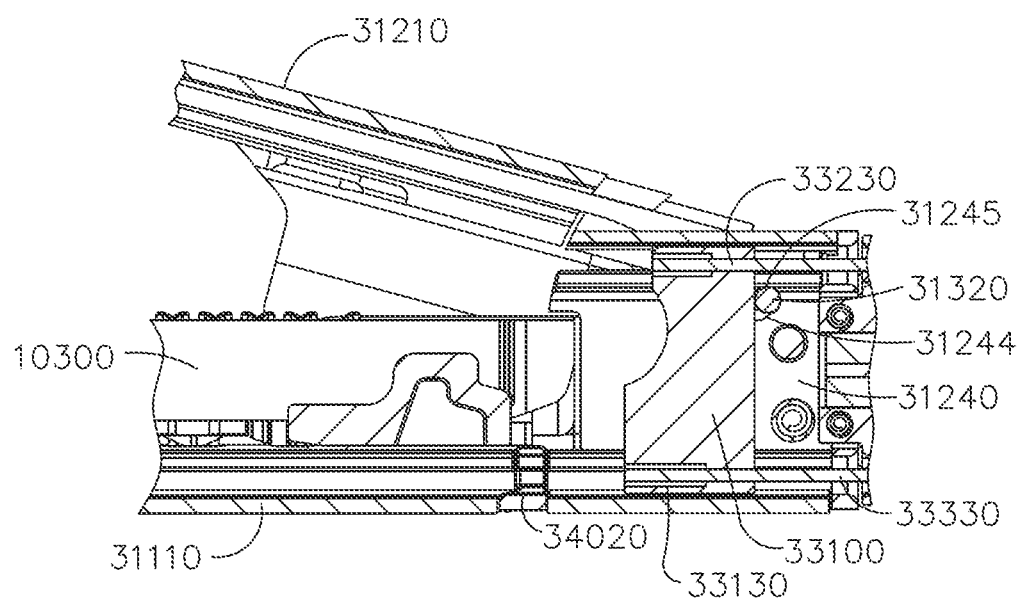
FIG. 41 is a cross-sectional side view of the surgical end effector of FIG. 26 with the anvil thereof in an open position.

Referring to FIGS. 36 and 40, an exemplary surgical staple cartridge 10300 comprises a cartridge body 10312 that defines a cartridge deck surface 10314 that is configured to face or confront the staple-forming underside 31218 of the anvil body 31212. An elongate cartridge slot 10316 extends axially through the cartridge body 10312 to accommodate passage of the firing member 33100 therethrough. The cartridge slot 10316 divides the cartridge deck surface 10314 into a left portion and a right portion. In the illustrated arrangement, a plurality of surgical staples or surgical fasteners 10320 are stored in corresponding staple pockets 10318 in each of the left and right portions that open through the cartridge deck surface 10314. One or more surgical staples 10320 are supported on a staple driver 10322 that is movably supported in the corresponding staple pocket 10318. Three lines of surgical staples 10320 are stored in the cartridge body 10312 on each side of the cartridge slot 10316. In one arrangement, the surgical staples 10320 and staple drivers 10322 are loaded from the bottom of the cartridge body 10312 and then retained therein by a cartridge tray that is attached to the cartridge body 10312.

The surgical staple cartridge 10300 further includes a camming assembly 10330 also known as a "sled" that is movably supported within the cartridge body 10312. See FIG. 36. The camming assembly 10330 is movable from a proximal-most "starting" position in the surgical staple cartridge 10300 to a "fully-fired" position in the distal end of the staple cartridge body 10312. The camming assembly 10330 is formed with a series of cams 10332 that correspond to each line of surgical staples 10320 in the surgical staple cartridge 10300. When the firing member 33100 is distally advanced from the intermediate closure position corresponding to the closed position of the anvil 31210, the firing member 33100 operably interfaces with or contacts the camming assembly 10330 and drives the camming assembly 10330 distally through the surgical staple cartridge 10300. As the camming assembly 10330 is driven distally from the starting position, the cams 10332 serially contact the lines of staple drivers 10322 to drive the staple drivers 10322 in a direction toward the anvil 31210. As the staple drivers 10322 are driven toward the anvil 31210, the surgical staples 10320 that are supported thereon are driven into the target tissue and into forming contact with the staple-forming underside 31218 of the anvil 31210. The tissue cutting blade 33114 of the firing member 33100 is located proximal to the camming assembly 10330 so that the surgical staples 10320 are fired and formed before the corresponding portion of target tissue is cut.

Once the target tissue has been cut and stapled, the clinician (or robotically-controlled system) may then activate the differential drive assembly 27400 to retract the firing member 33100 from the fully-fired position back to the beginning position wherein the anvil 31210 is moved to the open position to release the stapled target tissue from the surgical end effector 31000. Thereafter, the clinician may again activate the differential drive assembly 24700 to move the anvil 31210 to the closed position to permit the surgical end effector 31000 to exit back through the trocar cannula. Of course, the surgical instrument 30010 may also be effectively employed in a similar manner in "open" surgical applications wherein trocars are not employed to access the surgical area within the patient.

Figure 43:
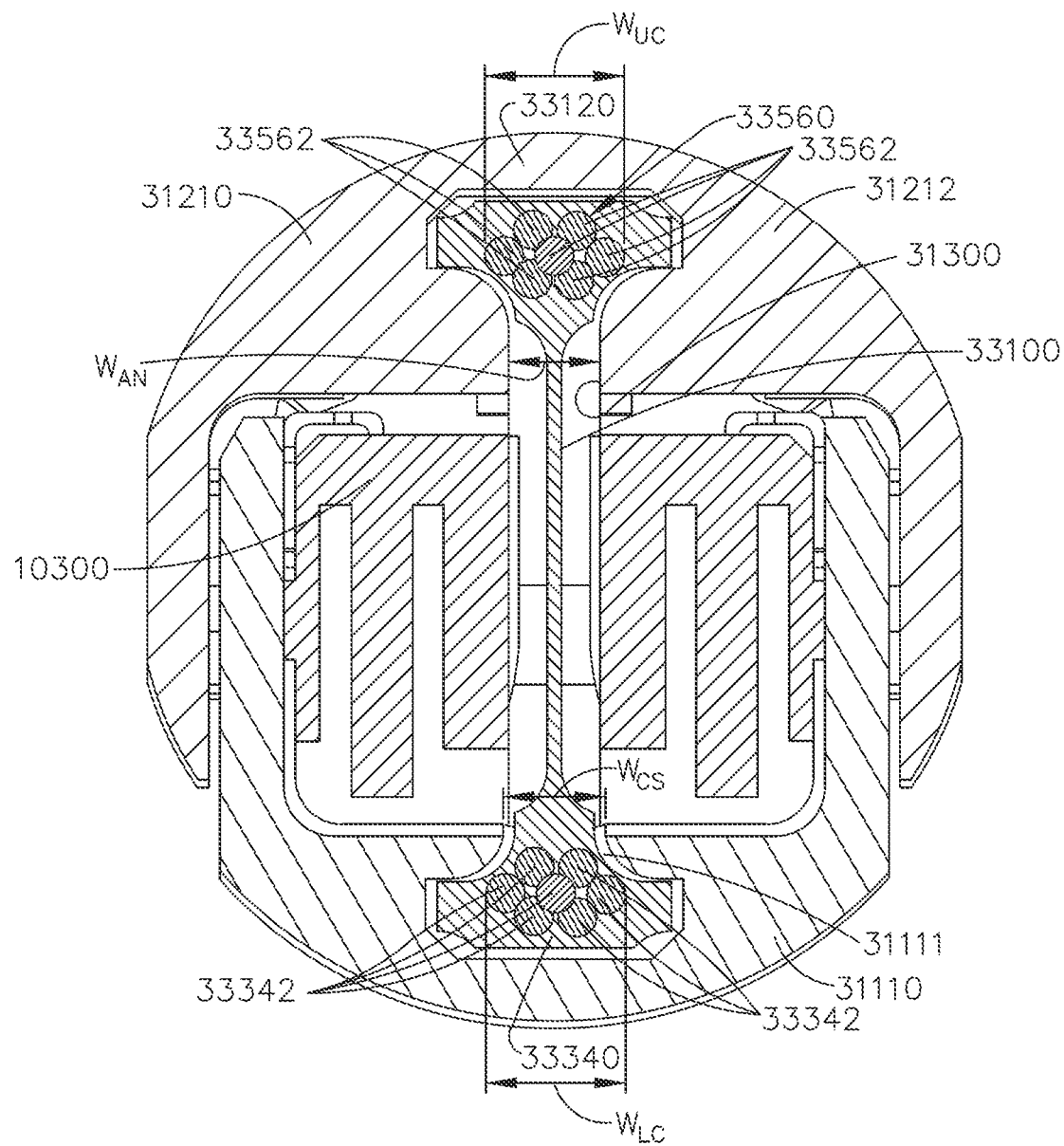
FIG. 43 is a cross-sectional end view of another surgical end effector in accordance with another general aspect of the present disclosure.

As described above, the upper firing assembly 33200 comprises an upper push coil 33230 that may be supported in an inner flexible upper sleeve 33231 which extends through the upper flexible outer tube or conduit 33210. The lower firing assembly 33300 comprises a lower push coil 33330 that is supported in an inner flexible lower sleeve 33341 which extends through the lower flexible outer tube or conduit 27310. In the embodiment depicted in FIG. 43, instead of an upper push coil, an upper push cable arrangement 33560 is employed and instead of a lower push coil, a lower push cable arrangement 33340 is employed. In at least one arrangement, the upper push cable arrangement 33560 comprises a cluster or bundle of upper push cables 33562 and the lower push cable arrangement 33340 comprises a cluster or bundle of lower push cables 33342. Such upper push cable arrangement 33560 and lower push cable arrangement 33340 may prevent any kinking of the push cable arrangements as the firing member 33100 is driven distally. Such configuration reduces or completely avoids any tendency of the upper push cable arrangement 33550 and lower push cable arrangement 33340 from falling out of the anvil slot 31300 and the channel slot 31111, respectively. As can be seen in FIG. 43, for example the width $W_{uc}$ of the upper push cable arrangement 33560 is wider that a width $W_{an}$ of the anvil slot 31300 which prevents the upper push cable arrangement 33560 from falling into (and potentially out of) the anvil slot 31300. Similarly, the width $W_{LC}$ of the lower push cable arrangement 33340 is greater than the width $W_{CS}$ of the channel slot 31111 which prevents the lower push cable arrangement 33340 from falling into (and potentially out of) the channel slot 31111. Such arrangement also favorably alters the internal strains commonly experienced by the push cables by employing a "non-circular" cross-section of each push cable arrangement.

In the example illustrated in FIG. 43, the upper push cable arrangement 33560 comprises seven upper push cables 33562 that have the same circular cross-sectional shape and are identical in size. In other arrangements, the upper push cables 33562 may have different cross-sectional shapes and have different cross-sectional sizes. The upper push cable arrangement 33560 may be coated or over-molded with a flexible material that can also reduce friction. Similarly, the lower push cable arrangement 33340 comprises seven lower push cables 33342 that have the same circular cross-sectional shape and are identical in size. In other arrangements, the lower push cables 33342 may have different cross-sectional shapes and have different cross-sectional sizes. The lower push cable arrangement 33340 may be coated or over-molded with a flexible material that can also reduce friction. The upper push cable arrangement 33560 may be attached to or otherwise operably interface with the upper push rod 33220 in the various manners described herein to facilitate distal advancement and proximal retraction thereof by the differential drive assembly 27400. Similarly, the lower push cable arrangement 33340 may be attached to or otherwise operably interface with the lower push rod 33320 in the various manners described herein to facilitate distal advancement and proximal retraction thereof by the differential drive assembly 27400.

Figure 43A:
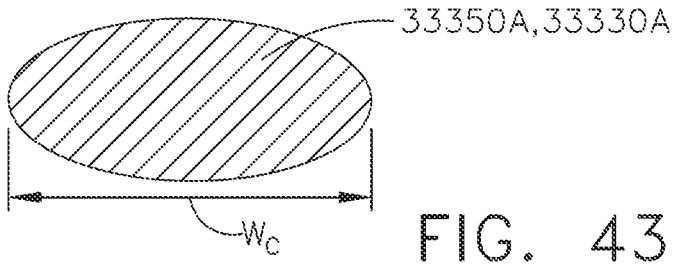
FIG. 43A is a cross-sectional view of an alternative push cable in accordance with another general aspect of the present disclosure.

FIG. 43A illustrates a cross-sectional shape of an alternative upper push cable 33350A and lower push cable 33330A that may be employed. The width $W_c$ of the upper push cable 33350A and lower push cable 33330A is greater than the width $W_{an}$ of the anvil slot 31300 and the width $W_{cs}$ of the channel slot 31111.

Figure 43B:
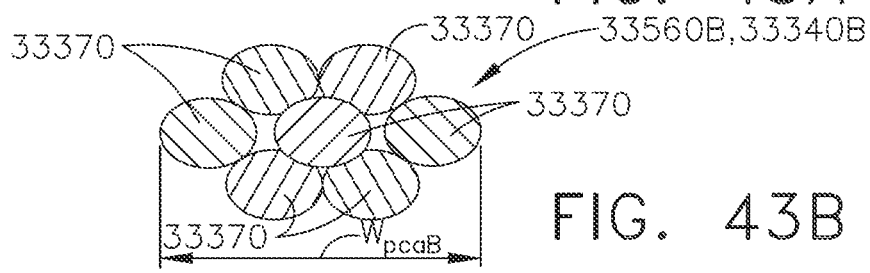
FIG. 43B is a cross-sectional view of an alternative push cable arrangement in accordance with another general aspect of the present disclosure.

FIG. 43B illustrates a cross-sectional shape of an alternative upper push cable arrangement 33560B and lower push cable arrangement 33340B that may be employed. This example employs a total of seven push cables 33370 that are equal in size and have an oval cross-sectional shape. The width $W_{pcaB}$ of each alternative upper push cable arrangement 33560B and lower push cable arrangement 33340B is greater that the width $W_{an}$ of the anvil slot 31300 and the width $W_{cs}$ of the channel slot 31111.

Figure 43C:
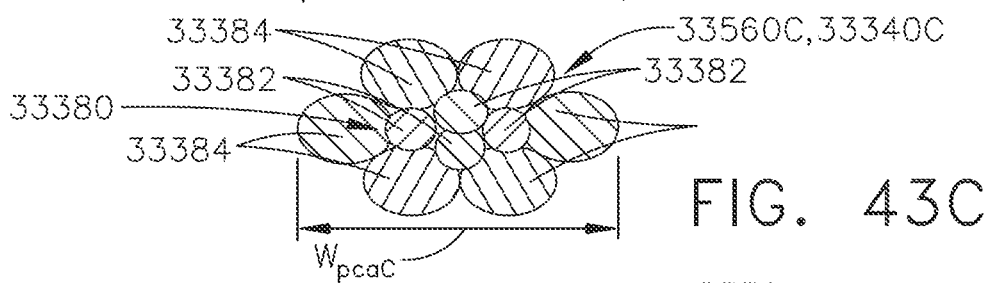
FIG. 43C is a cross-sectional view of an alternative push cable arrangement in accordance with another general aspect of the present disclosure.

FIG. 43C illustrates a cross-sectional shape of an alternative upper push cable arrangement 33560C and lower push cable arrangement 33340C that may be employed. This example employs a central cluster 33380 of central push cables 33382 that is surrounded by six outer push cables 33384 that are larger than central push cables 33382. In the illustrated example, the central push cables 33382 each have a circular cross-sectional shape and each of the outer push cables 33384 have an oval cross-sectional shape. The width $W_{pcaC}$ of each alternative upper push cable arrangement 33560C and lower push cable arrangement 33340C is greater that the width $W_{an}$ of the anvil slot 31300 and the width $W_{cs}$ of the channel slot 31111.

Figure 43D:
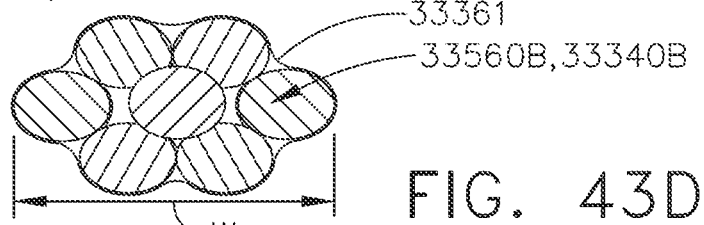
FIG. 43D is a cross-sectional view of an alternative push cable arrangement in accordance with another general aspect of the present disclosure.

FIG. 43D illustrates the upper push cable arrangement 33560B and lower push cable arrangement 33340B described above that has been encapsulated or over-molded with a friction-reducing flexible covering 33561.

Figure 43E:
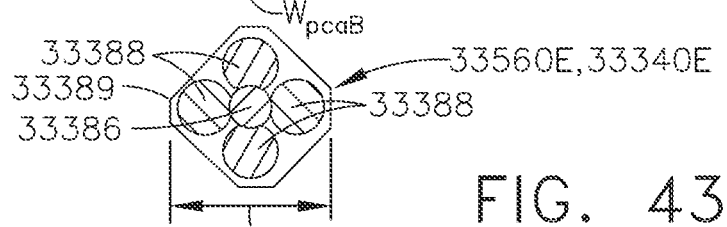
FIG. 43E is a cross-sectional view of an alternative push cable arrangement in accordance with another general aspect of the present disclosure.

FIG. 43E illustrates a cross-sectional shape of an alternative upper push cable arrangement 33560E and lower push cable arrangement 33340E that may be employed. This example has a somewhat diamond shape and comprises a central push cable 33386 that is surrounded by four outer push cables 33388 that are larger than central push cable 33386. In the illustrated example, the central push cable 33386 and the outer push cables 33388 each have a circular cross-sectional shape. The width $W_{pcaE}$ of each alternative upper push cable arrangement 33560E and lower push cable arrangement 33340E is greater that the width $W_{an}$ of the anvil slot 31300 and the width $W_{cs}$ of the channel slot 31111. In the illustrated arrangement, the upper push cable arrangement 33560E and lower push cable arrangement 33340E has been encapsulated or over-molded with a friction-reducing flexible covering 33389.

Figure 43F:
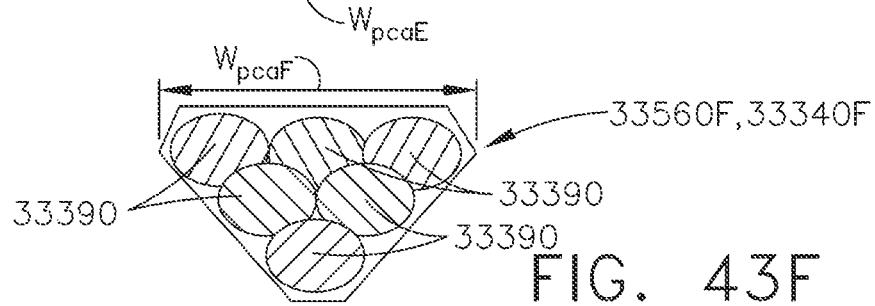
FIG. 43F is a cross-sectional view of an alternative push cable arrangement in accordance with another general aspect of the present disclosure.

FIG. 43F illustrates a cross-sectional shape of an alternative upper push cable arrangement 33560F and lower push cable arrangement 33340F that may be employed. This example has a somewhat triangular cross-sectional shape and comprises six push cables 33390 that are the same size and have an oval cross-sectional shape. The width $W_{pcaF}$ of each alternative upper push cable arrangement 33560F and lower push cable arrangement 33340F is greater that the width $W_{an}$ of the anvil slot 31300 and the width $W_{cs}$ of the channel slot 31111. In the illustrated arrangement, the upper push cable arrangement 33560F and lower push cable arrangement 33340F has been encapsulated or over-molded with a friction-reducing flexible covering 33392.

In the various embodiments described above, the push cables may comprise a Nitinol material, titanium, stainless steel or other suitable material. Other numbers of push cables and sizes of push cables having different cross-sectional shapes may be employed, provided that the overall width of the support cable or support cable arrangement is greater than the width of the anvil slot and the channel slot while also being sized to pass through the various openings in the various components of the surgical instrument 30010 in the manners disclosed herein. It will be further appreciated that the cross-sectional shapes, sizes, and compositions of the lower push cable(s) and lower push cable arrangements may differ from the cross-sectional shapes, sizes, and compositions of the upper push cable(s) and upper push cable arrangements.

Figure 44:
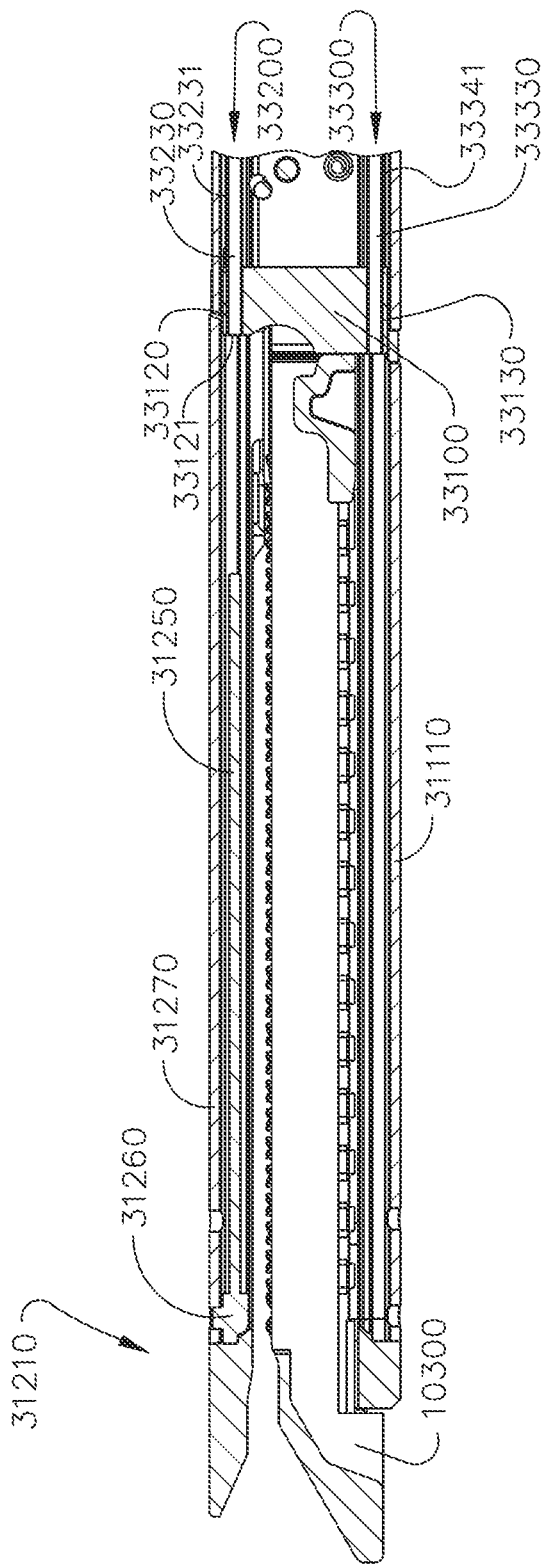
FIG. 44 is a cross-sectional side view of another surgical end effector in accordance with another general aspect of the present disclosure with an anvil thereof in a closed position and a firing member thereof in an intermediate closure position.

In the embodiments illustrated in FIGS. 38 and 44, the upper firing assembly 33200 comprises an upper push coil 33230 that may be supported in an inner flexible upper sleeve 33231 which extends through the upper flexible outer tube or conduit 33210. The upper push coil 33230 is hollow and may comprise a coil spring that is fabricated from Nitinol, titanium, stainless steel, etc. In other arrangements, the upper push coil 33230 comprises a laser cut "hypotube" that essentially comprises a hollow tubular member with offset laser cuts therein which enable the hypotube to flex and bend while being capable of transmitting axial forces or motions. The upper push coil 33230 may be received in a flexible upper sleeve 33231 that may be fabricated from a polymer or similar material and prevent tissue, fluid, and/or debris from infiltrating into the upper push coil 33230 which may hamper its ability to flex and bend during articulation of the surgical end effector relative to the elongate shaft assembly. The upper push coil 33230 is attached to the top firing member feature 33120 of the firing member 33100 and operably interfaces with the differential drive assembly 27400 for actuation thereof in the various manners described herein.

Also in the example depicted in FIGS. 38 and 44, the lower firing assembly 33300 comprises a lower push coil 33330 that is supported in an inner flexible lower sleeve 33341 which extends through the lower flexible outer tube or conduit 27310. The lower push coil 33330 is hollow and may comprise a coil spring that is fabricated from Nitinol, titanium, stainless steel, etc. In other arrangements, the lower push coil 33330 comprises a laser cut hypotube that essentially comprises a hollow tubular member with offset laser cuts therein which enable the hypotube to flex and bend. The inner flexible lower sleeve 33341 may be fabricated from a polymer or similar material and prevent tissue, fluid, and/or debris from infiltrating into the lower push coil 33330 which may hamper its ability to flex during articulation. The lower push coil 33330 is attached to the bottom firing member feature 33130 of the firing member 33100 and operably interfaces with the differential drive assembly 27400 for actuation thereof in the various manners described herein.

Figure 45:
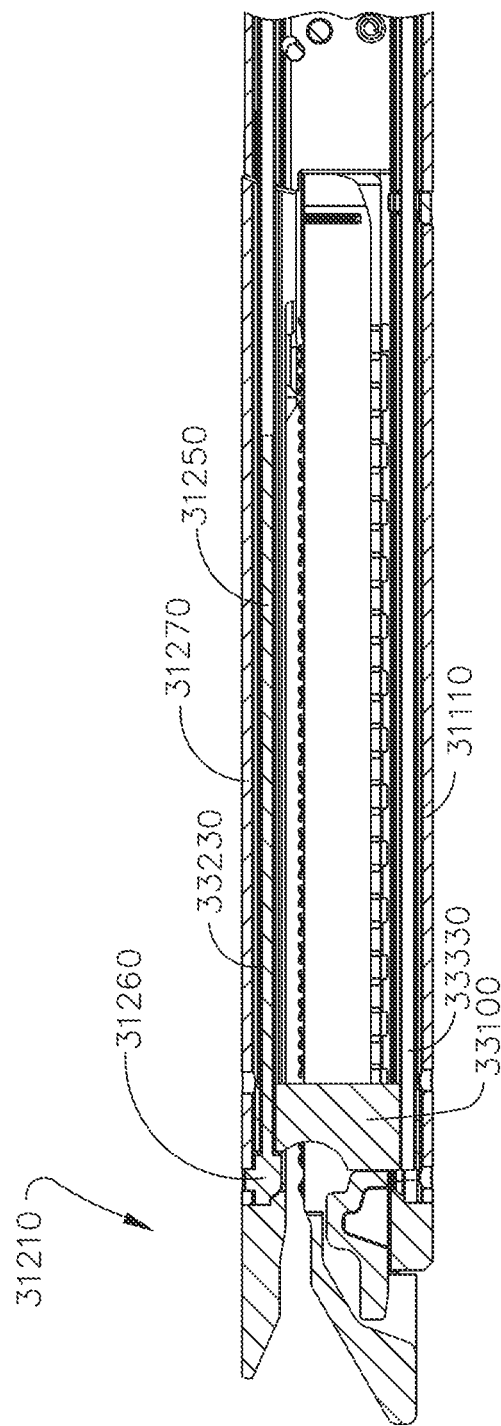
FIG. 45 is another cross-sectional side view of the surgical end effector of FIG. 44 with the firing member in an ending position.

Turning to FIGS. 30, 31, 37, and 44, the anvil 31210 comprises a stabilizing beam 31250 that is supported in the anvil body 31212 and is configured to enter the hollow upper push coil 33230 as the firing member 33100 is distally advanced through the surgical end effector 31000. As can be seen in FIGS. 30 and 37, a distal end 31252 is attached to a mounting bracket 31260 that is attached to an anvil cap 31270 that is attached to the anvil body 31212 by welding, adhesive, etc. The stabilizing beam 31250 may be fabricated from a material that is more flexible than the material comprising the anvil body 31212 to facilitate firing on thick tissue. The proximal end of the stabilizing beam 31250 may be tapered, pointed, etc. to facilitate passage through an opening 33121 in the top firing member feature 33120 and into the hollow upper push coil 33230. As the firing member 33100 is driven distally from the intermediate closure position, the stabilizing beam 31250 enters the hollow upper push coil 33230. The cantilevered stabilizing beam 31250 supports the upper push coil 33230 during firing of the firing member 33100 and prevents the upper push coil 33230 from buckling within the anvil slot 31300 during firing (movement from the intermediate closure position to the ending position). See FIG. 45.

Figure 46:
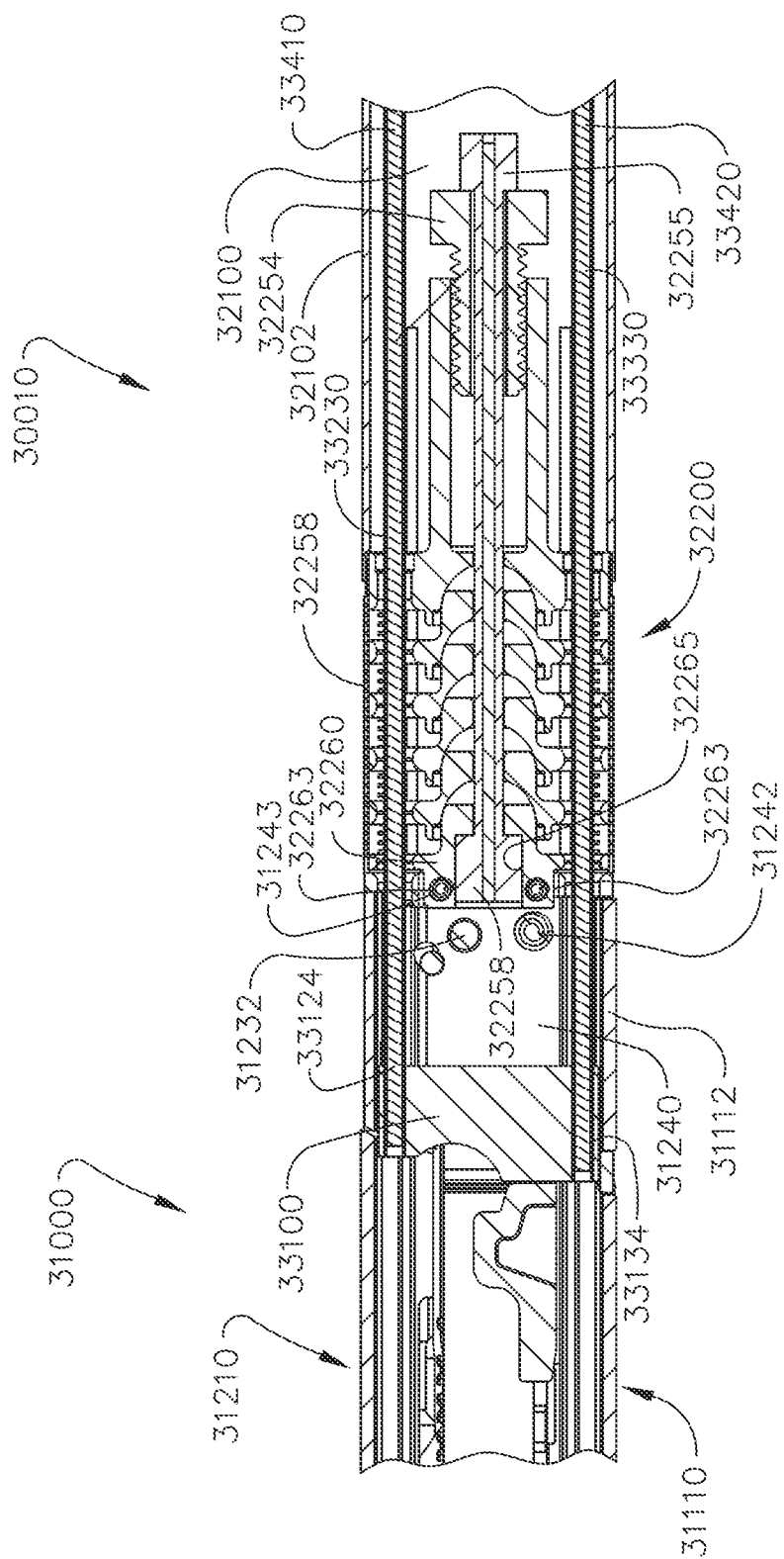
FIG. 46 is a cross-sectional side view of a portion of another surgical end effector in accordance with another general aspect of the present disclosure with an anvil thereof in a closed position and a firing member thereof in an intermediate closure position.

FIG. 46 illustrates use of an upper stabilizing beam 33410 that is coupled to the firing member 33100 and protrudes proximally therefrom to be received within the upper push coil 33230 and a lower stabilizing beam 33420 that is coupled to the firing member 33100 and protrudes proximally therefrom to be received with the lower push coil 33330. In this arrangement, the upper stabilizing beam 33410 and the lower stabilizing beam 33420 are fabricated from a material that is flexible enough to flexibly pass through the articulation joint 32200, but yet is stiff enough to resist bucking of the push coils 33230, 33330. In one example, each of the upper stabilizing beam 33410 and the lower stabilizing beam 33420 may comprise a combination of rigid and flexible sections that are configured to engage with a corresponding distal stabilizing beam (not shown). Arrangements wherein each of the upper stabilizing beam 33410 and the lower stabilizing beam 33420 are semi-rigid along their respective entire lengths from proximally in the shaft assembly to the distal end of the anvil (when the firing member 33100 is in the ending position) may serve to apply tension and rigidify the surgical end effector. The upper stabilizing beam 33410 and the lower stabilizing beam 33420 allow the firing drive system to push through the small diameter supports in the articulation joint and remain stable as the firing member moves distally through the end effector to prevent buckling.

FIGS. 47-50 illustrate an upper firing assembly 33200' that is similar to upper firing assembly 33200 and comprises an upper push coil 33230 that may be supported in an inner flexible upper sleeve 33231 which extends through the upper flexible outer tube or conduit 33210. In one arrangement, the upper push coil 33230 is hollow and may comprise a coil spring that is fabricated from Nitinol, titanium, stainless steel, etc. In other arrangements, the upper push coil 33230 comprises a laser cut "hypotube" that essentially comprises a hollow tubular member with offset laser cuts therein which enable the hypotube to flex and bend while being capable of transmitting axial forces or motions. The upper push coil 33230 may be received in a flexible upper sleeve 33231 that may be fabricated from a polymer or similar material and prevent tissue, fluid, and/or debris from infiltrating into the upper push coil 33230 which may hamper its ability to flex and bend during articulation of the surgical end effector relative to the elongate shaft assembly. The upper push coil 33230 is attached to the top firing member feature 33120 of the firing member 33100 and operably interfaces with the differential drive assembly 27400 for actuation thereof in the various manners described herein.

In this example, the lower firing assembly 33300' is similar to lower firing assembly 33300 described above and comprises a lower push coil 33330 that is supported in an inner flexible lower sleeve 33341 which extends through the lower flexible outer tube or conduit 27310. The lower push coil 33330 is hollow and may comprise a coil spring that is fabricated from Nitinol, titanium, stainless steel, etc. In other arrangements, the lower push coil 33330 comprises a laser cut hypotube that essentially comprises a hollow tubular member with offset laser cuts therein which enable the hypotube to flex and bend. The inner flexible lower sleeve 33341 may be fabricated from a polymer or similar material and prevent tissue, fluid, and/or debris from infiltrating into the lower push coil 33330 which may hamper its ability to flex during articulation. The lower push coil 33330 is attached to the bottom firing member feature 33130 of the firing member 33100 and operably interfaces with the differential drive assembly 27400 for actuation thereof in the various manners described herein.

In the illustrated embodiment, the upper firing assembly 33200' includes an upper stabilizing assembly 33500 that comprises a right upper cable or flexible member 33510 and a left upper cable or flexible member 33520. A distal end of the right upper cable 33510 and a distal end of the left upper cable 33520 are each attached to the top firing member feature 33120 of the firing member 33100. Similarly, the proximal end of the right upper cable 33510 and the proximal end of the left upper cable 33520 each operably interface with a portion of a cable control system of the various types described herein that is configured to manage the tensioning (pulling) and paying out of the cables 33510 and 33520 during operation of the surgical instrument. As can also be seen in FIG. 47, a right series 33512 of spaced upper right spring members 33514 are journaled on (attached to or otherwise supported on) the right upper cable 33510. Similarly, a left series of 33522 of spaced upper left spring members 33524 are journaled on (attached to or otherwise supported on) the left upper cable 33520.

Figure 47:
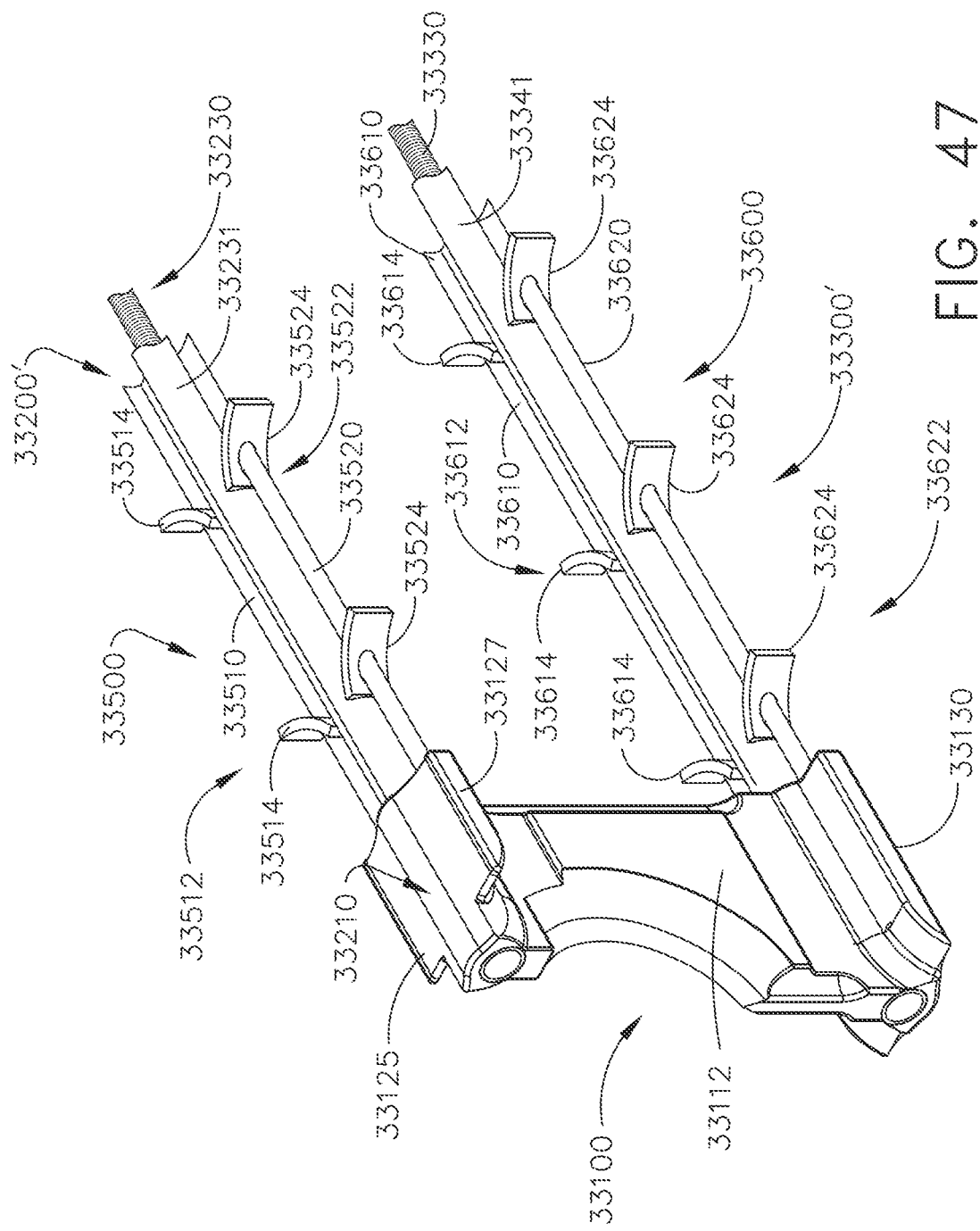
FIG. 47 is a perspective view of another firing member and upper and lower firing member assemblies in accordance with another general aspect of the present disclosure.

Still referring to FIG. 47, the lower firing assembly 33300' includes a lower stabilizing assembly 33600 that comprises a right lower cable or flexible member 33610 and a left lower cable or flexible member 33620. A distal end of the right lower cable 33610 and a distal end of the left lower cable 33620 are each attached to the bottom firing member feature bottom firing member feature 33130 of the firing member 33100. Similarly, the proximal end of the right lower cable 33610 and the proximal end of the left lower cable 33620 each operably interface with a portion of a cable control system of the various types described herein that is configured to manage the tensioning (pulling) and paying out of the cables 33610 and 33620 during operation of the surgical instrument. As can also be seen in FIG. 47, a right lower series 33612 of spaced lower right spring members 33614 are journaled on (attached to or otherwise supported on) the right lower cable 33610. Similarly, a left lower series of 33622 of spaced lower left spring members 33624 are journaled on (attached to or otherwise supported on) the left lower cable 33620.

Figure 48:
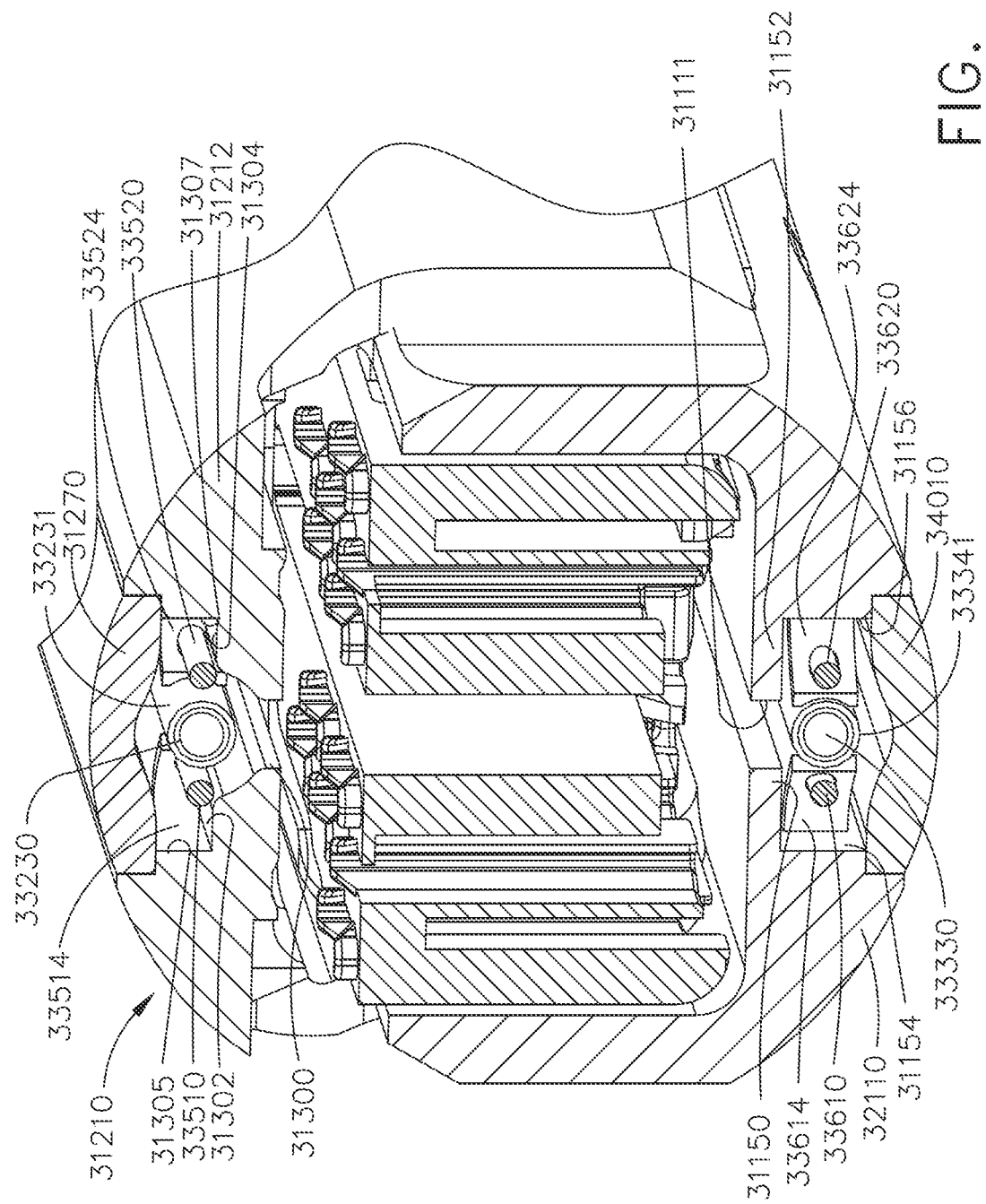
FIG. 48 is a cross-sectional end view of a portion of a surgical end effector that employs the firing member and upper and lower firing member assemblies of FIG. 47, with the firing member omitted for clarity.

Referring now to FIG. 48, the anvil body 31212 comprises a centrally-disposed axially extending anvil slot 31300 that is configured to permit the firing member body 33112 to pass therethrough during a firing stroke and a retraction stroke. The anvil body 31212 further includes axially extending ledges 31302, 31304 that are formed on opposite sides of the anvil slot 31300 that are configured to be slidably engaged by the first top tab 33125 and the second top tab 33127 of the firing member 33100, respectively during firing. An anvil cap 31270 is attached to the anvil body 31212 by welding, adhesive, etc. and cooperates with the ledge 31302 to define an upper right axial passage 31305 in the anvil body 31212. Similarly, the anvil cap 31270 cooperates with the ledge 31304 to define an upper left axial passage 31307 in the anvil body 31212.

Still referring to FIG. 48, the elongate channel 32110 comprises an axially extending channel slot 31111 that is configured to permit the firing member body 33112 to pass therethrough. The elongate channel 32110 further comprises axially extending ledges 31150, 31152 that are formed on each side of the channel slot 31111 and are configured to be slidably engaged by the first bottom tab 33135 and the second bottom tab 33137 of the firing member 33100. A channel cap 34010 is affixed to the elongate channel 32110 by welding or other suitable adhesive or fastener arrangement and cooperates with the axially extending ledge 31150 to define a lower right axial passage 31154 in the elongate channel 32110. The channel cap 30410 further cooperates with axially extending ledge 33152 to define a lower left axial passage 31156 in the elongate channel 32110.

When the firing member 33100 is distally advanced through the surgical end effector during a "firing" stroke, the upper right spring members 33514 on the right upper cable or flexible member 33510 flex outward to provide additional support within the upper right axial passage 31305. Likewise, the upper left spring members 33524 on the left upper cable or flexible member 33520 flex outward to provide additional support with the upper left axial passage 31307. Similarly, the lower right spring members 33614 on the right lower cable or flexible member 33610 flex outward to provide additional support within the lower right axial passage 31154 and the lower left spring members 33624 on the left lower cable or flexible member 33620 flex outward to provide additional support within the lower left axial passage 31156. Such arrangement serves to minimize or prevent buckling of the upper firing assembly 33200' in the anvil 31210 and the lower firing assembly 33300' in the elongate channel 32110 during the firing stroke. The firing member 33100 is retracted back to the beginning position by pulling on the cables 33510, 33520, 33610, 33620 in the proximal direction. As can be seen in FIG. 50, pulling of the cables 33510, 33520, 33610, 33620 in the proximal direction causes the spring members 33514, 33524 to flex back against the upper push coil 33230 and spring members 33614, 33624 to flex back against the lower spring coil 33330 to facilitate proximal transfer through the articulation joint. This design allows the upper firing assembly 33200' and the lower firing assembly 33300' to pass through the small diameter passages in the articulation joint during retraction and still substantially fill or occupy the axial passages 31305, 31307 in the anvil body 31212 and the axial passages 31154, 31156 in the elongate channel 32110 during firing to prevent or minimize buckling.

Figure 51:
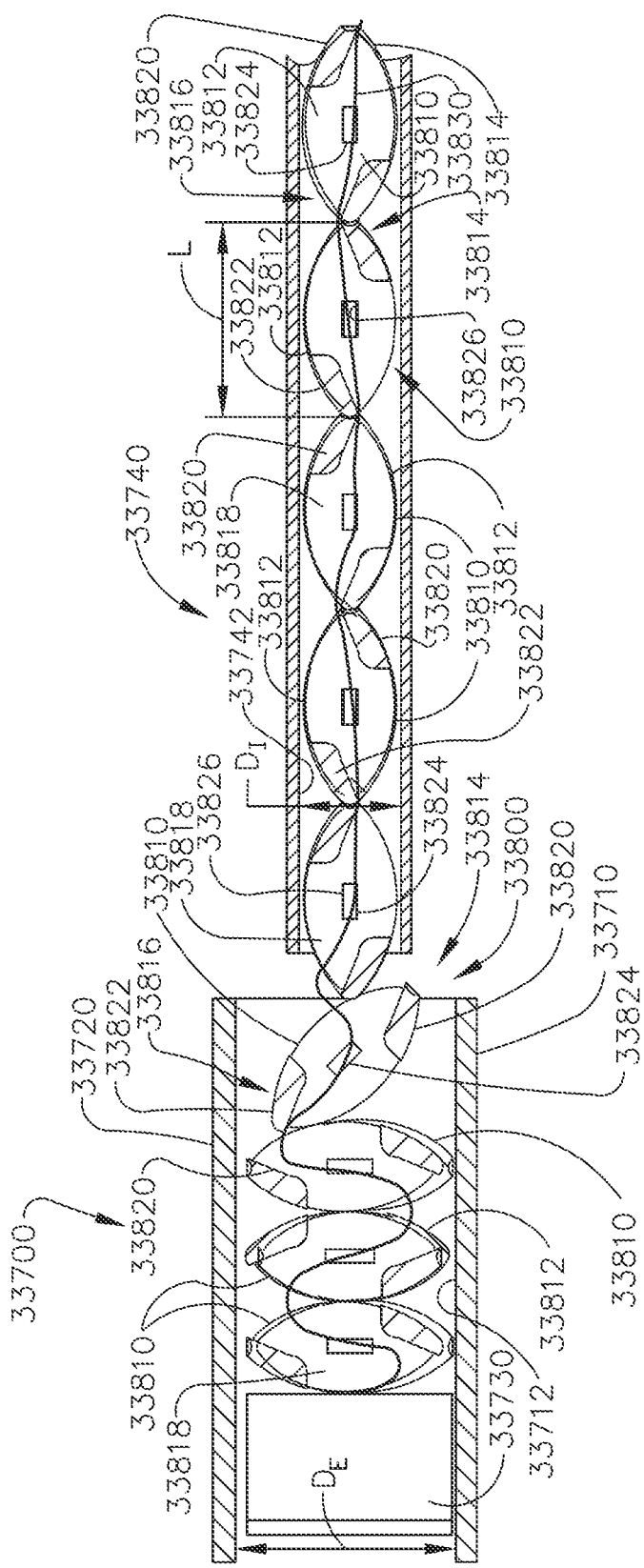
FIG. 51 is a view of another firing assembly embodiment passing through an articulation joint and portion of a surgical end effector in accordance with another general aspect of the present disclosure.

FIG. 51 depicts in somewhat diagrammatic form, a surgical end effector 33700 that comprises a pair of jaws that may consist of a channel 33710 and an anvil 33720. A firing member 33730 is supported for axial travel within the surgical end effector 33700 in the various manners described herein to cut tissue and fire staples contained in a staple cartridge (not shown) that is operably supported in the surgical end effector 33700. FIG. 51 also depicts in diagrammatical form an articulation joint 33740 that may comprise any one of the articulation joint arrangements disclosed herein as well as other articulation joint arrangements. In still other arrangements, the surgical end effector 33700 may comprise other surgical tool configurations that comprise at least one movable jaw and an axially movable firing member.

Figure 52:
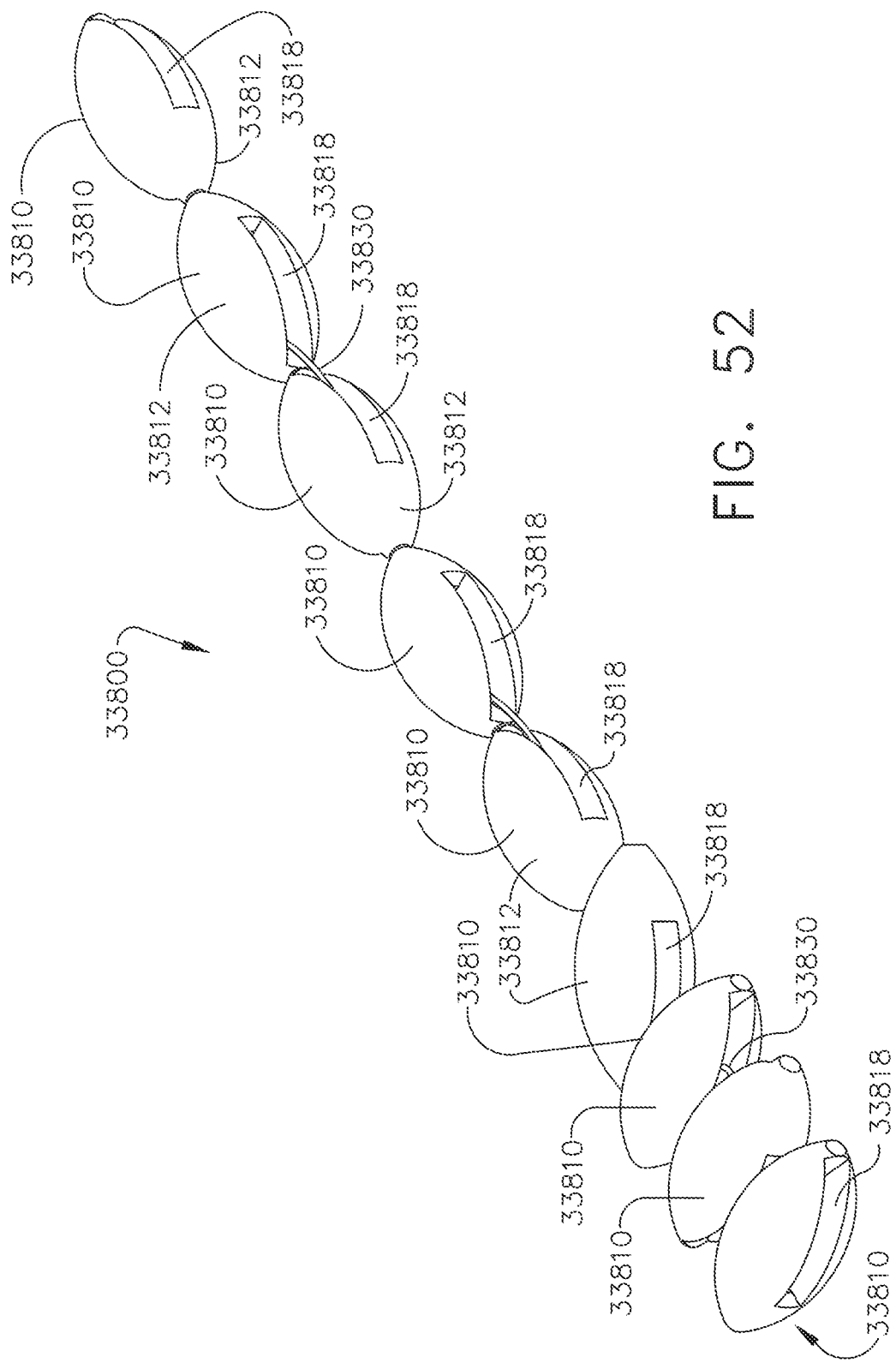
FIG. 52 is a perspective view of a portion of the firing assembly of FIG. 51.

FIGS. 51 and 52 further illustrate a firing assembly 33800 that may be employed to traverse through a narrow passage 33742 in the articulation joint 33740 while applying a pushing motion to the firing member 33730 and then assuming a larger or different "footprint" within the surgical end effector 33700 to prevent buckling of the firing assembly 33800 while continuing to apply pushing motions to the firing member 33730. In the illustrated arrangement, the firing assembly 33800 comprises a series of ovoid members 33810 that are loosely coupled together by a flexible member or cable 33830. In one example, each ovoid member 33810 comprises a prolate spheroid that comprises an ovoid body 33812 that defines a somewhat pointed or tapered proximal end 33814 and a somewhat pointed or tapered distal end 33816. As can be seen in FIG. 52, each ovoid body 33812 includes an open central area 33818 that is defined by a proximal ovoid portion 33820 and a distal ovoid portion 33822. Additionally, each open central area 33818 further defines a central lug 33824 that may have a passage 33826 therethrough for guiding the cable 33830 through the firing assembly 33800. The cable 33830 is threaded through the open central areas 33818 and through the passages 33826 in the central lugs 33824 as can be seen in FIG. 51.

Turning to FIG. 52, when the firing assembly 33800 passes through the passage 33742 in the articulation joint 33740, the ovoid members 33810 are constrained to be arranged lengthwise. The distal ovoid portion 33822 of one ovoid member 33810 is configured to be aligned with the proximal ovoid portion 33820 of the adjacent ovoid member 33810 in the manner depicted in FIG. 51 to form a rigid pushing arrangement as the firing assembly 33800 passes through the narrow passage 33742 in the articulation joint 33740. As used in this context, the term "narrow" means that an inner diameter $D_I$ of the passage 33742 is less than a length L of each ovoid member 33810. In at least one application, a pushing motion may be applied to the proximal-most ovoid member 33810 of the upper firing assembly 33800 by a gear rack and motor arrangement of the types disclosed herein. In alternative arrangements, the pushing motion may be applied to the firing assembly 33800 by a hydraulic or pneumatic cylinder or other suitable arrangement. The cable 33830 may operably interface with a portion of a cable control system of the various types described herein that is configured to manage the tensioning (pulling) and paying out of the cable 33830 during operation of the surgical instrument.

As can be seen in FIG. 51, as the ovoid members 33810 exit the passage 33742 in the articulation joint 33740, they enter a passage 33712 in the end effector 33700 that is configured to accommodate the passage of the firing member 33730 therethrough. The passage 33712 may be defined by the channel 33710 and anvil 33720 (or other jaw arrangements) and have an inner diameter $D_E$ that is greater than $D_I$ as well as the length L of each ovoid member 33810. Thus, $D_E>L>D_I$. As each of the ovoid members 33810 exit the passage 33742, their ovoid shape causes each ovoid member 33810 to assume the position shown in FIG. 51 to essentially fill or substantially fill the passage 33712 in the end effector 33700 to prevent buckling of the firing assembly 33800 as the firing assembly 33800 continues to push the firing member 33730 distally through the surgical end effector 33700 to its ending position therein. Stated another way, the ovoid members 33810 travel lengthwise through the narrower passage 33742. Once the ovoid members 33810 encounter the larger passage 33712, due to the instability of pushing on the lengthwise "stack" of ovoid members 33810, the ovoid members 33810 change their orientation to form a "widthwise" stack. In alternative configurations, flat surfaces may be strategically provided on the body members 33812 to force rotation of each ovoid member in a specific direction or to make pushing more efficient.

Once the firing member 33730 has reached the ending position within the surgical end effector 33700, the firing member 33700 may be retracted back to its beginning position within the surgical end effector 33700 by pulling on the cable 33830. Again, as the ovoid members 33810 exit the passage 33712 in the surgical end effector 33700, their ovoid shape will cause them to turn into and enter the passage 33742 in the articulation joint 33740. As can be appreciated from the foregoing, such firing assembly arrangement may successfully be employed to pass through a narrower first opening or passage in an instrument and then provide a pushing action to a member constrained to move within a second opening or passage that is larger than the first opening or passage.

In those embodiments wherein the firing member 33100 includes a tissue cutting surface or blade, it may be desirable for the surgical end effector to be configured in such a way so as to prevent the inadvertent advancement of the firing member unless an "unspent" surgical staple cartridge 10300 is properly supported in the elongate channel 31110 of the surgical end effector 31000. If, for example, no staple cartridge is present at all and the firing member 33100 is distally advanced through the surgical end effector 31000, the tissue would be severed, but not stapled. Similarly, if a spent staple cartridge (i.e., a staple cartridge wherein at least some of the surgical staples have already been fired therefrom) is present in the surgical end effector 31000 and the firing member is advanced, the tissue would be severed, but may not be completely stapled, if at all. It will be appreciated that such occurrences could lead to undesirable catastrophic results during the surgical procedure. U.S. Pat. No. 6,988,649 entitled SURGICAL STAPLING INSTRUMENT HAVING A SPENT CARTRIDGE LOCKOUT, U.S. Pat. No. 7,044,352 entitled SURGICAL STAPLING INSTRUMENT HAVING A SINGLE LOCKOUT MECHANISM FOR PREVENTION OF FIRING, U.S. Pat. No. 7,380,695 entitled SURGICAL STAPLING INSTRUMENT HAVING A SINGLE LOCKOUT MECHANISM FOR PREVENTION OF FIRING, U.S. Pat. No. 10,154,841, entitled SURGICAL STAPLING INSTRUMENTS WITH LOCKOUT ARRANGEMENTS FOR PREVENTING FIRING SYSTEM ACTUATION WHEN A CARTRIDGE IS SPENT OR MISSING, and U.S. Pat. No. 10,980,536, entitled NO-CARTRIDGE AND SPENT CARTRIDGE LOCKOUT ARRANGEMENTS FOR SURGICAL STAPLERS, each disclose various firing member lockout arrangements. Each of those references is hereby incorporated by reference in its entirety herein.

Conventional lockout arrangements employ a firing member that is biased downward into contact with a ledge on the channel unless an unspent cartridge has been loaded or seated in the channel. When the unspent cartridge is seated in the channel, the camming member or sled engages the firing member and lifts it out of alignment with the channel ledge so the firing member may thereafter be advanced distally to fire (drive the staples from) the staple cartridge. The various firing member arrangements disclosed herein may be driven by push cables or push coils that interface with a top portion and a bottom of the firing member. In such arrangements, the firing member is not well-suited to be biased downwardly making such conventional firing member lock arrangements unsuited for these surgical end effectors.

FIGS. 53-57 illustrate a firing member lockout system generally designated as 34000 that prevents the firing member 33100 from moving distally from an intermediate closure position to an ending position within the surgical end effector 31000 unless an "unfired", "unspent", "fresh" or "new" surgical staple cartridge 10300 has been properly seated within the elongate channel 31110. An "unfired", "unspent", "fresh" or "new" surgical staple cartridge 10300 means herein that the surgical staple cartridge 10300 has all of its surgical staples 10320 or fasteners in their "ready-to-be-fired" positions. In addition, the camming assembly or sled 10330 is located in its proximal-most, "starting" position within the cartridge body 10312. The unspent surgical staple cartridge 10300 is operably seated within the elongate channel 31110 and may be retained therein by snap features on the cartridge body 10312 that are configured to retainingly engage corresponding portions of the elongate channel 31110.

In the illustrated example, the firing member lockout system 34000 comprises a firing member lock 34020 that is configured to block the distal movement of the firing member 33100 from the intermediate closure position to the ending position unless the axially movable camming assembly 10330 in the surgical staple cartridge 10300 that is supported in the elongate channel 31110 is in the starting position. Turning to FIGS. 30, 53, and 54, the firing member lock 34020 is movably supported in a channel cap 34010 that is attached to the bottom of the elongate channel 31110. As can be seen in FIG. 30, a distal end 34012 of the channel cap 30410 may be attached to a channel fastener bracket 34014 that is affixed to the elongate channel 31110. Additionally or in the alternative, the channel cap 34010 may be affixed to the elongate channel 31110 by welding or other suitable adhesive or fastener arrangement.

As can be further seen in FIG. 30, the firing member lock 34020 is movably supported in a lock cavity 34016 that is formed in the channel cap 34010. In addition, the firing member lockout system 34000 comprises a biaser arrangement 34040 that is configured to bias the firing member lock 34020 between a locked position wherein the firing member lock 34020 blocks the distal advancement of the firing member 33100 from the intermediate closure position to the ending position to an unlocked position wherein the firing member lock 34020 does not block or prevent the firing member 33100 from distally moving from the intermediate closure position to the ending position.

Figure 55:
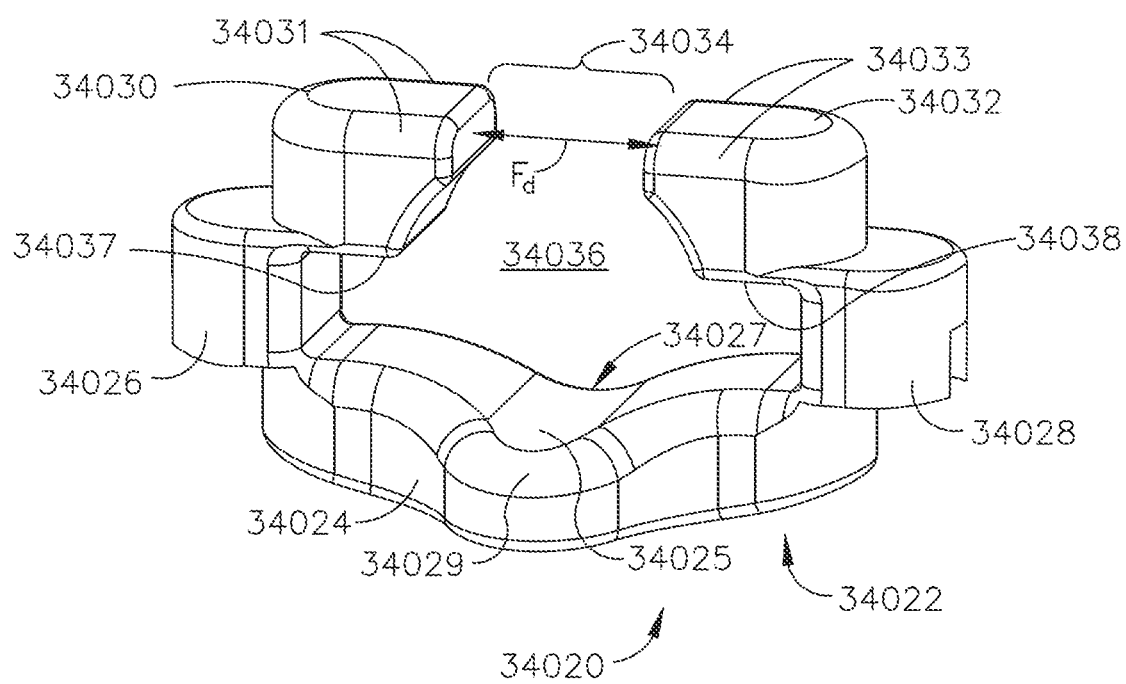
FIG. 55 is a perspective view of a firing member lock of the firing member lockout system of FIG. 53.

FIG. 55 illustrates one form of a firing member lock 34020 that may be employed. As can be seen in FIG. 55, the firing member lock 34020 comprises a lock body 34022 that comprises a bottom lock portion 34024 that is configured to span across a channel axis CA (FIGS. 53 and 54) that is defined by the axially extending channel slot 31111 in the elongate channel 31110. In one example, the biaser arrangement 34040 comprises a right or "first" lock spring 34042 that is located on one (right) lateral side of the channel axis CA and a left or "second" lock spring 34044 located on the other lateral side (left) of the channel axis CA. See FIG. 30. To accommodate the first lock spring 34042, the lock body 34022 further comprises a first spring pocket 34026. See FIG. 55. The lock body 34022 also includes a second spring pocket 34028 that is configured to accommodate the second lock spring 34044. Additionally, the lock body 34022 further comprises a first upper body portion 34030 that is located on the right side of the channel axis CA and a second upper body portion 34032 that is located on the left side of the channel axis CA. The first upper body portion 34030 is spaced from the second upper body portion 34032 a distance $F_d$ that defines a firing member space 34034 that is wide enough to permit passage of the vertically extending firing member body portion 33112 therethrough. See FIGS. 55 and 56. Additionally, the lock body 34022 further defines a central opening 34036 that includes a first or right channel portion 34037 that is configured to accommodate passage of the first bottom tab 33125 therethrough when the firing member lock is in the unlocked position and a second or left channel portion 34038 that is configured to accommodate passage therethrough of the second bottom tab 33127 therethrough when the firing member lock 34020 is in the unlocked position.

Figure 56:
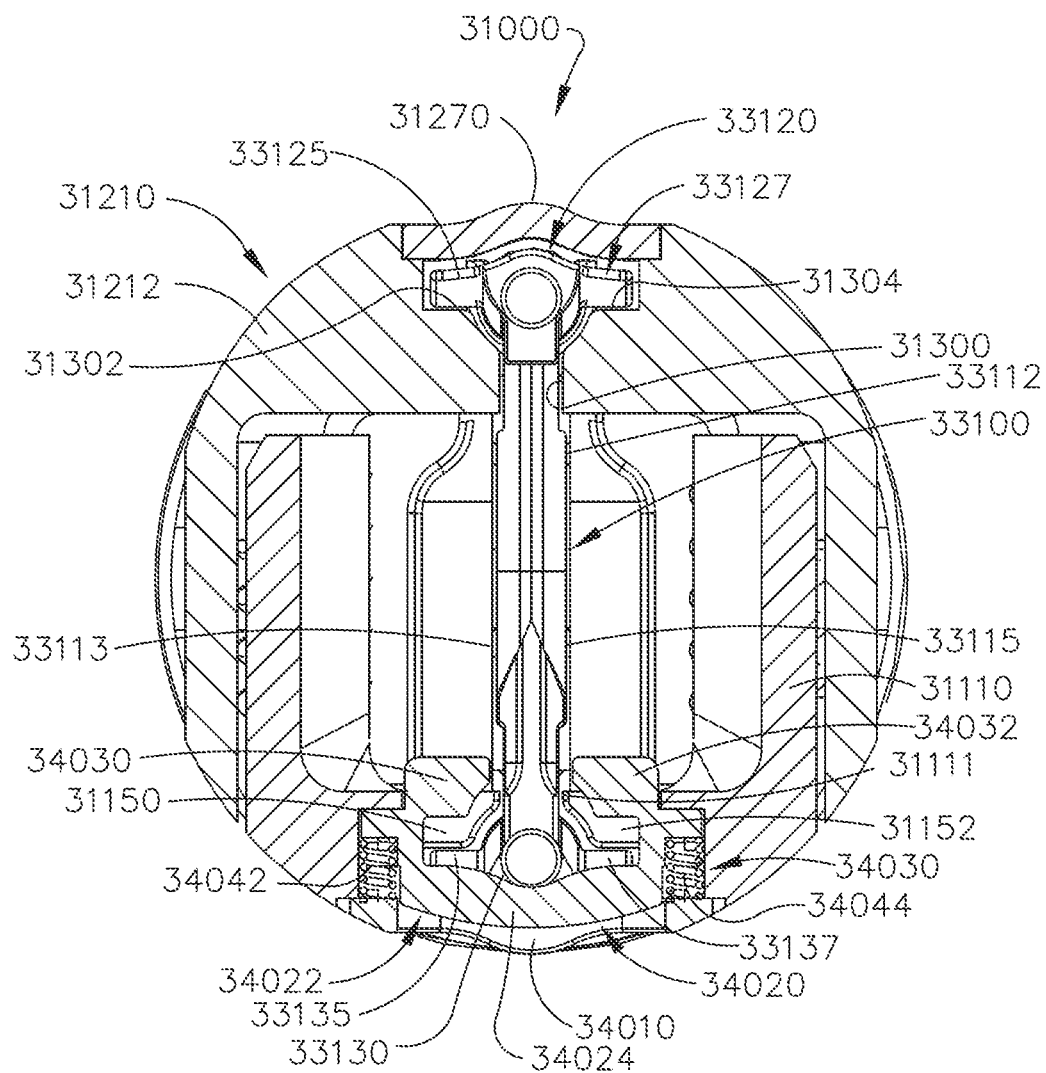
FIG. 56 is a cross-sectional end view of the surgical end effector of FIG. 53 with the firing member lockout system in the locked orientation.

FIGS. 53 and 56 illustrate the surgical end effector 31000 before a staple cartridge has been operably seated in the elongate channel 31110 and when the firing member 33100 is in the intermediate closure position. As can be seen in FIGS. 53 and 56, the biaser arrangement 34030 has biased the firing member lock 34020 upward into a "locked" position. As can be most particularly seen in FIG. 56, when the firing member lock 34020 is in the locked position, the bottom lock portion 34024 is positioned in a blocking orientation relative to the bottom firing member feature 33130. When in that locked position, should the clinician attempt to distally advance the firing member 33100 from the intermediate closure position, the bottom firing member feature 33130 will contact the firing member lock 34020 and be prevented from moving distally beyond that point.

Figure 57:
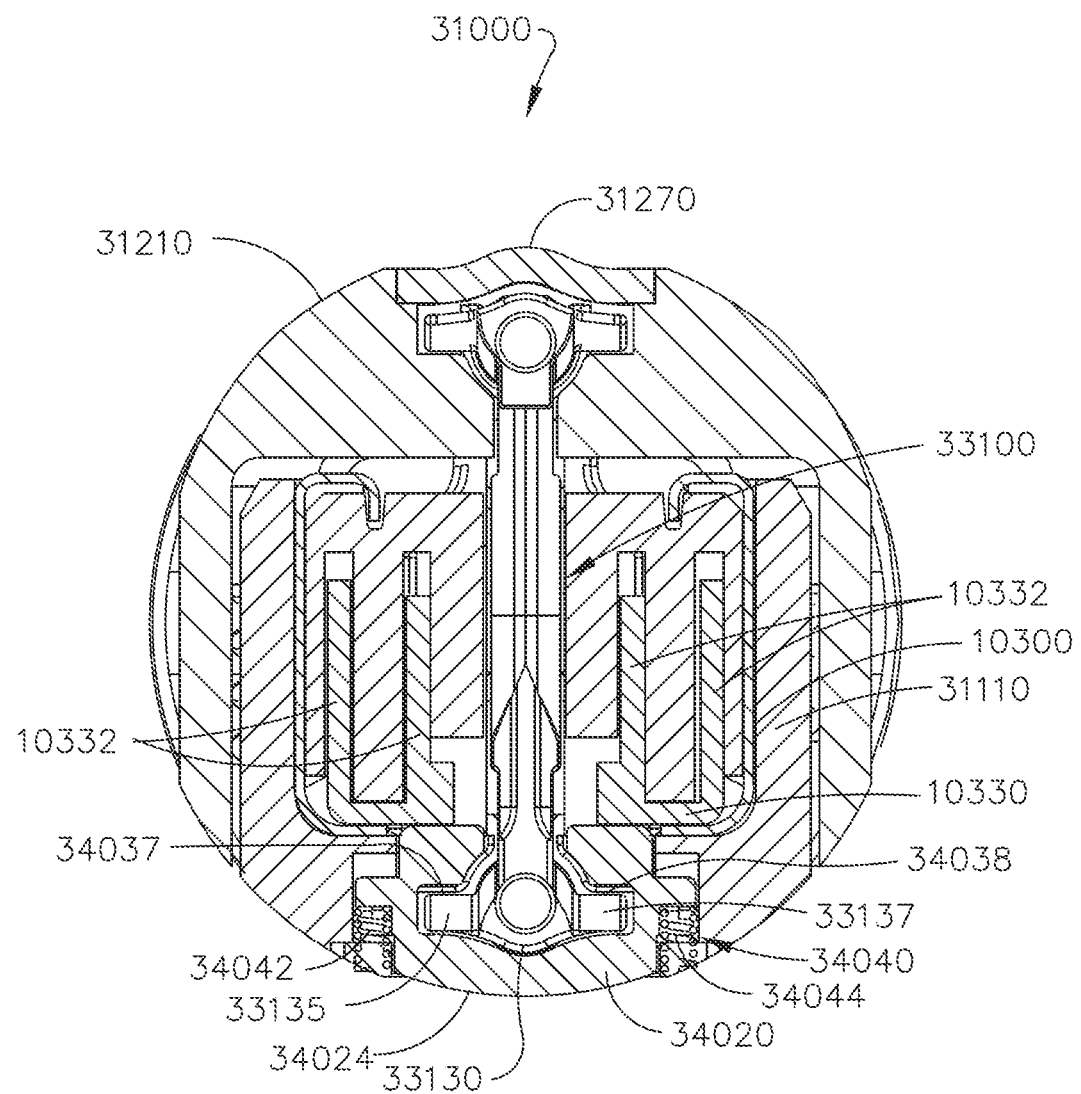
FIG. 57 is another cross-sectional end view of the surgical end effector of FIG. 54 with the firing member lockout system in the unlocked orientation.

FIGS. 54 and 57 illustrate the surgical end effector 31000 after an unspent (new, unfired) surgical staple cartridge 10300 has been operably seated in the elongate channel 31110. As can be seen in FIGS. 54 and 57, the camming assembly 10330 is in the starting position and has biased the firing member lock 34020 into an "unlocked" position against the bias of the biaser arrangement 34040. As can be seen in FIG. 57, when the firing member lock 34020 is in the unlocked position, the central opening 34036 is aligned with the bottom firing member feature 33130. The first channel portion 34037 is aligned with the first bottom tab 33135 of the bottom firing member feature 33130 to permit passage of the first bottom tab 33135 therethrough and the second channel portion 34038 is aligned with the second bottom tab 33137 of the bottom firing member feature 33130 to permit passage of the second bottom tab 33137 therethrough. Thus, when the firing member lock 34020 has been biased into the unlocked position by the camming assembly 10330 in the starting position, the clinician can then distally advance the firing member 33100 from the intermediate closure position to the ending position in the surgical end effector 31000.

As can be seen in FIG. 55, in at least one arrangement, the bottom lock portion 34024 is formed with a central depression or trough 34025 that has a rounded proximal edge 34027 and a rounded distal edge 34029 to allow the bottom push cable or push coil to glide over the bottom lock portion 34024. The rounded proximal edge 34027 may have a radius that is smaller than a radius of the rounded distal edge 34029 to help block the firing member 33100 when the firing member lock 34020 is in the locked position. Also in at least one arrangement, the first upper body portion 34030 is formed with rounded first edges 34031 and the second upper body portion 34032 is formed with rounded second edges 34033. The rounded first edges 34031 and the rounded second edges 34033 enable the camming assembly 10330 to glide over the firing member lock 34020 during the installation of the unspent staple cartridge 10300 into the elongate channel 31110.

Figure 58:
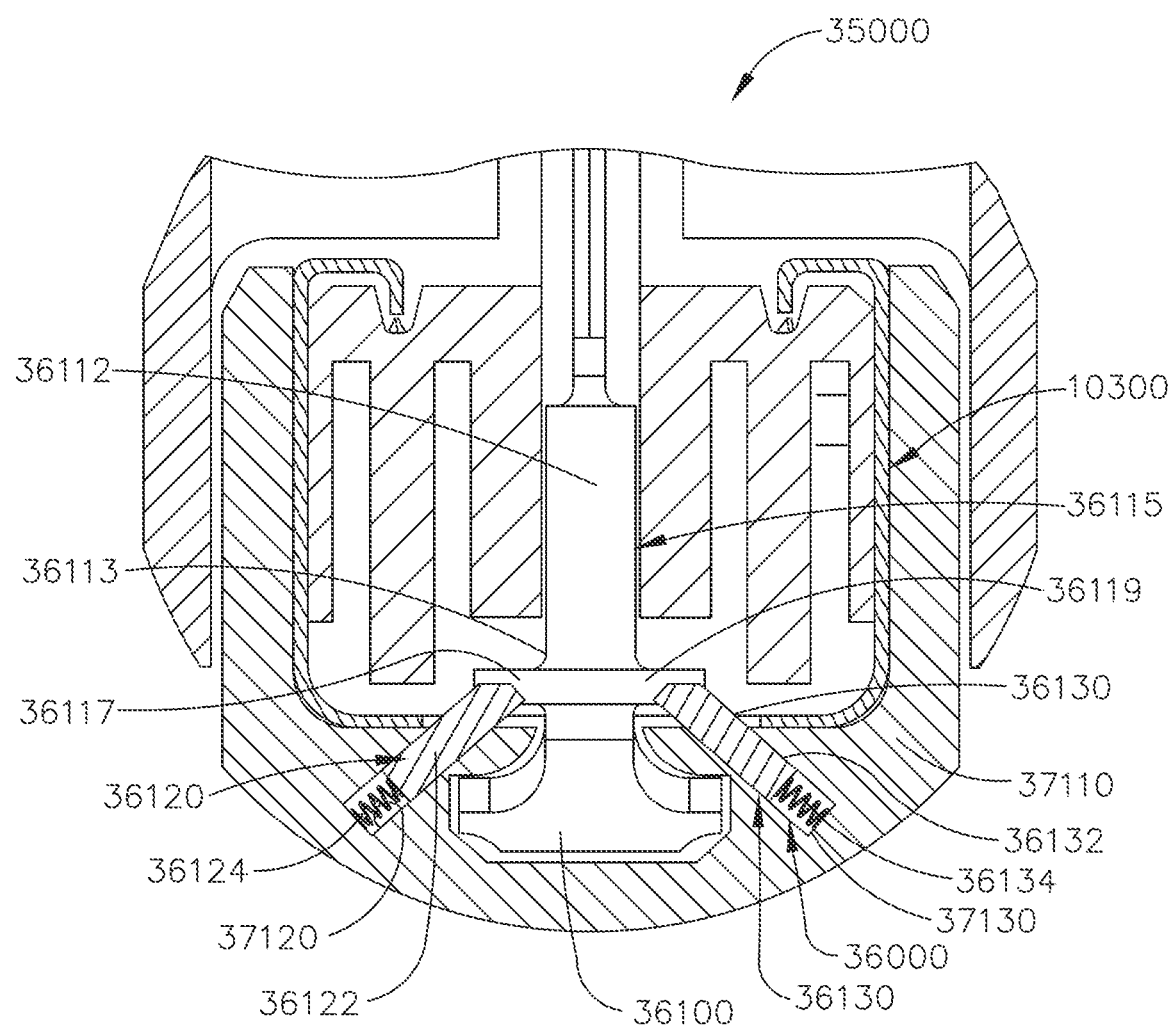
FIG. 58 is a cross-sectional end view of a portion of another surgical end effector with a firing member lockout system thereof in a locked orientation.
Figure 59:
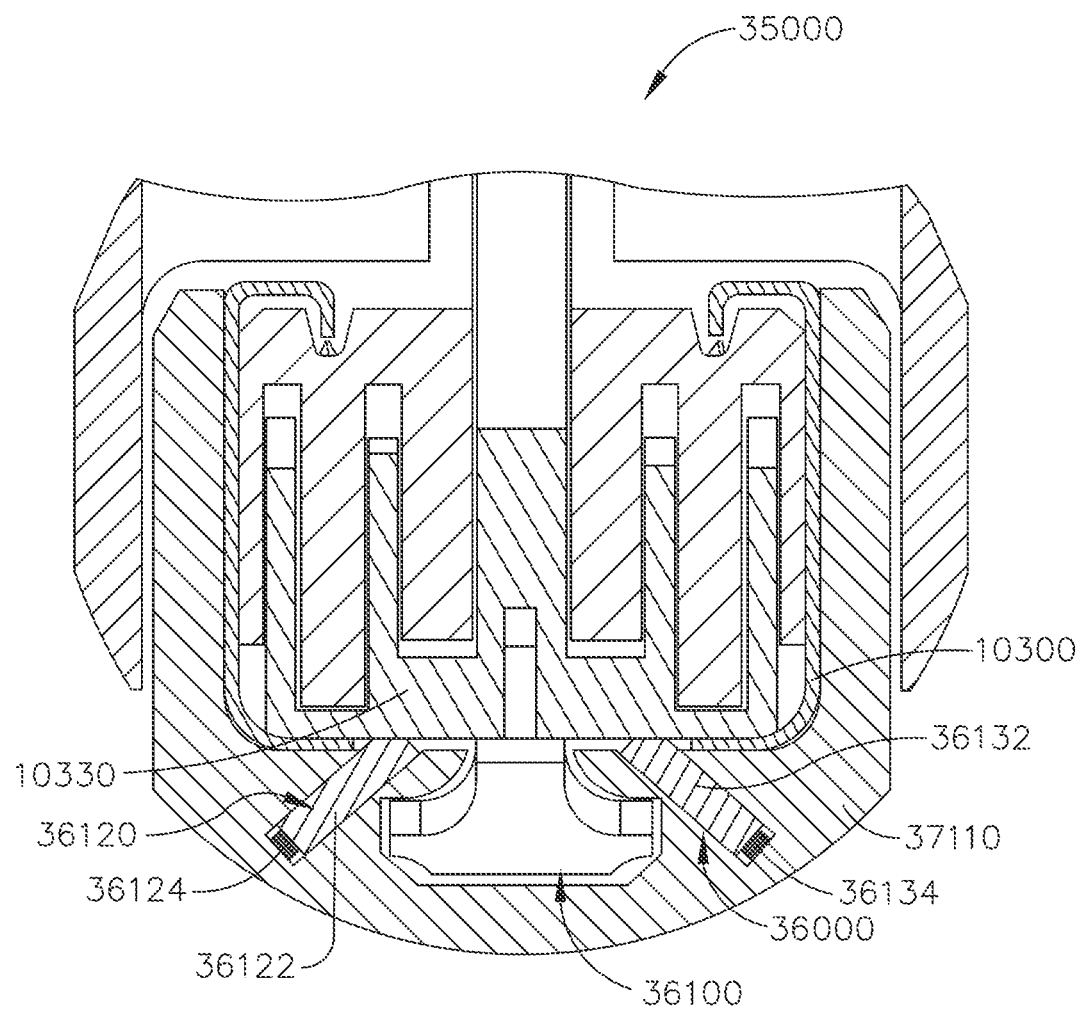
FIG. 59 is another cross-sectional end view of the surgical end effector of FIG. 58 with an unspent surgical staple cartridge installed therein and with the firing member lockout system in an unlocked orientation.

FIGS. 58 and 59 illustrate an alternative firing member lock system generally designated as 36000 that prevents a firing member 36100 from moving distally from its intermediate closure position to its ending position within the surgical end effector 35000 unless an "unfired", "unspent", "fresh" or "new" surgical staple cartridge 10300 has been properly seated within an elongate channel 37110 of the surgical end effector 35000. In the illustrated example, the firing member lockout system 36000 comprises a right firing member lock 36120 that is configured to contact a first portion or first formation 36117 formed on a first lateral side 36113 of the firing member body 36112. In one arrangement, the right firing member lock 36120 comprises a right or "first" lock feature 36122 that is slidably received in a first lock channel 37120 formed in the elongate channel 37110. A first biasing member in the form of a first spring 36124 is attached to the bottom surface of the channel 37120 and the end of the right lock feature 36122 as shown. Such arrangement serves to bias the first lock feature 36122 into engagement with the first formation 36117 on the firing member body 36112 when the firing member 36100 is in the intermediate closure position and either no surgical staple cartridge has been seated in the elongate channel 37110 or a spent or partially-fired surgical staple cartridge (a surgical staple cartridge that has a camming assembly that is not in the starting position—see FIG. 58) has been seated in the elongate channel 31110. However, when an unspent surgical staple cartridge 10300 has been seated into the elongate channel 37110 (FIG. 59), a camming assembly 10330 in the surgical staple cartridge 10300 will bias the first lock feature 36122 into an unlocked position wherein the firing member 36100 and the camming assembly 10330 may be advanced distally from the closure or beginning position. See FIG. 59.

As can be seen in FIG. 58, the firing member lockout system 36000 may further comprises a left or "second" firing member lock 36130 that is configured to contact a second portion or second formation 36119 formed on a second lateral side 36115 of the firing member body 36112. In one arrangement, the second firing member lock 36130 comprises a left or "second" lock feature 36132 that is slidably received in a second lock channel 37130 formed in the elongate channel 37110. A second biasing member in the form of a second spring 36134 is attached to the bottom surface of the channel 37130 and the end of the second lock feature 36132 as shown. Such arrangement serves to bias the second lock feature 36132 into engagement with the second formation 36119 on the firing member body 36112 when the firing member 36100 is in the intermediate closure position and either no staple cartridge has been seated in the elongate channel 37110 or a spent or partially fired cartridge (a cartridge wherein the camming assembly thereof is not in the starting position—see FIG. 58) has been seated in the elongate channel 31110. However, when an unspent surgical staple cartridge 10300 has been seated into the elongate channel 31110 (FIG. 59), the camming assembly 10330 will bias the second lock feature 36132 into an unlocked position wherein the firing member 36100 and the camming assembly 10330 may be advanced distally from the beginning and closure position. The first formation 36117 on the firing member 36100 is configured to bias the first lock feature 36122 into the unlocked position when the firing member 36100 is being retracted from the ending position back to the beginning position. Similarly, the second formation 36119 on the firing member 36100 is configured to bias the second lock feature into the unlocked position when the firing member 36100 is being retracted from the ending position back to the beginning position. Once the first formation 36117 disengages the first lock feature 36122 and the second formation disengages the second lock feature 36132, the first lock feature 36122 and the second lock feature 36132 return to the locked position. In an alternative arrangement, only one of the first lock feature 36122 and second lock feature 36132 may be employed and otherwise operate in the manner disclosed above.

Figure 60:
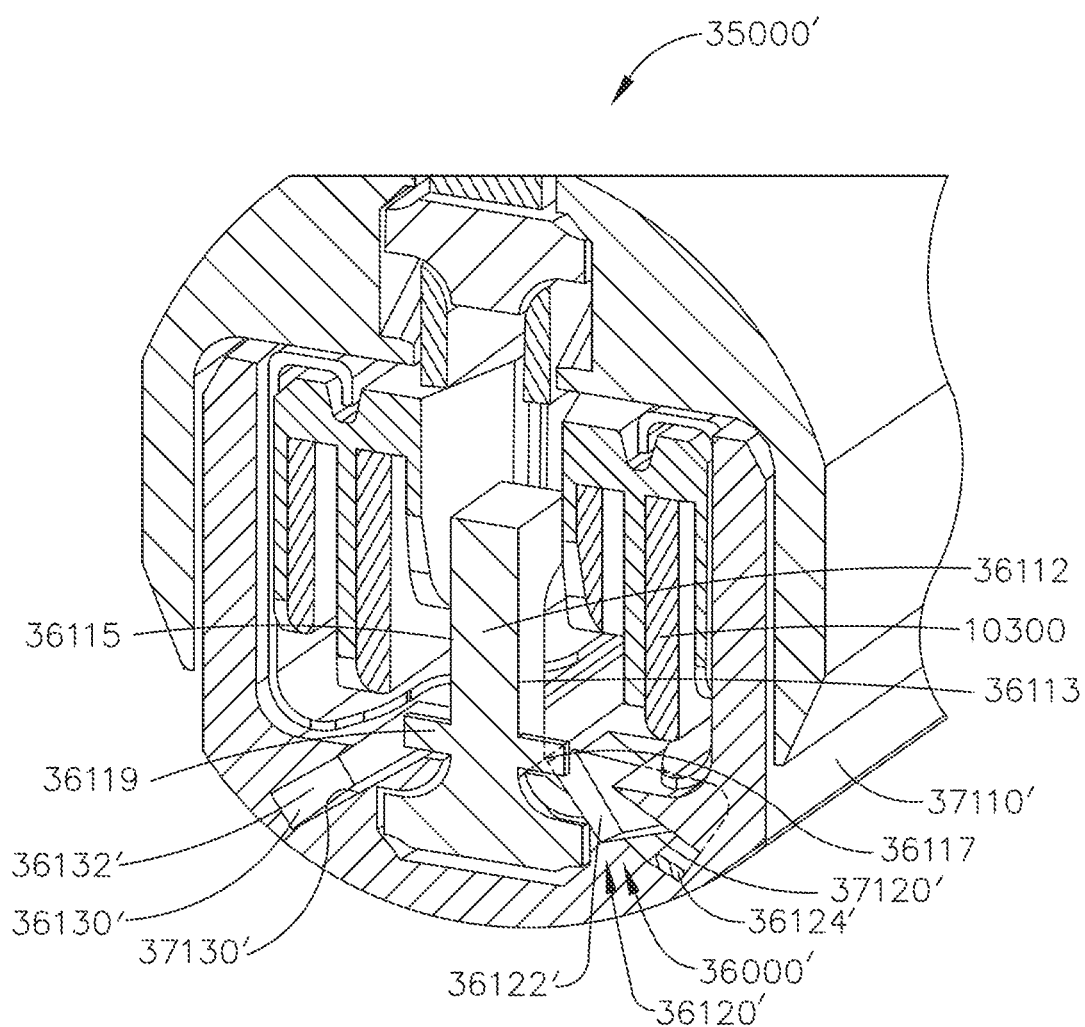
FIG. 60 is a partial cross-sectional perspective view of a portion of another surgical instrument with a firing member lockout system thereof in a locked orientation.

FIG. 60 illustrates an alternative surgical end effector 35000' that employs an alternative firing member lock system generally designated as 36000' that prevents a firing member 36100 from moving distally from its intermediate closure position to its ending position within the surgical end effector 35000' unless an "unfired", "unspent", "fresh" or "new" surgical staple cartridge 10300 has been properly seated within an elongate channel 37110' of the surgical end effector 35000'. In the illustrated example, the firing member lockout system 36000' comprises a right firing member lock 36120' that is configured to contact a first portion or first formation 36117 formed on a first lateral side 36113 of the firing member body 36112. In one arrangement, the right firing member lock 36120' comprises a right or "first" lock feature 36122' that is pivotably supported in a first lock channel 37120' that is formed in the elongate channel 37110'. A first biasing member in the form of a first spring 36124' is supported within the first lock channel 37120' to pivotably bias the first lock feature 36122' into engagement with the first formation 36117 on the firing member body 36112 when the firing member 36100 is in the closed or beginning position and either no staple cartridge has been seated in the elongate channel 37110' or a spent or partially fired cartridge (a cartridge wherein the camming assembly thereof is not in the starting position—see FIG. 60) has been seated in the elongate channel 31110'. However, when an unspent surgical staple cartridge 10300 has been seated into the elongate channel 37110', a camming assembly 10330 (in its starting position) in the surgical staple cartridge 10300 will bias the first lock feature 36122' into an unlocked position wherein the firing member 36100 and the camming assembly 10330 may be advanced distally from the closure or beginning position.

As can be seen in FIG. 60, the firing member lockout system 36000' may further comprises a left or "second" firing member lock 36130' that is configured to contact a second portion or second formation 36119 formed on a second lateral side 36115 of the firing member body 36112. In one arrangement, the second firing member lock 36130' comprises a left or "second" lock feature 36132' that is slidably received in a second lock channel 37130 formed in the elongate channel 37110. A second biasing member in the form of a second spring 36134 is supported within the second lock channel 37130'. Such arrangement serves to bias the second lock feature 36132' into engagement with the second formation 36119 on the firing member body 36112 when the firing member 36100 is in the closed position and either no staple cartridge has been seated in the elongate channel 37110' or a spent or partially fired cartridge (a cartridge wherein the camming assembly thereof is not in the starting position—see FIG. 60) has been seated in the elongate channel 31110'. However, when an unspent surgical staple cartridge 10300 has been seated into the elongate channel 31110, the camming assembly 10330 will bias the second lock feature 36132' into an unlocked position wherein the firing member 36100 and the camming assembly 10330 may be advanced distally from the beginning and closure position. The first formation 36117 on the firing member 36100 is configured to bias the first lock feature 36122' into the unlocked position when the firing member 36100 is being retracted from the ending position back to the closure and/or beginning position. Similarly, the second formation 36119 on the firing member 36100 is configured to bias the second lock feature into the unlocked position when the firing member 36100 is being retracted from the ending position back to the beginning position. Once the first formation 36117 disengages the first lock feature 36122' and the second formation disengages the second lock feature 36132, the first lock feature 36122' and the second lock feature 36132' return to the locked position. In an alternative arrangement, only one of the first lock feature 36122' and second lock feature 36132' may be employed and otherwise operate in the manner disclosed above.

Figure 61:
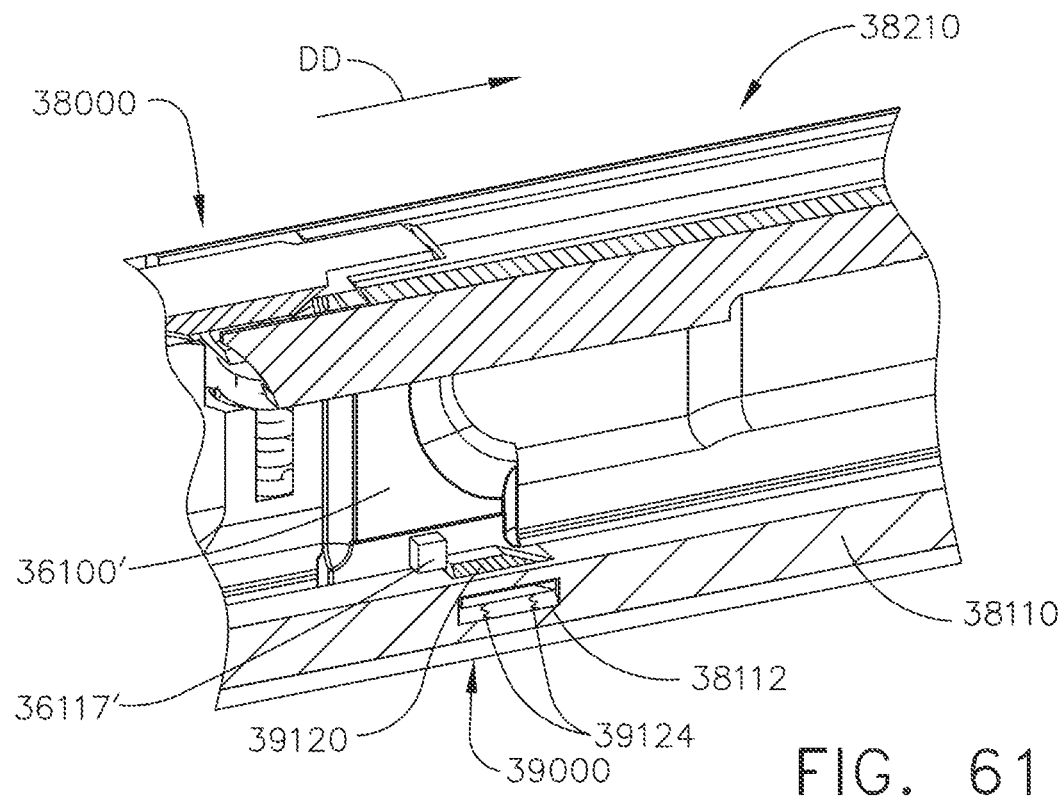
FIG. 61 is a cross-sectional side view of a portion of another surgical end effector with the firing member lockout system thereof in a locked orientation.
Figure 62:
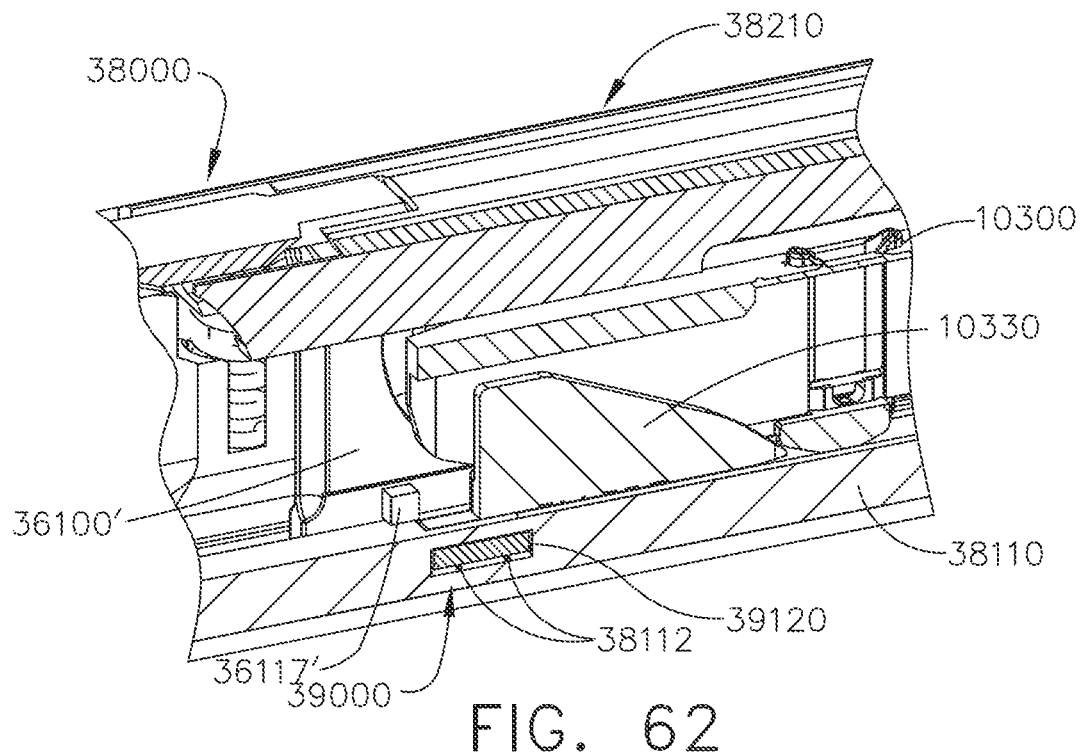
FIG. 62 is another cross-sectional side view of the surgical end effector of FIG. 61 with the firing member lockout system in an unlocked orientation.

FIGS. 61 and 62 illustrate an alternative firing member lock system generally designated as 39000 that is configured to prevent a firing member 36100' from moving distally from its intermediate closure position to its ending position within a surgical end effector 38000 unless an "unfired", "unspent", "fresh" or "new" surgical staple cartridge 10300 has been properly seated within an elongate channel 38110 of the surgical end effector 38000. In the illustrated example, the firing member lock system 39000 comprises a firing member lock 39120 that is configured to contact a lock portion 36117' that is formed on or otherwise protrudes from the firing member body 36100'. In one arrangement, the firing member lock 39120 is movably supported in a lock cavity 38112 that is formed in the elongate channel 38110. In the illustrated example, a pair of biasing members in the form of springs 39124 serve to bias the firing member lock 39120 into a locked position wherein the firing member lock 39120 blockingly engages the lock portion 36117' on the firing member body 36112'. FIG. 61 illustrates the surgical end effector 38000 with the firing member 36100' in an intermediate closure position that corresponds to the closed position of an anvil 38210 of the surgical end effector, but no staple cartridge has been seated into the elongate channel 38110. As can be seen in FIG. 61, the firing member lock 39120 is blocking the distal advancement of the firing member 36100' from the intermediate closure position. FIG. 62 illustrates the surgical end effector 38000 after an unspent surgical staple cartridge 10300 has been seated in the elongate channel 38110 and the firing member 36100' is in the intermediate closure position. As can be seen in FIG. 62, a camming assembly 10330 of the unspent surgical staple cartridge 10300 is in a starting position wherein the camming assembly 10330 has depressed or otherwise moved the firing member lock 39120 into an "unlocked" position wherein the firing member 36100" may be distally advanced from the intermediate closure position. As can be seen in FIGS. 61 and 62, the firing member lock 39120 is formed with a distally-facing tapered surface or ramp 39126 that facilitates the depression of the firing member 39120 by the lock portion 36117' on the firing member 36100' into the lock cavity 38112 to permit the firing member 36100' to be retracted back to the beginning position. In an alternative arrangement, another lock portion 36117' protrudes from an opposite side of the firing member 36100' and is configured to operably interact in the above-described manner with another corresponding firing member lock 39120. The another firing member lock 39120 is configured to be moved from the locked position to the unlocked position by the camming assembly 10330 in the above-described manner.

Figure 63:
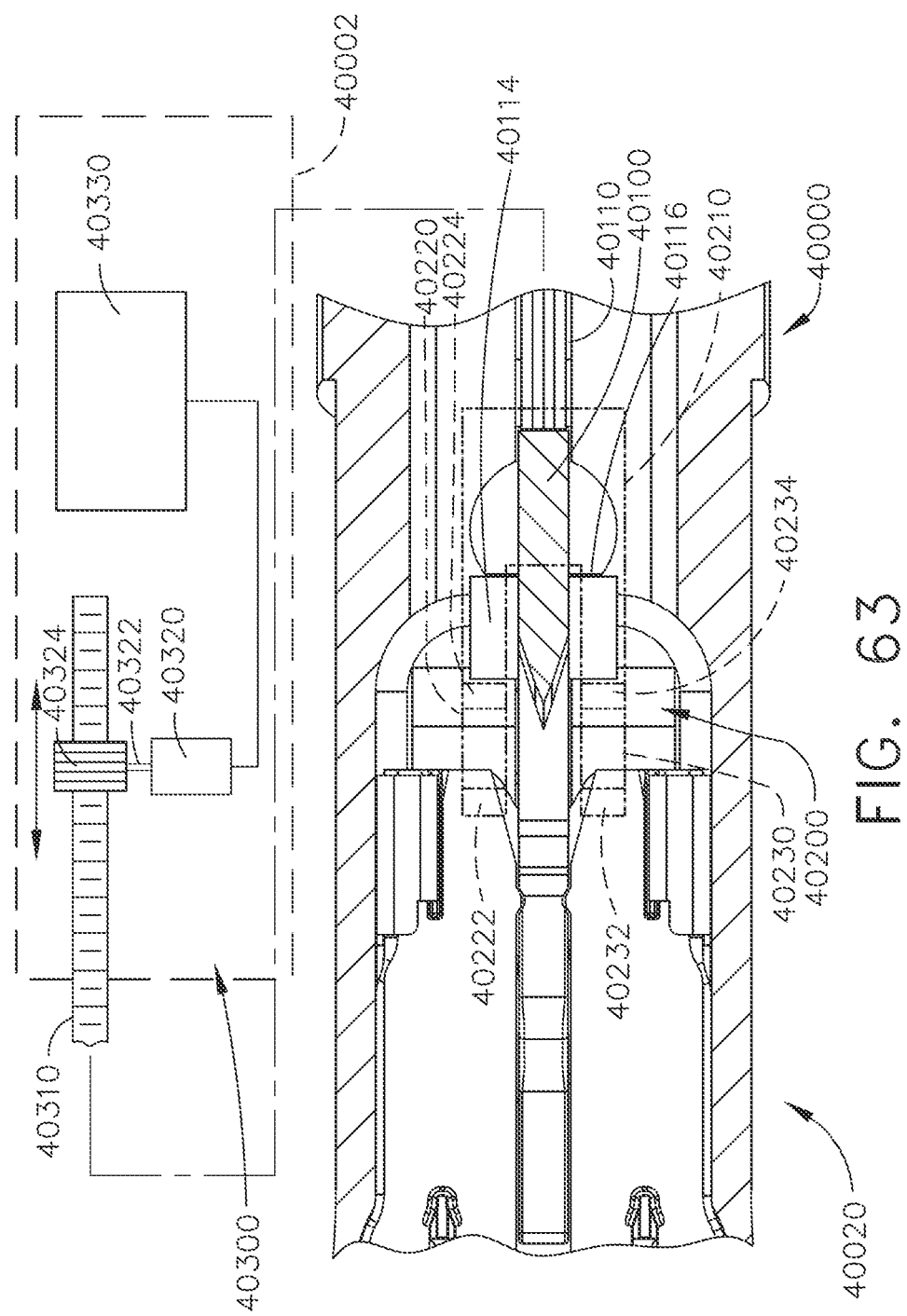
FIG. 63 is a partial cross-sectional top view of portion of another surgical end effector of a surgical instrument in accordance with another general aspect of the present disclosure.
Figure 64:
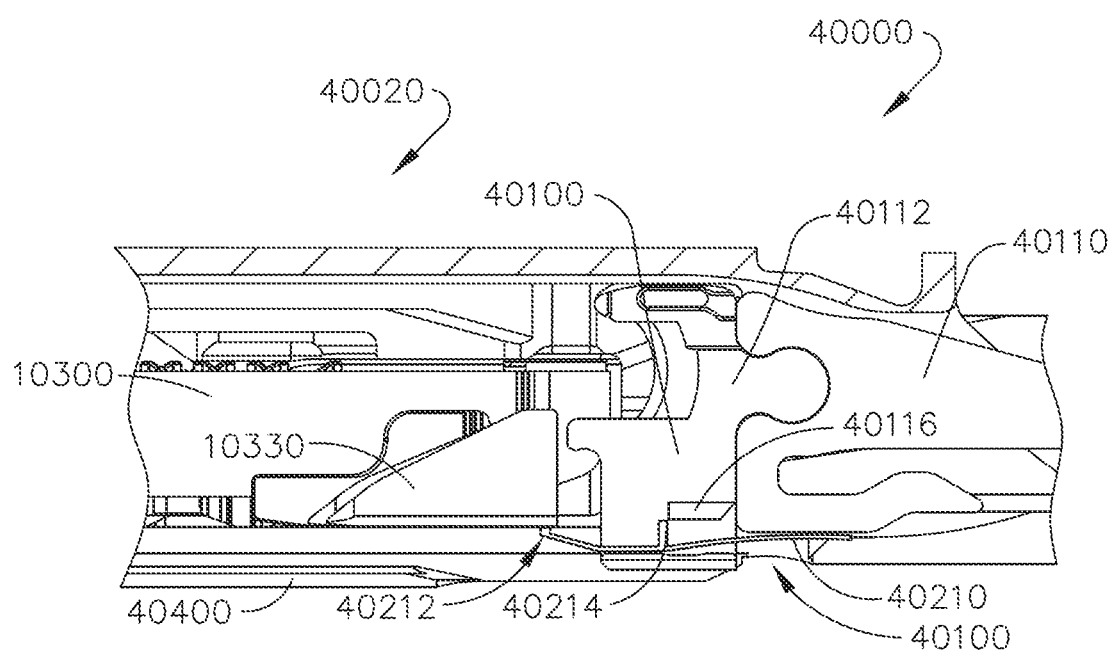
FIG. 64 is a partial cross-sectional side view of the surgical end effector of FIG. 63 with a firing member lockout system thereof in an unlocked orientation.
Figure 65:
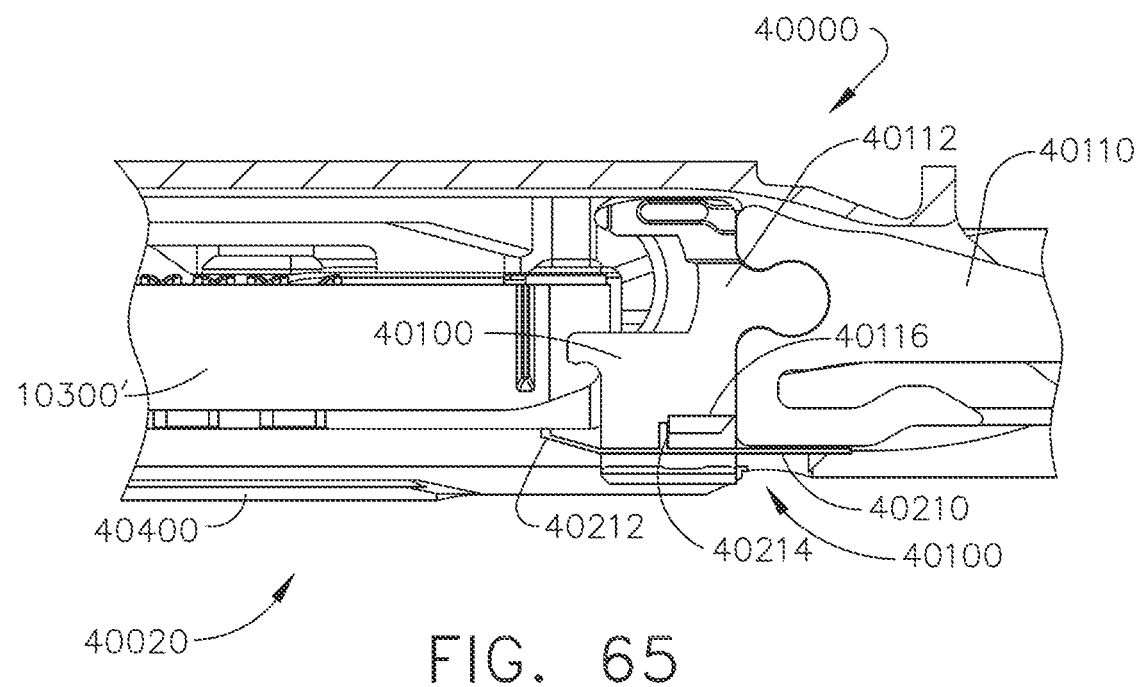
FIG. 65 is another partial cross-sectional side view of the surgical end effector of FIG. 63 with the firing member lockout system in a locked configuration.

An alternative firing member lockout system 40200 that is configured to prevent a firing member 40100 of surgical end effector 40020 of a surgical instrument 40000 from distally advancing from an intermediate closure position to an ending position unless an unspent staple cartridge has been seated in the surgical end effector 40000 is depicted in FIGS. 63-65. FIG. 63 illustrates one form of firing member drive system 40300 that may be employed to drive and retract the firing beam 40110 and the firing member 40100 that is coupled thereto. As can be seen in FIG. 63, the firing beam 40110 may comprise a firing beam gear rack 40310 that is attached to or otherwise associated with the firing beam 40110. The firing member drive system 40300 may further comprise a firing drive motor 40320 that is configured to drive a drive gear 40324 that is in meshing engagement with the firing beam gear rack 40310. The drive gear 40322 is coupled to an output shaft 40322 of the drive motor 40320. Rotation of the output shaft 40322 in a first rotary direction will drive the firing member 40100 distally between a beginning position, an intermediate closure position, and an ending position within the surgical end effector 40000 and rotation of the output shaft 40322 of the firing drive motor 40320 in a second opposite rotary direction will drive the firing member 40100 proximally from the ending position back to the beginning position. In one arrangement, the firing drive motor 40320 is controlled by a motor control system 40330 that may comprise a microprocessor-controlled control circuit 40332 that may be housed in an instrument housing 40002, associated with an instrument housing, and/or comprise a portion of a robotic system or other automated surgical system. For example, in one arrangement, the motor control system 40330 monitors the amount of firing current $I_F$ drawn by the drive motor 40320 during the initiation of the firing stroke in which the firing member drive system 40300 drives the firing member 40110 distally from the intermediate closure position to the ending position.

Turning to FIGS. 64 and 65, the firing member lockout system 40200 may further comprise a friction-generating spring 40210 that is supported within an elongate channel 40400 of the surgical end effector 40020. In the example depicted in FIGS. 64 and 65, the friction-generating spring 40210 comprises a right spring arm 40220 corresponding to a right side of the firing member 40110 and a left spring arm 40230 corresponding to a left side of the firing member 40110. The right spring arm 40220 comprises a right actuator end portion 40222 and a right upstanding retention tab portion 40224. Similarly, the left spring arm 40230 comprises a left actuator end portion 40232 and a left upstanding retention tab portion 40234. The friction-generating spring 40210 is mounted in the elongate channel 40400 with a normal bias such that the right retention tab portion 40214 is biased into a "locked" position wherein the right retention tab portion 40224 is in confronting alignment with a right lock lug 40114 on the firing member body 40112 and the left retention tab portion 40234 is on confronting alignment with a left lock lug 40116 on the firing member body 40112. See FIG. 65.

FIG. 64 depicts an unspent surgical staple cartridge 10300 properly seated in the elongate channel 40400. As indicated above, an unspent surgical staple cartridge 10300 contains surgical staples in their respective ready-to-fire positions and comprises a camming assembly 10330 in a starting position. When the camming assembly 10330 is in the unfired or starting position, the camming assembly 10330 will contact the right actuator end portion 40222 and the left actuator end portion 40232 of the friction-generating spring 40210 to thereby bias the right actuator end portion 40222 out of confronting alignment with the right lock lug 40114 and the left actuator end portion 40232 out of confronting alignment with the left lock lug 40116. See FIG. 64. When the friction-generating spring 40210 is in that "unlocked" position, the friction-generating spring 40210 may not apply any meaningful frictional resistance to the firing member 40110 as the firing member 40110 is driven distally from the intermediate closure position.

FIG. 65 illustrates the position of the friction-generating spring 40210 after the camming assembly 10330 in the surgical staple cartridge 10300 has been advanced distally out of the starting position which may be indicative of the staple cartridge being partially or completely fired. In either case, the surgical staple cartridge 10300' depicted in FIG. 65 is no longer an unspent surgical staple cartridge. As can be seen in FIG. 65, because the "spent" surgical staple cartridge 10300' in the surgical end effector 40020 lacks the camming assembly 10330 in the ready-to-fire or starting position, the friction-generating spring 40210 is in the locking position (e.g., the right retention tab portion 40224 is in confronting alignment with a right lock lug 40114 on the firing member body 40112 and the left retention tab portion 40234 is on confronting alignment with a left lock lug 40116 on the firing member body 40112). If the clinician attempts to fire (distally advance the firing member 40110 from the intermediate closure position) when the retention tab portions 40224, 40234 are in the locking position) the right lock lug 40114 will contact the right retention tab portion 40224 and the left lock lug 40116 will contact left retention portion 40234 which will increase an amount of frictional resistance experienced by the firing member 40110. Thus, the amount of drive force required to be generated by the firing drive motor 40320 to overcome such additional frictional resistance must also be increased which may require the firing drive motor 40320 to draw an increased amount of firing current $I_F$. The motor controlled system 40330 may be configured to discontinue actuation of the firing drive motor 40320 when the firing current exceeds a predetermined magnitude that is indicative of the increased frictional resistance applied to the firing member 40110 by the firing member lockout system 40200 when an unspent staple cartridge has not been properly seated in the surgical end effector 40020.

Figure 66:
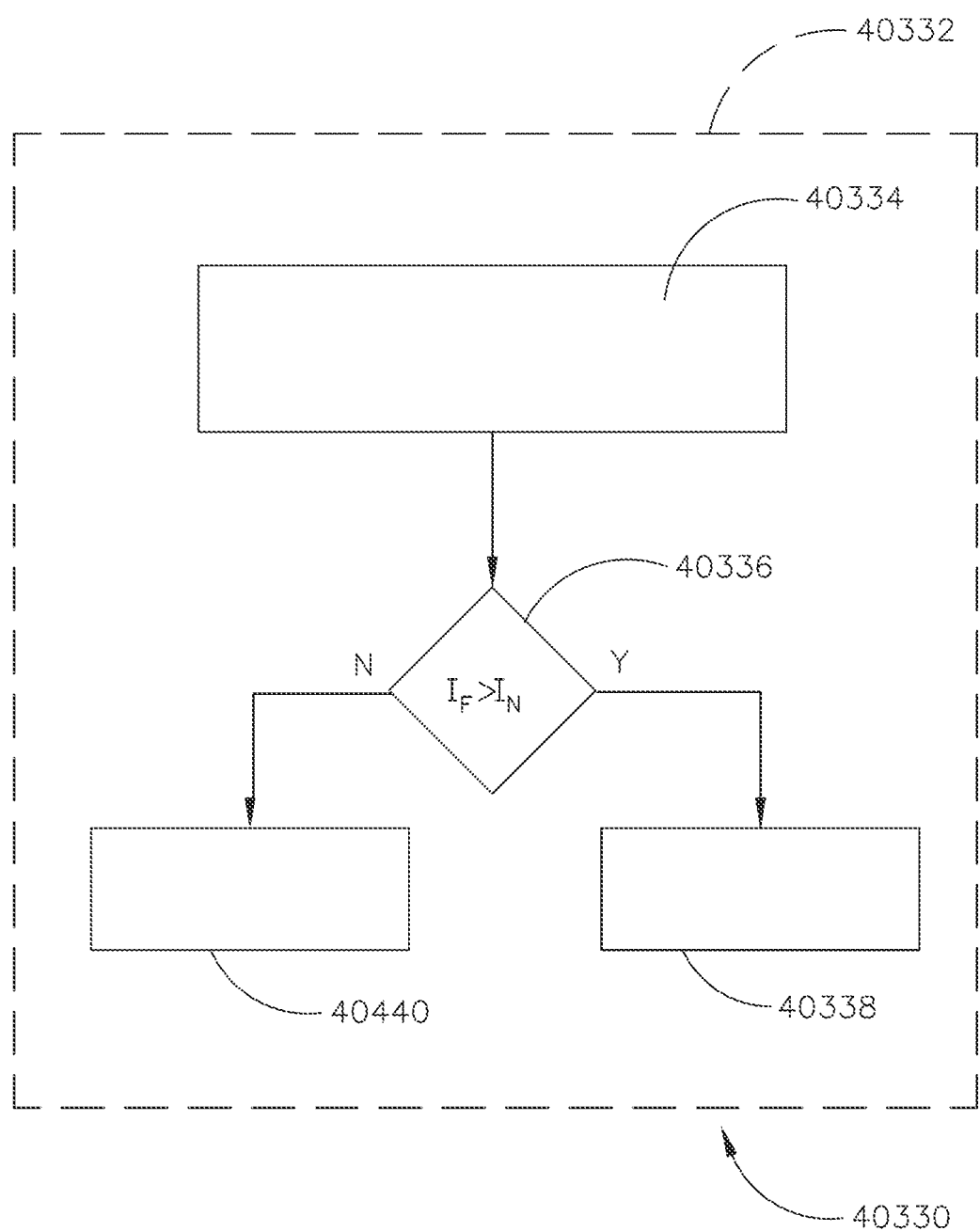
FIG. 66 depicts an example of a control circuit arrangement of the surgical instrument of FIG. 63.

FIG. 66 illustrates one form of a motor controlled system 40330 that may be implemented by a corresponding microprocessor and/or control circuit 40332. As can be seen in FIG. 66, the control circuit 40332 implements an action 40334 to determine an amount of firing current $I_F$ that is being drawn by the firing drive motor 40320 when attempting to drive the firing member 40110 distally from the intermediate closure position. Stated another way, in action 40334, the control circuit 40332 powers the firing drive motor 40320 to drive the firing member 40110 distally from the intermediate closure position. In action 40336, the control circuit compares the firing current $I_F$ drawn by the firing drive motor 40320 in action 40334 to an acceptable range of firing current $I_N$ that the firing drive motor 40320 would normally draw when the firing drive motor 40320 is driving the firing member 40110 distally from the intermediate closure position and the right retention tab 40222 and the left retention tab 40232 are in the unlocked positions. If $I_F > I_N$, which is indicative of no unspent staple cartridge being loaded into the surgical end effector, the control circuit 40332 stops actuation of the firing drive motor 40320 in action 40338. If $I_F \leq I_N$, which is indicative of an unspent surgical staple cartridge 10300 loaded into the surgical end effector, the control circuit 40332 continues to power the firing drive motor 40320 to drive the firing member 40110 from the intermediate closure position to the ending position. In another arrangement, when the monitored firing current $I_F$ exceeds the acceptable range of current $I_N$ by a predetermined amount, the control circuit 40332 will stop the firing drive motor 40320. This "load" monitoring arrangement may be employed in connection with any of the firing member lock arrangements disclosed herein. In robotic systems, the control circuit will perform a "homing" operation on the surgical instrument whenever the surgical instrument is installed on the robot. During this homing step, the control system will check current loads and other loads and positions of its different drive systems to ensure that the surgical instrument is ready for use. Thus, if during this homing operation, the firing drive motor attempts to distally advance the firing member and a spike in the motor current is detected, the control circuit will stop powering the firing drive motor. Such spike in current is caused by the frictional resistance that is applied to the firing member by the firing member lock system when an unspent cartridge has not been loaded into the surgical end effector of the surgical instrument.

Figure 67:
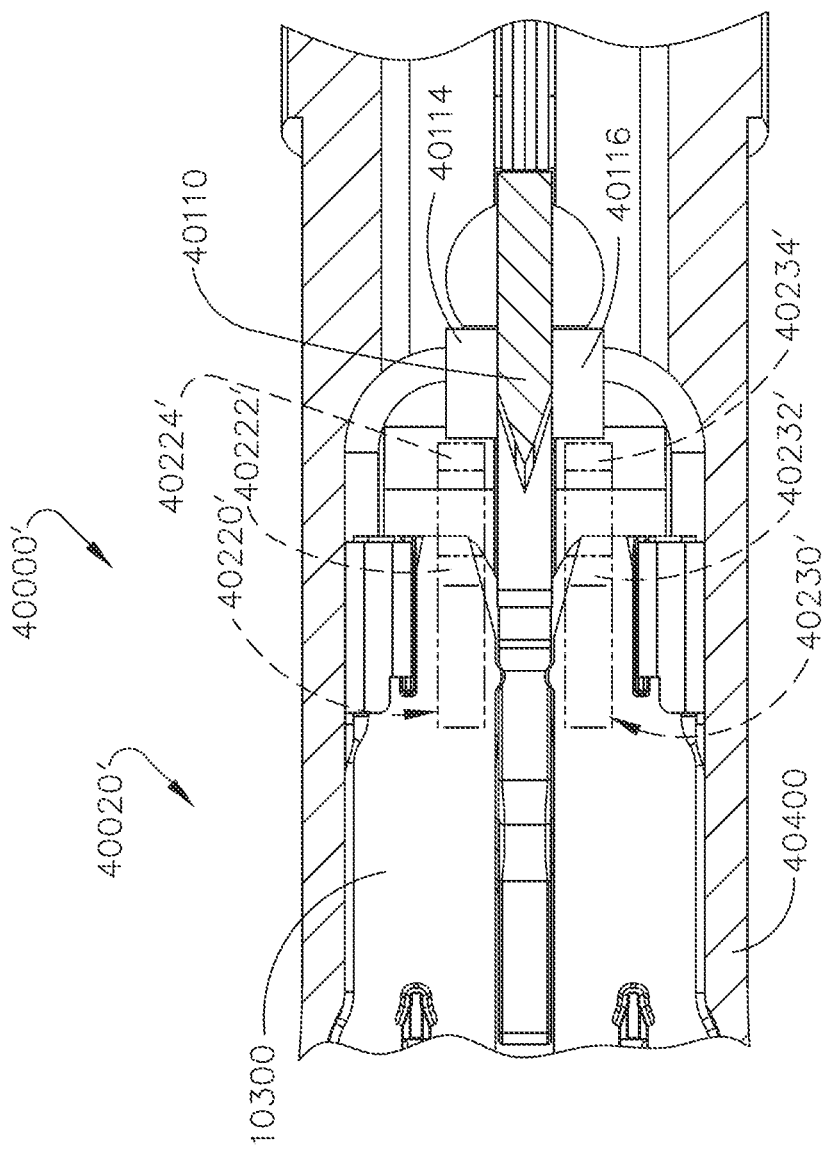
FIG. 67 is a partial cross-sectional top view of portion of another surgical end effector of a surgical instrument in accordance with another general aspect of the present disclosure.
Figure 68:
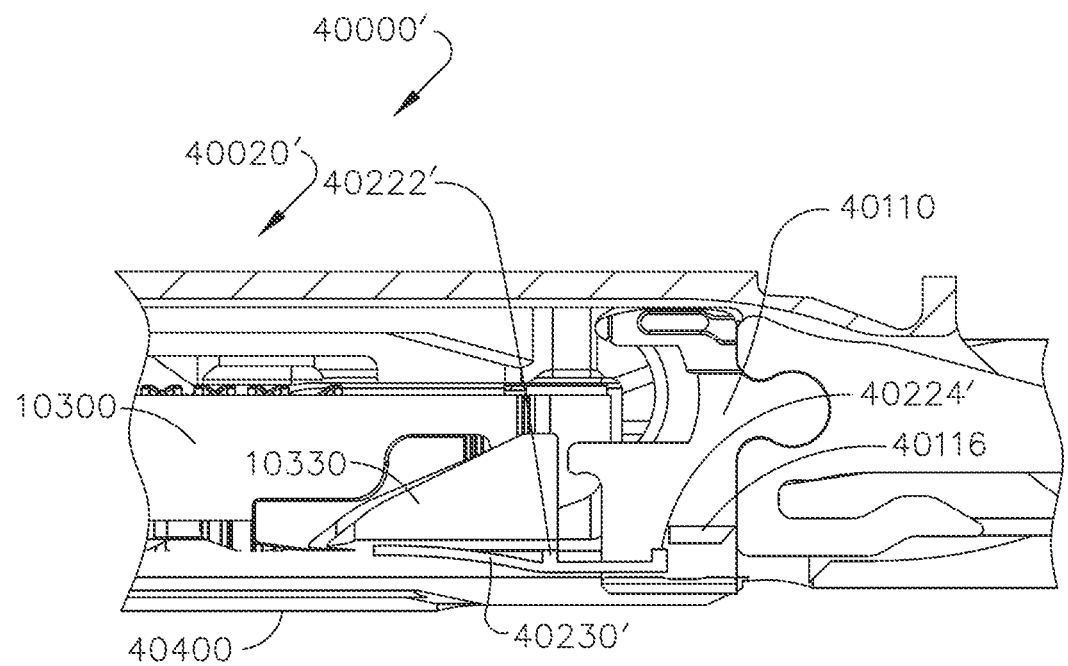
FIG. 68 is a partial cross-sectional side view of the surgical end effector of FIG. 67 with a firing member lockout system thereof in an unlocked orientation.
Figure 69:
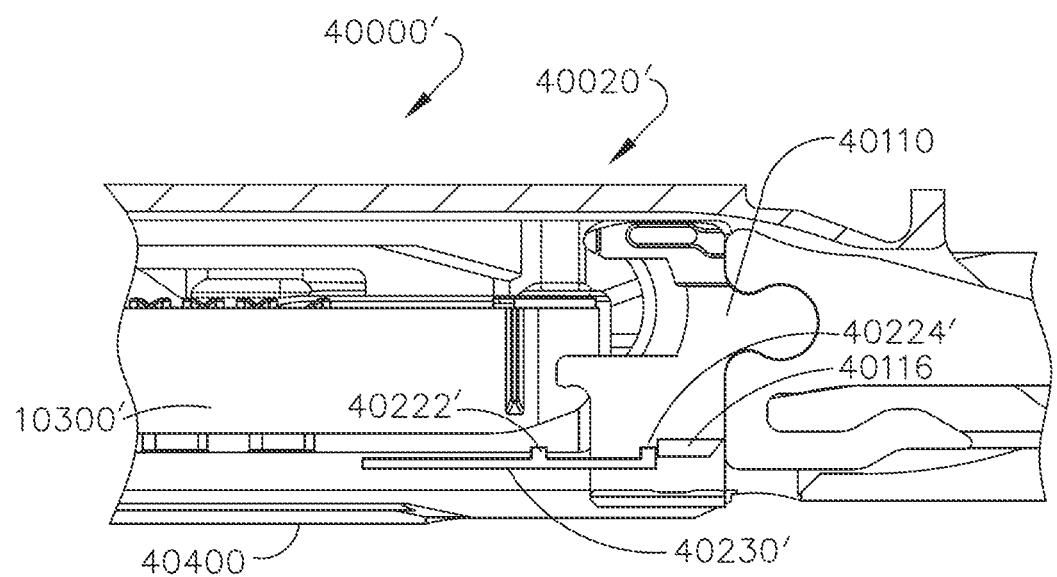
FIG. 69 is a partial cross-sectional side view of the surgical end effector of FIG. 67 with a firing member lockout system thereof in a locked orientation.

FIGS. 67-69 illustrate another surgical instrument 40000' and surgical end effector 40020' that is identical or very similar to the surgical end effector 40020 and surgical instrument 40000 described in detail above except for the differences discussed below. For example, the surgical end effector 40020' comprises an alternative friction-generating arrangement that comprises a right friction-generating spring 40220' that corresponds to a right side of the firing member 40110 and a left friction-generating spring 40230' that corresponds to a left side of the firing member 40110. The right friction-generating spring 40220' is mounted in the elongate channel 40400 and comprises a right actuator portion 40222' and a right upstanding retention tab portion 40224'. Similarly, the left friction-generating spring arm 40230' comprises a left actuator portion 40232' and a left upstanding retention tab portion 40234'. The right friction-generating spring 40220' is mounted in the elongate channel 40400 such that the right retention tab portion 40224' is in a "locked" position wherein the right retention tab portion 40224' is in confronting alignment with a right lock lug 40114 on the firing member body 40112. Similarly, the left friction-generating spring 40230' is mounted in the elongate channel 40400 such that the left retention tab portion 40234' is in confronting alignment with a left lock lug 40116 on the firing member body 40112. See FIG. 67.

FIG. 68 depicts an unspent surgical staple cartridge 10300 properly seated in the elongate channel 40400. As indicated above, an unspent surgical staple cartridge 10300 contains surgical staples in their respective ready-to-fire positions and comprises a camming assembly 10330 in a starting position. When the camming assembly 10330 is in the unfired or starting position, the camming assembly 10330 will contact the right actuator end portion 40222' of the right friction-generating spring 40220' and the left actuator end portion 40232' of the left friction-generating spring 40230' to thereby bias the right actuator end portion 40222' out of confronting alignment with the right lock lug 40114 and the left actuator end portion 40232' out of confronting alignment with the left lock lug 40116. See FIG. 68. When the right friction-generating spring 40220' and the left friction-generating spring 40230' are in those "unlocked" positions, the right friction-generating spring 40220' and the left friction-generating spring 40230' may not apply any meaningful frictional resistance to the firing member 40110 as the firing member 40110 is driven distally from the intermediate closure position.

FIG. 69 illustrates the position of the left friction-generating spring 40230' after the camming assembly in a surgical staple cartridge 10300' has been advanced distally out of the ready-to-fire or starting position which may be indicative of the surgical staple cartridge being partially or completely fired. In either case, the staple cartridge 10300' depicted in FIG. 69 no longer comprises an "unspent" surgical staple cartridge, but instead comprises a "spent" or fired staple cartridge. As can be seen in FIG. 69, because the "spent" surgical staple cartridge 10300' in the surgical end effector lacks the camming assembly 10330 in the ready-to-fire or starting position, the right friction-generating spring 40220' and the left friction-generating spring 40230' are in the locking positions (e.g., the right retention tab portion 40224' is in confronting alignment with a right lock lug 40114 on the firing member body 40112 and the left retention tab portion 40234' is in confronting alignment with a left lock lug 40116 on the firing member body 40112). If the clinician attempts to fire (distally advance the firing member 40110 from the intermediate closure position) when the retention tab portions 40224', 40234' are in the locking positions) the right lock lug 40114 will contact the right retention tab portion 40224' and the left lock lug 40116' will contact the left retention tab portion 40234' which will increase an amount of frictional resistance experienced by the firing member 40110. Thus, the amount of drive force required to be generated by the firing drive motor 40320 to overcome such additional frictional resistance must also be increased which may require the firing drive motor 40320 to draw an increased an amount of firing current $I_F$. The motor controlled system 40330 may be configured to discontinue actuation of the firing drive motor 40320 when the firing current exceeds a predetermined magnitude that is indicative of the increased frictional resistance applied to the firing member 40110 by the firing member lockout system when an unspent staple cartridge has not been properly seated in the surgical end effector in the manner described above.

Figure 70:
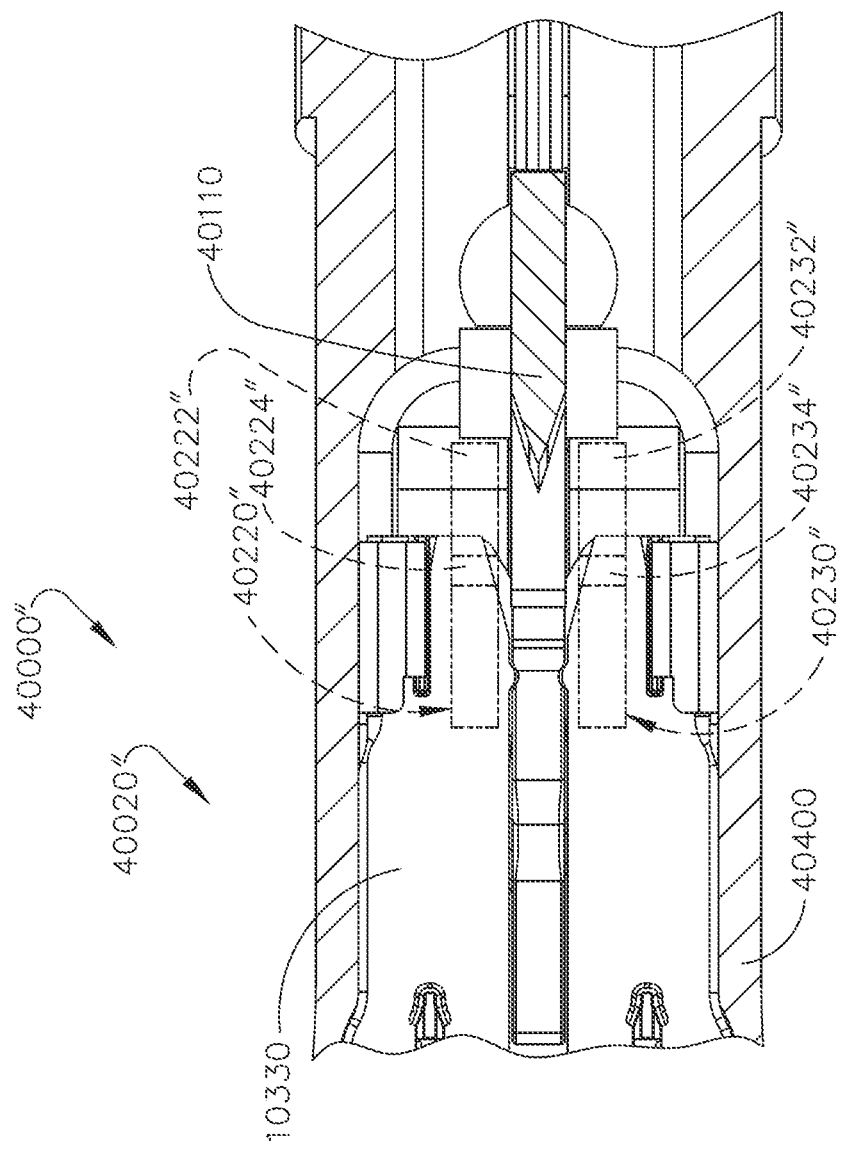
FIG. 70 is a partial cross-sectional top view of portion of another surgical end effector of a surgical instrument in accordance with another general aspect of the present disclosure.
Figure 71:
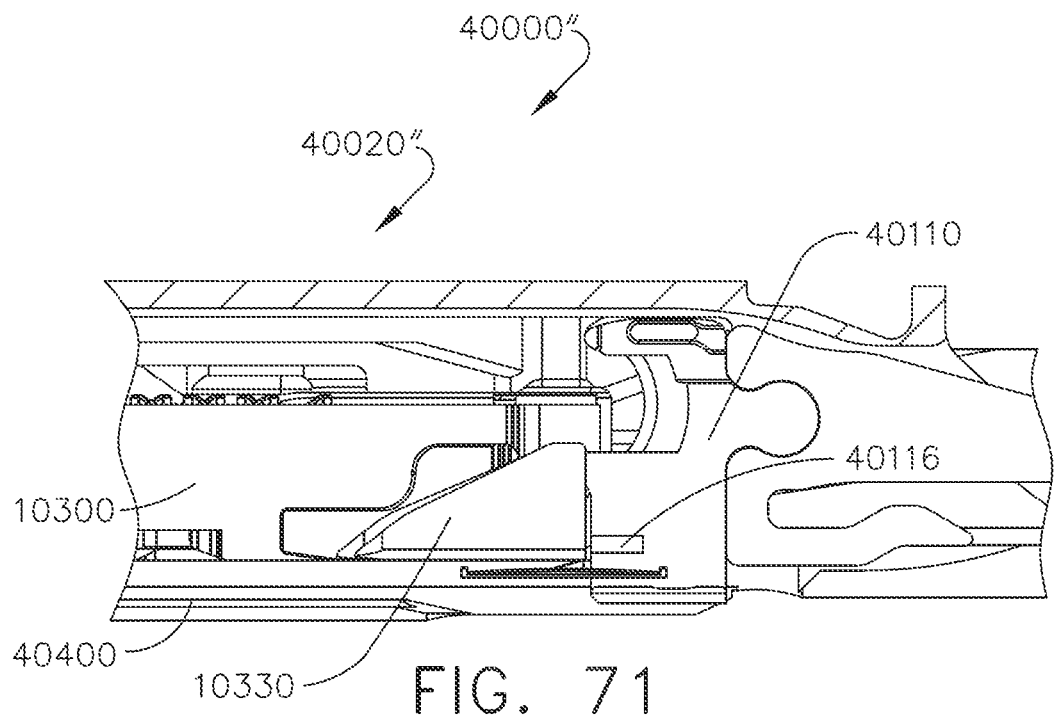
FIG. 71 is a partial cross-sectional side view of the surgical end effector of FIG. 70 with a firing member lockout system thereof in an unlocked orientation.
Figure 72:
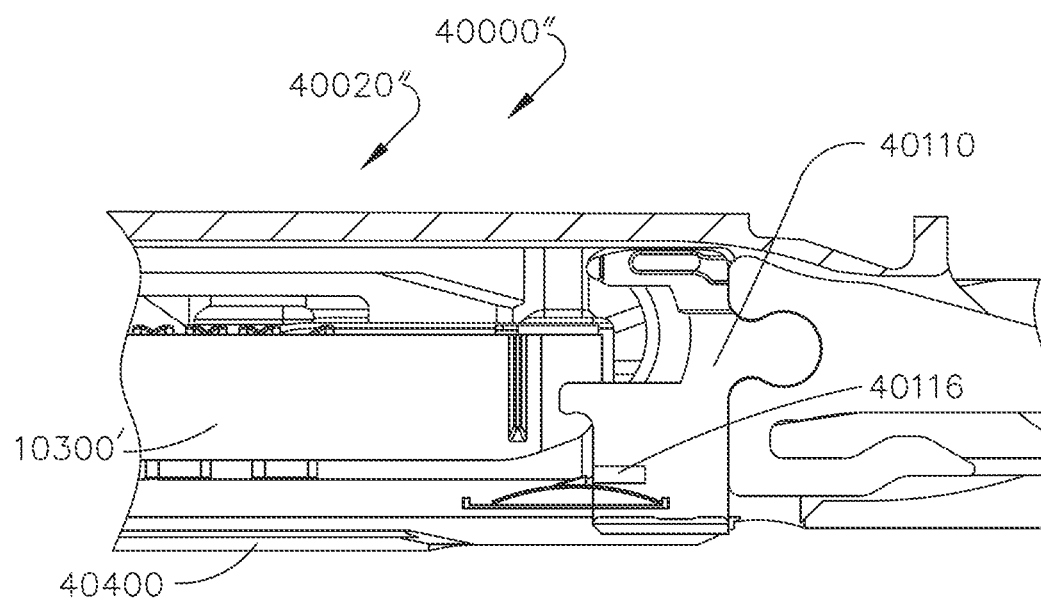
FIG. 72 is a partial cross-sectional side view of the surgical end effector of FIG. 70 with a firing member lockout system thereof in a locked orientation.

FIGS. 70-72 illustrate another surgical instrument 40000" and surgical end effector 40020" that is identical or very similar to the surgical end effector 40020 and surgical instrument 40000 described in detail above except for the differences discussed below. For example, the surgical end effector 40020" comprises an alternative friction-generating arrangement that comprises a right friction-generating spring 40220" that corresponds to a right side of the firing member 40110' and a left friction-generating spring 40230" that corresponds to a left side of the firing member 40110. The right friction-generating spring 40220" is mounted in the elongate channel 40400 and comprises a right spring body 40222" and an upstanding right retention tab portion 40224". Similarly, the left friction-generating spring 40230" comprises a left spring body portion 40232" and a left upstanding retention tab portion 40234". The right friction-generating spring 40220' is mounted in the elongate channel 40400 such that the right retention tab portion 40224' is in a "locked" position wherein the right retention tab portion 40224' is in confronting alignment with a right lock lug 40114 on the firing member body 40112. Similarly, the left friction-generating spring 40230" is mounted in the elongate channel 40400 such that the left retention tab portion 40234' is in confronting alignment with a left lock lug 40116 on the firing member body 40112. See FIG. 70.

FIG. 71 depicts an unspent surgical staple cartridge 10300 properly seated in the elongate channel 40400. As indicated above, an unspent surgical staple cartridge 10300 contains surgical staples in their respective ready-to-fire positions and comprises a camming assembly 10330 in a starting position. When the camming assembly 10330 is in the unfired or starting position, the camming assembly 10330 will depress the right retention tab portion 40224" out of confronting alignment with the right lock lug 40114 (unlocked position) and the left retention tab portion 40234" out of confronting alignment with the left lock lug 40116 (unlocked position). See FIG. 71. When the right friction-generating spring 40220" and the left friction-generating spring 40230" are in those "unlocked" positions, the right friction-generating spring 40220" and the left friction-generating spring 40230" may not apply any meaningful frictional resistance to the firing member 40110 as the firing member 40110 is driven distally from the intermediate closure position.

FIG. 72 illustrates the position of the left friction-generating spring 40230" after the camming assembly in the surgical staple cartridge 10300' has been advanced distally out of the ready-to-fire or starting position which may be indicative of the staple cartridge being partially or completely fired. In either case, the surgical staple cartridge 10300' depicted in FIG. 72 is no longer an unspent surgical staple cartridge. As can be seen in FIG. 72, because the "spent" surgical staple cartridge 10300' in the surgical end effector lacks the camming assembly in the ready-to-fire or starting position, the right friction-generating spring 40220" and the left friction-generating spring 40230" are in the locking positions (e.g., the right retention tab portion 40224" is in confronting alignment with a right lock lug 40114 on the firing member body 40112 and the left retention tab portion 40234" is in confronting alignment with a left lock lug 40116 on the firing member body 40112). If the clinician attempts to fire (distally advance the firing member 40110 from the intermediate closure position) when the retention tab portions 40224", 40234" are in the locking positions) the right lock lug 40114 will contact the right retention tab portion 40224" and the left lock lug 40116 will contact the left retention tab portion 40234" which will increase an amount of frictional resistance experienced by the firing member 40110. Thus, the amount of drive force required to be generated by the firing drive motor 40320 to overcome such additional frictional resistance must also be increased which may require the firing drive motor 40320 to draw an increased an amount of firing current $I_F$. The motor controlled system 40330 may be configured to discontinue actuation of the firing drive motor 40320 when the firing current exceeds a predetermined magnitude that is indicative of the increased frictional resistance applied to the firing member 40110 by the firing member lockout system when an unspent staple cartridge has not been properly seated in the surgical end effector in the manner described above. Other arrangements are contemplated wherein sensors are employed to detect the amount of drive forces that are being applied to the firing member or the drive components operably interfacing therewith. For example, strain gauges may be applied to the firing member and or drive components to detect these forces and loads. The control system would monitor these loads and compare them to loads normally encountered during the actuation of the firing member through an unspent surgical staple cartridge. If the control system detects a spike in such loads, the firing drive motor or other drive mechanism would be deactivated by the control system.

The firing member lockout systems described above are configured to prevent distal movement of the firing member from an intermediate closure position unless an unspent staple cartridge is operably seated in the surgical end effector. In such embodiments, the firing member is selectively movable from a beginning position which enables the anvil to pivot or otherwise move to an open position to the intermediate closure position. As the firing member is distally advanced from the beginning position, in various embodiments, the firing member applies closure motions to the anvil to move the anvil to a closed position. When the firing member has been distally moved to the intermediate closure position, the anvil has been moved to the closed position. Such arrangements enable the surgical end effector to be employed as a grasping instrument for grasping and positioning tissue without cutting and stapling the tissue by moving the firing member between the beginning position to the intermediate closure position. In various embodiments, the anvil may be configured with tissue stops to prevent the target tissue from infiltrating proximally beyond the proximal-most staples in the surgical staple cartridge. When the firing member is in the intermediate closure position, the firing member is proximal to the tissue and proximal-most staples in the surgical staple cartridge such that the firing member is unable to cut the tissue and fire staples. The firing member must be distally advanced from the intermediate closure position to cut tissue and fire staples. Other configurations are contemplated, however, wherein independently actuatable closure member(s) are employed to apply closure motions to the anvil. Such arrangements facilitate movement of the anvil between open and closed positions without moving the firing member from the beginning position. In such applications, the firing member may be positioned to cut tissue and fire staples when the firing member is distally advanced from the beginning position and not an intermediate closure position, for example. In such applications, the firing lockout systems disclosed herein are configured to prevent distal movement of the firing member from the beginning position unless an unspent staple cartridge is operably seated in the surgical end effector.

Example 1—A surgical instrument configured for use in connection with a staple cartridge comprising a plurality of surgical staples stored therein and an axially movable camming member that is configured to eject the surgical staples therefrom when the axially movable camming member is moved from a starting position to a fully fired position in the staple cartridge. The surgical instrument comprises a surgical end effector comprising a first jaw that is configured to operably support the staple cartridge therein and a second jaw that is movable between an open position and a closed position relative to the first jaw. The surgical instrument further comprises an axially movable firing member that is configured to move between a beginning position in the surgical end effector and an ending position in the surgical end effector. A first flexible drive member operably interfaces with a first portion of the axially movable firing member to apply first axial drive motions thereto and a second flexible drive member operably interfaces with a second portion of the axially movable firing member to apply second axial drive motions thereto. A firing member lock is supported in the surgical end effector and is configured to prevent the firing member from moving distally from the beginning position to the ending position unless the axially movable camming member in the staple cartridge is in the starting position in engagement with the firing member lock.

Example 2—The surgical instrument of Example 1, wherein the axially movable firing member is configured to move the second jaw from the open position to the closed position when the axially movable firing member is distally moved from the beginning position to an intermediate closure position, and wherein the firing member lock is configured to prevent the axially movable firing member from moving distally from the intermediate closure position to the ending position unless the axially movable camming member is in the starting position in engagement with the firing member lock.

Example 3—The surgical instrument of Examples 1 or 2, wherein the firing member lock comprises a lock member movably supported in the first jaw. The lock member is movable between a locked position wherein the lock member blocks distal movement of the axially movable firing member from the intermediate closure position and an unlocked position wherein the axially movable firing member is distally movable from the intermediate closure position to the ending position. A biaser arrangement is configured to bias the lock member into the locked position.

Example 4—The surgical instrument of Example 3, wherein the first jaw defines a first jaw axis, and wherein the biaser arrangement comprises a first lock spring located on a first lateral side of the first jaw axis and a second lock spring located on a second lateral side of the first jaw axis.

Example 5—The surgical instrument of Examples 1, 2, 3 or 4, wherein the axially movable firing member comprises a firing member body that comprises a first lateral body side and a second lateral body side. A first firing member bottom tab protrudes from the first lateral body side and a second firing member bottom tab protrudes from the second lateral body side. The lock member comprises a first lateral channel portion that is configured to permit the first firing member bottom tab to pass therethrough when the firing member is in the unlocked position. A second lateral channel portion is configured to permit the second firing member bottom tab to pass therethrough when the firing member is in the unlocked position.

Example 6—The surgical instrument of Examples 1, 2, 3, 4 or 5, wherein the first flexible drive member operably interfaces with a top portion of the axially movable firing member to apply top axial drive motions thereto, and wherein the second flexible drive member operably interfaces with a bottom portion of the axially movable firing member to apply bottom axial drive motions thereto.

Example 7—The surgical instrument of Example 1, wherein the firing member lock comprises a friction-generating spring arrangement that is supported in the surgical end effector. The friction-generating spring arrangement is movable between a locked position wherein the friction-generating spring arrangement is in confronting alignment with a portion of the axially movable firing member and an unlocked position wherein the friction-generating spring arrangement is not in confronting alignment with the portion of the axially movable firing member. The axially movable camming member in the starting position is configured to move the friction-generating spring arrangement into the unlocked position.

Example 8—The surgical instrument of Example 7, wherein the axially movable firing member comprises a firing member body that comprises a first lateral body side and a second lateral body side. A firing member first lateral tab protrudes from the first lateral body side and a firing member second lateral tab protrudes from the second lateral body side. The friction-generating spring arrangement comprises a first retention tab that is configured to engage the firing member first lateral tab when the friction-generating spring arrangement is in the locked position. A second retention tab is configured to engage the firing member second lateral tab when the friction-generating spring arrangement is in the locked position.

Example 9—The surgical instrument of Examples 7 or 8, further comprising a firing drive motor that operably interfaces with the first flexible drive member and the second flexible drive member to apply first axial drive motions to the first flexible drive member and second axial drive motions to the second flexible drive member to drive the axially movable firing member between the beginning position and the ending position. A control circuit operably interfaces with the firing drive motor and is configured to deactivate the firing drive motor when an amount of current drawn by the firing drive motor exceeds a predetermined amount.

Example 10—The surgical instrument of Example 9, wherein when the friction-generating spring arrangement is in the locked position, the amount of current drawn by the firing drive motor exceeds the predetermined amount.

Example 11—A surgical instrument configured for use in connection with a staple cartridge comprising a plurality of surgical staples stored therein and an axially movable camming member that is configured to eject the surgical staples therefrom when the axially movable camming member is moved from a starting position to a fully fired position in the staple cartridge. The surgical instrument comprises a surgical end effector comprising a first jaw that operably supports the staple cartridge therein and a second jaw that is movable between an open position and a closed position relative to the first jaw. The surgical instrument further comprises an axially movable firing member that is configured to move between a beginning position in the surgical end effector and an ending position in the surgical end effector. An electrical drive arrangement operably interfaces with the axially movable firing member to apply axial drive motions thereto. A controller operably interfaces with the electrical drive arrangement and is configured to monitor an amount of electrical current drawn by the electrical drive arrangement required to drive the axially movable firing member from the beginning position to the ending position. The controller is further configured to cause the electrical drive arrangement to discontinue applying the axial drive motions to the axially movable firing member when the amount of electrical current exceeds a predetermined threshold. A firing member lock arrangement is operably supported in the surgical end effector and is configured to move between a locked position in which the firing member lock arrangement applies an amount of frictional resistance to the axially movable firing member to cause the amount of electrical current drawn by the electrical drive arrangement to exceed the predetermined threshold and an unlocked position wherein the firing member lock arrangement discontinues the application of the frictional resistance to the axially movable firing member. The firing member lock arrangement is biased into the locked position unless the axially movable camming member in the staple cartridge is in the starting position.

Example 12—The surgical instrument of Example 11, wherein the firing member lock arrangement comprises a lock member that is movably supported in the first jaw. The lock member is movable between the locked position in which the lock member frictionally contacts a corresponding portion of the axially movable firing member and the unlocked position. A biaser arrangement is configured to bias the lock member into the locked position.

Example 13—The surgical instrument of Example 12, wherein the lock member is configured to be moved from the locked position to the unlocked position by the axially movable camming member in the staple cartridge when the axially movable camming member is in the starting position.

Example 14—The surgical instrument of Examples 12 or 13, wherein the axially movable firing member comprises a firing member body and wherein the corresponding portion of the axially movable firing member is on a first lateral side of the firing member body. The firing member lock arrangement further comprises another lock member that is movably supported in the first jaw and is movable between another locked position wherein the another lock member frictionally contacts another corresponding portion on a second lateral side of the axially movable firing member and another unlocked position. Another biaser arrangement is configured to bias the another lock member into the another locked position.

Example 15—The surgical instrument of Example 14, wherein the lock member is configured to be moved from the locked position to the unlocked position and the another lock member is configured to be moved from the another locked position to the another unlocked position by the axially movable camming member in the staple cartridge when the axially movable camming member is in the starting position.

Example 16—The surgical instrument of Examples 14 or 15, wherein the axially movable firing member comprises a first locking tab and a second locking tab. The lock member is configured to engage the first locking tab when the lock member is in the locked position and the another lock member is configured to engage the second locking tab when the another lock member is in the another locked position.

Example 17—The surgical instrument of Examples 11, 12, 13, 14 15 or 16, further comprising an upper flexible drive member that operably interfaces with the electrical drive arrangement and a top portion of the axially movable firing member to apply top axial drive motions thereto. A lower flexible drive member operably interfaces with the electrical drive arrangement and a bottom portion of the axially movable firing member to apply bottom axial drive motions thereto.

Example 18—The surgical instrument of Example 17, wherein the upper flexible drive member comprises an upper hollow coil member that operably interfaces with the top portion of the axially movable firing member. An upper cable arrangement extends through the upper hollow coil member and is attached to the top portion of the axially movable firing member. A lower hollow coil member operably interfaces with the bottom portion of the axially movable firing member. A lower cable arrangement extends through the lower hollow coil member and is attached to the bottom portion of the axially movable firing member.

Example 19—A surgical instrument configured for use in connection with a staple cartridge comprising a plurality of surgical staples stored therein and an axially movable camming member that is configured to eject the surgical staples therefrom when the axially movable camming member is moved from a starting position to a fully fired position in the staple cartridge. The surgical instrument comprises a surgical end effector that comprises a first jaw that operably supports the staple cartridge therein. A second jaw is movable between an open position and a closed position relative to the first jaw. The surgical instrument further comprises an axially movable firing member that is configured to move between a beginning position in the surgical end effector and an ending position in the surgical end effector. An upper flexible drive member operably interfaces with a top portion of the axially movable firing member to apply axial drive motions thereto. A lower flexible drive member operably interfaces with a bottom portion of the axially movable firing member to apply other axial drive motions thereto. The surgical instrument further comprises means for preventing the axially movable firing member from moving from the beginning position to the ending position unless the axially movable camming member in the staple cartridge is in the starting position.

Example 20—The surgical instrument of Example 19, wherein the axially movable firing member is configured to move the second jaw from the open position to the closed position when the axially movable firing member is distally moved from the beginning position to an intermediate closure position, and wherein the means for preventing is configured to prevent the axially movable firing member from moving distally from the intermediate closure position to the ending position unless the axially movable camming member in the staple cartridge is in the starting position.

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

Many of the surgical instrument systems described herein are motivated by an electric motor; however, the surgical instrument systems described herein can be motivated in any suitable manner. In various instances, the surgical instrument systems described herein can be motivated by a manually-operated trigger, for example. In certain instances, the motors disclosed herein may comprise a portion or portions of a robotically controlled system. Moreover, any of the end effectors and/or tool assemblies disclosed herein can be utilized with a robotic surgical instrument system. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail.

The entire disclosures of:
U.S. Pat. No. 5,403,312, entitled ELECTROSURGICAL HEMOSTATIC DEVICE, which issued on Apr. 4, 1995;
U.S. Pat. No. 7,000,818, entitled SURGICAL STAPLING INSTRUMENT HAVING SEPARATE DISTINCT CLOSING AND FIRING SYSTEMS, which issued on Feb. 21, 2006;
U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;
U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;
U.S. Pat. No. 7,670,334, entitled SURGICAL INSTRUMENT HAVING AN ARTICULATING END EFFECTOR, which issued on Mar. 2, 2010;
U.S. Pat. No. 7,753,245, entitled SURGICAL STAPLING INSTRUMENTS, which issued on Jul. 13, 2010;
U.S. Pat. No. 8,393,514, entitled SELECTIVELY ORIENTABLE IMPLANTABLE FASTENER CARTRIDGE, which issued on Mar. 12, 2013;
U.S. patent application Ser. No. 11/343,803, entitled SURGICAL INSTRUMENT HAVING RECORDING CAPABILITIES, now U.S. Pat. No. 7,845,537;
U.S. patent application Ser. No. 12/031,573, entitled SURGICAL CUTTING AND FASTENING INSTRUMENT HAVING RF ELECTRODES, filed Feb. 14, 2008;
U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;
U.S. patent application Ser. No. 12/235,782, entitled MOTOR-DRIVEN SURGICAL CUTTING INSTRUMENT, now U.S. Pat. No. 8,210,411;
U.S. patent application Ser. No. 12/235,972, entitled MOTORIZED SURGICAL INSTRUMENT, now U.S. Pat. No. 9,050,083;
U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;
U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009, now U.S. Pat. No. 8,220,688;
U.S. patent application Ser. No. 12/893,461, entitled STAPLE CARTRIDGE, filed Sep. 29, 2012, now U.S. Pat. No. 8,733,613;
U.S. patent application Ser. No. 13/036,647, entitled SURGICAL STAPLING INSTRUMENT, filed Feb. 28, 2011, now U.S. Pat. No. 8,561,870;
U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;
U.S. patent application Ser. No. 13/524,049, entitled ARTICULATABLE SURGICAL INSTRUMENT COMPRISING A FIRING DRIVE, filed on Jun. 15, 2012, now U.S. Pat. No. 9,101,358;
U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;
U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;
U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one or more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

What is claimed is:

1. A surgical instrument configured for use in connection with a staple cartridge comprising a plurality of surgical staples stored therein and an axially movable camming sled configured to eject the surgical staples therefrom when the axially movable camming sled is moved from a starting position to a fully fired position in the staple cartridge, wherein said surgical instrument comprises:
a surgical end effector, comprising:
 a first jaw configured to operably support the staple cartridge therein; and
 a second jaw movable between an open position and a closed position relative to said first jaw, and wherein said surgical instrument further comprises:
an axially movable firing member configured to move between a beginning position in said surgical end effector and an ending position in said surgical end effector, wherein said axially movable firing member comprises:
 a distal head comprising a top portion, a bottom portion, and a vertically-extending body intermediate the top portion and the bottom portion, wherein the top portion and the bottom portion are integrally formed with the body;
 a first flexible drive coil extending proximally from said top portion of said distal head, wherein said first flexible drive coil is to apply top axial drive motions to said distal head; and
 a second flexible drive coil extending proximally from said bottom portion of said distal head, wherein said second flexible drive coil is vertically spaced from said first flexible drive coil, and wherein said second flexible drive coil is to apply bottom axial drive motions to the distal head; and
a firing member lock supported in said surgical end effector, wherein said firing member lock is configured to prevent said axially movable firing member from moving distally from the beginning position to the ending position unless the axially movable camming sled in the staple cartridge is in the starting position and in engagement with said firing member lock.

2. The surgical instrument of claim 1, wherein said axially movable firing member is configured to move said second jaw from the open position to the closed position when said axially movable firing member is distally moved from the beginning position to an intermediate closure position, and wherein said firing member lock is configured to prevent said axially movable firing member from moving distally from the intermediate closure position to the ending position unless the axially movable camming sled is in the starting position in engagement with said firing member lock.

3. The surgical instrument of claim 2, wherein said firing member lock comprises:
a lock member movably supported in said first jaw, wherein said lock member is movable between a locked position wherein said lock member blocks distal movement of said axially movable firing member from the intermediate closure position and an unlocked position wherein said axially movable firing member is distally movable from the intermediate closure position to the ending position; and
a biaser arrangement configured to bias said lock member into the locked position.

4. The surgical instrument of claim 3, wherein said first jaw defines a first jaw axis, and wherein said biaser arrangement comprises:
a first lock spring located on a first lateral side of the first jaw axis; and
a second lock spring located on a second lateral side of the first jaw axis.

5. The surgical instrument of claim 3, wherein said distal head comprises:
a first lateral side and a second lateral side;
a first firing member bottom tab protruding from said first lateral side; and a second firing member bottom tab protruding from said second lateral side, and wherein said lock member comprises:
a first lateral channel portion configured to permit said first firing member bottom tab to pass therethrough when said lock member is in the unlocked position; and
a second lateral channel portion configured to permit said second firing member bottom tab to pass therethrough when said lock member is in the unlocked position.

6. The surgical instrument of claim 1, wherein said firing member lock comprises a friction-generating spring arrangement supported in said surgical end effector, wherein said friction-generating spring arrangement is movable between a locked position wherein said friction-generating spring arrangement is in confronting alignment with a portion of said axially movable firing member and an unlocked position wherein said friction-generating spring arrangement is not in confronting alignment with said portion of said axially movable firing member, and wherein said axially movable camming sled in the starting position is configured to move said friction-generating spring arrangement into the unlocked position.

7. The surgical instrument of claim 6, wherein said distal head further comprises:
a first lateral body side and a second lateral body side;
a firing member first lateral tab protruding from said first lateral body side; and
a firing member second lateral tab protruding from said second lateral body side, and wherein said friction-generating spring arrangement comprises:
a first retention tab configured to engage said firing member first lateral tab when said friction-generating spring arrangement is in the locked position; and
a second retention tab configured to engage said firing member second lateral tab when said friction-generating spring arrangement is in the locked position.

8. The surgical instrument of claim 6, further comprising:
a firing drive motor operably interfacing with said first flexible drive coil and said second flexible drive coil to apply said top axial drive motions to said first flexible drive coil and bottom axial drive motions to said second flexible drive coil to drive said axially movable firing member between the beginning position and the ending position; and
a control circuit operably interfacing with said firing drive motor, wherein said control circuit is configured to deactivate said firing drive motor when an amount of current drawn by said firing drive motor exceeds a predetermined amount.

9. The surgical instrument of claim 8, wherein when said friction-generating spring arrangement is in the locked position, said amount of current drawn by said firing drive motor exceeds the predetermined amount.

10. A surgical instrument configured for use in connection with a staple cartridge comprising a plurality of surgical staples stored therein and an axially movable camming sled configured to eject the surgical staples therefrom when the axially movable camming sled is moved from a starting position to a fully fired position in the staple cartridge, wherein said surgical instrument comprises:
a surgical end effector, comprising:
a first jaw operably supporting the staple cartridge therein; and
a second jaw movable between an open position and a closed position relative to said first jaw, and wherein said surgical instrument further comprises:
an axially movable firing member configured to move between a beginning position in said surgical end effector and an ending position in said surgical end effector;
an electrical drive arrangement operably interfacing with said axially movable firing member to apply axial drive motions thereto;
a controller operably interfacing with said electrical drive arrangement, wherein said controller is configured to monitor an amount of electrical current drawn by said electrical drive arrangement to drive said axially movable firing member distally from the beginning position to the ending position, wherein said controller is further configured to cause said electrical drive arrangement to discontinue applying the axial drive motions to said axially movable firing member when said amount of electrical current exceeds a predetermined threshold; and
a firing member lock arrangement comprising a lock body supported in said first jaw, wherein said lock body is configured for slidable movement between a locked position in which said lock body engages a locking tab protruding from said axially moving firing member to apply an amount of frictional resistance to said locking tab on said axially movable firing member to cause the amount of electrical current drawn by said electrical drive arrangement when driving said axially movable firing member distally from said beginning position to exceed the predetermined threshold and an unlocked position wherein the lock body discontinues the application of the frictional resistance to said locking tab on said axially movable firing member, and wherein said lock body is biased into the locked position unless the axially movable camming sled in the staple cartridge is in the starting position.

11. The surgical instrument of claim 10, wherein said firing member lock arrangement comprises a biaser arrangement configured to bias said lock body into the locked position.

12. The surgical instrument of claim 11, wherein said lock body is configured to be moved from the locked position to the unlocked position by said axially movable camming sled in the staple cartridge when said axially movable camming sled is in the starting position.

13. The surgical instrument of claim 11, wherein said axially movable firing member comprises a firing member body, wherein said locking tab of said axially movable firing member protrudes from a first lateral side of said firing member body, and wherein said lock body frictionally contacts another locking tab protruding from a second lateral side of said firing member body when said lock body is in the locked position and said axially movable firing member is moved distally from said beginning position.

14. The surgical instrument of claim 13, wherein said lock body is configured to be non-pivotally moved from the locked position to the unlocked position by the axially movable camming sled in the staple cartridge when the axially movable camming sled is in the starting position.

15. The surgical instrument of claim 10, further comprising:
an upper flexible drive member operably interfacing with said electrical drive arrangement and a top portion of said axially movable firing member to apply top axial drive motions thereto; and
a lower flexible drive member vertically spaced from said upper flexible drive member and operably interfacing with said electrical drive arrangement and a bottom portion of said axially movable firing member to apply bottom axial drive motions thereto.

16. The surgical instrument of claim 15, wherein said upper flexible drive member comprises:
- an upper hollow coil member operably interfacing with said top portion of said axially movable firing member;
- an upper cable arrangement extending through said upper hollow coil member and attached to said top portion of said axially movable firing member;
- a lower hollow coil member operably interfacing with said bottom portion of said axially movable firing member; and
- a lower cable arrangement extending through said lower hollow coil member and attached to said bottom portion of said axially movable firing member.

17. A surgical instrument configured for use in connection with a staple cartridge comprising a plurality of surgical staples stored therein and an axially movable camming sled configured to eject the surgical staples therefrom when the axially movable sled member is moved from a starting position to a fully fired position in the staple cartridge, wherein said surgical instrument comprises:
- a surgical end effector, comprising:
  - a first jaw operably supporting the staple cartridge therein; and
  - a second jaw movable between an open position and a closed position relative to said first jaw, and wherein said surgical instrument further comprises:
- an axially movable firing member configured to move between a beginning position in said surgical end effector and an ending position in said surgical end effector, wherein said axially movable firing member comprises:
- a distal head comprising a top portion, a bottom portion, and a body intermediate the top portion and the bottom portion, wherein the top portion and the bottom portion are integrally formed with the body;
- an upper flexible drive coil extending proximally from said top portion, wherein said upper flexible drive member is to apply upper axial drive motions to said distal head; and
- a lower flexible drive coil extending proximally from said bottom portion, wherein said lower flexible drive coil is vertically spaced from said upper flexible drive coil, wherein said lower flexible drive coil is to apply lower axial drive motions to said distal head; and
- means for preventing said axially movable firing member from moving from the beginning position to the ending position unless the axially movable camming sled in the staple cartridge is in said starting position.

18. The surgical instrument of claim 17, wherein said axially movable firing member is configured to move said second jaw from the open position to the closed position when said axially movable firing member is distally moved from the beginning position to an intermediate closure position, and wherein said means for preventing is configured to prevent said axially movable firing member from moving distally from the intermediate closure position to the ending position unless the axially movable camming sled in the staple cartridge is in the starting position.

19. A surgical instrument configured for use in connection with a staple cartridge comprising a plurality of surgical staples stored therein and an axially movable camming member configured to eject the surgical staples therefrom when the axially movable camming member is moved from a starting position to a fully fired position in the staple cartridge, wherein said surgical instrument comprises:
- a surgical end effector, comprising:
  - a first jaw operably supporting the staple cartridge therein; and
  - a second jaw movable between an open position and a closed position relative to said first jaw, and wherein said surgical instrument further comprises:
- an axially movable firing member configured to move between a beginning position in said surgical end effector and an ending position in said surgical end effector;
- an upper flexible drive member operably interfacing with an electrical drive arrangement and a top portion of said axially movable firing member to apply top axial drive motions thereto, wherein said upper flexible drive member comprises an upper hollow coil member operably interfacing with said top portion of said axially movable firing member and an upper cable arrangement extending through said upper hollow coil member and attached to said top portion of said axially movable firing member;
- a lower flexible drive member operably interfacing with said electrical drive arrangement and a bottom portion of said axially movable firing member to apply bottom axial drive motions thereto, wherein said lower flexible drive member comprises a lower hollow coil member operably interfacing with said bottom portion of said axially movable firing member and a lower cable arrangement extending through said lower hollow coil member and attached to said bottom portion of said axially movable firing member;
- a controller operably interfacing with said electrical drive arrangement, wherein said controller is configured to monitor an amount of electrical current drawn by said electrical drive arrangement to drive said axially movable firing member from the beginning position to the ending position, wherein said controller is further configured to cause said electrical drive arrangement to discontinue applying the axial drive motions to said axially movable firing member when said amount of electrical current exceeds a predetermined threshold; and
- a firing member lock arrangement operably supported in said surgical end effector, wherein said firing member lock arrangement is configured to move between a locked position in which said firing member lock arrangement engages a lock tab protruding from said axially moving firing member to apply an amount of frictional resistance to said axially movable firing member to cause the amount of electrical current drawn by said electrical drive arrangement to exceed the predetermined threshold and an unlocked position wherein the firing member lock arrangement discontinues the application of the frictional resistance to said axially movable firing member, and wherein said firing member lock arrangement is biased into the locked position unless the axially movable camming member in the staple cartridge is in the starting position.

20. A surgical instrument configured for use in connection with a staple cartridge comprising a plurality of surgical staples stored therein and an axially movable camming sled configured to eject the surgical staples therefrom when the axially movable camming sled is moved from a starting position to a fully fired position in the staple cartridge, wherein said surgical instrument comprises:
- a surgical end effector, comprising:
  - a first jaw configured to operably support the staple cartridge therein; and a second jaw movable between an open position and a closed position relative to said first jaw, and wherein said surgical instrument further comprises:

an axially movable firing member configured to move between a beginning position in said surgical end effector and an ending position in said surgical end effector, wherein said axially movable firing member comprises:
- a distal head comprising a top portion, a bottom portion, and a body intermediate the top portion and the bottom portion, wherein the top portion and the bottom portion are integrally formed with the body;
- a top flexible drive member extending proximally from said top portion of said axially movable firing member to apply upper axial drive motions to said distal head;
- a bottom flexible drive member extending proximally from said bottom portion of said distal head, wherein said bottom flexible drive member is vertically spaced from said top flexible drive member, and wherein said bottom flexible drive member is to apply lower axial drive motions to said distal head; and a firing member lock supported in said surgical end effector, wherein said firing member lock defines a central opening therein, wherein said central opening comprises an opening shape that is similar to a shape of a said bottom portion of said axially movable firing member such that when said firing member lock is in an unlocked position, said central opening is axially aligned with said bottom portion of said axially movable firing member to enable said bottom portion of said axially movable firing member to pass through said central opening and when said firing member lock is in a locked position, said central opening is not axially aligned with said bottom portion of said axially movable firing member to prevent said axially moving firing member from moving distally from the beginning position.

* * * * *